United States Patent
Kolkman et al.

(10) Patent No.: US 7,960,150 B2
(45) Date of Patent: Jun. 14, 2011

(54) **PRODUCTION OF A LIPID ACYLTRANSFERASE FROM TRANSFORMED *BACILLUS LICHENIFORMIS* CELLS**

(75) Inventors: Marc Kolkman, Oegstgeest (NL); Jørn Dalgaard Mikkelsen, Hvidovre (DK); Rikke Høegh Lorentsen, Randers (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 12/505,935

(22) Filed: Jul. 20, 2009

(65) Prior Publication Data

US 2010/0081169 A1    Apr. 1, 2010

Related U.S. Application Data

(63) Continuation-in-part of application No. PCT/IB2007/000558, filed on Jan. 25, 2007.

(51) Int. Cl.
*C12P 7/64* (2006.01)
*C07H 21/04* (2006.01)
*C12N 1/20* (2006.01)
*C12N 15/00* (2006.01)

(52) U.S. Cl. ............ 435/134; 435/252.31; 435/320.1; 536/23.2

(58) Field of Classification Search .............. None
See application file for complete search history.

(56) References Cited

U.S. PATENT DOCUMENTS

| | | | |
|---|---|---|---|
| 2,888,385 A | 5/1959 | Grandel |
| 3,260,606 A | 7/1966 | Azuma |
| 3,368,903 A | 2/1968 | Johnson |
| 3,520,702 A | 7/1970 | Menzi |
| 3,634,195 A | 1/1972 | Melachouris |
| 3,652,397 A | 3/1972 | Pardun |
| 3,677,902 A | 7/1972 | Aunstrup |
| 3,817,837 A | 6/1974 | Rubenstein et. al. |
| 3,850,752 A | 11/1974 | Wilhelmus et al. |
| 3,852,260 A | 12/1974 | Knutsen |
| 3,939,350 A | 2/1976 | Kronick et al. |
| 3,973,042 A | 8/1976 | Kosikowski |
| 3,996,345 A | 12/1976 | Ullman et al. |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,275,149 A | 6/1981 | Litman et al. |
| 4,277,437 A | 7/1981 | Maggio |
| 4,366,241 A | 12/1982 | Tom et al. |
| 4,399,218 A | 8/1983 | Gauhl |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,816,567 A | 3/1989 | Cabilly et al. |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,310,679 A | 5/1994 | Artiss et al. |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,674,707 A | 10/1997 | Hintz et al. |
| 5,677,160 A | 10/1997 | Oester |

(Continued)

FOREIGN PATENT DOCUMENTS

AR    249546    12/1996

(Continued)

OTHER PUBLICATIONS

Juan Anguita, et al., Purification, Gene Cloning, Amino Acid Sequence Analysis, and Expression of an Extracellular Lipase from an *Aeromonas hydrophila* Human Isolate, Applied And Environmental Microbiology (1993) vol. 59, No. 8, p. 2411-2417.

Laetitia Brunel, et al., High-level Expression of *Candida parapsilosis* Lipase/Acyltransferase in *Pichia pastoris*, Journal of Biotechnology (2004) vol. 111, p. 41-50.

Rainer Kalscheuer, Synthesis of Novel Lipids in *Saccharomyces cerevisiae* by Heterologous Expression of an Unspecified Bacterial Acyltransferase, Applied And Environmental Microbiology (2004) vol. 70, No. 12, p. 7119-7125.

(Continued)

*Primary Examiner* — Nashaat T Nashed
(74) *Attorney, Agent, or Firm* — Vedder Price P.C.; Thomas J. Kowalski; Heidi Lunasin

(57) ABSTRACT

The present invention relates to a method for the production of a lipid acyltransferase comprising the steps of: (i) providing a *Bacillus licheniformis* cell; (ii) transforming the *Bacillus licheniformis* cell with a heterologous nucleotide sequence encoding a lipid acyltransferase; and (iii) expressing the lipid acyltransferase in the cell under the control of a promoter sequence. In addition, the present invention further relates to the use of *Bacillus licheniformis* to express a lipid acyltransferase, a *Bacillus licheniformis* host cell comprising a heterologous lipid acyltransferase and a vector comprising a nucleotide sequence encoding a lipid acyltransferase operably linked to a promoter sequence homologous to *B. licheniformis*.

11 Claims, 41 Drawing Sheets

U.S. PATENT DOCUMENTS

| | | | |
|---|---|---|---|
| 5,695,802 A | 12/1997 | Van Den Ouweland |
| 5,716,654 A | 2/1998 | Groenendaal |
| 5,741,665 A | 4/1998 | Kato et al. |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,824,354 A | 10/1998 | Ritter et al. |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,254,903 B1 | 7/2001 | Schuster et al. |
| 6,255,076 B1 | 7/2001 | Widner et al. |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Soe et al. |
| 6,730,346 B2 | 5/2004 | Rey |
| 6,815,190 B1 | 11/2004 | Abo |
| 6,852,346 B2 | 2/2005 | Soe |
| 6,866,837 B2 | 3/2005 | Reubi et al. |
| 6,936,289 B2 | 8/2005 | Olsen et al. |
| 6,964,944 B1 | 11/2005 | Callisen et al. |
| 6,967,035 B2 | 11/2005 | Bojsen et al. |
| 7,226,771 B2 | 6/2007 | Gramatikova et al. |
| 7,718,204 B2 | 5/2010 | Soe et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2002/0182734 A1 | 12/2002 | Diaz-Torres et al. |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0142441 A1 | 7/2004 | Weiss et al. |
| 2004/0235106 A1 | 11/2004 | Kapeller-Libermann |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell |
| 2006/0040357 A1 | 2/2006 | Bandaru et al. |
| 2006/0075518 A1 | 4/2006 | Yaver et al. |
| 2006/0141457 A1 | 6/2006 | Lindqvist et al. |
| 2007/0026106 A1 | 2/2007 | Kreij et al. |
| 2007/0122525 A1 | 5/2007 | Kreij et al. |
| 2008/0063783 A1 | 3/2008 | Kreij et al. |
| 2008/0070287 A1 | 3/2008 | Soe et al. |
| 2008/0131936 A1 | 6/2008 | Miasnikov et al. |
| 2008/0187643 A1 | 8/2008 | Horlacher |

FOREIGN PATENT DOCUMENTS

| | | |
|---|---|---|
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224142 | 12/1996 |
| CA | 2403025 | 4/2004 |
| CA | 2403025 | 8/2004 |
| CN | 101200754 | 12/2007 |
| DE | 2817087 | 11/1978 |
| DE | 4429018 | 3/1995 |
| DE | 19620649 | 11/1997 |
| DE | 69129988 | 3/1999 |
| DE | 69330066 | 10/2001 |
| DE | 10119972 | 5/2002 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69531538 | 6/2004 |
| DE | 69819782 | 9/2004 |
| DK | 3106200 | 1/1989 |
| DK | 157560 | 1/1990 |
| DK | PA0888/92 | 7/1992 |
| DK | 96-704602 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | EP0746608 | 10/2003 |
| DK | EP1042458 | 3/2004 |
| EP | 0064855 | 11/1982 |
| EP | 0010296 | 12/1982 |
| EP | 0109244 | 5/1984 |
| EP | 0130064 | 1/1985 |

| | | | | | |
|---|---|---|---|---|---|
| EP | 0140542 | 5/1985 | EP | 0897423 | 10/2004 |
| EP | 0167309 | 1/1986 | EP | 1466980 | 10/2004 |
| EP | 0171995 | 2/1986 | EP | 0839186 | 11/2004 |
| EP | 0205208 | 12/1986 | EP | 1162889 | 2/2005 |
| EP | 0206390 | 12/1986 | EP | 1532863 | 5/2005 |
| EP | 0214761 | 3/1987 | EP | 1559788 | 8/2005 |
| EP | 0257388 | 3/1988 | EP | 1363506 | 11/2005 |
| EP | 0258068 | 3/1988 | EP | 01624047 A1 | 2/2006 |
| EP | 0260573 | 3/1988 | EP | 01624047 B1 | 2/2006 |
| EP | 0334462 | 9/1989 | EP | 1762622 | 3/2007 |
| EP | 0195311 | 6/1990 | EP | 1788080 | 5/2007 |
| EP | 0426211 | 5/1991 | ES | 535608 | 9/1984 |
| EP | 0445692 | 9/1991 | ES | 535602 | 10/1984 |
| EP | 0449375 | 10/1991 | ES | 535609 | 3/1985 |
| EP | 0468731 | 1/1992 | GB | 1086550 | 10/1967 |
| EP | 0493045 | 7/1992 | GB | 1442418 | 7/1976 |
| EP | 0583265 | 10/1992 | GB | 1577933 | 10/1980 |
| EP | 0513709 | 11/1992 | GB | 2264429 | 9/1993 |
| EP | 0542351 | 5/1993 | GB | 0028701.1 | 11/2000 |
| EP | 0558112 | 9/1993 | GB | 2358784 | 8/2001 |
| EP | 0238023 | 12/1993 | GB | 0301117.8 | 1/2003 |
| EP | 0575133 | 12/1993 | GB | 0301118.6 | 1/2003 |
| EP | 0580252 | 1/1994 | GB | 0301119.4 | 1/2003 |
| EP | 0258068 | 8/1994 | GB | 0301120.2 | 1/2003 |
| EP | 0622446 | 11/1994 | GB | 0301121.0 | 1/2003 |
| EP | 0652289 | 5/1995 | GB | 0301122.8 | 1/2003 |
| EP | 0654527 | 5/1995 | GB | 2379165 | 3/2003 |
| EP | 0396162 | 9/1995 | GB | 2267033 | 11/2003 |
| EP | 0687414 | 12/1995 | GB | 0330016.7 | 12/2003 |
| EP | 0585988 | 3/1996 | JP | 59183881 | 4/1960 |
| EP | 0721981 | 7/1996 | JP | 48-16612 | 5/1973 |
| EP | 0752008 | 1/1997 | JP | 5476892 | 6/1979 |
| EP | 0776604 | 6/1997 | JP | 55131340 | 10/1980 |
| EP | 0531104 | 8/1997 | JP | 57-189638 | 11/1982 |
| EP | 0808903 | 11/1997 | JP | 57-189637 | 12/1982 |
| EP | 0682116 | 12/1997 | JP | 60078529 | 5/1985 |
| EP | 0812910 | 12/1997 | JP | 62118883 | 11/1985 |
| EP | 0305216 | 3/1998 | JP | 63042691 | 8/1986 |
| EP | 0847701 | 6/1998 | JP | 62061590 | 3/1987 |
| EP | 0548228 | 8/1998 | JP | 62285749 | 12/1987 |
| EP | 0866796 | 9/1998 | JP | 10203974 | 8/1988 |
| EP | 0869167 | 10/1998 | JP | 1252294 | 10/1989 |
| EP | 0702712 | 12/1998 | JP | 2-49593 | 2/1990 |
| EP | 0882797 | 12/1998 | JP | 2-153997 | 6/1990 |
| EP | 0897667 | 2/1999 | JP | 04075592 | 3/1992 |
| EP | 0913092 | 5/1999 | JP | 6014773 | 3/1992 |
| EP | 0913468 | 5/1999 | JP | 4121186 | 4/1992 |
| EP | 0375102 | 6/1999 | JP | 15626492 | 6/1992 |
| EP | 0321811 | 12/1999 | JP | 04200339 | 7/1992 |
| EP | 1131416 | 6/2000 | JP | 4300839 | 10/1992 |
| EP | 0739985 | 11/2000 | JP | 4327536 | 11/1992 |
| EP | 1057415 | 12/2000 | JP | 04-370055 | 12/1992 |
| EP | 0659049 | 3/2001 | JP | 5211852 | 8/1993 |
| EP | 1103606 | 5/2001 | JP | 6345800 | 12/1994 |
| EP | 1108360 | 6/2001 | JP | 07-079687 | 3/1995 |
| EP | 1138763 | 10/2001 | JP | 8268882 | 4/1995 |
| EP | 1145637 | 10/2001 | JP | 7231788 | 9/1995 |
| EP | 0191217 | 2/2002 | JP | 7330794 | 12/1995 |
| EP | 1193314 | 4/2002 | JP | 8143457 | 6/1996 |
| EP | 0746618 | 8/2002 | JP | 8266213 | 10/1996 |
| EP | 1233676 | 8/2002 | JP | 9040689 | 2/1997 |
| EP | 0648263 | 9/2002 | JP | 10155493 | 6/1998 |
| EP | 0784674 | 9/2002 | JP | 10155493 A | 6/1998 |
| EP | 1073339 | 11/2002 | JP | 11-228986 | 8/1999 |
| EP | 1275711 | 1/2003 | JP | 11290078 | 10/1999 |
| EP | 1285969 | 2/2003 | JP | 2000226335 | 8/2000 |
| EP | 1298205 | 4/2003 | JP | 03/024096 | 7/2001 |
| EP | 0635053 | 6/2003 | JP | 3553958 | 5/2004 |
| EP | 0675944 | 6/2003 | KR | 93-700773 | 3/1993 |
| EP | 0817838 | 6/2003 | KR | 94-10252 | 10/1994 |
| EP | 1280919 | 6/2003 | KR | 95-700043 | 1/1995 |
| EP | 0746608 | 8/2003 | KR | 95-702583 | 6/1995 |
| EP | 0851913 | 5/2004 | KR | 96-704602 | 8/1996 |
| EP | 1262562 | 6/2004 | KR | 2001-7012115 | 9/2001 |
| EP | 1433852 | 6/2004 | KR | 2003-7008997 | 10/2003 |
| EP | 0977869 | 7/2004 | NL | 0784674 | 12/2002 |
| EP | 0743017 | 9/2004 | NL | 0869167 | 1/2003 |
| EP | 0675949 | 10/2004 | NL | 1073339 | 2/2003 |
| EP | 0880590 | 10/2004 | NL | 0746608 | 11/2003 |

| | | | | | | |
|---|---|---|---|---|---|---|
| PH | 31068 | 11/1984 | | WO | 00/34450 | 6/2000 |
| RU | 2140751 | 6/1997 | | WO | 00/36114 | 6/2000 |
| RU | 2235775 | 11/1999 | | WO | 00/43036 | 7/2000 |
| RU | 2001117497 | 6/2001 | | WO | 00/49164 | 8/2000 |
| SE | 9802548 | 7/1998 | | WO | 00/58517 | 10/2000 |
| TR | 200101551 | 12/1999 | | WO | 00/59307 | 10/2000 |
| WO | 88/02775 | 4/1988 | | WO | 00/60063 | 10/2000 |
| WO | 88/03365 | 5/1988 | | WO | 00/61771 | 10/2000 |
| WO | 89/01969 | 3/1989 | | WO | WO 00/63346 | 10/2000 |
| WO | 89/06803 | 7/1989 | | WO | 00/71808 | 11/2000 |
| WO | 91/00920 | 1/1991 | | WO | 00/75295 | 12/2000 |
| WO | 91/06661 | 5/1991 | | WO | 01/16308 | 3/2001 |
| WO | 91/14772 | 10/1991 | | WO | 01/27251 | 4/2001 |
| WO | WO 91/17243 | 11/1991 | | WO | 01/29222 | 4/2001 |
| WO | 92/05249 | 4/1992 | | WO | WO 00/23461 | 4/2001 |
| WO | 92/14830 | 9/1992 | | WO | 01/34835 | 5/2001 |
| WO | 92/18645 | 10/1992 | | WO | WO 01/39544 | 5/2001 |
| WO | 93/01285 | 1/1993 | | WO | 01/39602 | 6/2001 |
| WO | 93/11249 | 6/1993 | | WO | 01/42433 | 6/2001 |
| WO | 93/12812 | 7/1993 | | WO | 01/47363 | 7/2001 |
| WO | 94/01541 | 1/1994 | | WO | 01/66711 | 9/2001 |
| WO | 94/04035 | 3/1994 | | WO | 01/78524 | 10/2001 |
| WO | 94/14940 | 7/1994 | | WO | WO 01/75083 | 10/2001 |
| WO | 94/14951 | 7/1994 | | WO | 01/83559 | 11/2001 |
| WO | 94/26883 | 11/1994 | | WO | 01/83770 | 11/2001 |
| WO | 95/06720 | 3/1995 | | WO | 01/92502 | 12/2001 |
| WO | 95/09909 | 4/1995 | | WO | 02/00852 | 1/2002 |
| WO | 95/22606 | 8/1995 | | WO | 02/03805 | 1/2002 |
| WO | 95/22615 | 8/1995 | | WO | 02/06457 | 1/2002 |
| WO | 95/22625 | 8/1995 | | WO | WO 02/06508 | 1/2002 |
| WO | 95/29996 | 11/1995 | | WO | WO 02/14490 | 2/2002 |
| WO | 95/30744 | 11/1995 | | WO | 02/24881 | 3/2002 |
| WO | 96/09772 | 4/1996 | | WO | 02/30207 | 4/2002 |
| WO | 96/13578 | 5/1996 | | WO | WO 02/29113 | 4/2002 |
| WO | 96/13579 | 5/1996 | | WO | WO 02/39828 | 5/2002 |
| WO | 96/13580 | 5/1996 | | WO | 02/055679 | 7/2002 |
| WO | 96/27002 | 9/1996 | | WO | 02/062973 | 8/2002 |
| WO | 96/28542 | 9/1996 | | WO | 02/065854 | 8/2002 |
| WO | 96/30502 | 10/1996 | | WO | 02/066622 | 8/2002 |
| WO | 96/32472 | 10/1996 | | WO | 02/094123 | 11/2002 |
| WO | 96/39851 | 12/1996 | | WO | WO 03/006644 | 1/2003 |
| WO | 97/04079 | 2/1997 | | WO | 03/020923 | 3/2003 |
| WO | 97/05219 | 2/1997 | | WO | WO 03/020923 | 3/2003 |
| WO | 97/07202 | 2/1997 | | WO | WO 03/020941 | 3/2003 |
| WO | 97/11083 | 3/1997 | | WO | 03/040091 | 5/2003 |
| WO | 97/14713 | 4/1997 | | WO | 03/60112 | 7/2003 |
| WO | 97/27237 | 7/1997 | | WO | 03/070013 | 8/2003 |
| WO | 97/27276 | 7/1997 | | WO | 03/089260 | 10/2003 |
| WO | 97/41212 | 11/1997 | | WO | WO 03/087142 | 10/2003 |
| WO | 97/41735 | 11/1997 | | WO | WO 03/087148 | 10/2003 |
| WO | 97/41736 | 11/1997 | | WO | WO 03/087149 | 10/2003 |
| WO | WO 98/00029 | 1/1998 | | WO | 03/097825 | 11/2003 |
| WO | 98/08939 | 3/1998 | | WO | WO 03/093453 | 11/2003 |
| WO | 98/14594 | 4/1998 | | WO | WO 03/97835 | 11/2003 |
| WO | WO 98/13479 | 4/1998 | | WO | 03/099016 | 12/2003 |
| WO | WO 98/16112 | 4/1998 | | WO | 03/100044 | 12/2003 |
| WO | 98/18912 | 5/1998 | | WO | 03/102118 | 12/2003 |
| WO | 98/26057 | 6/1998 | | WO | WO 03/100044 | 12/2003 |
| WO | WO 98/23162 | 6/1998 | | WO | 2004/004467 | 1/2004 |
| WO | 98/31790 | 7/1998 | | WO | 2004/018660 | 3/2004 |
| WO | WO 98/31790 | 7/1998 | | WO | 2004/053039 | 6/2004 |
| WO | 98/41623 | 9/1998 | | WO | 2004/053152 | 6/2004 |
| WO | 98/44804 | 10/1998 | | WO | 2004/059075 | 7/2004 |
| WO | 98/45453 | 10/1998 | | WO | WO 2004/064537 | 8/2004 |
| WO | 98/50532 | 11/1998 | | WO | WO 2004/064987 | 8/2004 |
| WO | 98/51163 | 11/1998 | | WO | WO 2004/084638 | 10/2004 |
| WO | 98/59028 | 12/1998 | | WO | 2004/097012 | 11/2004 |
| WO | 99/33964 | 7/1999 | | WO | 2004/111216 | 12/2004 |
| WO | 99/34011 | 7/1999 | | WO | 2005/003339 | 1/2005 |
| WO | 99/37782 | 7/1999 | | WO | 2005/005977 | 1/2005 |
| WO | 99/42566 | 8/1999 | | WO | 97/07205 | 2/2005 |
| WO | 99/50399 | 10/1999 | | WO | 2005/056782 | 6/2005 |
| WO | 99/53001 | 10/1999 | | WO | 2005/066347 | 7/2005 |
| WO | 99/53769 | 10/1999 | | WO | 2005/066351 | 7/2005 |
| WO | WO 99/53001 | 10/1999 | | WO | WO 2005/066347 | 7/2005 |
| WO | 99/55883 | 11/1999 | | WO | WO 2005/066351 | 7/2005 |
| WO | 00/05396 | 2/2000 | | WO | 2005069762 | 8/2005 |
| WO | 00/28044 | 5/2000 | | WO | WO 2005/069762 | 8/2005 |
| WO | 00/32758 | 6/2000 | | WO | 2005/080540 | 9/2005 |

| WO | 2005/087918 | 9/2005 |
| WO | WO 2005/111203 | 11/2005 |
| WO | 2006/008508 | 1/2006 |
| WO | 2006/008653 | 1/2006 |
| WO | WO 2006/008508 | 1/2006 |
| WO | 2006018205 | 2/2006 |
| WO | WO 2006/018205 | 2/2006 |
| WO | 2006/032279 | 3/2006 |
| WO | WO 2006/031699 | 3/2006 |
| WO | WO 2006/045354 | 5/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

Saul B. Needleman, et al., A General Method Applicable to the Search for Similarities in the Amino Acid Sequence of Two Proteins, J. Mol. Biology (1970) vol. 48, p. 443-453.

A. H. Nerland, The Nucleotide Sequence of the Gene Encoding GCAT From *Aeromonas salmonicida* ssp. Salmonicida, Journal of Fish Diseases (1996) vol. 19, p. 145-150.

Aji Sutrisno, et al., Express of a Gene Encoding Chitinase (pCA 8 ORF) from *Aeromonas* sp. No. 10S-24 in *Escherichia coli* and Enzyme Characterization, Journal of Bioscience And Bioengineering (2001) vol. 91, No. 6, p. 599-602.

U.S. Appl. No. 60/039,791, dated Mar. 4, 1997, Clausen.

U.S. Appl. No. 60/189,780, dated Mar. 16, 2000, Soe.

U.S. Appl. No. 60/489,441, dated Jul. 23, 2003, Kreij.

Acker, L. "Die Lipide des Getreides, ihre Zusammense und inre Bedeutung", Getreide Mehl Brot (1974) 28:181-187.

Adamzcak, Marek, et al., "Application of Enzymatic Glycerolysis for Production of Monoglycerides from Waste Fats", Polish Journal of Food and Nutrition Science, Mar. 1994, pp. 129-133.

Adhikari, B., et al., "Stickiness in Foods: A Review of Mechanisms and Test Methods", International Journal of Food Properties, vol. 4, No. 1, 2001, 1pg.

Aisaka, Kazuo et al., "Production of Lipoprotein Lipase and Lipase by Rhizopus japonicu", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the Pseudomonas family", Biochimica et Biophysica Acta, vol. 1259, 1995, pp. 9-17.

Al-Obaidy, K A, "Dough and Gluten Characteristics of Good and Poor Quality Flours: Lipid-Protein Bindings affected by Mixing time, water absorption, chemicals and heat," Dissertation Abstracts International B (1987) vol. 47(9) 3597, order No. DA8624641, pp. 266.

Amano Enzyme Inc., http://www.amano-enzyme.co.jp/english/productuse/oil_fat.html. Date of visit: Jun. 21, 2004; (Copyright 2003) pp. 1-2.

Amano Enzymes "Enzymes for Gastrointestinal Digestion" Oct. 1997, pp. 1-2.

Amano Enzymes, Amano Enzyme Europe Ltd, Sep. 1994, pp. 1-4.

Amin, Neelam S., et al., "Direct transformation of site-saturation libraries in Bacillus subtilis", BioTechniques, Dec. 2003, vol. 35 pp. 1134-1140.

Andersson, L., et al., "Hydrolysis of galactolipids by human pancreatic lipolytic enzymes and duidenal contents", Journal of Lipid Research, 1995, vol. 36, pp. 1392-1400.

Sander, Andreas, et al., "Herstellung und Anwendungsmoelichkeiten von Eiweiss-Fettsaeurekondensaten/Production and application of acylated proten hydrolysates", Fett/Lipid 99 (1997) Nr. 4, pp. 115-120.

An-I Yeh et al., "Effects of Oxido-reductants on rheological properties of wheat flour dough and comparison with some characteristics of extruded noodles", Cereal Chemistry, 1999, vol. 76, No. 5, pp. 614-620.

Arbige, Michael A et al, "Novel lipase for cheddar cheese flavor development" Food Technology, vol. 40, 1996, pp. 91-98.

Archer, David B., et al., "Proteolytic degradation of heterologous proteins expressed in Aspergillus Niger", Biotechnology Letter, vol. 14, No. 5, May 1992, pp. 357-362.

Arcos J.A. et al, "Quantative Enzymatic Production of 6.O-Acylglucose Esters", Biotechnology and Bioengineering 1998 vol. 57, No. 5, pp. 505-509.

Arpigny Jean Louis et al, "Bacterial lipolytic enzymes: Classification and properties", Biochemical Journal, vol. 343, No. 1, Oct. 1, 1999, pp. 177-183, XP002375631.

Assignment Document for Enzymatisk detergent additiv, detergent og vaskemetode, executed Aug. 13, 1986 pp. 1-3.

Atomi H, et al., "Microbial lipases-from screening to design", In: Barnes PJ, ed. Oils-Fats-Lipids, 21st World Congress Int Soc Fat Res. England: Bridgwater, 1995: pp. 49-50, vol. 1. NZAS-0016055-NZAS-0016056.

August C.A.P.A. et al. "The use of genetic engineering to obtain efficient production of porcine pancreatic phospholipase A2", Biochimica et Biophysica Acta, vol. 1089, 1991, pp. 345-351.

Aunstrup, Knud et al., "Production of Microbiol Enzymes", Microbiol Technology, Academic Press, 1979, 2nd edition, vol. 1, chap. 9, pp. 281-309.

Ausubel, Frederick M., et al. (editors), "Short Protocols in Molecular Biology- A Compendium of Methods from Current Protocols in Molecular Biology", 1995, John Wiley & Sons, Inc, NZAS-0028441-NZAS-002844.

Bachmatova, I., et al., "Lipase of Pseudomonas mendocina 3121-1 and its Substrate Specificty", Biologija, 1995, pp. 57-59.

"Fat Splitting, Esterification, and Interesterification", in Bailey's Industrial Oils and Fat Products, vol. 2, 4th Edition, John Wiley and Sons, New York pp. 97-173, 1982.

Balcao V.M et. al., "Bioreactors with immobilized lipase: State of the art," Enzyme Microb Technhol, May 1, 1996; 18(6):392-416.

Balcao, V. et. al. "Lipase Catalyzed Modification of Milkfat," (1998), Biotechnology Advances, vol. 16, No. 2, pp. 309-341.

Ballance, D.J., et al., "Transformation of Aspergillus Nidulans by the orotidine-5'-phosphate decarboxylase gene of neurospora crassa", Biochemical and biophysical Research Communications, vol. 112, No. 1, 1983, pp. 284-289.

Ballance, "Transformation Systems for Filamentous Fungi and an Overview of Fungal Gene Structure", Molecular Industrial Mycology, Systems and Applications for Filamentous Fungi, Leong and Berka (eds.), Marcel Dekker Inc, New York 1991, pp. 1-29.

Barbesgaard, Peder et al, "On the safety of Aspergillus oryzae: a review," Applied Microbiology and Biotechnology (1992) 36: 569-572.

Barnes, P.J., "Lipids in Cereal Technology", Food and Science Technology, Academic Press, 1983, pp. 167-171.

Basrl, M., et al., "Amidination of Lipase with Hyrdophobic Imidoesters", JAOCS, vol. 69, No. 6, Jun. 1992, pp. 579-582.

Bateman A et. al., "HMM-based databases in InterPro," Briefings in Bioinformatics vol. 3,No. 3, pp. 236-245 (2002).

Bateman A et al, (2002), "The Pfam Protein Families Database," Nucleic Acids Res. vol. 30, No. 1, pp. 276-280.

Becker T. "Separation and Purification Processes for Recovery of Industrial Enzymes" in R.K. Singh, S.S.H. Rizvi (eds): Bioseparation processes in Foods, Marcel Dekker, New York, pp. 427-445.

Bekkers et al, "The use of genetic engineering to obtain efficient production of porcine pancreatic phospholipase A2 by Saccharomyces cerevisiae," (1991) Biochim Biophys Acta vol. 1089 No. 3 , pp. 345-351.

Bengtsson Olivecrona Gunilla et al. "Phospholipase activity of milk lipoprotein lipase," Methods in Enzymology, vol. 197, 1991 pp. 345-356.

Bentley S D et al, Complete genome sequence of the model actinomycete Streptomyces coelicolor A3(2), Nature vol. 417, 2002, pp. 141-147.

Berger K.G. (1990) "Recent developments in palm oil." Oleagineux, vol. 45, pg. 437-443.

Berks, Ben C., "A common export pathway for proteins binding complex redox cofactors?" Molecular Microbiology, 1996, vol. 22, pp. 393-404.

Beucage S.L. et al, (1981), "Deoxynucleoside Phosphoramidites- A New class of Key Intermediates for Deoxypolynucleotide Synthesis," Tetrahedron Letters 22, pp. 1859-1869.

Bieleski R.L., Sugar Alcohols, in Loewus F A & Tanner W (eds), Plant Carbohydrates I. Intercellular Carbohydrates Encyclopedia Plant Physiol. N.S., 1982, 13A, chapter 5, pp. 158-192, Springer, Berlin.

Bilyk, Alexander, et al., "Lipase-catalyzed triglyceride Hydrolysis in Organic Solvent", pp. 320-323, J, vol. 68, No. 5, May 1991.

Biocatalysts, Limited, Product Sheet for Lipomod(TM) 627P-L627P, published Jan. 9, 2002, Pontypridd UK, p. 1.

Jakobsen, Soren, "Biotekkomet falder hardt til jorden", Borsens, p. 6, Aug. 28, 2002. NZAS-0564031.

Birch et al., "Evidence of Multiple Extracellular Phospholipase Activities of Aspergillus fumigatus", Infection and Immunity, Mar. 1996, vol. 64, No. 3, 1996.

Birgitte Hugh-Jensen et al., "Rhizomucor miehei Triglyceride Lipase is Processed and Secreted from Transformed Aspergillus oryzae", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.

Bjorkling, F., et al., "Lipase Catalyzed Organic Synthesis", S. Servie (ed.), Microbial Reagents in Organic Synthesis, pp. 249-260, 1992.

Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.

Bjorkling, Frederik, et al., "Lipase -mediated Formation of Peroxycarboxylic acids used in Catalytic Epoxidation of Alkenes", J. Chem. Soc., Chemical Communications, Issue 19, 1990.

Bjurlin et al. Identification of carboxylesterase activities of commercial triacylglycerol hydrolase (lipase) preparations, Eur. J. Lipid Sci. Technol. 104 (2002) 143-155.

Blain JA et al, The Nature of Mycelial Lipolytic enzymes in filamentous fungi, Fems Microbiol. Lett., 1978, vol. 3, 85-87.

Blecker et al, Improved emulsifying and foaming of whey proteins after enzymic fat hydrolysis, (1997) J Food Science, vol. 62, No. 1.

Blumenthal, Cynthia Z., "Production of toxic metabolites in *Aspergillus niger, Aspergillus oryzae*, and *Trichoderma reesei*: justification of mycotoxin testing in food grade enzyme preparations derived from the three fungi", Regulatory Toxicology and Pharmacology, vol. 39, 2004, pp. 214-228.

Boel, Esper, et al.; "Rhizomucor miehei Triglyceride Lipase is Synthesized as a Precursor"; Novo Research Institute; vol. 23; No. 7; Jul. 1988.

Bornscheuer U T et al, "Optimizing lipases and related enzymes for efficient application," Trends in Biotechnology, Elsevier Publications, Cambridge GB, vol. 20, No. 10, Oct. 1, 2002, pp. 433-437.

Bornscheuer, Uwe T., "Lipase-catalyzed syntheses of monoacylglycerols", Enzyme and Microbiol Technology, vol. 17, pp. 578-586, 1995.

Brady, Leo, et al., "A serine protease triad forms the catalytic centre of a triacylglycerol lipase", Nature, vol. 343, 1990, pp. 767-770.

Brockerhoff, Hans, et al., "Lipolytic Enzymes", Academic Press, 1974, 1 page.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor complex", Nature, vol. 351, 1991, pp. 491-494.

Buckley J. Thomas et al, "Purification and Partial Characterization of a Bacterial Phospholipid: Cholesterol Acyltransferase," Journal of Biological Chemistry, vol. 257, No. 6, pp. 3320-3325, 1982.

Buckley, "Mechanism of action of a bacterial glycerophospholipid cholesterol acyltransferase," Biochemistry 1983, 22, 5490-5493.

Bulkacz J et al, "Phospholipase A activity in supernatants from cultures of Bacteroides melaninogenicus," Biochim. Biophys. Acta (1981) vol. 664, pp. 148-155.

Van Den Berg. G, Regulatory status and use of lipase in various countries, Bulletin of the IDF 294/1994—The use of lipases in cheesemaking, pp. 19-20, (1994).

Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.

Butcher, Bronwyn G., et al., "The divergent chromosomal ars operon of *Acidithiobacillus ferrooxidans* is regulated by an atypical ArsR protein," Microbiology, 2002, vol. 148, pp. 3983-3992.

Buxton et al, "Transformation of *Aspergillus niger* using the argB gene of *Aspergillus nidulans*," Gene, 1985, 37:207-214.

Cao, Shu-Gui, et al., "Enzymatic Preparation of Monoglycerides via Glycerolysis of Fats and Oils Catalyzed by Lipase from Pseudomonas Species" National Laboratory of Enzyme Engineering. Monoglycerides, Enzyme Engine, Annals New York Academy of Sciences, 1996, vol. 799, issue 1, pp. 670-677.

Carriere et al, "Pancreatic Lipase Structure—Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) "New Chemical methods for Synthesizing polynucleotides," Nuc Acids Res Symp Ser 215-223.

Casimir C A et al "GDSL family of serine esterases/lipases," Progress in Lipid Research, 2004, pp. 534-552.

Castello, P., et al., "Technological and Biochemical effects of exogenous lipases in breadmaking", 2nd European Symposium on enzymes in Grain Processing, Dec. 8-10, 1999, Helsinki, pp. 193-199. Published by VTT, Espoo, 2000.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4, pp. 476-482.

Chakravarti DN et al, Biol. Abstracts, 1981, vol. 72, abstract No. 012592.

Cheng Cheng et al., "Transformation of Trichoderma viride using the Neurospora crassa pyr4 gene and its use in the expression of a Taka-amylase A gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from Arabidopsis", Phytochemical Analysis, vol. 9, pp. 53-57, 1998.

Christophersen, Claus, et al., "Enzymatic Characterisation of Novamyl a Thermostable α-Amylase", Starch/Stärke, vol. 50, 1998, pp. 39-45.

Chung O K et al, "Defatted and Reconstituted wheat flours. VI. Response to shortening addition and Lipid Removal in Flours that vary in Bread-making Quality" Cereal Chemistry (1980), vol. 57(2), pp. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science And Technology, vol. 103, 2001, pp. 333-340.

Clausen, Kim, "New enzyme for degumming", Oils and Fats International, vol. 17, No. 4, Jun. 2001, pp. 24-25.

Cloning of rad51 and rad52 homologues from *Aspergillus oryzae* and the effect of their overexpression on homologous recombination, Novozymes internal document Feb. 9, 2001.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), pp. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998, pp. 657-660.

Council Directive of Dec. 21, 1988 (89/107/EEC).

Council Regulation (EC) No. 2991/94 May 12, 1994 Official Journal of the European Communities, Sep. 12, 1994, No. L316/2-7.

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan, Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, "Heterologous expression of the *Aspergillus nidulans* regulatory gene nirA in *Fusarium oxysporum*," (1991) Gene vol. 109, No. 1, pp. 155-160.

Daboussi et al., "Transformation of seven species of filamentous fungi using the nitrate reductase gene of *Aspergillus nidulans*", Curr. Genet., 15:453-456, 1989.

Daftary R.D. et al., Functional Bread-making Properties of Wheat Flour Lipids, Functional Bread-Making Properties of Lipids chapter 2, in Food Technology, Mar. 1968m vol. 22, No. 327, pp. 79-82, NZAS-0487568.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).

Danisco, Hexose oxidase—nyt enzym med mange mulingheder (advert) Mar. 15, 1999.

Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.

Accession No., P10480 "Glycerophosphopholipid-cholesterol acyltransferase" created Jul. 1, 1989, available at www.ncbi.nlm.nih.gov/entrez.

Database accession No. Q44268 -& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.

Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.

Database Uniprotkb Jun. 1, 2003, S. Omura et al: "putative secreted hydrolase from streptomyces avermitilis" XP002376340 retrieved from EBI, Hinxton, UK Database accession No. Q828T4 abstract.

Database Uniprotkb May 1, 2000, S.D. Bentley et al: "Putative Secreted Hydrolase from Streptomyces coelicolor" XP002376339 retrieved from EBI, Hinxton, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.

Declaration by Clive Graham Phipps Walter (Dec. C) Jul. 4, 2003.

Declaration by Dr Jorn Borch Soe (Dec. F) Dec. 2, 2003.

Declaration by Dr Mark Turner (Dec. G) Feb. 4, 2005, pp. 1-6.

Declaration by Henrik Pedersen (Dec. A) Jul. 7, 2003, pp. 1-3.

Declaration by Henrik Pedersen, Masoud Rajabi Zargahi and Clive Graham Phipps Walter (Dec. 2) Feb. 7, 2005, pp. 1-26, D46.

Declaration by Janne Brunstedt (Dec. D) Jul. 4, 2003.

Declaration by Kazuko Kato, Henrik Pedersen, Masoud Rajabi Zaghari, Clive Phipps Walter, and Janne Brunstedt (Dec. I) Feb. 7, 2005.

Declaration by Kim Borch Oct. 17, 2005.

Declaration by Luise Erlandsen Oct. 21, 2005.

Declaration by Masoud Rajabi Zargahi (Dec. B) Jul. 7, 2003.

Declaration by Masoud Rajabi Zargahi (Dec. E) Jul. 15, 2003.

Declaration by Tina Spendler Oct. 14, 2005.

Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.

Dellaporta, et al.; "A Plant DNA Minipreparation Version II"; Plant Molecular Biology Reporter(1983); vol. 1(4); pp. 19-21.

Derewenda et al, "The crystal and molecular structure of the Rhizomuxor miehei Triacylglyceride Lipase at 1•9 Å Resolution", J. Mol. Biol. 1992, 227:818-839.

Derewenda, Urszula, et al., "Catalysis at the Interface: The Anatomy of a Conformational Change in a Triglyceride Lipase", Biochemistry, vol. 31, pp. 1532-1541, 1992.

Dictionary of Biochemistry and Molecular Biology, Stenesh, J. Second Edition, John Wiley, 1975, p. 16, ISBN 0471840890, pp. 1-3.

Dinkci. N, Mucor miehei den elde edilen lipaz, Ege Univeraitesi Ziraat Fakultesi Dergisi Cilt, 37, Saiy 2-3, 2000, 141-148.

Direct, "The Road to Success: New Stabilizers Rouses Big Interest," A Newsletter from Danisco Ingredients, Sep. 1996, pp. 1-4.

Directive 2000/36/EC. Http://europa.eu.int/scadplus/leg/en/lvb/121122b.htm. Dato: Jun. 16, 2004.

Drost-Lustenberger, C and Spendler T Lipopan F BG—Application and Mechanism of a new lipase for baking, Novozymes. Spanish version of EP869167, Novozymes, Oct. 7, 1998.

Drost-Lustenberger, C. et al., Novozymes, "Lipopan F BG—application and mechanism of a new lipase for bread baking" Cereal Food (2003), Novozymes internal draft.

Drost-Lustenberger, Cornelia, et al., "Lipopan F BG—unlocking the natural strengthening potential in dough", Cereal Food, 2004. Novozymes internal draft, pp. 1-6.

Duan, Rui Dong, Fat Digestion and Absorption (2000), pp. 25-46, publisher AOCS Press, Champaign III CODEN 69ACBA Conference; general review written in English.

Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.

Ducancel, Frederic, et al., "Complete amino acid sequence of a PLA2 from the tiger snake *Notechis sculatus scutatus* as deduced from a complementary DNA", Nucleic Acids Research, vol. 16, No. 18, 1988.

Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.

Lorber B & Giegé R, Preparation and handling of biological macromolecules, in Dugruix (Ed), Crystallization of Nucleic Acids and Proteins A Practical Approach, 1992, Oxford University of Press, ISBN 0199632456.

Dutilh & Groger, "Improvement of Product Attributes of Mayonnaise by Enzymic Hydrolysis of Egg Yolk with Phospholipase A2", 1981 J. Sci. Food Agric. 32, 451-458.

Eddine et al, "Cloning and expression analysis of NhL1, a gene encoding an extracellular lipase from the fungal pea pathogen *Nextria haematococca* MP VI (Fusarium solani f. sp. pisi) that is expressed in planta", Mol. Genet. Genomics (2001) 265: 215-224.

EFEMA Index of Food Emulsifiers Jan. 2004, 4th Edition.

Efthymiou CC et al., "Development of domestic feta cheese", Journal of Dairy Science 1964, vol. 47, No. 6, pp. 593-598.

Ellaiah et al., "Production of lipase by immobilized cells of *Aspergillus niger*", Process Biochemistry, vol. 39, 2004, pp. 525-528.

Elyk, Alexander, et al., "Lipase-Catalyzed ", JAOCS, vol. 8, No. 5, May 1991, pp. 320-323.

Engelhorn and Raab, "Rapid Electroblotting of Small DNA Fragments from Polyacrylamide Gels", Biotechniques (1991) 11(5):594-6.

Engelhorn et al., "Rapid Electroblotting of Small DNA Fragments from Polyacrylamide Gels"; Biotechniques(1991); vol. 11(5); pp. 594-596.

Nagodawithana, T. "Enzymes in food processing" (3rd Ed.), Academic press 1993, pp. 205-219.

EPO, Mobay Chemical Corporation—Decision of the Technical Board of Appeal 3.3.1 dated Jul. 1, 1982, *Official Journal EPO*, Oct. 1982, pp. 394-402.

Ettinger, William F. et al., "Structure of Cutinase Gene, cDNA, and the Derived Amino Acid Sequence from Phytopathogenic Fungi", Biochemistry, vol. 26, pp. 7883-7892, 1987.

Euromonitor International, "The World Market for Dairy Products—Introduction, Executive Summary, Operating Environment, World Market Overview, Key Trends and Developments" in *Euromonitor, Strategy* 2000, Feb. 2001.

European Parliament and Council Directive No. 95/2/EC of Feb. 20, 1995 on food additives other than colours and sweeteners. OJ No. L61 Mar. 18, 1995 pp. 1-53.

European Parliament and Council Directive No. 98/72/EC of Oct. 15, 1998 amending Directive 95/2/EC on food additives other than colours and sweeteners. OJ No. L295 Nov. 4, 1998 pp. 18-30.

Ezra, David, et al., "Coronamycins, peptide antibiotics produced by a *verticillate Streptomyces sp.* (MSU-2110) endophytic on *Monstera sp.*", Microbiology, 2004, vol. 150, pp. 785-793.

Fauvel, et al.; "Purification of Two Lipases With High Phospholipase A, Activity from Guinea-Pig Pancreas"; Biochimica et Biophysica Acta(198I); vol. 663; pp. 446-456.

Fernandez-Garcia et al., "The use of lipolytic and proteolytic enzymes in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, "Purification and properties of a lipase from *Penicillium chrysogenum* isolated from industrial wastes," J. Chem. Technol. Biotechnol. 75, 569-576.

Finizym Technical Information, Novo Enzymes, 1981.

Fødevarenubusteriet (2003). Bekendtgørelse om indhold of transfedtsyrer I olier og fedtstoffer. Bekendtgørelse nr. 160 af Nov. 3, 2003.

Vafiades D, "Embracing Enzymes", Food R&D, Dairy Fields ingredient technology section, Mar. 1996, pp. 39-44.

Forman, Todd, "Enzymes Used in Bread Baking: An Application Update", Technical Bulletin, vol. XXVI, Issue 10, Oct. 2004.

Fox, et al.; "Isolation and some Properties of Extracellular Heat-Stable Lipases: from *Pseudomonas Fluorescens* Strain AFT 36"; Journal of Dairy Research (1988); vol. 50; pp. 77-89.

Frenken N. et al (1992) "cloning of the Pseudomonas glumae Lipase Gene and Determination of the Active Site Residues," Appl. Envir. Microbiol. 58 3787-3791.

Freshzyme™, Novozymes Product Sheet Baking/2000-11814, NZAS—0265916. Mar. 12, 2001, pp. 1-3.

Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

Frost & Sullivan leaflet for report #7954-88 U.S. Market for Enzymes for Food Applications, May 2001, NZAS-0413133.

Fugman, Douglas A et al "Lipoprotein Lipase and phospholipase A2—Catalyzed hydrolysis of phospholipid vesicles with an encapsulated fluorescent dye," Biochemica et Biophysica acia 795 (1984) 191-195.

Daftary, R. D. et. al "Functional Bread-Making Properties of Wheat Flour Lipids", Food Technology, vol. 22, pp. 327-330.

Galliard T and Dennis S (1974) Phospholipase, Galactolipase, and Acyl Transferase Activities of a Lipolytic Enzyme from Potatoe, Phytochemistry vol. 13, pp. 1731-1735.

Galliard, "The Enzymic Breakdown of Lipids in Potato Tuber by Phospholipid- And Galactolipid- Acyl Hydrolase Activities and by Lipoxygenase", Phytochemistry, 1970, vol. 9, pp. 1725-1734.

Gan, Z. et al., "Rapid Communication—Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.

Gemel J et al., "Comparison of galactoplipase activity and free fatty acid levels in chloroplasts of chill-sensitve and chill-resistant plants", European Journal of Biochemistry, vol. 166, 1987, Published by Springer International on behalf of the Federation of European Biochemical Societies, pp. 229-233.

Geus et al (1987) Nucleic Acids Research 15(9) pp. 3743-3759.

Gilbert, E. Jane, et al., "Purification and properties of extracellular lipase from Pseudomonal aeruginosa EF2", Journal of General Microbiology, 1991, vol. 137, pp. 2223-2229.

Gillian, B., Turgeon et al., "*Cochliobolus heterostrophus* using the *Aspergillus nidulans* amdS gene", Mol Gen Genet, 201: 450-453, 1985.

Godfrey, Tony, et al., "Industrial Enzymology Second Edition", Macmillan Press, 1996, ISBN 0333594649, Chapter 2.17, Olive and other Edible Oils, pp. 299-300.

Goodey et al, "Expression and secretion of foreign polypeptides in Yeast," Yeast Biotechnology, Berry et al (eds.), Allen and Unwin, London 1987, pp. 401-429.

Graille J, "Possible applications of acyltransferases in Oleotechnology," Lipid Technology, vol. 5, No. 1, 1993, pp. 11-16.

GRAS Notification dated Apr. 11, 2001 by Novozymes for LecitaseR and LipopanTM F. Gregg L. et al., A lipases preparation produced by *Aspergillus oryzae* expressing the gene encoding a lipases from Fusarium oxyporum. Novo Nordisk A/S product Sheet for Lecitase Novo, Oct. 2000.

Greenough et al (1996) "Safety evaluation of a lipase expressed in *Aspergillus oryzae*," Food Chem Toxicology 34:161-166 and PubMed abstract in respect thereof.

Haas and Berka, 1991, "cloning, expression and characterization of a cDNA encoding a lipase from Phizopus delemar," Gene, 109:107-113.

Haas, et al., "Enzymatic Phosphatidylcholine Hydrolysis in Organic Solvents: An Examination of Selected Commercially Available Lipases", JAOCS, vol. 71, No. 5, May 1994, pp. 483-490.

Haas, et al.; "Lipases of the Genera *Rhizopus* and *Rhizomucor*: Versatile Catalysts in Nature and the Laboratory"; Food Biotechnology Micro-organisims (1995); pp. 549-588.

Haggag H F et al. Egypt J Food Sci vol. 22, No. 1 pp. 99-107 (1994).

Marion D et al., "Lipids, Lipid-protein interactions and the quality of baked cereal products", chapter 6 in Hamer, Rob J., et al., "Interaction: The Keys to Cereal Quality", American Association of Cereal Chemists, S Paul, Minnesota, 1998, ISBN 0913250996, pp. 131-167.

Hanlin, Richard T., "Illustrated Genera of Ascomycetes"; The American Phytopathological Society, 1992, St Paul, Minnesota, pp. 48, 49, 234, 235, 244, 245.

Hansen, Chr., Danisco and Novozymes, Apr. 3, 2002, Food Ingredients day, R&D—the main ingredients for growth.

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the Neurospora crassa nit-4 pathway- specific regularotory gene for nitrate assimilation in *Aspergillus nidulans*", Gene., vol. 100, pp. 237-240, 1991.

Helmsing, "Purification and Properties of Galactolipase", Biochim., Biophys., Acta, vol. 178, pp. 519-533, 1969.

Henderson, H.E., et al., "Structure-function relationships of lipoprotein lipase: mutation analysis and mutagenesis of the loop region", Journal of Lipid Research, vol. 34, 1993, pp. 1593-1602.

Henke, Erik, et al., "Activity of Lipases and Esterases towards Tertiary Alcohols: Insights into Structure-Function Relationships", Angew. Chem. Int. Ed., 2002, vol. 41, No. 17.

Hernquist L & Anjou K (1993) Diglycerides as a stabilizer of the β'-crystal form in margarines and fats, in Fette Seifen Anstrichmittel 2:64-66.

Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.

Hilton S et al, "Purification and spectral study of a microbial fatty acyltransferase:activation by limited proteolysis," Biochemistry vol. 29, No. 38, 1990, pp. 9072-9078.

Hilton S, Buckley JT, "Studies on the reaction mechanism of a microbial lipase/acyltransferase using chemical modification and site-directed mutagenesis," J Biol Chem. Jan. 15, 1991; 266(2): 997-1000.

Hirayama O et al, "Purification and properties of a lipid acyl-hydrolase from potatoe tubers," Biochim Biophys Acta. 1975, vol. 384(1), pp. 127-137.

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.

Holmquist et al., "Lipases from Rhizomucor miehei and Humicola lanuginosa: Modification of the Lid covering the active site alters enantioselectivity", Journal of Protein Chemistry, vol. 12, No. 6, 1993.

Holmquist et al., "Trp89 in the Lid of Humicola lanuginosa Lipase is Important for Efficient Hydrolysis of Tributyrin", Lipids, vol. 29, No. 9, 1994.

Horn T et al, Synthesis of oligonucleotides on cellulose. Part II: design and synthetic strategy to the synthesis of 22 oligodeoxynucleotides coding for Gastric Inhibitory Polypeptide (GIP), Nuc Acids Res Symp Ser No. 7, pp. 225-232 (1980).

Hoshino, et al.; "Calcium Ion Regulates the Release of Lipase of *Fusarium oxysporum*"; J. Biochem (1991); vol. 110; pp. 457-461.

Hoshino, Tamotsu, et al., "Purfication and Some Characteristics of Extracellular Lipase from *Fusarium oxysporum*", Biosci. Biotech. Biochem., vol. 56, No. 4, pp. 660-664, 1992.

Hossen, Monjur and Hernandez, Ernesto, "Phospolipase D-Catalyzed Synthesis of Novel Phospholipid-Phytosterol Conjugates", Lipids, vol. 39, Aug. 2004, pp. 777-782.

Hou, Ching T, "pH dependence and thermostability of lipases from cultures from the ARS Culture Collection", Journal of Industrial Microbiology, vol. 13, No. 4, 1994, pp. 242-248.

Hübner et al., "Interactions at the lipid-water interface", Chemistry and physics of Lipids, vol. 96, 1998, pp. 99-123.

Hugh-Jensen, Birgitte, et al., "Rhizomucor miehei Triglyceride Lipase is Processed and Secreted from Transformed *Aspergillus oryzae*", Lipids, vol. 24, No. 9, pp. 781-785, 1989.

Humum et al., "Enzyme Catalysed Synthesis in Ambient Temperature Ionic Liquids", Biocatalysis and Biotransformation, 2001, vol. 19, pp. 331-338, NZAS-0215170.

Icard-Verniere, Christele, et al., "Effects of mixing conditions on pasta dough development on biochemical changes", Cereal Chemistry, 1999, vol. 76, No. 4, pp. 558-565.

Igrejas, Gilberto, et al., "Genetic and Environmental Effects on Puroindoline-a and Puroindoline-b Content and their Relationship to Technological Properties in French Bread Wheats", Journal of Cereal Science, vol. 34, 2001, pp. 37-47.

Ikeda H et al, "Complete genome sequence and comparative analysis of the industrial microorganism *Streptomyces avermitilis*", Nature Biotech, vol. 21, pp. 526-531, May 2003.

Godfrey, Tony, et al., editors, Industrial enzymology (2nd Ed.), The Macmillan press, pp. 299-300, (1996).

Ishihara et al., "Studies on Lipase from *Mucor Javanicus* * I. Purification and Properties", Biochimica et Biophysica Acta vol. 388, pp. 413-422, (1975).

Isobe and Nokihara, "Primary structure determination of mono- and diacylglycerol lipase from *Penicillium camembertti*", Febs. Lett., Federation of European Biochemical Societies, vol. 320, No. 2, pp. 101-106, (1993).

Isobe K et al, "A new enzymatic method for glycoaldehyde production from ethylene glycol", Journal of Molecular Catalysis B: Enzymatic 1 (1995), pp. 37-43.

Iwai and Tsujisaka, "Fungal lipase", (in Lipases, Borgström and Brockman (eds.), Elsevier, Amsterdam, 1984, pp. 443-468.

Iwai, Mieko, et al., "Hydrolytic and Esterifying Actions of Crystalline Lipase of *Aspergillus Niger*", J. Gen. Appl. Microbiol., 1964, vol. 10, No. 1, pp. 13-21.

Izco et al., "Capillary electrophoresis: Evaluation of the effect of added enzymes on casein proteolysis during the ripening of a ewe's-milk cheese", Adv Food Sci, vol. 21, No. 3/4, pp. 110-116, (1999).

Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53: pp. 609-616.

Jan-Willem F. A. Simons et al., "Cloning, purification and characterisation of the lipase from *Staphylococcus epidermidis*", Eur. J. Biochem., vol. 253, pp. 675-683, 1998.

Jeng-yen Lin, Matthew, "Wheat Polar Lipids—A Theseis Submitted to the Graduate Faculty of the North Dakota State University of Agriculture and Applied Science", May 1972, pp. 34-45.

Jensen B et al "Effect and Activity of Lipases in Dough and Bread" (translation), 48th Conference on Baking technology and 3rd Conference on Cake & Pastry Technology, Nov. 4-6, 1997, pp. 67-76.

Jensen, B., et al., "Effekt and Wirksamkeit von Lipasen in Teig and Brot" 48th Conference on Baking technology and 3rd Conference on Cake & Pastry Technology, Nov. 4-6, 1997, pp. 67-76.

Owens JJ, "Lecithinase Positive Bacteria in Milk", Process Biochemistry, Jan. 1978, vol. 13, pp. 13-14, 30.

Joerger et al., "Alteration of Chain Length Selectivity of a Rhizopus delemar Lipase through Site-Directed Mutagenesis", Lipids, vol. 29, No. 6, 1997, pp. 377-384.

Jong et al.; "American Type Culture Collection Catalogue of Filamentous FUNGI"; Eighteenth edition (1991) p. 80.

Joshi, et al.; "Specificity of Fungal Lipase in Hydrolytic Cleavage of Oil"; Acta Microbiologica Hungarica (1987); vol. 34(2); pp. 111-114.

Joshi, Sunita, et al., "Specificity of Lipase isolated from *Fusarium oxysporum*", Department of Chemistry, Indian Institute of Technology, vol. 25, No. 1 & 2, pp. 76-78, (Jan.-Jun. 1985).

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.

Kaniuga Z, "Galactolipase and chilling sensitivity of plants", Acta Biochim Pol. (1997), vol. 44(1), pp. 21-35.

Kapur J & Sood ML, J. "Effect of pH and Temperature on Lipase and Phospholipase of Adult *Haemonchus contortus* (*Nematoda: Trichostrongylidae*)" J. Parasit., 1986, vol. 72, No. 2, pp. 346-347.

Kasai, Naoya, et al., "Chiral C3 epoxides and halophydrins: Their preparation and synthetic application", Journal of Molecular Catalysis B: Enzymatic, vol. 4, 1998, pp. 237-252.

Kasai, Naoya, et al., "Optically Active Chlorohydrins as Chiral C3 and C4 Building Units: Microbial Resolution and Synthetic Applications", Chirality, vol. 10, pp. 682-692, (1998).

Kawamura, F., et al., "Construction of a *Bacillus subtilis* Double Mutant Deficient in Extracellular Alkaline and Neutral Proteases", J. of Bacteriology, vol. 160, No. 1, Oct. 1984, pp. 442-444.

Keller, R.C.A., et al., "Competitive Adsorption Behaviour of Wheat Flour Components and Emulsifiers at an Air-Water Interface", Journal of Cereal Science, vol. 25, 1997, pp. 175-183.

Keum J S et al., "Effect of Commercial Protease and Lipase on the Ripening of Cheddar Cheese", Korean J Dairy Sci 15 (2): pp. 103-117, (1993).

Kim, Hyung Kwoun, et al., Expression and characterization of Ca2+-independent lipase from *Bacillus pumilus* B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.

Kimura, Yoshiharu, et al., "Application of Immobilized Lipase to Hydrolysis of Triacylglyceride", Eur J. Appl Microbiol Biotechnol, 1983, vol. 17, pp. 107-112.

Kindstedt et al., Rapid Quantative test for free oil (Oiling off) in melted Mozzarella cheese, J. Dairy Sci., 1990, vol. 73, p. 867-873.

King et al, "The production of proteins and peptides from *Saccharomyces cervisiae*", Molecular and Cell Biology of Yeasts, Walton and Yarronton (eds.), Blackie, Glasgow, 1989, pp. 107-133.

Kirk, Ole, et al., "Fatty Acid Specificity in Lipase-Catalyzed Synthesis of Glucoside Esters" Biocatalysis, 1992, vol. 6, pp. 127-134.

Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.

Klein, Robert R., et al., "Additive Effects of Acyl-Binding Site Mutations on the Fatty Acid Selectivity of Rhizopus delemar Lipase", JAOCS, vol. 74, No. 11, 1997, pp. 1401-1407.

Kocak et al., Effect of lipase enzyme (palatase A 750 L) on the ripening of tulum cheese, Tr. J. of Agriculture and Forestry, 1995, vol. 19, pp. 171-177.

Kocak et at., Effect of added fungal lipase on the ripening of Kasar cheese, Milchwissenschaft 51(1), 1996, pp. 13-17.

Kochubei et al., Role of lipids in the organization of the closest surroundings of the reaction centers, Molekulyarnaya Biologiya vol. 12, No. 1, pp. 47-54, Jan.-Feb. 1978.

Kochubei S M et al, "Nature of Longwave Fluorescence of Particles Enriched with Photosytem I", Biophysics (1981), vol. 26(2), pp. 299-304.

Kochubei S M et al, "Differences in the Structure of Long Wave Fluorescence Molecular Aggregates in Photosytems I and II" Institute of Plant Physiology, Academy of Sciences of the Ukranian SSR, Kiev, (Translated from Molekulyarnaya Biologiya vol. 9, No. 2, pp. 190-193, Mar.-Apr. 1975) pp. 150-153, (1975).

Kochubei SM et al, "Role of Lipids in the Organization of the Closest Surroundings of the Reaction Centers of Photosytem 1", Institute of Plant Physiology, Academy of Sciences of the Ukranian SSR, Kiev, (Translated from Molekulyarnaya Biologiya vol. 12, No. 1, pp. 47-54, Jan.-Feb. 1978) pp. 32-37, (1978).

Kolkovski et al., "The Effect of Dietary Enzymes with Age on Protein and Lipid Assimilation and Deposition in *Sparus Aurata Larvae*", in Fish Nutrition in Practice, Biarritz (France), Jun. 24-27 1991, Ed. INRA Paris, 1993, les Colloques, No. 61, pp. 569-578.

Kostal, Jan, et al., "Enhanced Arsenic Accumulation in Engineered Bacterial Cells Expressing ArsR", Applied and Environmental Microbiology, Aug. 2004, vol. 70, No. 8, pp. 4582-4587.

Kouker, et al.; "Specific and Sensitive Plate Assay for Bacterial Lipases"; Applied and Environmental Microbiology (1987); vol. 53(1); pp. 211-213.

Krishna, Sajja Hari, et al., "Enantioselective transesterification of a tertiary alcohol by lipase A from *Candida antarctica*", Tetrahedron: Asymmetry, vol. 13, 2002, pp. 2693-2696.

Kristensen A.C.J., "Preparation of margarine and spreads by enzyme-generated emulsifiers", Master thesis, The Royal Veterinary and Agricultural University, Frederiksberg, Copenhagen, (Jan. 2004) pp. 1-154.

Krog, Niels J., "Dynamic and Unique Monoglycerides", Cereal Foods World, The American Association of Cereal Chemists, Jan. 1979, vol. 24, No. 1, p. 10.

Krupa, Zbigniew et al., "Requirement of Galactolipids for Photosystem J Activity in Lyophilized Spinach Chloroplasts", Biochimica et Biophysica Acta, 408, pp. 26-34, 1975.

Kuipers, Oscar P., et al., "Enhanced Activity and Altered Specificity of Phospholipase A2 by Deletion of a Surface Loop", Science, vol. 244, 1989, pp. 82-85 NZAS-0668767.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from *Torulaspora delbrueckii*", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, pp. 1072-1076, 1994.

Larsen N G et al, "The Effect of Ball-milling on Phospholipid Extractability and the Breadmaking Quality of Flour", Journal of Cereal Science (1990), vol. 12(2), pp. 155-164.

Lecointe et al., "Ester Synthesis in Aqueous Media in the Presence of Various Lipases" Biotechnology Letters, vol. 18, No. 8 (Aug.) pp. 869-874, (1996).

Lee, Keun Hyeung, et al., "Identification and characterization of the antimicrobial peptide corresponding to C-terminal B-sheet domain of tenecin 1, an antibacterial protein of larvae of Tenebrio molitor", Biochem. J., 1996, vol. 334, pp. 99-105.

Lee, Kyung S., et al., The Saccharomyces cerevisiae PLB1 Gene Encodes a Protein Required for Lysophospholipase and Phospholipase B Activity, The Journal of Biological Chemistry, vol. 269, No. 31, Issue of Aug. 5, pp. 19725-19730, (1994).

Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of *Candida albicans*", The Journal of Biological Chemistry, vol. 273, No. 40, pp. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, "Inhibition of *Listeria monocytogenes* by monoacylglycerols synthesized from coconut oil and milkfat by lipase-catalyzed glycerolysis." Journal of Agricultural Food Chemistry (1993), vol. 41, No. 8, pp. 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M JY et al, "Effect on quality of bread and pasta products" Cereal Chemistry (1974), vol. 51(1), pp. 34-45.

Lin S et al, "Purification and characterization of a glycerol oxidase from *Penicillium* sp. TS-622" Enzyme and Microbial Technology 18 (1996), pp. 383-387.

"Lipase A Amano" Technical Bulletin No Lez-1 (Product Specification from Armano Pharmaceutical Co Ltd Nagoya Japan), Dec. 16, 1985, pp. 1-6.

Lipase A "Amano" 6 Assay Note from Armano Pharmaceutical Co Ltd Nagoya Japan, Aug. 27, 1985, p. 1.

Lipase A "Amano" 6 product sheet, Amano Enzyme Inc, Apr. 1, 1999, pp. 1-2.

Lipase SP677 as a Baking Enzyme, from Novo Nordisk, Denmark, Mar. 17, 1994, pp. 1-5.

Lipopan F: Keep the quality—cut your costs 2000 Novozymes A/S. www.enzymes.novo.dk/cgl-bin/bvisapi.dll/biotimes/one_article.jsp?id-16947&lang=en&t=b1, pp. 1-2. (2000).

Litthauer, Derek, et al., "*Pseudomonas luteola* lipase: A new member of the 320- residue *Pseudomonas* lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Lo Y-C et al. Crystal structure of *Escherichia coli* Thioesterase I/ProteaseI/Lysophospholipase L1: Consensus sequence blocks constitute the catalytic center of SGNH-hydrolases through a conserved hydrogen bond network. Journal of Molecular Biology, London, GB, vol. 330, No. 3, 539-551.

Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.

Lozano et al., "Over-stabilization of *Candida antarctica* lipase B by ionic liquids in ester synthesis", Biotechnology Letters, vol. 23, pp. 1529-1533, 2001.

Lustenberger, Cornelia et al., Abstract of "Application of lipase in Asian Noodles and Non-durum Pasta" AACC 2000 Annual Meeting, Nov. 5-9, 2000, pp. 1-2, available at http://aaccnet.org/meetings/2000/Abstracts/a00ma031.htm.

Luzi, Paola et al "Structure and organization of the human galactocerebrosidase (GALC) gene",Genomics (1995), vol. 26, No. 2, pp. 407-409.

Madsen J.S. & Qvist K.B., "Hydrolysis of milk protein by *Bacillus licheniformis* protease specific for acidic amino acid residues" Journal of Food Science, vol. 62, pp. 579-582, (1997).

Mao, Cungui, et al., "Cloning and Characterization of a Saccharomyces cerevisiae Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, University of Aalborg, pp. 1-13, Sep. 2002.

Marion D et al., "Lipids, Lipid-protein Interactions and the Quality of Baked Cereal Products" from Interactions The Keys to Cereal Quality, Chapter 6, Editors Hamer & Hoseney, American Association of Cereal Chemists, Inc., St. Paul, Minnesota, pp. 131-167, (1998). ISBN 0 913250-99-6.

Marion D et al., Wheat Lipids and Lipid-binding proteins: structure and function, in "Wheat Structure Biochemistry & Functionality", editor Schofield JP, 2000, Royal Society of Chemistry Special publication 212 pp. 245-260 ISBN 085404777-8 (It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of Humicola lanuginosa lipase", Protein Engineering, vol. 9, No. 6, 1996, pp. 519-524.

Martinez, Chrislaine, et al., "Engineering cysteine mutants to obtain crystallographic phases with a cutinase from Fusarium solani pisi", Protein Engineering, vol. 6, No. 2, pp. 157-165, 1993.

Martinez, Diego, et al., "Genome sequence of the lignocellulose degrading fungus Phanerochaete chrysosporium strain RP78", Nature Biotechnology, Nature Publishing Group, pp. 1-6, published online on May 2, 2004.

Mason, "Use of Lipolytic Enzyme From *Aeromonas* in Detergents", Research Disclosure, Kenneth Mason Publications, Westbourne GB No. 390, Oct. 1996, pp. 661-662.

Masuda, Naoko, et al., "Primary structure of protein moiety of Penicillium notatum phospholipase B deduced from the Cdna", Eur. J. Biochem., vol. 202, pp. 783-787, 1991.

Matos, A.R., et al., "A patatin-like protein with galactolipase activity is induced by drought stress in Vigna unguiculata leaves", Biochemical Society Transactions, Lipid Catabolism: Lipid Degradation, vol. 28, part 6, pp. 779-781, Jun. 30, 2000.

Matos, AR et al, "A novel patatin-like gene stimulated by drought stress encodes a galactolipid acyl hydrolase", FEBS Letters, 491, pp. 188-192, (First published online Feb. 9, 2001).

Matsuoka, et al.; "Purification and properties of a Phospholipase C That has High Activity toward Sphingomyelin from *Aspergillus Saitoi*"; Biotechonology and Applied Biochemistry (1987); vol. 9, pp. 401-409.

Matthes et al, "Simultaneous rapid chemical synthesis of over one hundred oligonucleotides on a microscale" The Embo Journal, vol. 3, No. 4, pp. 801-805, (1984).

Reetz M.T., Max-Planck-Institut fur Kohlenforschung et al., "Controlling the enantioselectivity of enzymes by directed evolution: Practical and theoretical ramifications", PNAS, Apr. 20, 2004, vol. 101, No. 16, pp. 5716-5722, NZAS-0441867.

McAuley, Katherine E., et al., "Structure of a feruloyl esterase from Aspergillus niger", Acta Crystallographica, Section D, D60, Biological Crystallography, pp. 878-887, 2004.

McCoy M G et al, "Characterization of the lipolytic activity of endothelial lipase", Journal of Lipid Research (2002), vol. 43, pp. 921-929.

McNeill G.P. & Berger R.G., Enzymatic glycerolysis of palm oil fractions and palm oil based model mixture: Relationship between fatty acid composition and monoglyceride yield, in Food Biotechnology 7: pp. 75-87, (1993).

McNeill, Gerald P., et al., "Further Improvements in the Yield of Monoglycerides During Enzymatic Glycerolysis of Fats and Oils", JAOCS, Jan. 1991, vol. 68, No. 1, pp. 6-10. NZAS-0213370.

McNeill, Gerald P., et al., "High-Yield Enzymatic Glycerolysis of Fats and Oils", JAOCS, vol. 68, No. 1, pp. 1-5, Jan. 1991.

McNeill, Gerald P., et al., "Selective Distribution of Saturated Fatty Acids into the Monoglyceride Fraction During Enzymatic Glycerolysis", JAOCS, vol. 69, No. 11, pp. 1098-1103, Nov. 1992.

McNeill, Gerald P., et al., "Solid Phase Enzymatic Glycerolysis of Beef Tallow Resulting in a High Yield of Monoglyceride", JAOCS, vol. 67, No. 11, pp. 779-783, (Nov. 1990).

Memo: From Charlotte Johanson, "Short introduction/ status on Ferulic Acid Esterases and Acetyl Xylan Esterases", Protein Biochemistry, pp. 1-2, Jan. 9, 2004.

Meyer, V., et al., "Transcriptional regulation of the Antifungal Protein in Aspergillus giganteus", Mol Genet Genomics, 2002, vol. 266, pp. 747-757.

Meyers, Robert A., "Molecular Biology and Biotechnology—A Comprehensive Desk Reference" VCH Publishers, pp. 731-737, (1995). ISBN1560815698, NZAS-015769.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from Phanerochaete chrysosporium and Bjerkandera sp. BOS55", Enzyme and Microbial Technology, vol. 32, pp. 769-775 (2003).

Miller, Byron S., et al., "A Comparison of Cereal, Fungal, and Bacterial Alpha-Amylases as Supplements for Breadmaking", Food Technology, pp. 38-42, (Jan. 1953). NZAS 0225991.

Mine Y, "Application of the enzymatic methods to the determination of contaminated yolk in egg white", Food Research International, vol. 29, No. 1, pp. 81-84, (1996).

Ministerio da Ciencia e Tecnologia, *Diario Oficial da Uniao*, No. 134, p. 6, Jul. 15, 2003. ISSN 1677-7042, NZNA-0046369.

Mohsen et al., "Specificity of Lipase Produced by Rhyopus Delemar and Its Utilization in Bread Making", Egypt. J Food. Sci. vol. 14, No. 1, pp. 175-182 (1986).

Molecular Biological Methods for Bacillus—Chapter 3 Plasmids (Ed. C.R. Harwood and S.M. Cutting) John Wiley and Sons Ltd, Chichester, UK, pp. 75-174, 1990.

Mølgaard, Anne, et al., "Rhamnogalacturonan acetylesterase elucidates the structure and function of a new family of hydrolases", Structure, vol. 9, No. 4, pp. 373-383, 2000, NZNA-0056695.

Umanskii M.S. et al., Effect on quality of Kostroma cheese of bacterial cultures selected on phospholipase activity, Molochnaya Promyshlennost 1980 No. 11 21-25, 47—abstract from Food Sci & Tech Abs.

Monick John A., Alcohols, Their Chemistry, Properties and Manufacture, Reinhold Book Cooperation, pp. 3, 6, 14, 47, 48, (1968).

"Mono- and Diglycerides of Edible Fatty Acids", in Monographs for Emulsifiers for Foods, 2nd Edition, The European Food Emulsifier Manufacturers' Association (EFEMA), pp. 47-51, Nov. 1985.

Moore, Charles M., et al., "Metal ion homeostasis in Bacillus subtilis", Current Opinion in Microbiology, vol. 8, pp. 188-195, 2005.

Morgan, Keith R., et al., "Stalling in Starch Breads: the Effect of Antistaling a-Amylase", Starch/Stärke, vol. 49, pp. 59-66,1997.

Morgan-Jones, Gareth; "Notes on Coelomycetes.II. Concerning the Fusicoccum Anamorph of Botryosphaneria Ribis"; Mycotoxon, vol. 30, pp. 117-125; Oct.-Dec. 1987.

Morinaga et al., "Improvement of Oligonucleotide-Directed Site-Specific Mutagenesis Using Double-Stranded Plasmid DNA", Biotechnology 2, pp. 636-639, (1984).

Morten, T. & A., Letter, Rodovre, Jul. 2004.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Mototake, et al., "Transesterification of Oil by Fatty Acid-Modified Lipase", Technical Research Institute, JAOCS, Jun. 1993, vol. 70, No. 6, pp. 571-574 NZAS-0457255.

Murakami, Nobutoshi, et al., "Enzymatic Transformation of Glyceroglycolipids into sn-1 and sn-2 Lysoglyceroglycolipids by use of Rhizopus arrhizus Lipase", Tetrahedron, vol. 50, No. 7, pp. 1993-2002, (1994).

Mustranta, Annikka, et al., "Comparison of Lipases and Phosphlipases in the Hydrolysis of Phospholipids", Process Biochemistry, vol. 30, No. 5, pp. 393-401, 1995.

General Conditions of the company limited by shares N.V. Nederlandsch Octrooibureau, Terms and Conditions, Jan. 2004. NZAS-0012567.

Nagano, et al.; "Cloning and Nucleotide Sequence of cDNA Encoding a Lipase from *Fusarium keteroporum*"; J. Biochem (1994); vol. 116; pp. 535-540.

Nagao T. et al., "C-Terminal Peptide of Fusarium heterosporum Lipase is Necessary for its Increasing Thermostability", J. Biochem., vol. 124, 1124-1129, 1998.

Nagao, T., et al, "Amino Acid Residues Contributing to Stabilization of *Fusarium heterosporum* Lipase", J. of Bioscience and Bioengineering, vol. 89, No. 5, pp. 446-450, 2000.

Nagao, T., et al, "Review: Increase in stability of *Fusarium heterosporum* lipase", J. of Molecular Catalysis B: Enzymatic 17 (2002) pp. 125-132.

Nagao, T., et al, "Use of Thermostable *Fusarium heterosporum* Lipase for Production of Structured Lipid Containing Oleic and Palmitic Acids in Organic Solvent-Free System", JAOCS vol. 78, No. 2, pp. 167-172, (2001).

Nagao, Toshihiro et al., "Cloning and Nucleotide Sequence of CDNA Encoding a Lipase from Fusarium heterosporum", J. Biochem., vol. 116, pp. 535-540, 1994.

Nagao, Toshihiro et al., "Expression of Lipase cDNA from Fusarium heterosporum by Saccharomyces cereviisiae: High-Level Production and Purification", Journal of Fermentation and Bioengineering, 1996, vol. 81, No. 6, pp. 488-492.

Godtfredsen S E, "Lipases", in "Enzymes in food processing" (3rd Ed.), Nagodawithana T and Red G (editors), Academic Press, New York, 1993, ISBN 0125136307, chapter 8, pp. 205-219 NZAS-0665885.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, pp. 147-151.

Nerland A H, Journal of Fish Diseases, vol. 19, No. 2, 1996, pp. 145-150.

Néron, et al., "Effects of lipase and the phosphlipase on the lipids hydrolysis during mixing in correlation with the oxygen consumption by wheat flour dough during kneading", poster 125 Ko at AACC/Tia, San Diego, Calfornia, Sep. 20-22, 2004, available at http://www.cnam.fr/biochimie.

Ness, Jon. E., et al., "DNA shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences Candida albicans Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nielsen et al., "Lipases A and B from the yeast Candida antarctica", in "Biotechnological Applications of Cold-Adapted Organisms" Margesin R & Shimmer F (editors), Springer, 1999, ISBN 3540649727 pp. 49-61 NZAS-0214451.

Nierle W et al, Fette Seifen Anstrichmittel (1981), vol. 83(10), pp. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi Met al, Tetrahedron Letters (1991), vol. 31(1), pp. 1331-1334.

Novozymes data dated Jul. 17, 2005 entitled "Baking performance of prior art lipases from *Humicola lanuginosa, Aspergillus tubigensis, Rhizopus delemar and Rhizomucor miehei*, and their activity on galactolipids in dough".

Novozymes Memo—Test of lipases for EP1193314B1, Jul. 6, 2005, pp. 1-5.

Novozymes Report 2002 Annual Report, "Successfor new baking enzyme," pp. 1-2.

Novozymes journal BioTimes, "Biowhitening—a new concept for steamed bread", Jan. 2005 http://www.biotimes.com/en/Articles/2005/March/Pages/Biowhitening—anewconceptforsteamedbread.aspx, pp. 1-2.

Novozymes, "Breakthrough: Less Fattening Fried Food" *BioTimes*, Jun. 2001, No. 2, pp. 1-12.

Novozymes, "Enzymes for dough strengthening", 2001, pp. 16-21.

Novozymes, "Lipopan F BG—application and mechanism of a new lipase for bread baking" (Draft) Cereal Food (2003) (Author: Drost-Lustenberger, C. et al.), pp. 1-29.

Novozymes article, "Mechanism studies of the new lipase,"Cereal Foods, No. 14, pp. 1-9.

Novozymes, "Product Sheet for Lipopan F BG", *Cereal Food*, (2001), pp. 1-3.

Novozymes, "Product Sheet for Lipopan FS BG", *Cereal Food* (2002), pp. 1-3.

Novozymes, "Product Sheet for Lipopan S BG", *Cereal Food* (2002), pp. 1-3.

Novozymes, "Product Sheet for Noopazyme", Cereal Food (2002) pp. 1-3.

Novozymes, "Product Sheet for Novozym 27016," Baking (2000), pp. 1-6.

Novozymes, "Product Sheet for Novozym 27019," Baking (2000), pp. 1-6.

Novozymes, "Product Sheet for Novozym 27080," Cereal Food (2003), pp. 1-3.

Novozymes, "Revolutionizing baking", *BioTimes* (Dec. 2002) pp. 6-7.

Novozymes, "Strong sales for lipase that makes dough stronger" *BioTimes*, Dec. 2003, pp. 1-2.

Novozymes, "The Novozyme Touch: Make your mark on the future," pp. 1-3.

Novozymes, "The perfect roll every time for steers", *BioTimes*, Sep. 2003, pp. 1-2.

Novozymes, "The value of innovation", *BioTimes*, Mar. 2004, pp. 8-9.
Novozymes, "The vital role of technical service in baking", *BioTimes*, Jun. 2004, pp. 8-9.
Novozymes, Lipopan 50 BG, Product Sheet, pp. 1-3.
Novozymes, Lipopan 50 BG, Product Specification, pp. 1-3.
Novozymes, Lipopan F BG, Product Data Sheet, pp. 1-2.
Novozymes, Lipopan FS Bg, Product Sheet, Cereal Food, pp. 1-3.
Novozymes brochure "Enzymes at work" 2004, pp. 1-60.
Nylander et al., "Interaction between lipids and lipases A collection of papers presented at the European Meeting on lipid and lipase interaction at Lund University" Sep. 2000.
Ognjenovic Radomir et al, Acceleration of ripening of semi-hard cheese by proteolytic and lipolytic enzymes, Proceedings for Natural Sciences, 1996, vol. 91, pp. 5-17.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30th-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) "Partial glycerides and palm oil Crystallisation," in Journal of Science and Food Agriculture vol. 28, p. 955.
Okiy D.A. (1978) "Interaction of triglycerides and diglycerides of palm oil," in Oleagineux, vol. 33 pp. 625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
O'Mahony et al. "Hydrolysis of the lipoprotein fractions of milk by Phospholipase C," Journal of Dairy Science, 1972, vol. 55, No. 4, pp. 408-412.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004, pp. 287-296.
Osman, Mohamed, et al., "Lipolytic activity of Alternaria alternata and Fusarium oxysporum and certain properties of their lipids", Microbios Letters, vol. 39, pp. 131-135, 1988.
Ostrovskaya L K et al, "Spectral Features of the Action of Galactolipase on Native Forms of Chlorophyll," Dokl Akad Nauk SSSR, (vol. 186(4), pp. 961-963) pp. 59-61.
O'Sullivan et al, "A Galactolipase activity associated with the thylakoids of Wheat Leaves (Triticum aestivum L.)," J Plant Physiol, vol. 313, (1987) pp. 393-404.
Outtrup, Günther H., et al., "Properties and Application of a Thermostable Maltogenic Amylase Produced by a Strain of Bacillus Modified by Recombinant-DNA Techniques", Starch/Starke, vol. 36, No. 12, pp. 405-411.
Palomo, Jose M., et al., "Enzymatic production of (3S, 4R)-(−)-4-(4'-fluorophenyl)-6-oxo-piperidin-3-carboxylic acid using a commerical preparation of lipase A from Candida antarctica: the role of a contaminant esterase" Tetrahedron: Asymmetry, vol. 13, 2002, pp. 2653-2659.
Palomo, Jose M., et al., "Enzymatic resolution of (±)-glycidyl butyrate in aquenous media. Strong modulation of the properties of the lipase from Rhizopus oryzae via immobilization techniques", Tetrahedron: Asymmetry, vol. 15, 2004, pp. 1157-1161.

Palomo, Jose M., et al., "Modulation of the enantioselectivity of Candida antarctica B lipase via conformational engineering: kinetic resolution of (±)-α-hydroxy-phenylacetic acid derivatives", Tetrahedron: Asymmetry, vol. 13, 2002, pp. 1337-1345.
Pariza, Michael, et al., "Evaluating the safety of Microbiol Enzyme Preparations Used in Food Processing: Update for a New Century", Regulatory Toxicology and Pharmacology, vol. 33, pp. 173-186.
Patent Abstracts of Japan vol. 016, No. 528 (C-1001), Oct. 29, 1992 & JP 04 200339 A see abstract.
Patent Abstracts of Japan vol. 095, No. 001, Feb. 28, 1995 & JP 06 296467 A see abstract.
Penninga et al, "Site-directed mutations in Tyrosine 195 of Cyclodextrin Glycosyltransferase from Bacillus circulans Strain 251 affect qctivity and product Specificity," Biochemistry (1995), 3368-3376.
Persson, Manias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the Humicola lanuginosa Lipase", Biochemistry, 1998, vol. 37, pp. 12375-12383.
Peters, G.H., et al.; "Dynamics of Rhizomucor miehei lipase in a lipid or aqueous environment: Functional role of glycines"; Draft for Biophys. J, 1996 Nov., vol. 71, No. 5, pp. 2245-2255 NZAS-0031441.
Peters, G.H., et al.; "Essential motions in lipases and their relationship to the biological function", Proceedings of the German Conference on Bioinformatics, GCB '96, Leipzig, Germany, Sep. 30-Oct. 2, 1996, poster, pp. 280-282 NZAS-0031438.
Peters, Günther H., et al., "Theoretical Investigation of the Dynamics of the Active Site Lid in Rhizomucor miehei Lipase", Biophysical Journal, vol. 71, 1996, pp. 119-129.
*Harborne J.B. et al. (editors), Phytochemical Dictionary: A Handbook of Bioactive Compounds from Plants, Taylor & Francis*, 1993, *ISBN* 978050667363 *Chapter 4, "Sugar Alcohols and Cyclitols"*, pp. 20-23.
Picon et al., "Release of Encapsulated Proeinase from Dehydration-Rehydration Liposomes by a Co-encapsulated Phospholipase," Biotechnology Letters, Oct. 1995, vol. 17, No. 10, pp. 1051-1056.
Plijter J and JHGM Mutsaers, "The surface rheological properties of dough and the influence of lipase on it, Gist-brocades," Bakery Ingredients Division, Oct. 1994.
Plou et al, "Enzymatic acylation of di- and trisaccharides with fatty acids: choosing approiate enzyme, support and solvent," J. Biotechnology 92 (2002) 55-66.
Ponte J G, "Note on the Separation and Baking properties of Polar and Nonpolar Wheat Flour Lipids," Cereal Chemistry (1969), vol. 46(3), pp. 325-329.
Poulsen, C.H., et al., "Effect and Functionality of Lipases in Dough and Bread", in Angelino SAGF, Hamer RJ, van Hartingsveldt W, Heidekamp F, van der Lugt JP (editors), First European Symposium on Enzymes and Grain Processing, Zeist, The Netherlands, TNO Nutrition and Food Research Institute, ISBN 90-75202-04-0, pp. 204-214. Proceedings of ESEGP-1, Noordwijkerhout, The Netherlands, Dec. 2-4, 1996, NZAS-0158559.
Poulsen, Charlotte, et al. "Purification and Characterization of a Hexose Oxidase with Excellent Strenghening Effects in Bread" Cereal Chem. (1998) vol. 75(1); pp. 51-57.
Product Sheet B1324a-GB—"Lecitase$^R$ Novo", Novo Nordisk, Oct. 2000, pp. 1-4.
Punt, P. et. al., "Transformation of Filamentous Fungi Based on Hygromycin B and Phleomycin Resistance Markers," Meth. Enzym., 1992, 216:447-457.
Pyler, E.J., "Baking Science and Technology," Third Edition vol. 1, 1988, p. 588.
Pyler, E.J., "Baking Science and Technology," Third Edition, vol. II, 1988, pp. 589-801.
Queener et al. (1994), "Improved Expression of a Hybrid: Streptomyces clavuligerus cefE Gene in Penicillium chrysogenum," Ann N Y Acad Sci. 721, pp. 178-193.
Rambosek, J., "Recombinant DNA in Filamentous Fungi: Progress and Prospects," CRC Crit. Rev. Biotechnol., 1987, vol. 6, No. 4, pp. 357-393.

Rapp, Peter, et al., "Formation of extracellular lipases by filamentous fungi, yeasts, and bacteria", Enzyme Microb. Technol., 1992, vol. 14, November.

Rapp, Peter; "Production, regulation, and some properties of lipase activity from *Fusarium Oxysporum f.* sp. *vasinfectum*"; Enzyme and Microbial Technolo (1995); vol. 17; pp. 832-838.

Reetz M.T et. al., "Overexpression, immobilization and biotechnological application of Pseudomonas lipases," Chem Phys Lipids. Jun. 1998; 93(1-2): 3-14.

Reetz Manfred T, "Lipases as practical biocatalysts," Current Opinion in Chemical Biology, Apr. 2002, vol. 6, No. 2, pp. 145-150.

Reiser J et al.(1990). "Transfer and Expression of Heterologous Genes in Yeasts other than Saccharomyces cerevisiae," Adv Biochem Eng Biotechnol. 43, pp. 75-102.

Richardson & Hyslop, "Enzymes", pp. 371-476 in "Food Chemistry Second Edition, Revised and Expanded", 1985, second edition, Owen R. Fennema (ed), Marcel Dekker, Inc, New York and Basel.

Richardson and Hyslop, "Enzymes: XI—Enzymes Added to Foods During Processing" in *Food Chemistry*, Marcel Dekker, Inc., New York, NY 1985.

Arskog and Joergensen, "Baking performance of prior art lipases from *Candida cylindraceaand Aspergillus foeditus* and their actiivty on galactolipids in dough", Novozymes Report 2005.

Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.

Richardson, Toby H., et al., "A Novel, High Performance Enzyme for Starch Liquefaction", The Journal of Biological Chemistry, vol. 277, No. 29, Issue of Jul. 19, pp. 25501-26507, 2002.

Roberts et al. (1992). "Heterologous gene expression in *Aspergillus niger*: a glucoamylase-porcine pancreatic prophospholipase A2 fusion protein is secreted and processed to yield mature enzyme," Gene 122(1), 155-161.

Roberts, et al.; "Extracellular Lipase Production by Fungi from Sunflower Seed"; Mycologia(1987); vol. 79(2); pp. 265-273.

Robertson et al, "Influence of Active Site and Tyrosine Modification on the Secretion and Activity of the Aeromonas hydrophila Lipase/Acyltransferase," Journal of Biological Chemistry, 1994, vol. 259, No. 3, pp. 2146-2150.

Rodrigues, et al.;"Short Communication: Bioseparations with Permeable Particles"; Journal of Chromatography & Biomedical Applications(1995); vol. 655; pp. 233-240.

Rogalska, Ewa, et al., "Stereoselective Hydrolysis of Triglycerides by Animal and Microbial Lipases", Chirality, vol. 5, pp. 24-30, 1993.

Rose, et al.;"CODEHOP (Consensus-Degenerate Hybrid Oligonucleotide Primer) PCR primer design"; Nucleic Acids Research(2003); vol. 31(13); pp. 3763-3766.

Rousseau, Derick, et al., "Tailoring the Textural Attributes of Butter Fat/Canola Oil Blends via Rhizopus arrhizus Lipase-Catalyzed Interesterification. 2. Modifications of Physical Properties", J. Agric. Food Chem., vol. 1998, vol. 46, pp. 2375-2381.

Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.

Sahsah, Y., et al., "Enzymatic degradation of polar lipids in Vigna unguiculata leaves and influence of drought stress", Physiologia Plantarum, vol. 104, pp. 577-586, 1998.

Sahsah, Y., et al., "Purification and characterization of a soluble lipolytic acylhydrolase from Cowpea (vigna unguiculata L.) leaves", Biochimica et Biophysica Acta, vol. 1215, pp. 66-73, 1994.

Saiki R.K. et al, "Primer-Directed Enzymatic Amplification of DNA with a Thermostable DNA Polymerase," Science (1988) 239, pp. 487-491.

Saito, Kunihiko, et al., "Phospholipase B from Penicillium notatum", Methods in Enzymology, 1991, vol. 197, pp. 446-456 NZAS-0418833.

Sakai, Norio, et al., "Human glactocerebrosidase gene: promoter analysis of the 5'-flanking region and structural organization", Biochimica et Biophysica Acta, vol. 1395, pp. 62-67, 1998.

Sakaki T et al, Advanced Research on Plant Lipids, Proceedings of the International Symposium on Plant Lipids, 15th, Okazaki, Japan, May 12-17 2002 (2003) pp. 291-294, Publisher Kluwer Academic Publishers.

Sambrook et al, Chapters 1, 7, 9, 11, 12 and 13—Molecular Cloning a laboratory manual, vol. 3, pp. 1.1-13.104, Cold Spring Harbor Laboratory Press (1989).

Sambrook, J., et al. "Molecular Cloning: A Laboratory Manual, Second Edition", Plasmid Vectors, 1989, pp. 1-462.

Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.

Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).

Saxena, et al.; "Purification Strategies for Microbial Lipases"; Journal of Microbilogical Methods (2003); pp. 1-18.

Scheib et al.; "Stereoselectivity of Mucorales lipases toward triradylglycerols—A simple solution to a complex problem"; Protein Science (1999); vol. 8; pp. 215-221.

Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.

Schofield, J. David, "Wheat Structure, Biochemistry and Functionality", Department of Food Science and Technologw, pp. 243-260.

Scopes, Robert K., "Section 8.4: Ultrafiltration" in *Protein Purification Principles and Practice, Third Edition* (1994) Springer-Verlag, New York, pp. 267-269.

Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.

Shillcock, Julian C., et al., "Tension-induced fusion of bilayer membranes and vesicles", Advance Online Publication Feb. 13, 2005, Nat. Mater., 2005, vol. 4, No. 3, pp. 225-228 NZAS-0231181.

Shimada et al, "Enzymatic Purification of Polyunsaturated Fatty Acids," J. Of Bioscience and Bioengineering vol. 91, No. 6, 529-538 (2001).

Shimada et al, "Purification and Characterization of a Novel Solvent-Tolerant Lipase from Fusarium heterosporum," J. of Fermentation and Bioengineering vol. 75, No. 5, 349-352 (1993).

Shimada et al, "Enrichment of Polyunsaturated Fatty Acids with Geotrichum candidum Lipase," JAOCS vol. 71, No. 9, (Sep. 1994), pp. 951-954.

Shin, et al.; "Butyl-Toyopearl 650 as a New Hydrophobic Adsorbent for Water-Soluable Enzyme Proteins"; Analytical Biochemistry(1984); vol. 138; pp. 259-261.

Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969, pp. 93-103.

Si, Joan Qi, "Enzymes, Baking, Bread-Making", Encyclopedia of Bioprocess Technology, Wiley, 1999, ISBN 0471138223 NZAS-0255053, pp. 1-18.

Si, Joan Qi, "Synergistic Effect of Enzymes for Breadbaking", Novo Nordisk publication A-06513b, pp. 1-18, based on presentation No. 300 at AACC Annual Meeting 1996, Baltimore. Also Encyclopedia of Bioprocess Technology, Wiley, 1999, ISBN 0471138223.

Si, Joan Qi, et al. "Enzymes for bread, noodles and non-durum pasta", Cereal Food 2002 pp. 1:3 - 3:4. Also in Enzymes in Food Technology, RJ Whitehurst & BA Law, Enzymes in Food Technology, Sheffield Academic Press, ISBN 1-84127-223-X, pp. 19-54.

Si, Joan Qi, et al., "Novamyl—A true Anti-Staling Enzyme", Cereal Food, Oct. 2001, pp. 1-20.

Si, Joan Qi, et al., "Synergistic Effect of Enzymes for Breadbaking", Cereal Food, Oct. 2001, p. 1:21, based on presentation No. 300 at AACC Annual Meeting 1996, Baltimore. Also Encyclopedia of Bioprocess Technology, Wiley, 1999, ISBN 0471138223.

Si, Joan Qi; "New Enzymes for the Baking Industry"; Food Tech Europe (1996) pp. 60-64.

Sias B et al, "Human Pancreatic Lipase-Related Protein 2 Is a Galactolipase," Biochemistry, (2004), vol. 43(31), pp. 10138-10148.

Siew W.L. et. al. (1999) "Influence of diglycerides on crystalisation of palm oil," in Journal of Science of Food and Agriculture 79:722-726.

Siew W.L. & Ng W.L. (2000) Differential scanning thermograms of palm oil triglycerides in the presence of diglycerides, in Journal of Oil Palm Research 12:107.

Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.

Skovgaard, et al.;"Comparison of Intra- and extracellualr isozyme banding patterns of Fusarium Oxysporum"; Mycol. Res. (1998); vol. 102(9); pp. 1077-1084.

Slotboom et al, "Hydrolysis of Phosphoglycerides by Purified Lipase Preparation," Chem. Phys. Lipids vol. 4 (1970) 15-29.

Smith, George P.; "The Progeny of sexual PCR"; Nature; vol. 370; No. 18; Aug. 4, 1994 pp. 324-325.

Smith, Timothy L., et al., "The promoter of the glucoamylase-encoding gene of Aspergillus niger functions in Ustilago maydis", Gene. 88, 259-262, 1990.

Soe, J.B., "Analyses of Monoglycerides and Other Emulsifiers by Gaschromatography", Fette, Seifen, Anstrichmittel, 1983, 85 Jahrgang, nr. 2, pp. 72-76NZNA-0005896.

Solares, Laura F., et al., "Enzymatic resolution of new carbonate intermediates for the synthesis of (S)-(+)zopiclone", Tetrahedron: Asymmetry, vol. 13, 2002, pp. 2577-2582.

Sols and De Le Fuente, "On the substrate specificity of glucose oxidase", Biochem et Biophysica Acta (1957) 24:206-7.

Sonntag N.O.V. (1982a) Glycerolysis of Fats and methyl esters—status, review and critique, in Journal of American Oil Chemist Society 59:795-802A.

Soragni, Elisabetta, et al., "A nutrient-regulated, dual localization phospholipase A2 in the symbiotic fungus" The EMBO Journal, vol. 20, No. 18, pp. 5079-5090, 2001.

Sorensen, H.R., et al., "Effects of added enzymes on the physicochemical characteristics on fresh durum-pasta", Internal # A-6780.

Sosland, Josh, "Alive and kicking", Milling & Baking News, Feb. 24, 2004. http://www.bakingbusiness.com/co_articles.asp?ArticleID=70026 downloaded Sep. 16, 2004 pp.1-13.

Soumanou, Mohamed M., et al., "Two-Step Enzymatic Reaction for the Synthesis of Pure Structured Triacylglycerides", JAOCS, vol. 75, No. 6, 1998.

Spendler, et al., "Functionality and mechanism of a new 2nd generation lipase for baking industry" —Abstract. 2001 AACC Annual Meeting; Symposia at Charlotte, NC. Oct. 14-18, 2001.

Spradling J.E., "Tailoring Enzyme Systems for Food Processing, in"Biocatalysis in Agricultural Biotechnology, ACS Symposium Series 389, ed. Whitaker, John R. et al., 1989, ISBN 0-8412-1571-5 pp. 24-43 NZAS-0213683.

Sreekrishna K et al (1988) "High level expression of heterologous proteins in methylotrophic yeast Pichia pastoris," J Basic Microbiol. 28(4), 265-78.

Stadler et al., "Understanding Lipase Action and Selectivity", CCACAA, vol. 68, No. 3, pp. 649-674, 1995.

Steinstraesser, et al., "Activity of Novispirin G10 against Pseudomonas aeruginosa in Vitro and in Infected Burns", Antimicrobial Agents and Chemotherapy, Jun. 2002, vol. 46, No. 6, pp. 1837-1844.

Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.

Stemmer, Willem P.C.; "Rapid evolution of a protein in vitro by DNA shuffling"; Affymax Research Institute, Nature, vol. 370, Aug. 4, 1994.

Sternberg, M., "Purification of Industrial Enzymes with Polyacrylic Acids", Process Biochemistry, Sep. 1976.

Strickland, James A., et al., "Inhibition of Diabrotica Larval Growth by Patatin, the Lipid Acyl Hydrolase from Potato Tubers", Plant Physiol, vol. 109, pp. 667-674, 1995.

Sudbery et al (1988) Biochem Soc Trans. 16(6), 1081-3.

Sugatani, Junko, et al., "Studies of a Phospholipase B from Penicillium Notatum Substrate Specificity and Properties of Active Site", Biochimica et Biophysica Acta, vol. 620, 1980, pp. 372-386.

Sugimoto et al., Agric. Biol. Chem. 47(6), 1201-1206 (1983).

Sugiyama et al., "Molecular cloning of a second phospholipase B gene, caPLB2 from Candida albicans", Medical Mycology, vol. 37, 1999.

Svendsen, A. "Engineered lipases for practical use", INFORM (1994) 5(5):619-623.

Svendsen, Allan, "Lipase protein engineering" Biochimica et Biophysica Acta, vol. 1543, 2000, pp. 223-238.

Svendsen, Allan, et al., "Biochemical properties of cloned lipases from the Pseudomonas family", Biochimica et Biophysica Acta, vol. 1259, 1995, pp. 9-17.

Sweigard, James A., et al., "Cloning and analysis of CUT1, a cutinase gene from Magnaporthe grisea", Mol. Gen. Genet., 232:174-182, 1992.

Swinkels et al (1993) Antonie van Leeuwenhoek 64, 187-201.

Sztajer H et al Acta Biotechnol, vol. 8, 1988, pp. 169-175.

Talker-Huiber, Cynthia Z., et al., "Esterase EstE from Xanthomonas vesicatoria (Xv_EstE) is an outer membrane protein capable of hydrolyzing long-chain polar esters", Appl. Microbiol Biotechnol, 61:479-487, 2003.

Terasaki, Masai-14 et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.

The New Enzyme Operatives, Ingredient Technology, 50, Aug. 1997.

Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.

Thornton et al 1988 Biochem. Et Biophys. Acta. 959, 153-159.

Tiss, Aly, et al., "Effects of Gum Arabic on Lipase Interfacial Binding and Activity", Analytical Biochemistry, vol. 294, pp. 36-43, 2001.

Toida J et al, Bioscience, Biotechnology, and Biochemistry, Jul. 1995, vol. 59, No. 7, pp. 1199-1203.

Tombs and Blake, Biochim. Biophys (1982) 700:81-89.

Topakas, E., et al. "Purification and characterization of a feruloyl esterase from Fusarium oxysporum catalyzing esterification of phenolic acids in ternary water—organic solvent mixtures", Journal of Biotechnology, vol. 102, 2003, pp. 33-44.

Torossian and Bell (Biotechnol. Appl. Biochem., 1991, 13:205-211.

Tsao et al. (1973) J Supramol Struct. 1(6), 490-7.

Tsuchiya, Atsushi et al, Fems Microbiology Letters, vol. 143, pp. 63-67.

Tsuneo Yamane et al., "Glycerolysis of Fat by Lipase", Laboratory of Bioreaction Engineering, vol. 35, No. 8, 1986.

Tsychiya, Atsushi, et al., "Cloning and nucleotide sequence of the mono- and diacylglycerol lipase gene (mdlB) of Aspergillus oryzae", FEMS Microbiology Letters, vol. 143, pp. 63-67, 1996.

Turnbull, K.M., et al., "Early expression of grain hardness in the developing wheat endosperm", Planta, 2003, vol. 216, pp. 699-706.

Turner, Nigel a., et al., "At what temperature can enzymes maintain their catalytic activity?", Enzyme and Microbial Technology, vol. 27, 2000, pp. 108-113.

Turner, Progress in Industrial Microbiology, Martinelli and Kinghorn (eds.), Elsevier, Amsterdam, 1994, 29:641-666.

Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.

Uppenberg, Jonas, et al., "The Sequence, crystal structure determination and refinement of two crystal forms of lipase B from Candida antarctica", Structure 1994, vol. 2, No. 4.

Upton C et al TIBS Trends in Biochemical Sciences, Elsevier Publication (1995), vol. 20, pp. 178-179.

Uusitalo et al. (1991) J Biotechnol. 17(1), 35-49.

Uwajima T et al, Agricultural and Biological Chemistry, 43(12), pp. 2633-2634, 1979.

Uwajima T et al, Agricultural and Biological Chemistry, 44(9), pp. 2039-2045, 1980.

Uwajima T et al, Methods in Enzymology, 89(41), pp. 243-248.

Vaidehi, et al.; "Lipase Activity of Some Fungi Isolated from Groundnut"; Current Science (1984); vol. 53(23); p. 1253.

van Binsbergen, Jan, et al., "Substitution of Phe-5 and Ile-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.

Van Den Berg. G, Regulatory status and use of lipase in various countries.

van Gemeren, I.A., et al., "Expression and Secretion of Defined Cutinase Variants by Aspergillus awamori" Applied and Environmental Microbiology, vol. 64, No. 8, pp. 2794-2799, Aug. 1998.

van Kampen, M.D., et al., "The phospholipase activity of Staphylococcus hyicus lipase strongly depends on a single Ser to Val mutation", Chemistry and Physics of Lipids, vol. 93, 1998, pp. 39-45.

van Nieuqenhuyzen W., "Lecithins Open Doors to baked goods", International Food Ingredients, 1998, No. 2, pp. 32-36.

van Oort, Maarten G et al, Biochemistry 1989 9278-9285.

van Solingen, Pieter, et al., "The cloning and characterization of the acyltransferase gene of penicillium chrysogenum", Agricultural University, Wageningen, The Netherlands.

Vaysse et al J. of Biotechnology 53 (1997) 41-46.

Villenueva, Inform, vol. 8, No. 6, Jun. 1997.

Vujaklija, Dušica, et al., "A novel streptomycete lipase: cloning, sequencing and high-level expression of the Streptomyces rimosus GDS (L)-lipase gene", Arch. Microbiol, vol. 178, pp. 124-130, 2002.

Wahnelt S.V., Meusel D, & Tülsner M, (1991) Zur kenntnis des diglyceride influsses auf das kristallisationsverhalten von Fetten, in Fat Science Technology 4:117-121.

Waninge, Rianne, et al., "Milk membrane lipid vesicle structures studied with Cryo-TEM", Colloids and Surfaces B: Biointerfaces 31 (2003), pp. 257-264.

Warmuth et al, 1992, Bio Forum 9, 282-283.

Watanabe et al. Bio sci Biochem 63(5) 820-826, 1999.

Watanabe, Yasuo et al., "Cloning and sequencing of phospholipase B gene from the yeast Torulaspora delbrueckii", FEMS Microbiology Letters, vol. 124, 1994, pp. 29-34.

Webb EC, Enzyme Nomenclature, 1992, p. 310.

Weber et al. J Agric Food Chem 1985, 33, 1093-1096.

Wen-Chen Suen et al., "Improved activity and thermostability of Candida antarctica lipase B by DNA family shuffling", Protein Engineering, Design & Selection, vol. 17, No. 2, pp. 133-140, 2004.

West S.; "Olive and Other Edible Oils"; Industrial Enzymology (1996); pp. 295-299.

Whitehead, Michael, et al., "Transformation of a nitrate reductase deficient mutant of Penicillium chrysogenum with the corresponding Aspergillus niger and A nidulans niaD genes", Mol Gen Genet, 216: 408-411, 1989.

Wilhelm et al., "A Novel Lipolytic Enzyme Located in the Outer Membrane of Pseudomonas aeruginosa", Journal of Bacteriology, vol. 181, No. 22, Nov. 1999, pp. 6977-6986.

Williams K.R. et al., "Protein Analysis by Integrated Sample Preparation, Chemistry, and Mass Spectrometry", in Molecular Biology and Biotechnology—A Comprehensive Desk Reference, VCH, 1995, ISBN 1-56081-569-8 edited by Meyers R.A., pp. 731-737.

Winnacker et al., "Identification of Recombinant DNA", chapter 11 in "From genes to clones: introduction to gene technology," by E. -L. Weinnacke, VCH, Weinheim, ISBN 0-89573-614-4, pp. 424-431.

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Helmerich G. et al., Strukur-Wirkungsbeziehehungen von Phospholipiden in Backwaren, Wirkung von Phospholipiden, Getreide Mehl and Brot, 2003, vol. 57, No. 5, pp. 270-273 NZAS-0301096.

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From Saccharomyces Cerevisiae", Biochimica et Biophysica Acta, vol. 795, 1984, pp. 117-124.

Kelley R.L. and Reddy C.A., Glucose Oxidase of Phanerochaete chrysosporium, in "Biomass, Part B, Lignin, Pectin, and Chitin", Wood et al., Eds., Methods in Enzymology (1988) vol. 161, Academic Press, San Diego, pp. 307-316.

WPI Acc no. 93-298906(38) Preparation of low fat content cream-by adding lipase to mixture of fat and water, Nisshin Oil and Fat Corp. Aug. 24, 1993.

Xu, Jun, et al., "Intron requirement for AFP gene expression in Trichoderma viride", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamano Y et al., Surface activity of lysophosphatidyl choline from soybean, 4th World Surfactants Congress, 1996, pp. 24-34.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model I. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Aires-Barros M.R. et al., "Isolation and purification of lipases," *Lipases their structure, biochemistry and application*, editors Woolley et al., Cambridge University Press, 1994, ISBN 0521445469 NZAS-00354436 pp. 242-270.

Bakezyme PH 800 Product Data Sheet, DSM Bakery ingredients, pp. 1-2. NZAS-0299424—NZAS-0299425, pp. 1-2, (Date after Mar. 19, 2002).

Courtin, Christophe M., et al., "Recent Advances in Enzymes in Grain Processing", Laboratory of Food Chemistry, Leuven, Belgium, 2003, ISBN 90-9016671-8, pp. 269-274, Sep. 2002.

Hedin, Eva M.K., et al., "Selective reduction and chemical modification of oxidized lipase cysteine mutants," vol. 80 pp. 529-539, 2002. Canadian J. Chemistry.

List of Cultures, Fungi and Yeasts, 32 edition, Institute of the Royal Netherlands Academy of Arts and Sciences, p. 38. (1990).

JCM Catalogue of Strains, Fifth Edition, "Filamentous Fungi & Yeasts", p. 246, (1992).

List of Cultures, 1992 Microorganisms Ninth Edition, Institute for Fermentation, Osaka, Japan, p. 325, (1992).

Larchenkova LP et al. "Effect of starter and souring temperature on reproduction of *E coli* and lactobacili in milk," International Dairy Congress XXI, vol. 1, book 2. Moscow, Jul. 12-16, 1982, Brief Communications, p. 539.

Lipomod L338P Data Sheet, Biocatalysts Limited, Aug. 15, 2003, pp. 1-2.

Mase T. et al., "Purification and Characterization of a new Lipase from Fusarium sp. TM-30", Biosci. Biotech. Biochem., vol. 59, No. 9, pp. 1771-1772, 1995.

Matsuda H et al, "Purification and properties of a lipolytic acyl-hydrolase from potato leaves", Biochimica et Biophysica Acta, vol. 573(1), pp. 155-165, (1979).

Mogensen, Jesper E., et al., "Activation, Inhibition, and Destabilization of Thermomyces lanuginosus Lipase by Detergents", Biochemistry, vol. 44, pp. 1719-1730, (2005).

Nierle, Von W. et al. "Weizenlipide: Funktion and Einfluβ bei der Verarbeitung des Mehles" with English abstract "Wheat lipids: Function and Effect in Flour Processing", vol. 83, No. 10, pp. 391-395, 1981.
Novozymes, "Product Sheet: Enzyme Business, Noopazyme" pp. 1-3, 2002.
Novozymes, "Product Sheet: Enzyme Business, Novozym 27019" pp. 1-2, 2001.
Novozymes, "Product Sheet: Enzyme Business, Novozym 677 BG," pp. 1-2, 1996.
Peelman F, et al, "A proposed architecture for lecithin cholesterol acyl transferase (LCAT): Identification of catalytic triad and molecular modeling," Protein Science, vol. 7 No. 3, pp. 587-599, 1998.
Product Data Sheet, Bakezyme P 500 BG, DSM Food Specialties, pp. 1-2, 2004.
Product Sheet, Enzyme Business Lipozyme® 10.000 L, Novo Nordisk, pp. 1-2, 1995.
Roberts, Ian N., et al., "Heterologous gene expression in Aspergillus niger: a glucoamylase-porcine pancreatic prophospholipase A2 fusion protein is secreted and processed to yield mature enzyme," Gene, vol. 122, pp. 155-161, 1992.
Shehata, A. "Manufacture of Blue Cheese by Direct Acidification Methods," University of Wisconsin pp. 1-90, May 20, 1966.
Iwai, M. et. al., Studies on Lipase II. Hydrolytic and esterifying actions of crystalline lipase of Aspergillus niger, Journal of Applied Microbiology, vol. 10 (1964) pp. 13-21.
Vaidehi, B.K. et al., "Lipase Activity of Some Fungi Isolated from Groundnut", Current Science, Dec. 5, 1984, vol. 53, No. 23, p. 1253.
Welter, et al; "Identification of Recombinant DNA" in From Genes to clones: Intro to gene technology, pp. 424-431, 1987.
Whitaker, John R., et al., "Biocatalysis in Agricultural Biotechnology", ACS Symposium Series, American Chemical Society, 1989, pp. 25-43.
Yount, Nannette Y., et al., "Multidimensional signatures in antimicrobial peptides," Proceedings of the National Academy of Sciences, vol. 101, No. 19, pp. 7363-7368, (2004).
U.S. Appl. No. 60/083,277, filed Apr. 28, 1998, Spender, Tina, et al.
AACC Method 54-21 Farinograph Method for Flour, from Physical Dough Tests supplied by the British Library, Nov. 3, 1999.
Anderson D, "A Primer in Oils Processing Technology" in Bailey's Industrial Oil and Fat Products, Sixth edition, John Wiley, 2005, vol. 5, chapter 1, pp. 1-56. ISBN 978047138401.
Anguita et al, "Purification, Gene Cloning, Amino Acid Sequence Analysis, and Expression of an Extracellular Lipase from an Aeromonas hydrophila Human Isolate", Appl. Environ. Microbiol., vol. 59, No. 8, pp. 2411-2417, Aug. 1993.
"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.
AOCS Method 2c-25 "1997 Moisture and Volatile Matter Air Oven Method" Sampling and Analysis of Commercial Fats and Oils, obtained from The British Library, p. 1, 1997.
AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.
Archer D.B. & Peberdy, The Molecular Biology of Secreted Enzyme Production by Fungi, Critical Reviews in Biotechnology, 1997, vol. 17, No. 4, pp. 273-306.
Arskog and Joergensen, "Baking performance of prior art lipases from Candida cylindracea and Aspergillus foeditus and their activity on galactolipids in dough", Novozymes Report Jul. 18, 2005, pp. 1-2.
Arskog and Joergensen, "Baking performance of prior art lipases from Humicola Lanuginosa, Aspergillus tubigensis, Rhizopus delemar and Rhizomucor miehei, and their activity on galactolipids in dougn", Novozymes Report Jul. 17, 2005, pp. 1-8.
Aust K., "Applications of lecithin in bakery foods," AIB Research Technical Bulletin, vol. XV, issue 12, Dec. 1993, pp. 1-6.
Banas a. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, pp. 34626-34634.
Beggs J.D., Transformation of yeast by a replicating hybrid plasmid, Nature (London), 1978, vol. 275, p. 104.
Bessette, "Efficient folding or proteins with multiple disulphide bonds in the Escherida coli cytoplasm", Proc. Natl. Acad. Sci. USA, 1999, vol. 96, pp. 13703-13708.
Bo Yang et al., "Optimization of Enzymatic Degumming Process for Rapseed Oil," JAOCS, 2006, vol. 83, No. 7, pp. 653-658.
Briand et al, "Substrate Specificity of the Lipase from Candida parapsilosis", Lipids, Aug. 1995, vol. 30, No. 8, pp. 747-754.
Bru R., López-Nicolás J.M., Garcia-Carmona F., (1995) "Aggregation of polyunsaturated fatty acid in the presence of cyclodextrins", Colloids and Surfaces A: Physiochemical and Engineering Aspects. 97, pp. 263- 269.
Brunel et al, "High-Level expression of Candida parapsilosis lipase/acyltransferase in Pichia pastoris," J Biotechnology, Jul 1, vol. 111, No. 1, pp. 41-50, 2004.
Buchold H. et. al., "Enzymatische Phosphatidentfernung aus Pfianzenolen" Technologies, 1993, vol. 95, No. 8, pp. 300-304, ISSN:0931-5985.
Buckley J. Thomas et al., Substrate specificity of bacterial glycerophospholipid: Cholesterol Acyltransferase, Biochemistry, 1982, vol. 21, pp. 6699-6703.
Bylund G. (ed), 1995, Dairy Processing Handbook, Chapter 2, pp. 17-42, Lund, Sweden.
Bylund G. (ed), 1995, Dairy Processing Handbook, Chapter 9, pp. 227-246, Lund, Sweden.
Ceci L.N. et al, Oil recovery and lecithin production using water degumming sludge of crude soybean oils, Journal of the Science of Food and Agriculture, 2008, vol. 88, No. 14, pp. 2460-2466.
Cereghino et al., Heterologous protein expression in the methylotrophic yeast Pichia pastoris, FEMS Microbiology Review, 2000, vol. 24, No. 1, pp. 45-66.
Chica et al, "Semi-rational approaches to engineering enzyme activity: combining the benefits of directed evolution and rational design" Current Opinion in Biotechnology, 2005, vol. 16, pp. 378-384.
Agro- Christou P., Genetic engineering of crop legumes and cereals: current status and recent advances, Agro-Food-Industry Hi-Tech, Mar./Apr. 1994, pp. 17-27.
Davis R.H. and de Serres, Genetic and Microbiological Research Techniques for Neurospora crassa, Methods Enzymology, 1971, vol. 17A, pp. 79-143.
EC 1.1.3.10 (downloaded—Jul. 12, 2010 from http://www.chem.qmul.ac.uk/iubmb/enzyme/EC1/1/3/10.html).
EC 1.1.3.4 (downloaded—Jul. 12, 2010 from http://wwvv.chem.qmul.ac.uk/iubmb/enzyme/EC1/1/3/4.html).
EC 1.1.3.5 (downloaded—Nov. 16, 2009 from http://www.chem.qmul.ac.uk/iubmb/enzyme/EC1/1/3/5.html).
EC 2.3.1.43 (downloaded Apr. 21, 2009 from http://www.chem.qmul.ac.uk/iubmb/enzyme/EC2/3/1/43.html).
EC 2.4.1.19 (Downloaded Jul. 12, 2010 from http://www.chem.qmul.ac.uk/iubmb/enzyme/EC2/4/1/19.html).
EC 3.1.1.26 (downloaded—Dec. 18, 2008 from http://www.chem.qmul.ac.uk/iubmb/enzyme/EC3/1/1/26.html).
EC 3.1.1.3 (downloaded— Dec. 18, 2008 from http://www.chem.qmul.ac.uk/iubmb/enzyme/EC3/1/1/3.html).
EC 3.1.1.32 (downloaded—May 22, 2008 from http://www.chem.qmul.ac.uk/iubmb/enzyme/EC3/1/1/32 .html).
EC 3.1.1.4 Phospholipase A2 enzyme Enzyme Entry 1983 (downloaded Apr. 21, 2009 from http://wwvv.chem.qmul.ac.uk/iubmb/enzyme/EC3/1/1/4.html).
EC 3.1.1.5 (downloaded Dec. 18, 2008 from http://www.chem.qmul.ac.uk/iubmb/enzyme/EC3/1/1/5.html).
EC 3.2.1.3 (downloaded Jul. 12, 2010 from http://www.chem.qmul.ac.uk/iubmb/enzyme/EC3/2/1/3.html).
EC 3.2.1.32 (Downloaded Jul. 12, 2010 from http://www.chem.qmul.ac.uk/iubmb/enzyme/EC3/2/1/32.html).
EC 3.2.1.60 (downloaded Apr. 28, 2009 from http://www.chem.qmul.ac.uk/iubmb/enzyme/EC3/2/1/60.html).

Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, pp. 31-45.
Garzillo et al, "Production, Purification, and Characterization of Glucose Oxidase from Penicillium Variable P16," Biotechnol. Appl. Biochem., 1995, vol. 22, pp. 169-178.
Genbank accession code NC_003888.1:8327480..8328367 (downloaded Apr. 21, 2009), p. 1.
Genbank accession No. AL646052 (downloaded Apr. 21, 2009), pp. 1-2.
Genbank accession No. AL939131.1:265480..266367 (downloaded Apr. 21, 2009), p. 1.
Genbank accession No. CAC42140 (downloaded Apr. 21, 2009), pp. 1-2.
Genbank accession No. P41734 (downloaded Apr. 21, 2009), pp. 1-4.
Genbank accession No. Z75034 (downloaded Apr. 21, 2009), pp. 1-2.
Hammond E.G. et al., "Soybean Oil" in Bailey's Industrial Oil and Fat Products, Sixth edition, John Wiley, 2005, vol. 3, chapter 13, pp. 577-653, ISBN 978047138401.
Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.
Hinnen A. et al., Transformation of yeast, Proceedings of the National Academy of Sciences USA, Apr. 1978, vol. 75, No. 4, pp. 1929-1933.
Hollenberg C.P. et al., Production of recombinant proteins by methylotrophic yeasts, Current Opinion in Biotechnology Oct. 1997, vol. 8, No. 5, pp. 554-560.
Horwell DC, "The 'peptoid' approach to the design of non-peptide, small molecular agonists and antogonists of neuropeptides", Trends Biotechnol., 1995, vol. 13, No. 4, pp. 132-134.
Hossen, Monjur, "Enzyme catalyzed synthesis of structured phospholipids with conjugated linoleic acid and plant sterols, " A Dissertation by MD Monjur Hossen, May 2005, pp. 1-152.
HUI, Bailey's Industrial Oil and Fat Products, 5th edition vol. 2 Edible Oil and Fat Products: Oils and Oilseeds, Wiley Interscience (1996), pp. 513-516. ISBN 0471594261.
International Dairy Federation Bulletin Document 116, 1979, p. 5, "Definition of recombined milk".
Ito H. et al., "Transformation of Intact Yeast Cells Treated with Alkali Cations," J. Bacteriology, 1983, vol. 153, pp. 163-168.
Jost R. et. al., "Milk and Dairy Products," Nestle Product Technology Center, 2007, Wiley-VCH, pp. 1-62, Konolfingen, Switzerland.
Kalscheuer et al, "Synthesis of Novel Lipids in Saccharomyces cerevisiae by Heterologous Expression of an Unspecific Bacterial Acyltransferase," Applied and Environmental Microbiology, vol. 70, No12, pp. 7119-7125, 2004.
Kane, "Effects of rare codon clusters on high-level expression of heterolgous proteins in *E. coli*" Current Opinion Biotechnology, 1995, vol. 6, pp. 494-500.
Kimmel, A, et al. "Preparation of cDNA and the Generation of cDNA Libraries: Overview," Methods in Enzymology, 1987, vol. 152, pp. 307-316.
LaVallie T.M., 2-Methoxyestradiol Inhibits Proliferation and Induces Apoptosis Independently of Estrogen Receptors α and β, Current Opinion in Biotechnology, 1995, vol. 6, No. 5, pp. 501-506.
Leon et al., "A new approach to study starchy changes occurring the double-baking process and during bread storage," Z. Lebensn. Unters Forsch A, 1997, vol. 204 pp. 316-320.
McIntyre et al., "Distribution of Glycerophospholipid-Cholesterol Acyltransferase in Selected Bacterial Species," Journal of Bacteriology, Jul. 1979, vol. 139, No. pp. 132-136.
NCBI protein accession code AAK84028.1 GI:15082088, (downloaded Dec. 18, 2009), pp. 1-2.
NCBI protein accession code CAB39707.1 GI:4529178, (downloaded Dec. 18, 2009), pp. 1-2.
NCBI protein accession code CAB62724.1 GI:6562793, (downloaded Dec. 18, 2009), pp. 1-2.
NCBI protein accession code CAB88833.1 GI:7635996, (downloaded Dec. 18, 2009), pp. 1-2.
NCBI protein accession code CAB89450.1; GI:7672261, (downloaded Dec. 18, 2009), pp. 1-2.
NCBI protein accession code CAC01477.1 GI:9716139, (downloaded Dec. 18, 2009), pp. 1-2.
NCBI's Genbank database accession No.: IIVN_A; GID:33357066, (downloaded Oct. 14, 2010), pp. 1-2.
Nerland A.H., "Glycerophospholipid-cholesterol acyltransferase precursor", SwissProt, Feb. 11, 2005 XP002318368 citing Nerland, A.H., "The nucleotide sequence of the gene encoding GCAT from Aeromonas salmonicida ssp. Salmonicida," Journal of Fish Diseases, vol. 19, pp. 145-150, 1996.
Oil Mill Gazetteer, "Enzymatic Degumming Improves Oil Refining in China," Jul. 2005 vol. 111, pp. 2-4.
Phospholipase C, E.C. 3.1.4.3, (downloaded Sep. 8, 2009 from http://www.chem.qmul.ac.uk/iubmb/enzyme/EC3/1/4/3.html), p. 1.
Poldermans B and Schoppink P, "Controlling the baking process and product quality with enzymes", Cereal Foods World, Mar. 1999, 44 (3), pp. 132-135.
Potrykus I., Gene Transfer to Plants: assessment of published approaches and results, Annu. Rev. Plant Physiol. Plant Mol. Biol., 1991, vol. 42, pp. 205-225.
PreSens Manual HydroPlate® HP96U and HydroPlate® HP96C, pp. 1-15, Aug. 17, 2004.
Seffernick et al, "Melamine Deaminase and Atrazine Chlorohydrolase: 98 Percent Identical but Functionally Different", Journal of Bacteriology, Apr. 2001, vol. 183, No. 8, pp. 2405-2410.
Seino et al, "Enzymatic Synthesis of Carbohydrate Esters of Fatty Acid (10 Esterification of Sucrose, Glucose, Fructose and Sorbitol", J. Am. Oil Chem. Soc., Nov. 1984, vol. 61, No. 11, pp. 1761-1765.
Sequence alignment of database accession No. Q44268 (database: UNIProtKB/TrEMBL) with Seq. ID No. 16, (downloaded Jan. 27, 2009), pp. 1-2.
Simon RJ et al.,"Peptoids: a modular approach to drug discovery", Proc. Natl. Acad. Sci. USA, 1992, vol. 89, No. 20, pp. 9367-9371.
Stryer, "Conformation and Dynamics," Biochemistry, 2nd Edition, 1981, WH Freeman & Co., San Francisco, p. 16.
Sutrisno, A. et al, "Expression of a gene Encoding Chitinase (pCA 8 ORF) from Aeromonas sp. No. 10S-24 in *Esxherichia coli* and Enzyme Characterization," Journal of Bioscience and Bioengineering, vol. 91, No. 6, pp. 599-602, 2001.
Szuhaj B.F., "Lecithins" in Bailey's Industrial Oil and Fat Products, Sixth edition, John Wiley, 2005, vol. 2, chapter 13, pp. 361-456. ISBN 978047138401.
Tanji M.et al., "Lipase hydrolysis of milk fat and its soft fractions", Research Bulletin of Obihiro University, 2001, vol. 22, No. 2, pp. 89-94.
Tilden E.B. and Hudson C.S., Preparation and Properties of the Amylases Produced by Bacillus Macerans and Bacillus Polymyxa, J. Bacteriology, 1942, vol. 43, pp. 527-544.
Torres C.F. et al., A two steps enzymatic procedure to obtain sterol esters, tocopherols and fatty acid ethyl esters from soybean oil deodorizer distillate, Process Biochemistry, 2007, vol. 42, No., 9, pp. 1335-1341.
Trueman L.J., "Heterologous Expression in Yeast," Methods Molecular Biology, vol. 49, pp. 341-354 (1995).
Turner G. Vectors for generic manipulation, in Martinelli S.D, Kinghorn J.R. (editors), *Aspergillus*: 50 years on. Progress in industrial microbiology, 1994, vol. 29, pp. 641-666.
Verenium Corporation leaflet Purifine® Enzyme"Convert Gums to Oils Significantly Increase Oil Yields no increase in Free Fatty Acids", San Diego, Jan. 2008.
Witkowski et al, "Conversion of a B-Ketoacyl Synthase to a Malonyl Decarboxylase by Replacement of the Active-Site Cysteine with Glutamine," Biochemistry, Sep. 7, 1999, vol. 38, No. 36, pp. 11643-11650.
Notification of Reasons for Refusal: JP Application No. 526105, Feb. 12, 2003 (Translation).
Notification of Reasons for Refusal: JP Application No. 526105, Jun. 4, 2002 (Translation).
Written Argument: JP Application No. 97181706.5, (Dec. 9, 1997) (Translation).

FIGURE 1 (SEQ ID No. 16)

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 2 (SEQ ID No. 1)

```
  1  MKKWFVCLLG LVALTVQAAD SRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL FNLPDLGQNP SARSQKVVEA VSHVSAYHNQ
201  LLLNLARQLA PTGMVKLFEI DKQFAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATFIANQY EFLAH*
```

FIGURE 3 (SEQ ID No. 2)

```
  1 ivafGDSlTd geayygdsdg ggwgagladr Ltallrlrar prgvdvfnrg isGrtsdGrl
 61 ivDalvallF laqslglpnL pPYLsgdflr GANFAsagAt Ilptsgpfli QvqFkdfksq
121 vlelrqalgl lqellrllpv ldakspdlvt imiGtNDlit saffgpkste sdrnvsvpef
181 kdnlrqlikr Lrsnngarii vlitlvilnl gplGClPlkl alalassknv dasgclerln
241 eavadfneal relaiskled qlrkdglpdv kgadvpyvDl ysifqdldgi qnpsayvyGF
301 ettkaCCGyG gryNynrvCG naglcnvtak aCnpssylls flfwDgfHps ekGykavAea
361 l
```

FIGURE 4 (SEQ ID No. 3)

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

FIGURE 5 (SEQ ID No. 4)

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIGURE 6 (SEQ ID No. 5)

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 7 (SEQ ID No. 6)

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 8 (SEQ ID No. 7)

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIGURE 9 (SEQ ID No. 8)

```
              10         20         30         40         50         60
               |          |          |          |          |          |
        MNLRQWMGAA TAALALGLAA CGGGGTDQSG NPNVAKVQRM VVFGDSLSDI GTYTPVAQAV 70         80         90        100        110        120
               |          |          |          |          |          |
        GGGKFTTNPG PIWAETVAAQ LGVTLTPAVM GYATSVQNCP KAGCFDYAQG GSRVTDPNGI 130        140        150        160        170        180
               |          |          |          |          |          |
        GHNGGAGALT YPVQQQLANF YAASNNTFNG NNDVVFVLAG SNDIFFWTTA AATSGSGVTP 190        200        210        220        230        240
               |          |          |          |          |          |
        AIATAQVQQA ATDLVGYVKD MIAKGATQVY VFNLPDSSLT PDGVASGTTG QALLHALVGT 250        260        270        280        290        300
               |          |          |          |          |          |
        FNTTLQSGLA GTSARIIDFN AQLTAAIQNG ASFGFANTSA RACDATKINA LVPSAGGSSL 310        320        330        340
               |          |          |          |
        FCSANTLVAS GADQSYLFAD GVHPTTAGHR LIASNVLARL LADNVAH
```

FIGURE 10 (SEQ ID No. 9)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIGURE 11 (SEQ ID No. 10)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIGURE 12 (SEQ ID No. 11)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

FIGURE 13 (SEQ ID No. 12)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

FIGURE 14 (SEQ ID No. 13)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIGURE 15 (SEQ ID No. 14)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

FIGURE 16 (SEQ ID No. 15)

```
  1 MKKWFVCLLG LIALTVQAAD TRPAFSRIVM FGDSLSDTGK MYSKMRGYLP
 51 SSPPYYEGRF SNGPVWLEQL TKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNK
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIETQY EFLAHG*
```

FIGURE 17 (SEQ ID No. 19)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIGURE 18 (SEQ ID No. 25)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLTKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

FIGURE 19 (SEQ ID NO. 26)

```
MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST
```

FIGURE 20 (SEQ ID No. 27)

```
ZP_00058717
    1 mlphpagerg evgaffallv gtpqdrrlrl echetrplrg rcgcgerrvp pltlpgdgvl
   61 cttsstrdae tvwrkhlqpr pdggfrphlg vgcllagqgs pgvlwcgreg crfevcrrdt
  121 pglsrtrngd ssppfragws lppkcgeisq sarktpavpr ysllrtdrpd gprgrfvgsg
  181 praatrrrlf lgipalvlvt altlvlavpt gretlwrmwc eatqdwclgv pvdsrgqpae
  241 dgeflllspv qaatwgnyya lgdsyssgdg ardyypgtav kggcwrsana ypelvaeayd
  301 faghlsflac sgqrgyamld aidevgsqld wnsphtslvt igiggndlgf stvlktcmvr
  361 vplldskact dqedairkrm akfettfeel isevrtrapd arilvvgypr ifpeeptgay
  421 ytltasnqrw lnetiqefnq qlaeavavhd eeiaasggvg svefvdvyha ldgheigsde
  481 pwvngvqlrd latgvtvdrs tfhpnaaghr avgervieqi etgpgrplya tfavvagatv
  541 dtlagevg
```

FIGURE 21 (SEQ ID No. 28)

```
    1 mgsgpraatr rrlflgipal vlvtaltlvl avptgretlw rmwceatqdw clgvpvdsrg
   61 qpaedgefll lspvqaatwg nyyalgdsys sgdgardyyp gtavkggcwr sanaypelva
  121 eaydfaghls flacsgqrgy amldaidevg sqldwnspht slvtigiggn dlgfstvlkt
  181 cmvrvpllds kactdqedai rkrmakfett feelisevrt rapdarilvv gyprifpeep
  241 tgayytltas nqrwlnetiq efnqqlaeav avhdeeiaas ggvgsvefvd vyhaldghei
  301 gsdepwvngv qlrdlatgvt vdrstfhpna aghravgerv ieqietgpgr plyatfavva
  361 gatvdtlage vg
```

FIGURE 22 (SEQ ID No. 29)

```
  1 mrttviaasa llllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 23 (SEQ ID No. 30)

ZP_00094165

```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk //
```

FIGURE 24 (SEQ ID No. 31)

NP_625998.

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
//
```

FIGURE 25 (SEQ ID No. 32)

NP_827753.

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
//
```

FIGURE 26 (SEQ ID No. 33)

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 27 (SEQ ID No. 34)

```
ADSRPAFSRIVMFGDSLSDTGKMYSKMRGYLPSSPPYYEGRFSNGPVWLEQLTNEFPGLTIANEAEGGPT
AVAYNKISWNPKYQVINNLDYEVTQFLQKDSFKPDDLVILWVGANDYLAYGWNTEQDAKRVRDAISDAAN
RMVLNGAKEILLFNLPDLGQNPSARSQKVVEAASHVSAYHNQLLLNLARQLAPTGMVKLFEIDKQFAEML
RDPQNFGLSDQRNACYGGSYVWKPFASRSASTDSQLSAFNPQERLAIAGNPLLAQAVASPMAARSASTLN
CE
GKMFWDQVHPTTVVHAALSEPAATFIESQYEFLAH
```

FIGURE 28 (SEQ ID No. 35)

```
  1  ADTRPAFSRI VMFGDSLSDT GKMYSKMRGY LPSSPPYYEG RFSNGPVWLE QLTKQFPGLT
 61  IANEAEGGAT AVAYNKISWN PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 29 (SEQ ID No. 36)

```
ACAGGCCGATGCACGGAACCGTACCTTTCCGCAGTGAAGCGCTCTCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGCTCGTACCGGATGATGTGCAGATCCAAAGAATT
```

FIGURE 30 (SEQ ID NO. 37):

```
MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST
```

FIGURE 31 (SEQ ID No. 38)

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 32 (SEQ ID No. 39)

```
   1 ggtggtgaac cagaacaccc ggtcgtcggc gtgggcgtcc aggtgcaggt gcaggttctt
  61 caactgctcc agcaggatgc cgccgtggcc gtgcacgatg gccttgggca ggcctgtggt
 121 ccccgacgag tacagcaccc atagcggatg gtcgaacggc agcggggtga actccagttc
 181 cgcgccttcg cccgcggctt cgaactccgc ccaggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcaccccga agtcggggga
 421 acaggacgac caggtcgcac cgatcgcggc gcaggcgagg aatgcggccg tcgcctcggc
 481 gatgttcggc aggtaggcca cgacccggtc gccgggcccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg gcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctcccctaa cgctccccgg tgacggagtg
1021 ttgtgcacca catctagcac gcgggacgcg gaaaccgtat ggagaaaaca cctacaaccc
1081 cggccggacg gtgggtttcg gccacactta ggggtcgggt gcctgcttgc cgggcagggc
1141 agtcccgggg tgctgtggtg cgggcgggag ggctgtcgct tcgaggtgtg ccggcgggac
1201 actccgggcc tcagccgtac ccgcaacggg gacagttctc ctcccttccg ggctggatgg
1261 tcccttcccc cgaaatgcgg cgagatctcc cagtcagccc ggaaaacacc cgctgtgccc
1321 aggtactctt gcttcgaac agacaggccg gacggtccac ggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agacgctgtg gcgcatgtgg
1501 tgtgaggcca cccaggactg gtgcctgggg gtgccggtcg actcccgcgg acagcctgcg
1561 gaggacggcg agtttctgct gctttctccg gtccaggcag cgacctgggg gaactattac
1621 gcgctcgggg attcgtactc ttcgggggac ggggcccgcg actactatcc cggcaccgcg
1681 gtgaagggcg gttgctggcg gtccgctaac gccatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact ccctcacac gtcgctggtg
1861 acgatcggga tcggcggcaa cgatctgggg ttctccacgg ttttgaagac ctgcatggtg
1921 cgggtgccgc tgctggacag caaggcgtgc acgaccagg aggacgctat ccgcaagcgg
1981 atggcgaaat cgagacgac gtttgaagag ctcatcagcg aagtgcgcac ccgcgcgccg
2041 gacgcccgga tccttgtcgt gggctacccc cggatttttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacgagat cggctcggac
2281 gagccgtggg tgaacggggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gcccgggccg tccgctctat gccactttcg cggtggtggc ggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc ggatcgttg agccgtcgt gtctttgacg agcacaccc gctgcaggag
2641 ccgttcgcac agttctcttc cgtggccag agtcgggtcg acgtcgatcc cagcccacag
2701 gccgatgctg cgggccgcga ccacgccgtt gccgaccagt tggtcgaggc gggcgcgcag
2761 cacggggcg agggcgcgga catggtccag gtaagggccg tcgcggacga ggctcaccac
2821 ggcagtgccg accgcgcagg cgagggcgtt gccgccgaag tgctgccgt gctggccggg
2881 gcggatcacg tcgaagactt ccgcgtcgcc taccgccgcc gccacgggca ggatgccgcc
2941 gcccagcgct ttgccgaaca ggtagatatc ggcgtcgact ccgctgtggt cgcaggcccg
```

FIGURE 33 (SEQ ID No. 40)

```
  1 vgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 34 (SEQ ID No. 41)

```
  1 mrttviaasa llllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 35 (SEQ ID No. 42)

```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggc ggcgggctct gtggtgcccc gcgaccccg
 181 gccccggtga gcggtgaatg aaatccggct gtaatcagca tcccgtgccc accccgtcgg
 241 ggaggtcagc gcccggagtg tctacgcagt cggatcctct cggactcggc catgctgtcg
 301 gcagcatcgc gctcccggt cttggcgtcc ctcggctgtt ctgcctgctg tccctggaag
 361 gcgaaatgat caccggggag tgatacaccg gtggtctcat cccggatgcc cacttcggcg
 421 ccatccggca attcggcag ctccgggtgg aagtaggtgg catccgatgc gtcggtgacg
 481 ccatagtggg cgaagatctc atcctgctcg agggtgctca ggccactctc cggatcgata
 541 tcggggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aatgggtgg tgggagccct ggtcgcggtt
 961 ccgtgggagg cgccgtgccc cgcaggatcg tcggcatcgg cggatctggc cggtaccccg
1021 cggtgaataa aatcattctg taaccttcat cacggttggt tttaggtatc cgcccctttc
1081 gtcctgaccc cgtcccggc gcgcgggagc ccgcgggttg cggtagacag gggagacgtg
1141 gacaccatga ggacaacggt catcgcagca agcgcattac tccttctcgc cggatgcgcg
1201 gatggggccc gggaggagac cgccggtgca ccgccgggtg agtcctccgg gggcatccgg
1261 gaggagggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg caggggggcg
1441 gtgaccgggg atctgctcga acccaggacg ctggggagc gcacgctgcc ggcgcaggtg
1501 gatgcgctga cggaggacac caccctggtc accctctcca tcggggcaa tgacctcgga
1561 ttcggggagg tggcgggatg catccgggaa cggatcgccg gggagaacgc tgatgattgc
1621 gtggacctgc tggggaaac catcggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactggggg atgtctccga ggcggatcgt
1801 cgttgggcgg ttgagctgac cgggcagatc aacgagaccg tgcgcgaggc ggccgaacga
1861 cacgatgccc tctttgtcct gcccgacgat gccgatgagc acaccagttg tgcaccccca
1921 cagcagcgct gggcggatat ccagggccaa cagaccgatg cctatccgct gcacccgacc
1981 tccgccggcc atgaggcgat ggccgccgcc gtccgggacg cgctgggcct ggaaccggtc
2041 cagccgtagc gccgggcgc gcttgtcga cgaccaaccc atgccaggct gcagtcacat
2101 cgcacatag cgcgcgggg cgatggagta cgcaccatag aggatgagc cgatgccgac
2161 gatgatgagc agcacactgc cgaagggttg ttccccgagg gtgcgcagag ccgagtccag
2221 acctgcggcc tgctccggat catgggccca accggcgatg acgatcaaca ccccaggat
2281 cccgaaggcg ataccacggg cgacataacc ggctgttccg gtgatgatga tcgcggtccc
2341 gacctgccct gaccccgcac ccgcctccag atcctcccgg aaatcccggg tggccccctt
2401 ccagaggttg tagacacccg ccccagtac caccagcccg gcgaccacaa ccagcaccac
2461 accccagggt tgggatagga cggtggcggt gacatcggtg gcggtctccc catcggaggt
2521 gctgccgccc cgggcgaagg tggaggtggt caccgccagg gagaagtaga ccatggccat
2581 gaccgccccc ttggcccttt ccttgaggtc ctcgcccgcc agcagctggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac gccggatccc
2761 agtggcgatg cgcaccgcga tccaccgat gaggatgtgc agtatgccca ggacaatgaa
2821 accacctctg gcaggtggg tcagcgcggg gtggtcctcg gcctggtcgg cagcccgttc
2881 gatcgtccgt ttcgcggatc tggtgtcgcc cttatccata gctcccattg aaccgccttg
2941 agggtgggc ggccactgtc agggcggatt gtgatctgaa ctgtgatgtt ccatcaaccc
```

FIGURE 36 (SEQ ID No. 43)

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
```

FIGURE 37 (SEQ ID No. 44)

```
   1 cccggcggcc cgtgcaggag cagcagccgg cccgcgatgt cctcgggcgt cgtcttcatc
  61 aggccgtcca tcgcgtcggc gaccggcgcc gtgtagttgg cccggacctc gtcccaggtg
 121 cccgcggcga tctggcgggt ggtgcggtgc gggccgcgcc gaggggagac gtaccagaag
 181 cccatcgtca cgttctccgg ctgcggttcg ggctcgtccg ccgctccgtc cgtcgcctcg
 241 ccgagcacct ctcggcgag tcggcgctg gtcgccgtca ccgtgacgtc ggcgccccgg
 301 ctccagcgcg agatcagcag cgtccagccg tcgccctccg ccagcgtcgc gctgcggtcg
 361 tcgtcgcggg cgatccgcag cacgcgcgcg ccgggcggca gcagcgtggc gccggaccgt
 421 acgcggtcga tgttcgccgc gtgcgagtac ggctgctcac ccgtggcgaa acggccgagg
 481 aacagcgcgt cgacgacgtc ggacggggag tcgctgtcgt ccacgttgag ccggatcggc
 541 agggcttcgt gcgggttcac ggacatgtcg ccatgatcgg gcacccggcc gccgcgtgca
 601 cccgcttcc cgggcacgca cgacaggggc tttctcgccg tcttccgtcc gaacttgaac
 661 gagtgtcagc catttcttgg catggacact tccagtcaac gcgcgtagct gctaccacgg
 721 ttgtggcagc aatcctgcta agggaggttc catgagacgt ttccgacttg tcggcttcct
 781 gagttcgctc gtcctcgccg ccggcgccgc cctcaccggg gcagcgaccg cccaggcggc
 841 ccaacccgcc gccgccgacg gctatgtggc cctcggcgac tcctactcct ccggggtcgg
 901 agcgggcagc tacatcagct cgagcggcga ctgcaagcgc agcacgaagg cccatcccta
 961 cctgtgggcg gccgcccact cgccctccac gttcgacttc accgcctgtt ccggcgcccg
1021 tacgggtgat gttctctccg gacagctcgg cccgctcagc tccggcaccg gctcgtctc
1081 gatcagcatc ggcggcaacg acgccggttt cgccgacacc atgacgacct gtgtgctcca
1141 gtccgagagc tcctgcctgt cgcggatcgc caccgccgag gcgtacgtcg actcgacgct
1201 gcccggcaag ctcgacggcg tctactcggc aatcagcgac aaggcgccga acgcccacgt
1261 cgtcgtcatc ggctacccgc gcttctacaa gctcggcacc acctgcatcg gcctgtccga
1321 gaccaagcgg acggcgatca acaaggcctc cgaccacctc aacaccgtcc tcgcccagcg
1381 cgccgccgcc cacggcttca ccttcggcga cgtacgcacc accttcaccg gccacgagct
1441 gtgctccggc agccctggc tgcacagcgt caactggctg aacatcggcg agtcgtacca
1501 ccccaccgcg gccggccagt ccggtggcta cctgccggtc ctcaacggcg ccgcctgacc
1561 tcaggcggaa ggagaagaag aaggagcgga gggagacgag gagtgggagg ccccgcccga
1621 cggggtcccc gtcccgtct ccgtctccgt cccggtcccg caagtcaccg agaacgccac
1681 cgcgtcggac gtggcccgca ccggactccg cacctccacg cgcacggcac tctcgaacgc
1741 gccggtgtcg tcgtgcgtcg tcaccaccac gccgtcctgg cgcgagcgct cgccgcccga
1801 cgggaaggac agcgtccgcc accccggatc ggagaccgac ccgtccgcgg tcacccaccg
1861 gtagccgacc tccgcgggca gccgccgac cgtgaacgtc gccgtgaacg cgggtgcccg
1921 gtcgtgcggc ggcggacagg cccccgagta gtgggtgcgc gagcccacca cggtcacctc
1981 caccgactgc gctgcggggc
```

FIGURE 38 (SEQ ID No. 45)

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

FIGURE 39 (SEQ ID No. 46)

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagccgg tgcccttctt gagcgtgacg atgtagctgc
 181 ccttgatcgc ggtggggagg ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctgggtg gggcgcacgg ctgtgggggg tgcgcgcgtc atcacgcaca cggccctgga
 421 gcgtcgtgtt ccgccctggg ttgagtaaag cctcggccat ctacggggt ggctcaaggg
 481 agttgagacc ctgtcatgag tctgacatga gcacgcaatc aacggggccg tgagcacccc
 541 gggcgacccc ggaaagtgc cgagaagtct tggcatggac acttcctgtc aacacgcgta
 601 gctggtacga cggttacggc agagatcctg ctaaagggag gttccatgag acgttcccga
 661 attacggcat acgtgacctc actcctcctc gccgtcggct gcgccctcac cggggcagcg
 721 acggcgcagg cgtccccagc cgccgcggcc acgggctatg tggccctcgg cgactcgtac
 781 tcgtccggtg tcggcgccgg cagctacctc agctccagcg gcgactgcaa gcgcagttcg
 841 aaggcctatc cgtacctctg gcaggccgcg cattcaccct cgtcgttcag tttcatggct
 901 tgctcgggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgccggg ccaactcgac agcgtgtaca cggcgatcag cacgaaggcc
1141 ccgtcggccc atgtggccgt gctgggctac ccccgcttct acaaactggg cggctcctgc
1201 ctcgcgggcc tctcggagac caagcggtcc gccatcaacg acgcggccga ctatctgaac
1261 agcgccatcg ccaagcgcgc cgccgaccac ggcttcacct cggcgacgt caagagcacc
1321 ttcaccggcc atgagatctg ctccagcagc acctggctgc acagtctcga cctgctgaac
1381 atcggccagt cctaccaccc gaccgcggcc ggccagtccg gcggctatct gccggtcatg
1441 aacagcgtgg cctgagctcc cacggcctga ttttttaagg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga acctgctt ctgctggtc tttccgccgc
1681 tcgccgggaa ggacagcgtc ttccagcccg gatccgggac ctcgcccttc ttggtcaccc
1741 agcggtactc cacctcgacc ggcacccggc ccaccgtgaa ggtcgccgtg aacgtgggcg
1801 cctggcggt gggcggcggg caggcaccgg agtagtcggt gtgcacgccg gtgaccgtca
1861 ccttcacgga ctgggccggc ggggtcgtcg taccgccgcc gccaccgccg cctcccggag
1921 tggagcccga gctgtggtcg ccccgccgt cggcgttgtc gtcctcgggg gttttcgaac
```

FIGURE 40 (SEQ ID No. 47)

```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 41 (SEQ ID No. 48)

```
1         ctgcagacac ccgccccgcc ttctcccgga tcgtcatgtt cggcgactcc ctcagcgaca
61        ccggcaagat gtactccaag atgcgcggct acctgccgtc ctccccgccg tactacgagg
121       gccgcttctc gaacggcccg gtctggctgg agcagctgac gaagcagttc ccggcctga
181       cgatcgccaa cgaggccgag ggggcgcga ccgcagtcgc ctacaacaag atctcctgga
241       acccgaagta ccaggtcatt aacaacctcg actacgaggt cacccagttc ttgcagaagg
301       actcgttcaa gcccgacgac ctggtcatcc tgtgggtggg cgccaacgac tacctggcct
361       acggttggaa cacggagcag gacgccaagc gggtgcgcga cgccatctcg gacgcggcaa
421       accgcatggt cctgaacggc gcgaagcaga tcctgctgtt caacctgccc gacctgggcc
481       agaacccgtc cgcccgctcc cagaaggtcg tcgaggccgt ctcgcacgtg tccgcctacc
541       acaacaagct gctcctcaac ctcgcccggc agctcgcccc gacgggcatg gtcaagctgt
601       tcgagatcga caagcagttc gcggagatgc tgcgcgaccc cagaacttc ggcctgagcg
661       acgtggagaa cccgtgctac gacggcggct acgtgtggaa gccgttcgcc acccggtccg
721       tctcgaccga ccggcagctg tcggccttct cgccccagga gcgcctggcg atcgctggca
781       acccgctcct ggcacaggcg gtagcttcgc cgatggcccg ccgtcggcc tcgcccctca
841       actgcgaggg caagatgttc tgggaccagg tccaccccac caccgtggtc cacgccgccc
901       tctcggagcg cgccgccacc ttcatcgaga cccagtacga gttcctcgcc cactagtcta
961       gaggatcc
```

FIGURE 42

1. L131
    2. S.avermitilis
    3. T.fusca
    4. Consensus

```
              1                                                 50
1    (1)   --------MRLTRSLSAASVIVFALLLALLGISPAQAAG-----------
2    (1)   --------MRRSRITAYVTSLLLAVGCALTGAATAQASPA----------
3    (1)   VGSGPRAATRRRLFLGIPALVLVTALTLVLAVPTGRETLWRMWCEATQDW
4    (1)           MRRSRFLA  ALILLTLA  AL GAA  ARAAP 51                                                100
1   (32)   ---------------------------P-AYVALGDSYSSGNGAGSYID
2   (33)   ---------------------------AAATGYVALGDSYSSGVGAGSYLS
3   (51)   CLGVPVDSRGQPAEDGEFLLLSPVQAATWGNYYALGDSYSSGDGARDYYP
4   (51)                              A A  YVALGDSYSSG GAGSY 101                                                150
1   (53)   SSGD---CHRSNNAYPARWAAANAP---SSFTFAACSGAVTTDVIN----
2   (57)   SSGD---CKRSSKAYPYLWQAAHSP---SSFSFMACSGARTGDVLA----
3  (101)   GTAVKGGCWRSANAYPELVAEAYDFA--GHLSFLACSGQRGYAMLDAIDE
4  (101)   SSGD   C RSTKAYPALWAAAHA   SSFSF ACSGARTYDVLA 151                                                200
1   (93)   --NQLGALNAST--GLVSITIGGNDAGFADAMTTCVTS------SDSTCL
2   (97)   --NQLGTLNSST--GLVSLTIGGNDAGFSDVMTTCVLQ------SDSACL
3  (149)   VGSQLDWNSPHT--SLVTIGIGGNDLGFSTVLKTCMVR------VPLLDS
4  (151)       QL LNS T   LVSIT IGGNDAGFAD MTTCVL        SDSACL 201                                                250
1  (133)   NRLATATNYINTTLLA-------RLDAVYSQIKARAPNARVVVLGYPRMY
2  (137)   SRINTAKAYVDSTLPG-------QLDSVYTAISTKAPSAHVAVLGYPRFY
3  (191)   KACTDQEDAIRKRMAKF----ETTFEELISEVRTRAPDARILVVGYPRIF
4  (201)     RIA AK YI  TLPA      RLDSVYSAI TRAP ARVVVLGYPRIY 251                                                300
1  (176)   LASNPWYCLGLSNTKRAAINTTADTLNSVISSRATAH----------GF
2  (180)   KLGG-SCLAGLSETKRSAINDAADYLNSAIAKRAADH----------GF
3  (237)   PEEPTGAYYTLTASNQRWLNETIQEFNQQLAEAVAVHDEEIAASGGVGSV
4  (251)       SG     LGLS TKRAAINDAAD LNSVIAKRAADH            GF 301                                                350
1  (215)   RFGDVRPTFNNHELFFGNDWLHSLTLP----------------VWESYH
2  (218)   TFGDVKSTFTGHEICSSSTWLHSLDLLN---------------IGQSYH
3  (287)   EFVDVYHALDGHEIGSDEPWVNGVQLRDLATG---------VTVDRSTFH
4  (301)   TFGDV  TF GHELCSA  PWLHSLTLP                V  SYH 351                                          395
1  (248)   PTSTGHQSGYLPVLNANSST------------------
2  (252)   PTAAGQSGGYLPVMNSVA--------------------
3  (328)   PNAAGHRAVGERVIEQIETGPGRPLYATFAVVAGATVDTLAGEVG
4  (351)   PTA GHAAGYLPVLNSI T
```

FIGURE 43

SEQ ID No 17 which is the amino acid sequence of a lipid acyltransferase from *Candida parapsilosis*;

```
MRYFAIAFLL  INTISAFVLA  PKKPSQDDFY  TPPQGYEAQP  LGSILKTRNV  PNPLTNVFTP  VKVQNAWQLL
VRSEDTFGNP  NAIVTTIIQP  FNAKKDKLVS  YQTFEDSGKL  DCAPSYAIQY  GSDISTLTTQ  GEMYYISALL
DQGYYVVTPD  YEGPKSTFTV  GLQSGRATLN  SLRATLKSGN  LTGVSSDAET  LLWGYSGGSL  ASGWAAAIQK
EYAPELSKNL  LGAALGGFVT  NITATAEAVD  SGPFAGIISN  ALAGIGNEYP  DFKNYLLKKV  SPLLSITYRL
GNTHCLLDGG  IAYFGKSFFS
RIIRYFPDGW  DLVNQEPIKT  ILQDNGLVYQ  PKDLTPQIPL  FIYHGTLDAI  VPIVNSRKTF  QQWCDWGLKS
GEYNEDLTNG  HITESIVGAP  AALTWIINRF  NGQPPVDGCQ  HNVRASNLEY  PGTPQSIKNY  FEAALHAILG
FDLGPDVKRD  KVTLGGLLKL  ERFAF
```

FIGURE 44

SEQ ID No 18 which is the amino acid sequence of a lipid acyltransferase from *Candida parapsilosis*;

```
MRYFAIAFLL  INTISAFVLA  PKKPSQDDFY  TPPQGYEAQP  LGSILKTRNV  PNPLTNVFTP  VKVQNAWQLL
VRSEDTFGNP  NAIVTTIIQP  FNAKKDKLVS  YQTFEDSGKL  DCAPSYAIQY  GSDISTLTTQ  GEMYYISALL
DQGYYVVTPD  YEGPKSTFTV  GLQSGRATLN  SLRATLKSGN  LTGVSSDAET  LLWGYSGGSL  ASGWAAAIQK
EYAPELSKNL  LGAALGGFVT  NITATAEAVD  SGPFAGIISN  ALAGIGNEYP  DFKNYLLKKV  SPLLSITYRL
GNTHCLLDGG  IAYFGKSFFS  RIIRYFPDGW  DLVNQEPIKT  ILQDNGLVYQ  PKDLTPQIPL  FIYHGTLDAI
VPIVNSRKTF  QQWCDWGLKS  GEYNEDLTNG  HITESIVGAP  AALTWIINRF  NGQPPVDGCQ  HNVRASNLEY
PGTPQSIKNY  FEAALHAILG  FDLGPDVKRD  KVTLGGLLKL  ERFAFHHHHH  H
```

```
1DEQm     T T V Y L   A G D S T M A K n - - - - - - - - - - - - - - - - - - - - - - - - - - - - - - - - - - - - - - - - - -
          s1s1s1- s1 s1s1h?h?h?h?
1IVNm   A D T L L I   L G D S L S A G - - - - - - - - - - - - - - - - - - - - - - - - - - - - - - - - - - - - G G G S G T N G W G E Y L
          s1s1s1- s1 s1s1h     h h h                                                                              h1h1h1h1h1
P10480m   I V M F G D S L S D T g k m - g y l p s s p p y y e G R F S N G P V W L E Q L   Y R M S A S A A W P A L L
                                                                                                                  h1h1h1h1h1

1DEOm   A S Y L S A T V - - - - - - - - - - V N D A V A G R S - - - - - - - A R S Y T R E G R F E N I A
          h1h1h1 s2 s2 s2                   s2s2s2s2s2s2s2                   h3h3h3h3h3h3h3h3h3h3h3h3h3h3
1IVNm   N D K W q s k - - - - - - - - - - t s v V N A S I S G D T - -       - S Q Q G L A   R L P A L L
          h1h1h1 s2?s2?                    s2?s2s2s2s2s2s2               h3                h3h3h3h3h3h3h3
P10480m T N E F P G   L T i a n e a e g g p p t a v a Y N K l S W N P A     y q v l N N L D Y E V T Q F L Q

1DEOm   D   V V T   A G D Y V I V E F G H N   D G g s l s t d n g     r t d c s g t g a E v C Y S V Y D G V N E T I
          h3h3         s4 s4s4s4s4s4                ? ?   ?   ? ? ?   ? ?   s?s?s?s?s?s?s?s? - L R G F Q P
1IVNm   K Q H Q P     R W V L V E L G G N   D G - -                       ? ? - - - - - - - - L R G F Q P
          h3h3h3        s4s4s4s4s4s4                                                                          h4
P10480m K D S F K   P D D L V I L W V G A N   D Y - - - - - - - - - - - - - - - - - - L A Y G W N T E Q D A

1DEOm   L T E P A Y   L E N A A K L F T A K     G A K V I L S S       Q T P N   N P W E T G T F V N S P T R
          h4h4h4h4 h4 h4h4h4h4h4h4h4h4h4h4      s5s5s5s5s5s5
1IVNm   Q Q T E Q T   L L R Q I L Q D V K a A   N A E P l l m q i R L P       A N Y G R     - R Y N E A
          h4h4h4h4 h4 h4h4h4h4h4h4h4h4h4h4      s?s5s5s5s5s5s5?s5?s5?                                           h5h5h5h5h5h5
P10480m K R V R D   A I S D A A N R M V L N     G A K E I L L F N L P d l g g n P S A R S Q K V V E A A S H V S A

1DEOm   F V E Y A   E L A A E V A - - - - - - - G     V E Y - V D H W S Y V D S I Y E T L G N A t v n - - -
          h5h5h5h5 h5 h5h5h5h5h5h5h5h5                s6 s6 s6?s6?s6h6h6h6h6h6h6h6h6h6h6 h h h h
1IVNm   F S A I Y   P K L A k e - - - - - - - f D   V P L L P F F M E E V Y                   L K P Q W
          h5h5h5h5 h5                               h5 s6s6s6s6?       h6 h6 h6 h6h6
P10480m Y H N Q L   L L N L A r g l a p t g m v k l = e i D K Q F A E M L R D P P Q N F G L S D Q R N a c y g g

1DEOm   - - - - - - - - - - - - - - - - - - - - - - - - - - - - - - - - - - - - - - - - - - - - - - - - - - - - -
1IVNm   - - - - - - - - - - - - - - - - - - - - - - - - - - - - - - - - - - - - - - - - - - - - - - - - - - - - -
P10480m s y v w k   p f a s r s a s t d s g   l s a f n p g e r l a   i a g n p l - a g a v a s p m a a r s a s t

1DEOm   - - - s   y F P I D H T   T S P A   G A E V V A E A   F L K A V V C T G T S L K S V L T T T S F E G T C
1IVNm   - - h - - - - - -         s?s?s?h7 h7h7h7h7h7h7h7    h7 h7 h7 h7h7h7h7 h?h?h?
        - - - -   M Q D D G I H   H P N R D A Q P F I A D W M A K Q L Q P L V N H D S L E
P10480m l n c e g k M F W D Q V H P T T V V H A A L S E P A T F I E S Q Y E F L A H -
```

```
                        10         20         30         40         50         60
              ....*....|....*....|....*....|....*....|....*....|....*....|
1IVN_A      4 LLILGDSLSAG------------------------YRMSASAAWPALLNDKWqsk----------  34
P10480     28 IVMFGDSLSDTgkmyskmrgylpsappyyaGRFSNGPVWLEQLTNEFPGLTianeaagqp  87

70         80         90        100        110        120
              ....*....|....*....|....*....|....*....|....*....|....*....|
1IVN_A     35 -ksvVNASISGDT-------------------------------SQQGLARLPALLKQHQPPW  65
P10480     88 asvaYNKISWNPKyq------------------------VINNLDYEVTQFLQKDSFKPDDL 125

130        140        150        160        170        180
              ....*....|....*....|....*....|....*....|....*....|....*....|
1IVN_A     66 VLVELGGNDG-------------------------------LRGFQPQQTEQT  87
P10480    126 VILWVGANDY-------------------------LA--YGWNTEQDAKRVRDA 152

190        200        210        220        230        240
              ....*....|....*....|....*....|....*....|....*....|....*....|
1IVN_A     88 LRQILQDVKaANAEPllmgiRLPANYGR----------------  115
P10480    153 ISDAANRMV-LNGAK-------EILLFNLPdlg---------qnF 180

250        260        270        280        290        300
              ....*....|....*....|....*....|....*....|....*....|....*....|
1IVN_A    116 ------------RYNEAFSAIYPKLAke-----------fDVPLLPFFME 142
P10480    181 GARSQKVVEAASHVSAYHNQLLLNLArqlaptg--------mvklfeiDKQFAEMLRD 230

310        320        330        340        350        360
              ....*....|....*....|....*....|....*....|....*....|....*....|
1IVN_A    143 EVYLKPQW----------------------------------------  150
P10480    231 PQNFGLSDQRNacyggsyvwkpfasrsastdsqlsafnpqerlalagnpllaqavaspma 290

370        380        390        400
              ....*....|....*....|....*....|....*....|
1IVN_A    151 ---------MQDDGI----------HPNRDAQPFIADWM 170
P10480    291 arsastlnoegkMFWLQV-------RPTTVVHAALSEPA 322
```

FIGURE 52

```
                     1                                                  50
    P10480    (1)  MKKWFVCLLGLVALTVQAADSRPAFSRIVMFGDSLSDTGKMYSKMRGYLP
    A. sal    (1)  -----------------ADTRPAFSRIVMFGDSLSDTGKMYSKMRGYLP
    A. hyd    (1)  -----------------ADSRPAFSRIVMFGDSLSDTGKMYSKMRGYLP
 Consensus    (1)                   AD*RPAFSRIVMFGDSLSDTGKMYSKMRGYLP
                    51                                                 100
    P10480   (51)  SSPPYYEGRFSNGPVWLEQLTNEFPGLTIANEAEGGPTAVAYNKISWNPK
    A. sal   (33)  SSPPYYEGRFSNGPVWLEQLTKQFPGLTIANEAEGGATAVAYNKISWNPK
    A. hyd   (33)  SSPPYYEGRFSNGPVWLEQLTKQFPGLTIANEAEGGATAVAYNKISWNPK
 Consensus   (51)  SSPPYYEGRFSNGPVWLEQLT**FPGLTIANEAEGG*TAVAYNKISWNPK
                   101                                                 150
    P10480  (101)  YQVINNLDYEVTQFLQKDSFKPDDLVILWVGANDYLAYGWNTEQDAKRVR
    A. sal   (83)  YQVINNLDYEVTQFLQKDSFKPDDLVILWVGANDYLAYGWNTEQDAKRVR
    A. hyd   (83)  YQVINNLDYEVTQFLQKDSFKPDDLVILWVGANDYLAYGWNTEQDAKRVR
 Consensus  (101)  YQVINNLDYEVTQFLQKDSFKPDDLVILWVGANDYLAYGWNTEQDAKRVR
                   151                                                 200
    P10480  (151)  DAISDAANRMVLNGAKEILLFNLPDLGQNPSARSQKVVEAASHVSAYHNQ
    A. sal  (133)  DAISDAANRMVLNGAKQILLFNLPDLGQNPSARSQKVVEAVSHVSAYHNK
    A. hyd  (133)  DAISDAANRMVLNGAKQILLFNLPDLGQNPSARSQKVVEAVSHVSAYHNQ
 Consensus  (151)  DAISDAANRMVLNGAK*ILLFNLPDLGQNPSARSQKVVEA*SHVSAYHN*
                   201                                                 250
    P10480  (201)  LLLNLARQLAPTGMVKLFEIDKQFAEMLRDPQNFGLSDQRNACYGGSYVW
    A. sal  (183)  LLLNLARQLAPTGMVKLFEIDKQFAEMLRDPQNFGLSDVENPCYDGGYVW
    A. hyd  (183)  LLLNLARQLAPTGMVKLFEIDKQFAEMLRDPQNFGLSDVENPCYDGGYVW
 Consensus  (201)  LLLNLARQLAPTGMVKLFEIDKQFAEMLRDPQNFGLSD**N*CY*G*YVW
                   251                                                 300
    P10480  (251)  KPFASRSASTDSQLSAFNPQERLAIAGNPLLAQAVASPMAARSASTLNCE
    A. sal  (233)  KPFATRSVSTDRQLSAFSPQERLAIAGNPLLAQAVASPMARRSASPLNCE
    A. hyd  (233)  KPFATRSVSTDRQLSAFSPQERLAIAGNPLLAQAVASPMARRSASPLNCE
 Consensus  (251)  KPFA*RS*STD*QLSAF*PQERLAIAGNPLLAQAVASPMA*RSAS*LNCE
                   301                          336
    P10480  (301)  GKMFWDQVHPTTVVHAALSEPAATFIESQYEFLAH-
    A. sal  (283)  GKMFWDQVHPTTVVHAALSERAATFIETQYEFLAHG
    A. hyd  (283)  GKMFWDQVHPTTVVHAALSERAATFIANQYEFLAH-
 Consensus  (301)  GKMFWDQVHPTTVVHAALSE*AATFI**QYEFLAH*
```

FIGURE 53

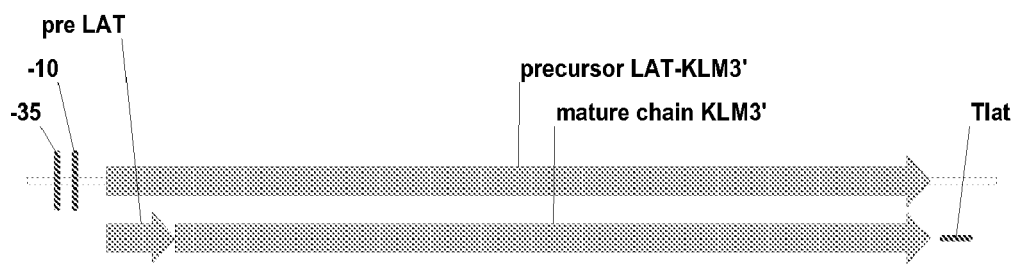

Gene construct for KLM3' expression 1225 bp

FIGURE 55

```
                                                         -35
    1  GCTTTTCTTT TGGAAGAAAA TATAGGGAAA ATGGTACTTG TTAAAAATTC GGAATATTTA
       CGAAAAGAAA ACCTTCTTTT ATATCCCTTT TACCATGAAC AATTTTTAAG CCTTATAAAT
       -10                                          M  K  Q  Q  K  R  L  .
   61  TACAATATCA TATGTTTCAC ATTGAAAGGG GAGGAGAATC ATGAAACAAC AAAAACGGCT
       ATGTTATAGT ATACAAAGTG TAACTTTCCC CTCCTCTTAG TACTTTGTTG TTTTTGCCGA
       .Y  A  R   L  L  T  L   L  F  A   L  I  F   L  L  P   H  S  A  A  .
  121  TTACGCCCGA TTGCTGACGC TGTTATTTGC GCTCATCTTC TTGCTGCCTC ATTCTGCAGC
       AATGCGGGCT AACGACTGCG ACAATAAACG CGAGTAGAAG AACGACGGAG TAAGACGTCG
       .S  A  A   D  T  R   P  A  F  S   R  I  V   M  F  G   D  S  L  S  .
  181  TTCAGCAGCA GATACAAGAC CGGCGTTTAG CCGGATCGTC ATGTTTGGAG ATAGCCTGAG
       AAGTCGTCGT CTATGTTCTG GCCGCAAATC GGCCTAGCAG TACAAACCTC TATCGGACTC
       .D  T  G   K  M  Y  S   K  M  R   G  Y  L   P  S  S   P  Y  Y  .
  241  CGATACGGGC AAAATGTATA GCAAAATGAG AGGCTATCTT CCGTCAAGCC CGCCGTATTA
       GCTATGCCCG TTTTACATAT CGTTTTACTC TCCGATAGAA GGCAGTTCGG GCGGCATAAT
       .E  G  R   F  S  N  G   P  V  W   L  E  Q   L  T  K   Q  F  P  G  .
  301  TGAAGGCCGC TTTAGCAATG GACCGGTCTG GCTGGAACAA CTGACGAAAC AATTTCCGGG
       ACTTCCGGCG AAATCGTTAC CTGGCCAGAC CGACCTTGTT GACTGCTTTG TTAAAGGCCC
       .L  T  I   A  N  E  A   E  G  G   A  T  A   V  A  Y   N  K  I  S  .
  361  ACTGACGATC GCTAATGAAG CAGAAGGAGG AGCAACAGCG GTCGCCTATA ACAAAATCAG
       TGACTGCTAG CGATTACTTC GTCTTCCTCC TCGTTGTCGC CAGCGGATAT TGTTTTAGTC
       .W  D  P   K  Y  Q  V   I  N  N   L  D  Y   E  V  T   Q  F  L  Q  .
  421  CTGGGACCCG AAATATCAGG TCATCAACAA CCTGGACTAT GAAGTCACAC AGTTTCTTCA
       GACCCTGGGC TTTATAGTCC AGTAGTTGTT GGACCTGATA CTTCAGTGTG TCAAAGAAGT
       .K  D  S   F  K  P   D  L  V  I   L  W  G   A  N  D   Y  L  .
  481  GAAAGACAGC TTTAAACCGG ATGATCTGGT CATCCTTTGG GTCGGCGCCA ATGATTATCT
       CTTTCTGTCG AAATTTGGCC TACTAGACCA GTAGGAAACC CAGCCGCGGT TACTAATAGA
       .A  Y  G   W  N  T  E   Q  D  A   K  R  V   R  D  A   I  S  D  A  .
  541  GGCGTATGGC TGGAACACAG AACAAGATGC CAAAAGAGTC AGAGATGCCA TCAGCGATGC
       CCGCATACCG ACCTTGTGTC TTGTTCTACG GTTTTCTCAG TCTCTACGGT AGTCGCTACG
       .A  N  R   M  V  L  N   G  A  K   Q  I  L   L  F  N   L  P  D  L  .
  601  CGCTAATAGA ATGGTCCTGA ACGGCGCCAA ACAAATCCTG CTGTTTAACC TGCCGGATCT
       GCGATTATCT TACCAGGACT TGCCGCGGTT TGTTTAGGAC GACAAATTGG ACGGCCTAGA
       .G  Q  N   P  S  A  R   S  Q  K   V  V  E   A  V  S   H  V  S  A  .
  661  GGGACAAAAT CCGAGCGCCA GAAGCCAAAA AGTCGTCGAA GCAGTCAGCC ATGTCAGCGC
       CCCTGTTTTA GGCTCGCGGT CTTCGGTTTT TCAGCAGCTT CGTCAGTCGG TACAGTCGCG
       .Y  H  N   K  L  L   N  L  A  R   Q  L  A   P  T  G   M  V  K  .
  721  CTATCATAAC AAACTGCTGC TGAACCTGGC AAGACAATTG GCACCGACGG GAATGGTTAA
       GATAGTATTG TTTGACGACG ACTTGGACCG TTCTGTTAAC CGTGGCTGCC CTTACCAATT
       .L  F  E   I  D  K  Q   F  A  E   M  L  R   D  P  Q   N  F  G  L  .
  781  ATTGTTTGAA ATTGACAAAC AGTTTGCCGA AATGCTGAGA GATCCGCAAA ATTTTGGCCT
       TAACAAACTT TAACTGTTTG TCAAACGGCT TTACGACTCT CTAGGCGTTT TAAAACCGGA
       .S  D  V   E  N  P  C   Y  D  G   G  Y  V   W  K  P   F  A  T  R  .
  841  GAGCGATGTC GAAAACCCGT GCTATGATGG CGGATATGTC TGGAAACCGT TTGCCACAAG
       CTCGCTACAG CTTTTGGGCA CGATACTACC GCCTATACAG ACCTTTGGCA AACGGTGTTC
       .S  V  S   T  D  R  Q   L  S  A   F  S  P   Q  E  R   L  A  I  A  .
  901  AAGCGTCAGC ACGGATAGAC AACTGTCAGC GTTTAGCCCG CAAGAAAGAC TGGCAATCGC
       TTCGCAGTCG TGCCTATCTG TTGACAGTCG CAAATCGGGC GTTCTTTCTG ACCGTTAGCG
       .G  N  P   L  L  A  Q   A  V  A   S  P  M   A  R  R   S  A  S  P  .
  961  CGGAAATCCG CTTTTGGCAC AAGCAGTTGC TTCACCGATG CAAGAAGAT CAGCAAGCCC
       GCCTTTAGGC GAAAACCGTG TTCGTCAACG AAGTGGCTAC CGTTCTTCTA GTCGTTCGGG
       .L  N  C   E  G  K  M   F  W  D   Q  V  H   P  T  T   V  V  H  A  .
 1021  GCTGAATTGC GAAGGCAAAA TGTTTTGGGA TCAGGTCCAT CCGACAACAG TTGTCCATGC
       CGACTTAACG CTTCCGTTTT ACAAAACCCT AGTCCAGGTA GGCTGTTGTC AACAGGTACG
       .A  L  S   E  R  A  A   T  F  I   E  T  Q   Y  E  F   L  A  H  G  .
 1081  TGCCCTTTCA GAAAGAGCGG CGACGTTTAT CGAAACACAG TATGAATTTC TGGCCCATGG
       ACGGGAAAGT CTTTCTCGCC GCTGCAAATA GCTTTGTGTC ATACTTAAAG ACCGGGTACC
       .stop
 1141  CTGAGTTAAC AGAGGACGGA TTTCCTGAAG GAAATCCGTT TTTTTATTTT AAGCTTGGAG
       GACTCAATTG TCTCCTGCCT AAAGGACTTC CTTTAGGCAA AAAAATAAAA TTCGAACCTC
 1201  ACAAGGTAAA GGATAAAACC TCGAG
       TGTTCCATTT CCTATTTTGG AGCTC
```

FIGURE 57 (SEQ ID No 49)

```
   1   ATGAAACAAC AAAAACGGCT TTACGCCCGA TTGCTGACGC TGTTATTTGC
       TACTTTGTTG TTTTTGCCGA AATGCGGGCT AACGACTGCG ACAATAAACG

51   GCTCATCTTC TTGCTGCCTC ATTCTGCAGC TTCAGCAGCA GATACAAGAC
       CGAGTAGAAG AACGACGGAG TAAGACGTCG AAGTCGTCGT CTATGTTCTG

101   CGGCGTTTAG CCGGATCGTC ATGTTTGGAG ATAGCCTGAG CGATACGGGC
       GCCGCAAATC GGCCTAGCAG TACAAACCTC TATCGGACTC GCTATGCCCG

151   AAAATGTATA GCAAAATGAG AGGCTATCTT CCGTCAAGCC CGCCGTATTA
       TTTTACATAT CGTTTTACTC TCCGATAGAA GGCAGTTCGG GCGGCATAAT

201   TGAAGGCCGC TTTAGCAATG GACCGGTCTG GCTGGAACAA CTGACGAAAC
       ACTTCCGGCG AAATCGTTAC CTGGCCAGAC CGACCTTGTT GACTGCTTTG

251   AATTTCCGGG ACTGACGATC GCTAATGAAG CAGAAGGAGG AGCAACAGCG
       TTAAAGGCCC TGACTGCTAG CGATTACTTC GTCTTCCTCC TCGTTGTCGC

301   GTCGCCTATA ACAAAATCAG CTGGGACCCG AAATATCAGG TCATCAACAA
       CAGCGGATAT TGTTTTAGTC GACCCTGGGC TTTATAGTCC AGTAGTTGTT

351   CCTGGACTAT GAAGTCACAC AGTTTCTTCA GAAAGACAGC TTTAAACCGG
       GGACCTGATA CTTCAGTGTG TCAAAGAAGT CTTTCTGTCG AAATTTGGCC

401   ATGATCTGGT CATCCTTTGG GTCGGCGCCA ATGATTATCT GGCGTATGGC
       TACTAGACCA GTAGGAAACC CAGCCGCGGT TACTAATAGA CCGCATACCG

451   TGGAACACAG AACAAGATGC CAAAAGAGTC AGAGATGCCA TCAGCGATGC
       ACCTTGTGTC TTGTTCTACG GTTTTCTCAG TCTCTACGGT AGTCGCTACG

501   CGCTAATAGA ATGGTCCTGA ACGGCGCCAA ACAAATCCTG CTGTTTAACC
       GCGATTATCT TACCAGGACT TGCCGCGGTT TGTTTAGGAC GACAAATTGG

551   TGCCGGATCT GGGACAAAAT CCGAGCGCCA GAAGCCAAAA AGTCGTCGAA
       ACGGCCTAGA CCCTGTTTTA GGCTCGCGGT CTTCGGTTTT TCAGCAGCTT

601   GCAGTCAGCC ATGTCAGCGC CTATCATAAC AAACTGCTGC TGAACCTGGC
       CGTCAGTCGG TACAGTCGCG GATAGTATTG TTTGACGACG ACTTGGACCG

651   AAGACAATTG GCACCGACGG GAATGGTTAA ATTGTTTGAA ATTGACAAAC
       TTCTGTTAAC CGTGGCTGCC CTTACCAATT TAACAAACTT TAACTGTTTG

701   AGTTTGCCGA AATGCTGAGA GATCCGCAAA ATTTTGGCCT GAGCGATGTC
       TCAAACGGCT TTACGACTCT CTAGGCGTTT TAAAACCGGA CTCGCTACAG

751   GAAAACCCGT GCTATGATGG CGGATATGTC TGGAAACCGT TTGCCACAAG
       CTTTTGGGCA CGATACTACC GCCTATACAG ACCTTTGGCA AACGGTGTTC

801   AAGCGTCAGC ACGGATAGAC AACTGTCAGC GTTTAGCCCG CAAGAAAGAC
       TTCGCAGTCG TGCCTATCTG TTGACAGTCG CAAATCGGGC GTTCTTTCTG

851   TGGCAATCGC CGGAAATCCG CTTTTGGCAC AAGCAGTTGC TTCACCGATG
       ACCGTTAGCG GCCTTTAGGC GAAAACCGTG TTCGTCAACG AAGTGGCTAC

901   GCAAGAAGAT CAGCAAGCCC GCTGAATTGC GAAGGCAAAA TGTTTTGGGA
       CGTTCTTCTA GTCGTTCGGG CGACTTAACG CTTCCGTTTT ACAAAACCCT

951   TCAGGTCCAT CCGACAACAG TTGTCCATGC TGCCCTTTCA GAAAGAGCGG
       AGTCCAGGTA GGCTGTTGTC AACAGGTACG ACGGGAAAGT CTTTCTCGCC

1001   CGACGTTTAT CGAAACACAG TATGAATTTC TGGCCCATGG CTGA
       GCTGCAAATA GCTTTGTGTC ATACTTAAAG ACCGGGTACC GACT
```

FIGURE 58 (SEQ ID No. 50)

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CCGTCTGGCT GGAGCAGCTG ACCAACGAGT CCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC GGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT TCTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

FIGURE 59 (SEQ ID No. 51)

```
  1  ATGAAAAAAT GGTTTGTTTG TTTATTGGGG TTGATCGCGC TGACAGTTCA GGCAGCCGAC
 61  ACTCGCCCCG CCTTCTCCCG GATCGTGATG TTCGGCGACA GCCTCTCCGA TACCGGCAAA
121  ATGTACAGCA AGATGCGCGG TTACCTCCCC TCCAGCCCGC CCTACTATGA GGGCCGTTTC
181  TCCAACGGAC CCGTCTGGCT GGAGCAGCTG ACCAAGCAGT TCCCGGGTCT GACCATCGCC
241  AACGAAGCGG AAGGCGGTGC CACTGCCGTG GCTTACAACA AGATCTCCTG GAATCCCAAG
301  TATCAGGTCT ACAACAACCT GGACTACGAG GTCACCCAGT TCTTGCAGAA AGACAGCTTC
361  AAGCCGGACG ATCTGGTGAT CCTCTGGGTC GGTGCCAATG ACTATCTGGC ATATGGCTGG
421  AATACGGAGC AGGATGCCAA GCGAGTTCGC GATGCCATCA GCGATGCGGC CAACCGCATG
481  GTACTGAACG GTGCCAAGCA GATACTGCTG TTCAACCTGC GGATCTGGG CCAGAACCCG
541  TCAGCCCGCA GTCAGAAGGT GGTCGAGGCG GTCAGCCATG TCTCCGCCTA TCACAACAAG
601  CTGCTGCTGA ACCTGGCACG CCAGCTGGCC CCCACCGGCA TGGTAAAGCT GTTCGAGATC
661  GACAAGCAAT TTGCCGAGAT GCTGCGTGAT CCGCAGAACT TCGGCCTGAG CGACGTCGAG
721  AACCCCTGCT ACGACGGCGG CTATGTGTGG AAGCCGTTTG CCACCCGCAG CGTCAGCACC
781  GACCGCCAGC TCTCCGCCTT CAGTCCGCAG GAACGCCTCG CCATCGCCGG CAACCCGCTG
841  CTGGCACAGG CCGTTGCCAG TCCTATGGCC CGCCGCAGCG CCAGCCCCCT CAACTGTGAG
901  GGCAAGATGT TCTGGGATCA GGTACACCCG ACCACTGTCG TGCACGCAGC CCTGAGCGAG
961  CGCGCCGCCA CCTTCATCGA GACCCAGTAC GAGTTCCTCG CCCACGGATG A
```

FIGURE 60 (SEQ ID No. 52)

```
  1  ATGCCGAAGC CTGCCCTTCG CCGTGTCATG ACCGCGACAG TCGCCGCCGT CGGCACGCTC
 61  GCCCTCGGCC TCACCGACGC CACCGCCCAC GCCGCGCCCG CCCAGGCCAC TCCGACCCTG
121  GACTACGTCG CCCTCGGCGA CAGCTACAGC GCCGGCTCCG GCGTCCTGCC CGTCGACCCC
181  GCCAACCTGC TCTGTCTGCG CTCGACGGCC AACTACCCCC ACGTCATCGC GGACACGACG
241  GGCGCCCGCC TCACGGACGT CACCTGCGGC GCCGCGCAGA CCGCCGACTT CACGCGGGCC
301  CAGTACCCGG GCGTCGCACC CCAGTTGGAC GCGCTCGGCA CCGGCACGGA CCTGGTCACG
361  CTCACCATCG GCGGCAACGA CAACAGCACC TTCATCAACC CCATCACGAC CTGCGGCACG
421  GCGGGTGTCC TCAGCGGCGG CAAGGGCAGC CCCTGCAAGG ACAGGCACGG CACCTCCTTC
481  GACGACGAGA TCGAGGCCAA CACGTACCCC GCGCTCAAGG AGGCGCTGCT CGGCGTCCGC
541  GCCAGGGCTC CCCACGCCAG GGTGGCGGCT CTCGGCTACC GTGGATCAC CCCGGCCACC
601  GCCGACCCGT CCTGCTTCCT GAAGCTCCCC CTCGCCGCCG GTGACGTGCC CTACCTGCGG
661  GCCATCCAGG CACACCTCAA CGACGCGGTC CGGCGGGCCG CCGAGGAGAC CGGAGCCACC
721  TACGTGGACT TCTCCGGGGT GTCCGACGGC ACGACGCCT GCGAGGCCCC CGGCACCCGC
781  TGGATCGAAC CGCTGCTCTT CGGGCACAGC CTCGTTCCGG TCCACCCCAA CGCCCTGGGC
841  GAGCGGCGCA TGGCCGAGCA CACGATGGAC GTCCTCGGCC TGGACTGA
```

FIGURE 61 (SEQ ID No. 53)

```
  1 TCAGTCCAGG CCGAGGACGT CCATCGTGTG CTCGGCCATG CGCCGCTCGC CCAGGGCGTT
 61 GGGGTGGACG GGAACGAGGC TGTGCCCGAA GAGCAGCGGT TCGATCCAGC GGGTGCCGGG
121 GGCCTCGCAG GCGTCGTGGC CGTCGGACAC CCCGGAGAAG TCCACGTAGG TGGCTCCGGT
181 CTCCTCGGCG GCCCGCCGGA CCGCGTCGTT GAGGTGTGCC TGGATGGCCC GCAGGTAGGG
241 CACGTCACCG GCGGCGAGGG GGAGCTTCAG GAAGCAGGAC GGGTCGGCGG TGGCCGGGGT
301 GATCCACGGG TAGCCGAGAG CCGCCACCCT GGCGTGGGGA GCCCTGGCGC GGACGCCGAG
361 CAGCGCCTCC TTGAGCGCGG GGTACGTGTT GGCCTCGATC TCGTCGTCGA AGGAGGTGCC
421 GTGCCTGTCC TTGCAGGGGC TGCCCTTGCC GCCGCTGAGG ACACCCGCCG TGCCGCAGGC
481 CGTGATGGCC TTGATGAAGG TGCTGTTGTC GTTGCCGCCG ATGGTGAGCG TGACCAGGTC
541 CGTGCCGGTC CCGAGCGCGT CCAACTGGGG TGCGACGCCC GGGTACTGGG CCCGCGTGAA
601 GTCGGCGGTC TGCGCGGCGC CGCAGGTGAC GTCCGTGAGG CGGGCGCCCG TCGTGTCCGC
661 GATGACGTGG GGGTAGTTGG CCGTCGAGCG CAGACAGAGC AGGTTGGCGG GGTCGACGGG
721 CAGGACGCCG GAGCCGGCGC TGTAGCTGTC GCCGAGGGCG ACGTAGTCCA GGGTCGGAGT
781 GGCCTGGGCG GGCGCGGCGT GGGCGGTGGC GTCGGTGAGG CCGAGGGCGA GCGTGCCGAC
841 GGCGGCGACT GTCGCGGTCA TGACACGGCG AAGGGCAGGC TTCGGCAT
```

FIGURE 62 (SEQ ID No. 54)

```
  1 ATGGATTACG AGAAGTTTCT GTTATTTGGG GATTCCATTA CTGAATTTGC TTTTAATACT
 61 AGGCCCATTG AAGATGGCAA AGATCAGTAT GCTCTTGGAG CCGCATTAGT CAACGAATAT
121 ACGAGAAAAA TGGATATTCT TCAAAGAGGG TTCAAAGGGT ACACTTCTAG ATGGGCGTTG
181 AAAATACTTC CTGAGATTTT AAAGCATGAA TCCAATATTG TCATGGCCAC AATATTTTTG
241 GGTGCCAACG ATGCATGCTC AGCAGGTCCC CAAAGTGTCC CCTCCCCGA ATTTATCGAT
301 AATATTCGTC AAATGGTATC TTTGATGAAG TCTTACCATA TCCGTCCTAT TATAATAGGA
361 CCGGGGCTAG TAGATAGAGA GAAGTGGGAA AAAGAAAAAT CTGAAGAAAT AGCTCTCGGA
421 TACTTCCGTA CCAACGAGAA CTTTGCCATT TATTCCGATG CCTTAGCAAA ACTAGCCAAT
481 GAGGAAAAAG TTCCCTTCGT GGCTTTGAAT AAGGCGTTTC AACAGGAAGG TGGTGATGCT
541 TGGCAACAAC TGCTAACAGA TGGACTGCAC TTTTCCGGAA AAGGGTACAA AATTTTTCAT
601 GACGAATTAT TGAAGGTCAT TGAGACATTC TACCCCCAAT ATCATCCCAA AAACATGCAG
661 TACAAACTGA AGATTGGAG AGATGTGCTA GATGATGGAT CTAACATAAT GTCTTGA
```

FIGURE 63 (SEQ ID No. 55)

```
     atgaacctgc gtcaatggat gggcgccgcc acggctgccc ttgccttggg cttggccgcg     60
     tgcggggcg gtgggaccga ccagagcggc aatcccaatg tcgccaaggt gcagcgcatg    120
     gtggtgttcg gcgacagcct gagcgatatc ggcacctaca ccccgtcgc gcaggcggtg    180
     ggcggcgca agttcaccac caacccgggc ccgatctggg ccgagaccgt ggccgcgcaa    240
     ctgggcgtga cgctcacgcc ggcggtgatg ggctacgcca cctccgtgca gaattgcccc    300
     aaggccggct gcttcgacta tgcgcagggc ggctcgcgcg tgaccgatcc gaacggcatc    360
     ggccacaacg gcggcgcggg ggcgctgacc tacccggttc agcagcagct cgccaacttc    420
     tacgcggcca gcaacaacac attcaacggc aataacgatg tcgtcttcgt gctggccggc    480
     agcaacgaca ttttcttctg gaccactgcg gcggccacca gcggctccgg cgtgacgccc    540
     gccattgcca cggcccaggt gcagcaggcc gcgacggacc tggtcggcta tgtcaaggac    600
     atgatcgcca agggtgcgac gcaggtctac gtgttcaacc tgcccgacag cagcctgacg    660
     ccggacgcg tggcaagcgg cacgaccggc caggcgctgc tgcacgcgct ggtgggcacg    720
     ttcaacacga cgctgcaaag cgggctgccc ggcacctcgg cgcgcatcat cgacttcaac    780
     gcacaactga ccgcggcgat ccagaatggc gcctcgttcg gcttcgccaa caccagcgcc    840
     cgggcctgcg acgccaccaa gatcaatgcc ctggtgccga gcgccggcgg cagctcgctg    900
     ttctgctcgg ccaacacgct ggtggcttcc ggtgcggacc agagctacct gttcgccgac    960
     ggcgtgcacc cgaccacggc cggccatcgc ctgatcgcca gcaacgtgct ggcgcgcctg   1020
     ctggcggata acgtcgcgca ctga                                          1044
```

FIGURE 64 (SEQ ID No. 56)

```
  1 gtgatcgggt cgtacgtggc ggtgggggac agcttcaccg agggcgtcgg cgaccccggc
 61 cccgacgggg cgttcgtcgg ctgggccgac cggctcgccg tactgctcgc ggaccggcgc
121 cccgagggcg acttcacgta cacgaacctc gccgtgcgcg gcaggctcct cgaccagatc
181 gtggcggaac aggtcccgcg ggtcgtcgga ctcgcgcccg acctcgtctc gttcgcggcg
241 ggcggcaacg acatcatccg gcccggcacc gatcccgacg aggtcgccga gcggttcgag
301 ctggcggtgg ccgcgctgac cgccgcggcc ggaaccgtcc tggtgaccac cgggttcgac
361 acccgggggg tgcccgtcct caagcacctg cgcggcaaga tcgccacgta caacgggcac
421 gtccgcgcca tcgccgaccg ctacggctgc ccggtgctcg acctgtggtc gctgcggagc
481 gtccaggacc gcagggcgtg ggacgccgac cggctgcacc tgtcgccgga ggggcacacc
541 cgggtggcgc tgcgcgcggg gcaggccctg ggcctgcgcg tcccggccga ccctgaccag
601 ccctggccgc ccctgccgcc gcgcggcacg ctcgacgtcc ggcgcgacga cgtgcactgg
661 gcgcgcgagt acctggtgcc gtggatcggg cgccggctgc ggggcgagtc gtcgggcgac
721 cacgtgacgg ccaaggggac gctgtcgccg gacgccatca gacgcggat cgccgcggtg
781 gcctga
```

FIGURE 65 (SEQ ID No. 57)

```
  1 atgcagacga accccgcgta caccagtctc gtcgccgtcg gcgactcctt caccgagggc
 61 atgtcggacc tgctgcccga cggctcctac cgtggctggg ccgacctcct cgccacccgg
121 atggcggccc gctcccccgg cttccggtac gccaacctgg cggtgcgcgg gaagctgatc
181 ggacagatcg tcgacgagca ggtggacgtg gccgccgcca tgggagccga cgtgatcacg
241 ctggtcggcg ggctcaacga cacgctgcgg cccaagtgcg acatggcccg ggtgcgggac
301 ctgctgaccc aggccgtgga acggctcgcc ccgcactgcg agcagctggt gctgatgcgc
361 agtcccggtc gccagggtcc ggtgctggag cgcttccggc cccgcatgga ggccctgttc
421 gccgtgatcg acgacctggc cgggcggcac ggcgccgtgg tcgtcgacct gtacggggcc
481 cagtcgctgg ccgaccctcg gatgtgggac gtggaccggc tgcaccgac cgccgagggc
541 caccgccggg tcgcggaggc ggtgtggcag tcgctcggcc acgagcccga ggacccccgag
601 tggcacgcgc cgatcccggc gacgccgccc ccggggtggg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc cctacgagga ccccgcacgg
781 tga
```

FIGURE 66 (SEQ ID No. 58)

```
   1 atgacccggg gtcgtgacgg gggtgcgggg gcgcccccca ccaagcaccg tgccctgctc
  61 gcggcgatcg tcaccctgat agtggcgatc tccgcggcca tatacgccgg agcgtccgcg
 121 gacgacggca gcaggacca cgcgctgcag gccggaggcc gtctcccacg aggagacgcc
 181 gcccccgcgt ccaccggtgc ctgggtgggc gcctgggcca ccgcaccggc cgcggccgag
 241 ccgggcaccg agacgaccgg cctgccgtgc cgcctccgtg ccaacgtcgt gcacacctcg
 301 gtcggcggca ccggcgcgcg gatcaccctc tcgaacctgt acgggcagtg gccgctgacc
 361 gtcacacacg cctcgatcgc cctgccgcc gggcccgaca ccgccgccgc gatcgccgac
 421 accatgcgcc ggctcacctt cggcggcagc gcccgggtga tcatcccggc ggggcggcag
 481 gtgatgagcg acaccgcccg cctcgccatc ccctacgggg cgaacgtcct ggtcaccacg
 541 tactccccca tcccgtccgg gccggtgacc taccatccgc aggcccggca gaccagctac
 601 ctggccgacg gcgaccgcac ggcggacgtc accgccgtcg cgtacaccac ccccacgccc
 661 tactggcgct acctgaccgc cctcgacgtg ctgacccacg aggccgacgt cacggtcgtg
 721 gcgttcggcg actccatcac cgacgcgcc cgctcgcaga gcgacgccaa ccaccgctgg
 781 accgacgtcc tcgccgcacg cctgcacgag gcggcgggcg acgcgggga cacgcccgc
 841 tacagcgtcg tcaacgaggg catcagcggc aaccggctcc tgaccagcag gccggggcgg
 901 ccggccgaca acccgagcgg actgagccgg ttccagcggg acgtgctgga acgcaccaac
 961 gtcaaggccg tcgtcgtcgt cctcggcgtc aacgacgtcc tgaacagccc ggaactcgcc
1021 gaccgcgtcg ccatcctgac cggcctgcgc acctcgtcg accgggcgca cgccggggga
1081 ctgcgggtcg tcggcgccac gatcacgcga ttcggcggct acggcggcta caccggagcc
1141 cgcgagacga tgcggcagga ggtcaacgag gagatccgct ccggccgggt cttcgacacg
1201 gtcgtcgact tcgacaaggc cctgcgcgac ccgtacgacc cgcgcggat gcgctccgac
1261 tacgacagcg gcgaccacct gcaccccggc gacaaggggt acgcgcgcat gggcgcggtc
1321 atcgacctgg ccgcgctgaa gggcgcggcg ccggtcaagg cgtag
```

FIGURE 67 (SEQ ID No. 59)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcagggtggg ggtgggcacg ccgacccggg tgccgaacgc gcagggactg
 181 tacggcggca ccctgcccac ggccggcgac ccgccgctgc ggctgatgat gctgggcgac
 241 tccacggccg ccgggcaggg cgtgcaccgg gccgggcaga cgccgggcgc gctgctggcg
 301 tccgggctcg cggcggtggc ggagcggtcg gtgcggctgg ggtcggtcgc ccagccgggg
 361 gcgtgctcgg acgacctgga ccggcaggtg gcgctggtgc tcgccgagcc ggaccggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgggcacg atcgagcggg tgcggcagcc gctgcgctgg
 601 ctggcccggc gggcctcacg gcagctcgcg gcggcacaga ccatcggcgc cgtcgagcag
 661 ggcgggcgca cggtgtcgct gggcgacctg ctgggtccgg agttcgcgca gaacccgcgg
 721 gagctcttcg gccccgacaa ctaccacccc tccgccgagg ggtacgccac ggccgcgatg
 781 gcggtactgc cctcggtgtg cgccgcgctc ggcctgtggc cggccgacga ggagcacccg
 841 gacgcgctgc cccgcgaggg cttcctgccg gtggcgcgcg cggccggcgg ggcggcgtcc
 901 gaggcgggta cggaggtcgc cgccgccatg cctacgggc ctcggggcc ctgggcgctg
 961 ctgaagcgcc ggagacggcg tcgggtgtcg gaggcggaac cgtccagccc gtccggcgtt
1021 tga
```

FIGURE 68 (SEQ ID No. 60)

```
   1 atgggtcgag ggacggacca gcggacgcgg tacggccgtc gccgggcgcg tgtcgcgctc
  61 gccgccctga ccgccgccgt cctgggcgtg gcgtggcgg ctgcgactc cgtgggcggc
 121 gactcacccg ctccttccgg cagccgtcg aagcggacga ggacggcgcc cgcctgggac
 181 accagccgg cgtccgtcgc cgccgtgggc gactccatca cgcgcggctt cgacgcctgt
 241 gcggtgctgt cggactgccc ggaggtgtcg tgggcgaccg gcagcagcgc gaaggtcgac
 301 tcgctggccg tacgctgct ggggaaggcg gacgcggccg agcacagctg gaactacgcg
 361 gtcaccgggg cccgatggc ggacctgacc gctcaggtga cgcgggcggc gcagcgcgag
 421 ccggagctgg tggcggtgat ggccggggc aacgacgcgt gccggtccac gacctcggcg
 481 atgacgccgg tggcggactt ccgggcgcag ttcgaggagg cgatggccac cctgcgcaag
 541 aagctccca aggcgcaggt gtacgtgtcg agcatcccgg acctcaagcg gctctggtcc
 601 cagggccgca ccaaccgct gggcaagcag gtgtggaagc tcggcctgtg cccgtcgatg
 661 ctgggcgacg cggactccct ggactcggcg gcgaccctgc ggcgcaacac ggtgcgcgac
 721 cgggtggcgg actacaacga ggtgctgcgg gaggtctgcg cgaaggaccg gcggtgccgc
 781 agcgacgacg cgcgtgca cgagttccgg ttcggcacgg accagttgag ccactgggac
 841 tggttccacc cgagtgtgga cggccaggcc cggctggcgg agatcgccta ccgcgcggtc
 901 accgcgaaga tccctga
```

FIGURE 69 (SEQ ID No. 61)

```
   1 ttcatcacaa cgatgtcaca acaccggcca tccgggtcat ccctgatcgt gggaatgggt
  61 gacaagcctt cccgtgacga aagggtcctg ctacatcaga aatgacagaa atcctgctca
 121 gggaggttcc atgagactgt cccgacgcgc ggccacggcg tccgcgctcc tcctcacccc
 181 ggcgctcgcg ctcttcggcg cgagcgcgca cgtgtccgcg ccgcgaatcc aggccaccga
 241 ctacgtggcc ctcggcgact cctactcctc ggggtcggc gcgggcagct acgacagcag
 301 cagtggctcc tgtaagcgca gcaccaagtc ctaccggcc ctgtgggccg cctcgcacac
 361 cggtacgcgg ttcaacttca ccgcctgttc gggcgccgc acaggagacg tgctggccaa
 421 gcagctgacc ccggtcaact ccggcaccga cctggtcagc attaccatcg cggcaacga
 481 cgcgggcttc gccgacacca tgaccacctg caacctccag ggcgagagcg cgtgcctggc
 541 gcggatcgcc aaggcgcgcg cctacatcca gcagacgctg cccgcccagc tggaccaggt
 601 ctacgacgcc atcgacagcc agccccccgc agccccgccg gtcgtcctgg gctaccccga
 661 cttctacaag ctgggcggca gctcgccgcc cggtctctcg gagaagtccc gcgcggccat
 721 caacgccgcc gccgacgaca tcaacgccgt caccgccaag cgccgcgcc accacggctt
 781 cgccttcggg gacgtcaaca cgaccttcgc cggcacgag ctgtgctccg gcgccccctg
 841 gctgcacagc gtcacccttc ccgtggagaa ctcctaccac cccacggcca acgacagtc
 901 caagggctac ctgcccgtcc tgaactccgc cacctgatct cgcggctact ccgcccctga
 961 cgaagtcccg ccccggcg gggcttcgcc gtaggtgcgc gtaccgccgt cgcccgtcgc
1021 gccggtggcc ccgccgtacg tgccgccgcc cccggacgcg tcggttc
```

FIGURE 70 (SEQ ID No. 62)

```
  1  ATGAAAAAAT GGTTTGTGTG TTTATTGGGA TTGGTCGCGC TGACAGTTCA
     TACTTTTTTA CCAAACACAC AAATAACCCT AACCAGCGCG ACTGTCAAGT

51  GGCAGCCGAC AGTCGCCCCG CCTTTTCCCG GATCGTGATG TTCGGCGACA
     CCGTCGGCTG TCAGCGGGGC GGAAAAGGGC CTAGCACTAC AAGCCGCTGT

101  GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201  GGAGCAGCTG ACCAAACAGT TCCCGGGTCT GACCATCGCC AACGAAGCGG
     CCTCGTCGAC TGGTTTGTCA AGGGCCCAGA CTGGTAGCGG TTGCTTCGCC

251  AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401  ACTATCTGGC CTATGGCTGG AACACGGAGC AGGATGCCAA GCGGGTTCGC
     TGATAGACCG GATACCGACC TTGTGCCTCG TCCTACGGTT CGCCCAAGCG

451  GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501  GATACTGCTG TTCAACCTGC CGGATCTGGG CCAGAACCCG TCAGCTCGCA
     CTATGACGAC AAGTTGGACG GCCTAGACCC GGTCTTGGGC AGTCGAGCGT

551  GTCAGAAGGT GGTCGAGGCG GTCAGCCATG TCTCCGCCTA TCACAACCAG
     CAGTCTTCCA CCAGCTCCGC CAGTCGGTAC AGAGGCGGAT AGTGTTGGTC

601  CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651  GTTCGAGATC GACAAGCAAT TGCCGAGAT GCTGCGTGAT CCGCAGAACT
     CAAGCTCTAG CTGTTCGTTA ACGGCTCTA CGACGCACTA GGCGTCTTGA

701  TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
     GGCAACGGTC AGGATACCGG GCGGCGTCGC GGTCGGGGGA GTTGACACTC

901  GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951  CCTGAGCGAG CGCGCCGCCA CCTTCATCGC GAACCAGTAC GAGTTCCTCG
     GGACTCGCTC GCGCGGCGGT GGAAGTAGCG CTTGGTCATG CTCAAGGAGC

1001 CCCAC TGA
     GGGTG ACT
```

FIGURE 71 (SEQ ID No. 63)

```
   1  ATGAAAAAAT GGTTTGTTTG TTTATTGGGG TTGATCGCGC TGACAGTTCA
      TACTTTTTTA CCAAACAAAC AAATAACCCC AACTAGCGCG ACTGTCAAGT

51  GGCAGCCGAC ACTCGCCCCG CCTTCTCCCG GATCGTGATG TTCGGCGACA
      CCGTCGGCTG TGAGCGGGGC GGAAGAGGGC CTAGCACTAC AAGCCGCTGT

101  GCCTCTCCGA TACCGGCAAA ATGTACAGCA AGATGCGCGG TTACCTCCCC
      CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
      AGGTCGGGCG GGATGATACT CCCGGCAAAG AGGTTGCCTG GGCAGACCGA

201  GGAGCAGCTG ACCAAGCAGT TCCCGGGTCT GACCATCGCC AACGAAGCGG
      CCTCGTCGAC TGGTTCGTCA AGGGCCCAGA CTGGTAGCGG TTGCTTCGCC

251  AAGGCGGTGC CACTGCCGTG GCTTACAACA AGATCTCCTG GAATCCCAAG
      TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
      ATAGTCCAGT AGTTGTTGGA CCTGATGCTC CAGTGGGTCA AGAACGTCTT

351  AGACAGCTTC AAGCCGGACG ATCGGTGAT CCTCTGGGTC GGTGCCAATG
      TCTGTCGAAG TTCGGCCTGC TAGACCACTA GGAGACCCAG CCACGGTTAC

401  ACTATCTGGC ATATGGCTGG AATACGGAGC AGGATGCCAA GCGAGTTCGC
      TGATAGACCG TATACCGACC TTATGCCTCG TCCTACGGTT CGCTCAAGCG

451  GATGCCATCA GCGATGCGGC CAACCGCATG GTACTGAACG GTGCCAAGCA
      CTACGGTAGT CGCTACGCCG GTTGGCGTAC CATGACTTGC CACGGTTCGT

501  GATACTGCTG TTCAACCTGC CGGATCTGGG CCAGAACCCG TCAGCCCGCA
      CTATGACGAC AAGTTGGACG GCCTAGACCC GGTCTTGGGC AGTCGGGCGT

551  GTCAGAAGGT GGTCGAGGCG GTCAGCCATG TCTCCGCCTA TCACAACAAG
      CAGTCTTCCA CCAGCTCCGC CAGTCGGTAC AGAGGCGGAT AGTGTTGTTC

601  CTGCTGCTGA ACCTGGCACG CCAGCTGGCC CCCACCGGCA TGGTAAAGCT
      GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
      CAAGCTCTAG CTGTTCGTTA AACGGCTCTA CGACGCACTA GGCGTCTTGA

701  TCGGCCTGAG CGACGTCGAG AACCCCTGCT ACGACGGCGG CTATGTGTGG
      AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
      TTCGGCAAAC GGTGGGCGTC GCAGTCGTGG CTGGCGGTCG AGAGGCGGAA

801  CAGTCCGCAG GAACGCCTCG CCATCGCCGG CAACCGCTG CTGGCACAGG
      GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
      GGCAACGGTC AGGATACCGG GCGGCGTCGC GGTCGGGGGA GTTGACACTC

901  GGCAAGATGT TCTGGGATCA GGTACACCCG ACCACTGTCG TGCACGCAGC
      CCGTTCTACA AGACCCTAGT CCATGTGGGC TGGTGACAGC ACGTGCGTCG

951  CCTGAGCGAG CGCGCCGCCA CCTTCATCGA GACCCAGTAC GAGTTCCTCG
      GGACTCGCTC GCGCGGCGGT GGAAGTAGCT CTGGGTCATG CTCAAGGAGC

1001  CCCACGGATG A
      GGGTGCCTAC T
```

FIGURE 72 (SEQ ID No. 24)

```
   1 ATGTTTAAGT TTAAAAAGAA TTTCTTAGTT GGATTATCGG CAGCTTTAAT
     TACAAATTCA AATTTTTCTT AAAGAATCAA CCTAATAGCC GTCGAAATTA

51 GAGTATTAGC TTGTTTTCGG CAACCGCCTC TGCAGCTAGC GCCGACAGCC
     CTCATAATCG AACAAAAGCC GTTGGCGGAG ACGTCGATCG CGGCTGTCGG

101 GTCCCGCCTT TTCCCGGATC GTGATGTTCG GCGACAGCCT CTCCGATACC
     CAGGGCGGAA AAGGGCCTAG CACTACAAGC CGCTGTCGGA GAGGCTATGG

151 GGCAAAATGT ACAGCAAGAT GCGCGGTTAC CTCCCCTCCA GCCCGCCCTA
     CCGTTTTACA TGTCGTTCTA CGCGCCAATG GAGGGGAGGT CGGGCGGGAT

201 CTATGAGGGC CGTTTCTCCA ACGGACCCGT CTGGCTGGAG CAGCTGACCA
     GATACTCCCG GCAAAGAGGT TGCCTGGGCA GACCGACCTC GTCGACTGGT

251 AACAGTTCCC GGGTCTGACC ATCGCCAACG AAGCGGAAGG CGGTGCCACT
     TTGTCAAGGG CCCAGACTGG TAGCGGTTGC TTCGCCTTCC GCCACGGTGA

301 GCCGTGGCTT ACAACAAGAT CTCCTGGAAT CCCAAGTATC AGGTCATCAA
     CGGCACCGAA TGTTGTTCTA GAGGACCTTA GGGTTCATAG TCCAGTAGTT

351 CAACCTGGAC TACGAGGTCA CCCAGTTCTT GCAGAAAGAC AGCTTCAAGC
     GTTGGACCTG ATGCTCCAGT GGGTCAAGAA CGTCTTTCTG TCGAAGTTCG

401 CGGACGATCT GGTGATCCTC TGGGTCGGTG CCAATGACTA TCTGGCCTAT
     GCCTGCTAGA CCACTAGGAG ACCCAGCCAC GGTTACTGAT AGACCGGATA

451 GGCTGGAACA CGGAGCAGGA TGCCAAGCGG GTTCGCGATG CCATCAGCGA
     CCGACCTTGT GCCTCGTCCT ACGGTTCGCC CAAGCGCTAC GGTAGTCGCT

501 TGCGGCCAAC CGCATGGTAC TGAACGGTGC CAAGCAGATA CTGCTGTTCA
     ACGCCGGTTG GCGTACCATG ACTTGCCACG GTTCGTCTAT GACGACAAGT

551 ACCTGCCGGA TCTGGGCCAG AACCCGTCAG CTCGCAGTCA GAAGGTGGTC
     TGGACGGCCT AGACCCGGTC TTGGGCAGTC GAGCGTCAGT CTTCCACCAG

601 GAGGCGGTCA GCCATGTCTC CGCCTATCAC AACCAGCTGC TGCTGAACCT
     CTCCGCCAGT CGGTACAGAG GCGGATAGTG TTGGTCGACG ACGACTTGGA

651 GGCACGCCAG CTGGCCCCCA CCGGCATGGT AAAGCTGTTC GAGATCGACA
     CCGTGCGGTC GACCGGGGGT GGCCGTACCA TTTCGACAAG CTCTAGCTGT

701 AGCAATTTGC CGAGATGCTG CGTGATCCGC AGAACTTCGG CCTGAGCGAC
     TCGTTAAACG GCTCTACGAC GCACTAGGCG TCTTGAAGCC GGACTCGCTG

751 GTCGAGAACC CCTGCTACGA CGGCGGCTAT GTGTGGAAGC CGTTTGCCAC
     CAGCTCTTGG GGACGATGCT GCCGCCGATA CACACCTTCG GCAAACGGTG

801 CCGCAGCGTC AGCACCGACC GCCAGCTCTC CGCCTTCAGT CCGCAGGAAC
     GGCGTCGCAG TCGTGGCTGG CGGTCGAGAG GCGGAAGTCA GGCGTCCTTG

851 GCCTCGCCAT CGCCGGCAAC CCGCTGCTGG CACAGGCCGT TGCCAGTCCT
     CGGAGCGGTA GCGGCCGTTG GGCGACGACC GTGTCCGGCA ACGGTCAGGA

901 ATGGCCCGCC GCAGCGCCAG CCCCCTCAAC TGTGAGGGCA AGATGTTCTG
     TACCGGGCGG CGTCGCGGTC GGGGGAGTTG ACACTCCCGT TCTACAAGAC

951 GGATCAGGTA CACCCGACCA CTGTCGTGCA CGCAGCCCTG AGCGAGCGCG
     CCTAGTCCAT GTGGGCTGGT GACAGCACGT GCGTCGGGAC TCGCTCGCGC

1001 CCGCCACCTT CATCGCGAAC CAGTACGAGT TCCTCGCCCA CTGATGA
     GGCGGTGGAA GTAGCGCTTG GTCATGCTCA AGGAGCGGGT GACTACT
```

PRODUCTION OF A LIPID ACYLTRANSFERASE FROM TRANSFORMED *BACILLUS LICHENIFORMIS* CELLS

INCORPORATION BY REFERENCE

This application is a continuation-in-part application of international patent application Serial No. PCT/IB2007/000558 filed Jan. 25, 2007, which published as PCT Publication No. WO 2008/090395 on Jul. 31, 2008.

Reference is made to the following related applications: US 2002-0009518, US 2004-0091574, WO2004/064537, WO2004/064987, WO2005/066347, WO2005/066351, U.S. Application Ser. No. 60/764,430 filed on 2 Feb. 2006 and WO2006/008508. Each of these applications and each of the documents cited in each of these applications ("application cited documents"), and each document referenced or cited in the application cited documents, either in the text or during the prosecution of those applications, as well as all arguments in support of patentability advanced during such prosecution, together with any manufacturer's instructions, descriptions, product specifications, and product sheets for any products mentioned herein are hereby incorporated herein by reference and may be employed in the practice of the invention. Various documents are also cited in this text ("herein cited documents"). Each of the herein cited documents, and each document cited or referenced in the herein cited documents, is hereby incorporated herein by reference.

SEQUENCE LISTING

The instant application contains a Sequence Listing which has been submitted via EFS-Web and is hereby incorporated by reference in its entirety. Said ASCII copy, created on Jun. 7, 2010, is named 67450920.txt and is 187,685 bytes in size.

FIELD OF THE PRESENT INVENTION

The present invention relates to the production of lipid acyltransferases. In particular, methods for the production of a lipid acyltransferase by expressing a lipid acyltransferase in a *Bacillus* host cell, preferably a *B. licheniformis* host cell. In addition, the present invention relates to the use of *Bacillus* (preferably *B. licheniformis*) to express a lipid acyltransferase and to a *Bacillus* host cell, preferably a *B. licheniformis* host cell, comprising in its genome a gene encoding a lipid acyltransferase.

BACKGROUND OF THE PRESENT INVENTION

Lipid acyltransferases are known to be advantageous in food applications. Lipid acyltransferases have been found to have significant acyltransferase activity in foodstuffs. This activity has surprising beneficial applications in methods of preparing foodstuffs.

For instance, WO 2004/064537 discloses a method for the in situ production of an emulsifier by use of a lipid acyltransferase and the advantages associated therewith.

Accordingly, there is a need for a method for the commercial production of lipid acyltransferases.

However, generally genes can be difficult to express in heterologous hosts and expression of lipid acyltransferases in host cells can be problematic.

WO 2004/064537 discloses the expression of two *Aeromonas* lipid acyltransferases in *Bacillus subtilis* and *Escherichia Coli*. However, expression in *B. subtilis* is low whilst *E. coli* is not a GRAS organism and is, therefore, unsuitable as a host for enzymes that are to be used in the food industry.

U.S. Pat. No. 6,255,076 discloses a method of producing a polypeptide in a *Bacillus* host cell. However, such a method requires the use of a tandem promoter in which each promoter sequence in operably linked to a single copy of a nucleic acid sequence encoding the polypeptide sequence. Thus, there is a need in the art for an improved method for the production of lipid acyltransferases.

Citation or identification of any document in this application is not an admission that such document is available as prior art to the present invention.

SUMMARY ASPECTS OF THE PRESENT INVENTION

Aspects of the present invention are presented in the claims and in the following commentary.

One aspect of the present invention relates to a method for the production of a lipid acyltransferase comprising the steps of:
  (i) providing a host cell, preferably a *Bacillus* host cell wherein the *Bacillus* host cell is one other than *Bacillus subtilis*, preferably a *Bacillus licheniformis* cell;
  (ii) transforming the host cell, preferably the *Bacillus* host cell wherein the *Bacillus* host cell is one other than *Bacillus subtilis*, preferably the *Bacillus licheniformis* cell, with a heterologous nucleotide sequence encoding a lipid acyltransferase and
  (iii) expressing the lipid acyltransferase in the cell under the control of a promoter sequence.

In another aspect, the present invention relates to a *Bacillus* host cell wherein the *Bacillus* host cell is one other than *Bacillus subtilis*, preferably a *Bacillus licheniformis* host cell, comprising a heterologous lipid acyltransferase.

In a further aspect, the present invention relates to the use of a *Bacillus* host cell wherein the *Bacillus* host cell is one other than *Bacillus subtilis*, preferably a *Bacillus licheniformis* host cell, in the production of a heterologous lipid acyltransferase.

Suitably expression in the *Bacillus* host wherein the *Bacillus* host is one other than *Bacillus subtilis*, and preferably wherein the *Bacillus* host is *B. licheniformis*, may result in increased expression when compared to expression in *B. subtilis*.

In yet another aspect, the present invention relates to an expression vector comprising a nucleotide sequence encoding a lipid acyltransferase operably linked to one or more regulatory sequence(s) such that the regulatory sequence(s) is capable of expressing the nucleotide sequence encoding a lipid acyltransferase in a suitable host or host cell, preferably in a *Bacillus* host (or cell) wherein the *Bacillus* host (or cell) is one other than *Bacillus subtilis*, preferably in *B. licheniformis* or a *B. licheniformis* cell.

Suitably the lipid acyltransferase may be a recombinant lipid acyltransferase.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

DETAILED DESCRIPTION OF THE PRESENT INVENTION

These and other embodiments are disclosed or are obvious from and encompassed by, the following Detailed Description.

According to a first aspect of the present invention there is provided a method for the production of a lipid acyltransferase comprising the steps of:
(i) providing a host cell, preferably a *Bacillus* host cell wherein the *Bacillus* host cell is one other than *Bacillus subtilis*, preferably a *Bacillus licheniformis* cell;
(ii) transforming the host cell, preferably a *Bacillus* host cell wherein the *Bacillus* host cell is one other than *Bacillus subtilis*, preferably a *Bacillus licheniformis* cell, with an heterologous nucleotide sequence encoding a lipid acyltransferase; and
(iii) expressing the lipid acyltransferase in the cell under the control of a promoter sequence.

Additionally, a nucleotide sequence encoding a signal peptide may be operably linked to said heterologous nucleotide sequence encoding a lipid acyltransferase.

Suitably, the method of the present invention may further comprise the additional step of isolating/recovering the lipid acyltransferase.

In another aspect, the present invention relates to a *Bacillus licheniformis* host cell comprising a heterologous lipid acyltransferase.

Suitably the lipid acyltransferase may be a recombinant lipid acyltransferase.

Suitably the promoter sequence used in accordance with the host cells, vectors, methods and/or uses of the present invention may be homologous to the host cell. "Homologous to the host cell" means originating within the host organism; i.e. a promoter sequence which is found naturally in the host organism. Suitably, the promoter sequence may be selected from the group consisting of a nucleotide sequence encoding: an α-amylase promoter, a protease promoter, a subtilisin promoter, a glutamic acid-specific protease promoter and a levansucrase promoter. Suitably the promoter sequence may be a nucleotide sequence encoding: the LAT (e.g. the alpha-amylase promoter from *B. licheniformis*, also known as AmyL), AprL (e.g. subtilisin Carlsberg promoter), Endo-GluC (e.g. the glutamic-acid specific promoter from *B. licheniformis*), AmyQ (e.g. the alpha amylase promoter from *B. amyloliquefaciens* alpha-amylase promoter) and SacB (e.g. the *B. subtilis* levansucrase promoter).

In one embodiment of the present invention the promoter sequence is the −35 to −10 sequence of an alpha amylase promoter, preferably the −35 to −10 sequence of a *B. licheniformis* α-amylase promoter. The "−35 to −10 sequence" describes the position relative to the transcription start site. Both the "−35" and the "−10" are boxes, i.e. a number of nucleotides, each comprising 6 nucleotides and these boxes are separated by 17 nucleotides. These 17 nucleotides are often referred to as a "spacer". This is illustrated in FIG. 55, where the −35 and the −10 boxes are underlined. For the avoidance of doubt, where "−35 to −10 sequence" is used herein it refers to a sequence from the start of the −35 box to the end of the −10 box i.e. including both the −35 box, the 17 nucleotide long spacer and the −10 box.

In some aspects, the nucleotide sequence encoding a lipid acyltransferase for use in anyone of the host cells, vectors, methods and/or uses of the present invention may comprise a GDSX (SEQ ID NO: 117) motif and/or a GANDY (SEQ ID NO: 118) motif.

Preferably, the lipid acyltransferase enzyme is characterised as an enzyme which possesses acyltransferase activity and which comprises the amino acid sequence motif GDSX (SEQ ID NO: 117), wherein X is one or more of the following amino acid residues l, A, V, I, F, Y, H, Q, T, N, M or S.

Suitably, the nucleotide sequence encoding a lipid acyltransferase for use in any one of the vectors, host cells, methods and/or uses of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*. Preferably, the lipid acyltransferase is obtainable, preferably obtained, from an organism from the genus *Aeromonas*.

In some aspects of the present invention, the nucleotide sequence encoding a lipid acyltransferase for use in any one of the vectors, host cells, methods and/or uses of the present invention encodes a lipid acyltransferase that comprises an aspartic acid residue at a position corresponding to N-80 in the amino acid sequence of the *Aeromonas hydrophila* lipid acyltransferase shown as SEQ ID No. 35.

In addition or in the alternative, the nucleotide sequence encoding a lipid acyltransferase for use in any one of the vectors, host cells, methods and/or uses of the present invention encodes a lipid acyltransferase that may comprise the amino acid sequence shown as SEQ ID No. 16, or an amino acid sequence which has 75% or more homology thereto. Suitably, the nucleotide sequence encoding a lipid acyltransferase encodes a lipid acyltransferase that may comprise the amino acid sequence shown as SEQ ID No. 16.

The term "heterologous" as used herein means a sequence derived from a separate genetic source or species. A heterologous sequence is a non-host sequence, a modified sequence, a sequence from a different host cell strain, or a homologous sequence from a different chromosomal location of the host cell.

A "homologous" sequence is a sequence that is found in the same genetic source or species i.e. it is naturally occurring in the relevant species of host cell.

The term "recombinant lipid acyltransferase" as used herein means that the lipid acyltransferase has been produced by means of genetic recombination. For instance, the nucleotide sequence encoding the lipid acyltransferase has been inserted into a cloning vector, resulting in a *B. licheniformis* cell characterised by the presence of the heterologous lipid acyltransferase.

Host Cell

In one embodiment of the present invention the host cell for use in the methods and/or uses of the present invention is a *Bacillus licheniformis* host cell.

It has been found that the use of a *Bacillus licheniformis* host cell results in increased expression of a lipid acyltransferase when compared with other organisms, such as *Bacillus subtilis*.

A lipid acyltransferase from *Aeromonas salmonicida* has been inserted into a number of conventional expression vectors, designed to be optimal for the expression in *Bacillus subtilis, Hansenula polymorpha, Schizosaccharomyces pombe* and *Aspergillus tubigensis*, respectively. Only very low levels were, however, detected in *Hansenula polymorpha, Schizosaccharomyces pombe* and *Aspergillus tubigensis*. The expression levels were below 1 µg/ml, and it was not possible to select cells which yielded enough protein to initiate a commercial production (results not shown). In contrast, *Bacillus licheniformis* was able to produce protein levels, which are attractive for an economically feasible production.

In particular, it has been found that expression in *B. licheniformis* is approximately 100-times greater than expression in *B. subtilis* under the control of aprE promoter or is approximately 100-times greater than expression in *S. lividans* under the control of an A4 promoter and fused to cellulose (results not shown herein).

In another embodiment the host cell may be any *Bacillus* cell other than *B. subtilis*. Preferably, said *Bacillus* host cell being from one of the following species: *Bacillus licheniformis; B. alkalophilus; B. amyloliquefaciens; B. circulans; B. clausii; B. coagulans; B. firmus; B. lautus; B. lentus; B. megaterium; B. pumilus* or *B. stearothermophilus*.

The term "host cell"—in relation to the present invention includes any cell that comprises either a nucleotide sequence encoding a lipid acyltransferase as defined herein or an expression vector as described above and which is used in the recombinant production of a lipid acyltransferase having the specific properties as defined herein.

Thus, a further embodiment of the present invention provides a host cell comprising (for example transformed or transfected with) a nucleotide sequence of the present invention or a nucleotide sequence that expresses a polypeptide having the specific properties as defined herein.

Suitably, in some embodiments, the host cell may be a protease deficient or protease minus strain and/or an α-amylase deficient or α-amylase minus strain.

Regulatory Sequences

In some applications, a lipid acyltransferase sequence for use in any one of the host cells, vectors, methods and/or uses of the present invention may be operably linked to a regulatory sequence which is capable of providing for the expression of the nucleotide sequence, such as by the chosen host cell (such as a *B. licheniformis* cell).

By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of regulatory regions, e.g. promoter, secretion leader and terminator regions that are not regulatory regions for the nucleotide sequence encoding the enzyme in nature.

Suitably, the nucleotide sequence of the present invention may be operably linked to at least a promoter.

Suitably, the nucleotide sequence encoding a lipid acyltransferase may be operably linked to at a nucleotide sequence encoding a terminator sequence. Examples of suitable terminator sequences for use in any one of the vectors, host cells, methods and/or uses of the present invention include: an α-amylase terminator sequence (for instance, CGGGACTTACCGAAAGAAACCATCAATGATGGTTTCTTTTTTGTTCATAAA—SEQ ID No. 64), an alkaline protease terminator sequence (for instance, CAAGACTAAAGACCGTTCGCCCGTTTTTG-CAATAAGCGGGCGAATCTTACATAAAAATA—SEQ ID No. 65), a glutamic-acid specific terminator sequence (for instance, ACGGCCGTTAGATGTGACAGCCCGTTC-CAAAAGGAAGCGGGCTGTCTTCGTGTATTATTGT—SEQ ID No. 66), a levanase terminator sequence (for instance, TCTTTTAAAGGAAAGGCTGGAATGCCCG-GCATTCCAGCCACATGATCATCGTTT—SEQ ID No. 67) and a subtilisin E terminator sequence (for instance, GCT-GACAAATAAAAAGAAGCAGGTATGGAG-GAACCTGCTTCTTTTTACTATTATTG—SEQ ID NO: 68). Suitably, the nucleotide sequence encoding a lipid acyltransferase may be operably linked to an α-amylase terminator, such as a *B. licheniformis* α-amylase terminator.

Promoter

The promoter sequence to be used in accordance with the present invention may be heterologous or homologous to the sequence encoding a lipid acyltransferase.

The promoter sequence may be any promoter sequence capable of directing expression of a lipid acyltransferase in the host cell of choice.

Suitably, the promoter sequence may be homologous to a *Bacillus* species, for example *B. licheniformis*. Preferably, the promoter sequence is homologous to the host cell of choice.

Suitable promoter sequences for use in the present invention include: the promoter of the *Bacillus licheniformis* alpha-amylase gene, the promoter of the *Bacillus licheniformis* subtilisin gene, the promoter of the *Bacillus subtilis* subtilisin gene, the promoter of the *Bacillus licheniformis* alkaline protease gene (subtilisin Carlsberg gene), the promoter of the *B. licheniformis* glutamic-acid specific protease gene, the promoter of *B. amyloliquefaciens* alpha-amylase gene; the promoter of *B. subtilis* levansucrase and a "consensus" promoter having the sequence TTGACA for the "−35" region and TATAAT for the "−10" region (i.e. the −35 to −10 promoter) of the alpha-amylase gene.

Other examples of promoters suitable for directing the transcription of a nucleic acid sequence in the methods of the present invention include: the promoter of the *Bacillus lentus* alkaline protease gene (aprH); the promoter of the *Bacillus subtilis* alpha-amylase gene (amyE); the promoter of the *Bacillus stearothermophilus* maltogenic amylase gene (amyM); the promoter of the *Bacillus licheniformis* penicillinase gene (penP); the promoters of the *Bacillus subtilis* xylA and xylB genes; and/or the promoter of the *Bacillus thuringiensis* subsp. *tenebrionis* CryIIIA gene.

In a preferred embodiment, the promoter sequence is an α-amylase promoter (such as a *Bacillus licheniformis* α-amylase promoter). Preferably, the promoter sequence comprises the −35 to −10 sequence of the *B. licheniformis* α-amylase promoter see FIGS. 53 and 55.

Signal Peptide

The lipid acyltransferase produced by a host cell by expression of the nucleotide sequence encoding the lipid acyltransferase may be secreted or may be contained intracellularly depending on the sequence and/or the vector used.

A signal sequence may be used to direct secretion of the coding sequences through a particular cell membrane. The signal sequences may be natural or foreign to the lipid acyltransferase coding sequence. For instance, the signal peptide coding sequence may be obtained form an amylase or protease gene from a *Bacillus* species, preferably from *Bacillus licheniformis*.

Suitable signal peptide coding sequences may be obtained from one or more of the following genes: maltogenic α-amylase gene, subtilisin gene, beta-lactamase gene, neutral protease gene, prsA gene, and/or acyltransferase gene.

Preferably, the signal peptide is a signal peptide of *B. licheniformis* α-amylase, *Aeromonas* acyltransferase (for instance, mkkwfvcllglialtvqa—SEQ ID No. 21), *B. subtilis* subtilisin (for instance, mrskklwisllfaltliftmafsnmsaqa—SEQ ID No. 22) or *B. licheniformis* subtilisin (for instance, mmrkksfwfgmltafmlvftmefsdsasa—SEQ ID No. 23). Suitably, the signal peptide may be the signal peptide of *B. licheniformis* α-amylase.

However, any signal peptide coding sequence capable of directing the expressed lipid acyltransferase into the secretory pathway of a *Bacillus* host cell (preferably a *B. licheniformis* host cell) of choice may be used.

In some embodiments of the present invention, a nucleotide sequence encoding a signal peptide may be operably linked to a nucleotide sequence encoding a lipid acyltransferase of choice.

The lipid acyltransferase of choice may be expressed in a host cell as defined herein as a fusion protein.

Expression Vector

The term "expression vector" means a construct capable of in vivo or in vitro expression.

Preferably, the expression vector is incorporated in the genome of the organism, such as a *B. licheniformis* host. The term "incorporated" preferably covers stable incorporation into the genome.

The nucleotide sequence encoding a lipid acyltransferase as defined herein may be present in a vector, in which the nucleotide sequence is operably linked to regulatory sequences such that the regulatory sequences are capable of providing the expression of the nucleotide sequence by a suitable host organism (such as *B. licheniformis*), i.e. the vector is an expression vector.

The vectors of the present invention may be transformed into a suitable host cell as described above to provide for expression of a polypeptide having lipid acyltransferase activity as defined herein.

The choice of vector, e.g. plasmid, cosmid, virus or phage vector, genomic insert, will often depend on the host cell into which it is to be introduced. The present invention may cover other forms of expression vectors which serve equivalent functions and which are, or become, known in the art.

Once transformed into the host cell of choice, the vector may replicate and function independently of the host cell's genome, or may integrate into the genome itself.

The vectors may contain one or more selectable marker genes such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein for use in any one of the vectors, host cells, other methods and/or uses of the present invention, by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Lipid Acyl Transferase

The nucleotide sequence encoding a lipid acyl transferase for use in any one of the methods, vectors and/or uses of the present invention may encode a natural lipid acyl transferase or a variant lipid acyl transferase.

For instance, the nucleotide sequence encoding a lipid acyl transferase for use in the present invention may be one as described in WO2004/064537, WO2004/064987, WO2005/066347, or WO2006/008508. These documents are incorporated herein by reference.

The term "lipid acyl transferase" as used herein preferably means an enzyme that has acyltransferase activity (generally classified as E.C. 2.3.1.x, for example 2.3.1.43), whereby the enzyme is capable of transferring an acyl group from a lipid to one or more acceptor substrates, such as one or more of the following: a sterol; a stanol; a carbohydrate; a protein; a protein subunit; a sugar alcohol, such as ascorbic acid and/or glycerol preferably glycerol and/or a sterol, such as cholesterol.

Preferably, the nucleotide sequence encoding a lipid acyl transferase for use in any one of the vectors, host cells, methods and/or uses of the present invention encodes a lipid acyltransferase that is capable of transferring an acyl group from a phospholipid (as defined herein) to a sugar alcohol, such as ascorbic acid and/or glycerol, most preferably glycerol.

For some aspects the "acyl acceptor" according to the present invention may be any compound comprising a hydroxy group (—OH), such as for example, polyvalent alcohols, including glycerol; sterols; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water. Preferably, the "acyl acceptor" according to the present invention is a sugar alcohol, such as a polyol, most preferably glycerol. For the purpose of this invention ascorbic acid is also considered a sugar-alcohol.

The acyl acceptor is preferably not a monoglyceride.

The acyl acceptor is preferably not a diglyceride

In one aspect, the nucleotide sequence encoding a lipid acyltransferase for use in any one of the host cells, vectors, methods and/or uses of the present invention encodes a lipid acyltransferase that may, as well as being able to transfer an acyl group from a lipid to glycerol, additionally be able to transfer the acyl group from a lipid to one or more of the following: a carbohydrate, a protein, a protein subunit, sterol and/or a stanol, preferably it is capable of transferring to both a sugar alcohol, such as ascorbic acid and/or glycerol, most preferably a sterol such as cholesterol, and/or plant sterol/stanols.

Preferably, the lipid substrate upon which the lipid acyl acts is one or more of the following lipids: a phospholipid, such as a lecithin, e.g. phosphatidylcholine.

This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the nucleotide sequence encoding a lipid acyl transferase for use in any one of the host cells, vectors, methods and/or uses of the present invention encodes a lipid acyltransferase that is incapable, or substantially incapable, of acting on a triglyceride and/or a 1-monoglyceride and/or 2-monoglyceride.

For some aspects, preferably the nucleotide sequence encoding a lipid acyl transferase for use in any one of the host cells, vectors, methods and/or uses of the present invention encodes a lipid acyltransferase that does not exhibit triacylglycerol lipase activity (E.C. 3.1.1.3) or does not exhibit significant triacylglycerol lipase activity (E.C. 3.1.1.3).

The ability to hydrolyse triglyceride (E.C. 3.1.1.3 activity) may be determined by lipase activity is determined according to Food Chemical Codex (3rd Ed., 1981, pp 492-493) modified to sunflower oil and pH 5.5 instead of olive oil and pH 6.5. The lipase activity is measured as LUS (lipase units sunflower) where 1 LUS is defined as the quantity of enzyme which can release 1 [mu]mol of fatty acids per minute from sunflower oil under the above assay conditions. Alternatively the LUT assay as defined in WO9845453 may be used. This reference is incorporated herein by reference.

The nucleotide sequence encoding a lipid acyl transferase for use in any one of the host cells, vectors, methods and/or uses of the present invention may encode a lipid acyltransferase that which is substantially incapable of acting on a triglyceride may have a LUS/mg of less than 1000, for example less than 500, such as less than 300, preferably less than 200, more preferably less than 100, more preferably less than 50, more preferably less than 20, more preferably less than 10, such as less than 5, less than 2, more preferably less than 1 LUS/mg. Alternatively LUT/mg activity is less than 500, such as less than 300, preferably less than 200, more preferably less than 100, more preferably less than 50, more preferably less than 20, more preferably less than 10, such as less than 5, less than 2, more preferably less than 1 LUT/mg.

The nucleotide sequence encoding a lipid acyl transferase for use in any one of the host cells, vectors, methods and/or uses of the present invention may encode a lipid acyltransferase that which is substantially incapable of acting on a monoglyceride may be determined by using mono-oleate (M7765 1-Oleoyl-rac-glycerol 99%) in place of the sunflower oil in the LUS assay. 1 MGHU is defined as the quantity of enzyme which can release 1 [mu]mol of fatty acids per minute from monoglyceride under the assay conditions.

The nucleotide sequence encoding a lipid acyl transferase for use in any one of the host cells, vectors, methods and/or uses of the present invention encodes a lipid acyltransferase that which is substantially incapable of acting on a triglyceride may have a MGHU/mg of less than 5000, for example less than 1000, for example less than 500, such as less than 300, preferably less than 200, more preferably less than 100, more preferably less than 50, more preferably less than 20, more preferably less than 10, such as less than 5, less than 2, more preferably less than 1 MGHU/mg.

Suitably, the nucleotide sequence encoding a lipid acyltransferase for use in any one of the host cells, vectors, methods and/or uses of the present invention encodes a lipid acyltransferase that may exhibit one or more of the following phospholipase activities: phospholipase A2 activity (E.C. 3.1.1.4) and/or phospholipase A1 activity (E.C. 3.1.1.32). The lipid acyl transferase may also have phospholipase B activity (E.C 3.1.1.5).

Suitably, for some aspects the lipid acyltransferase may be capable of transferring an acyl group from a phospholipid to a sugar alcohol, preferably glycerol and/or ascorbic acid.

For some aspects, preferably the nucleotide sequence encoding a lipid acyltransferase for use any one of the host cells, vectors, methods and/or uses of the present invention encodes a lipid acyltransferase that is capable of transferring an acyl group from a phospholipid to a sterol and/or a stanol to form at least a sterol ester and/or a stanol ester.

The lipid acyltransferase may be capable of transferring an acyl group from a lipid to a polyol such as glycerol, and/or a sterol such as cholesterol or plant sterol/stanols. Thus, in one embodiment the "acyl acceptor" according to the present invention may be glycerol and/or cholesterol or plant sterol/stanols.

Preferably, the lipid acyltransferase enzyme may be characterised using the following criteria:
the enzyme possesses acyl transferase activity which may be defined as ester transfer activity whereby the acyl part of an original ester bond of a lipid acyl donor is transferred to an acyl acceptor, preferably glycerol or cholesterol, to form a new ester; and
the enzyme comprises the amino acid sequence motif GDSX (SEQ ID NO: 117), wherein X is one or more of the following amino acid residues L, A, V, I, F, Y, H, Q, T, N, M or S.

Preferably, X of the GDSX (SEQ ID NO: 117) motif is L or Y. More preferably, X of the GDSX (SEQ ID NO: 117) motif is L.

Thus, preferably the enzyme according to the present invention comprises the amino acid sequence motif GDSL (SEQ ID NO: 119).

The GDSX (SEQ ID NO: 117) motif is comprised of four conserved amino acids. Preferably, the serine within the motif is a catalytic serine of the lipid acyl transferase enzyme. Suitably, the serine of the GDSX (SEQ ID NO: 117) motif may be in a position corresponding to Ser-16 in *Aeromonas hydrophila* lipid acyltransferase enzyme taught in Brumlik & Buckley (Journal of Bacteriology April 1996, Vol. 178, No. 7, P2060-2064).

To determine if a protein has the GDSX (SEQ ID NO: 117) motif according to the present invention, the sequence is preferably compared with the hidden markov model profiles (HMM profiles) of the pfam database in accordance with the procedures taught in WO2004/064537 or WO2004/064987, incorporated herein by reference.

Preferably the lipid acyl transferase enzyme can be aligned using the Pfam00657 consensus sequence (for a full explanation see WO2004/064537 or WO2004/064987).

Preferably, a positive match with the hidden markov model profile (HMM profile) of the pfam00657 domain family indicates the presence of the GDSL (SEQ ID NO: 119) or GDSX (SEQ ID NO: 117) domain according to the present invention.

Preferably when aligned with the Pfam00657 consensus sequence the lipid acyltransferase for use in the methods or uses of the invention may have at least one, preferably more than one, preferably more than two, of the following, a GDSX (SEQ ID NO: 117) block, a GANDY (SEQ ID NO: 118) block, a HPT block. Suitably, the lipid acyltransferase may have a GDSX (SEQ ID NO: 117) block and a GANDY (SEQ ID NO: 118) block. Alternatively, the enzyme may have a GDSX (SEQ ID NO: 117) block and a HPT block. Preferably the enzyme comprises at least a GDSX (SEQ ID NO: 117) block. See WO2004/064537 or WO2004/064987 for further details.

Preferably, residues of the GANDY (SEQ ID NO: 118) motif are selected from GANDY (SEQ ID NO: 118), GGNDA (SEQ ID NO: 120), GGNDL (SEQ ID NO: 121), most preferably GANDY (SEQ ID NO: 118).

Preferably, when aligned with the Pfam00657 consensus sequence the enzyme for use in the methods or uses of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophila* polypeptide sequence, namely SEQ ID No. 1: 28hid, 29hid, 30hid, 31hid, 32gly, 33Asp, 34Ser, 35hid, 130hid, 131Gly, 132Hid, 133Asn, 134Asp, 135hid, 309His.

The pfam00657 GDSX (SEQ ID NO: 117) domain is a unique identifier which distinguishes proteins possessing this domain from other enzymes.

The pfam00657 consensus sequence is presented in FIG. 3 as SEQ ID No. 2. This is derived from the identification of the pfam family 00657, database version 6, which may also be referred to as pfam00657.6 herein.

The consensus sequence may be updated by using further releases of the pfam database (for example see WO2004/064537 or WO2004/064987).

In one embodiment, the nucleotide sequence encoding a lipid acyl transferase enzyme for use in any one of the host cells, vectors, methods and/or uses of the present invention encodes a lipid acyltransferase that may be characterised using the following criteria:
  i) the enzyme possesses acyl transferase activity which may be defined as ester transfer activity whereby the acyl part of an original ester bond of a lipid acyl donor is transferred to acyl acceptor, preferably glycerol or cholesterol, to form a new ester, preferably monoglyceride or cholesterol ester respectfully;
  ii) the enzyme comprises the amino acid sequence motif GDSX (SEQ ID NO: 117), wherein X is one or more of the following amino acid residues L, A, V, I, F, Y, H, Q, T, N, M or S;
  iii) the enzyme comprises His-309 or comprises a histidine residue at a position corresponding to His-309 in the *Aeromonas hydrophila* lipid acyltransferase enzyme shown in FIGS. 2 and 4 (SEQ ID No. 1 or SEQ ID No. 3).

Preferably, the amino acid residue of the GDSX (SEQ ID NO: 117) motif is L (preferred embodiment "GDSL" disclosed as SEQ ID NO: 119).

In SEQ ID No. 3 or SEQ ID No. 1 the first 18 amino acid residues form a signal sequence. His-309 of the full length sequence, that is the protein including the signal sequence, equates to His-291 of the mature part of the protein, i.e. the sequence without the signal sequence.

In one embodiment, the nucleotide sequence encoding a lipid acyl transferase enzyme for use any one of the host cells, vectors, methods and uses of the present invention encodes a lipid acyltransferase that comprises the following catalytic triad: Ser-34, Asp-306 and His-309 or comprises a serine residue, an aspartic acid residue and a histidine residue, respectively, at positions corresponding to Ser-34, Asp-306 and His-309 in the *Aeromonas hydrophila* lipid acyl transferase enzyme shown in FIG. 4 (SEQ ID No. 3) or FIG. 2 (SEQ ID No. 1). As stated above, in the sequence shown in SEQ ID No. 3 or SEQ ID No. 1 the first 18 amino acid residues form a signal sequence. Ser-34, Asp-306 and His-309 of the full length sequence, that is the protein including the signal sequence, equate to Ser-16, Asp-288 and His-291 of the mature part of the protein, i.e. the sequence without the signal sequence. In the pfam00657 consensus sequence, as given in FIG. 3 (SEQ ID No. 2) the active site residues correspond to Ser-7, Asp-345 and His-348.

In one embodiment, the nucleotide sequence encoding a lipid acyl transferase enzyme for use any one of the host cells, vectors, methods and uses of the present invention encodes a lipid acyltransferase that may be characterised using the following criteria:
  the enzyme possesses acyl transferase activity which may be defined as ester transfer activity whereby the acyl part of an original ester bond of a first lipid acyl donor is transferred to an acyl acceptor to form a new ester; and
  the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-306 and His-309, respectively, in the *Aeromonas hydrophila* lipid acyltransferase enzyme shown in SEQ ID No. 3 or SEQ ID No. 1.

Suitably, the nucleotide sequence encoding a lipid acyltransferase enzyme for use in any one of the host cells, vectors, methods and uses of the present invention may be one of the following nucleotide sequences:
(a) the nucleotide sequence shown as SEQ ID No. 36 (see FIG. 29);
(b) the nucleotide sequence shown as SEQ ID No. 38 (see FIG. 31);
(c) the nucleotide sequence shown as SEQ ID No. 39 (see FIG. 32);
(d) the nucleotide sequence shown as SEQ ID No. 42 (see FIG. 35);
(e) the nucleotide sequence shown as SEQ ID No. 44 (see FIG. 37);
(f) the nucleotide sequence shown as SEQ ID No. 46 (see FIG. 39);
(g) the nucleotide sequence shown as SEQ ID No. 48 (see FIG. 41);
(h) the nucleotide sequence shown as SEQ ID No. 49 (see FIG. 57);
(i) the nucleotide sequence shown as SEQ ID No. 50 (see FIG. 58);
(j) the nucleotide sequence shown as SEQ ID No. 51 (see FIG. 59);
(k) the nucleotide sequence shown as SEQ ID No. 52 (see FIG. 60);
(l) the nucleotide sequence shown as SEQ ID No. 53 (see FIG. 61);
(m) the nucleotide sequence shown as SEQ ID No. 54 (see FIG. 62);
(n) the nucleotide sequence shown as SEQ ID No. 55 (see FIG. 63);
(o) the nucleotide sequence shown as SEQ ID No. 56 (see FIG. 64);
(p) the nucleotide sequence shown as SEQ ID No. 57 (see FIG. 65);
(q) the nucleotide sequence shown as SEQ ID No. 58 (see FIG. 66);
(r) the nucleotide sequence shown as SEQ ID No. 59 (see FIG. 67);
(s) the nucleotide sequence shown as SEQ ID No. 60 (see FIG. 68);
(t) the nucleotide sequence shown as SEQ ID No. 61 (see FIG. 69);
(u) the nucleotide sequence shown as SEQ ID No. 62 (see FIG. 70);
(v) the nucleotide sequence shown as SEQ ID No. 63 (see FIG. 71);
(w) or
a nucleotide sequence which has 70% or more, preferably 75% or more, identity with any one of the sequences shown as SEQ ID No. 36, SEQ ID No. 38, SEQ ID No. 39, SEQ ID No. 42, SEQ ID No. 44, SEQ ID No. 46, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62 or SEQ ID No. 63.

Suitably the nucleotide sequence may have 80% or more, preferably 85% or more, more preferably 90% or more and even more preferably 95% or more identity with any one of the sequences shown as SEQ ID No. 36, SEQ ID No. 38, SEQ ID No. 39, SEQ ID No. 42, SEQ ID No. 44, SEQ ID No. 46, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62 or SEQ ID No. 63.

In one embodiment, the nucleotide sequence encoding a lipid acyltransferase enzyme for use any one of the host cells, vectors, methods and uses of the present invention is a nucleotide sequence which has 70% or more, preferably 75% or more, identity with any one of the sequences shown as: SEQ ID No. 49, SEQ ID No. 50, SEQ ID No. 51, SEQ ID No. 62, and SEQ ID No. 63. Suitably the nucleotide sequence may have 80% or more, preferably 85% or more, more preferably 90% or more and even more preferably 95% or more identity with any one of the sequences shown as: SEQ ID No. 49, SEQ ID No. 50, SEQ ID No. 51, SEQ ID No. 62, and SEQ ID No. 63.

In one embodiment, the nucleotide sequence encoding a lipid acyltransferase enzyme for use in any one of the host cells, vectors, methods and uses of the present invention is a nucleotide sequence which has 70% or more, 75% or more, 80% or more, preferably 85% or more, more preferably 90% or more and even more preferably 95% or more identity the sequence shown as SEQ ID No. 49.

Suitably, the nucleotide sequence encoding a lipid acyl transferase enzyme for use any one of the host cells, vectors, methods and uses of the present invention may encode a lipid acyltransferase that comprises one or more of the following amino acid sequences:
(i) the amino acid sequence shown as SEQ ID No. 3
(ii) the amino acid sequence shown as SEQ ID No. 4
(iii) the amino acid sequence shown as SEQ ID No. 5
(iv) the amino acid sequence shown as SEQ ID No. 6
(v) the amino acid sequence shown as SEQ ID No. 7
(vi) the amino acid sequence shown as SEQ ID No. 8
(vii) the amino acid sequence shown as SEQ ID No. 9
(viii) the amino acid sequence shown as SEQ ID No. 10
(ix) the amino acid sequence shown as SEQ ID No. 11
(x) the amino acid sequence shown as SEQ ID No. 12
(xi) the amino acid sequence shown as SEQ ID No. 13
(xii) the amino acid sequence shown as SEQ ID No. 14
(xiii) the amino acid sequence shown as SEQ ID No. 1
(xiv) the amino acid sequence shown as SEQ ID No. 15 or an amino acid sequence which has 75%, 80%, 85%, 90%, 95%, 98% or more identity with any one of the sequences shown as SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, or SEQ ID No. 15.

Suitably, nucleotide sequence encoding a lipid acyl transferase enzyme for use in any one of the host cells, vectors, methods and uses of the present invention may encode a lipid acyltransferase that comprises either the amino acid sequence shown as SEQ ID No. 3 or as SEQ ID No. 4 or SEQ ID No. 1 or SEQ ID No. 15 or comprises an amino acid sequence which has 75% or more, preferably 80% or more, preferably 85% or more, preferably 90% or more, preferably 95% or more, identity with the amino acid sequence shown as SEQ ID No. 3 or the amino acid sequence shown as SEQ ID No. 4 or the amino acid sequence shown as SEQ ID No. 1 or the amino acid sequence shown as SEQ ID No. 15.

Suitably the nucleotide sequence encoding a lipid acyl transferase enzyme for use any one of the host cells, vectors, methods and uses of the present invention may encode a lipid acyltransferase that comprises an amino acid sequence which has 80% or more, preferably 85% or more, more preferably 90% or more and even more preferably 95% or more identity with any one of the sequences shown as SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, or SEQ ID No. 15.

Suitably, the nucleotide sequence encoding a lipid acyl transferase enzyme for use any one of the host cells, vectors, methods and uses of the present invention may encode a lipid acyltransferase that comprises one or more of the following amino acid sequences:
(a) an amino acid sequence shown as amino acid residues 1-100 of SEQ ID No. 3 or SEQ ID No. 1;
(b) an amino acid sequence shown as amino acids residues 101-200 of SEQ ID No. 3 or SEQ ID No. 1;
(c) an amino acid sequence shown as amino acid residues 201-300 of SEQ ID No. 3 or SEQ ID No. 1; or
(d) an amino acid sequence which has 75% or more, preferably 85% or more, more preferably 90% or more, even more preferably 95% or more identity to any one of the amino acid sequences defined in (a)-(c) above.

Suitably, lipid acyl transferase enzyme for use in methods and uses of the present invention may comprise one or more of the following amino acid sequences:
(a) an amino acid sequence shown as amino acid residues 28-39 of SEQ ID No. 3 or SEQ ID No. 1;
(b) an amino acid sequence shown as amino acids residues 77-88 of SEQ ID No. 3 or SEQ ID No. 1;
(c) an amino acid sequence shown as amino acid residues 126-136 of SEQ ID No. 3 or SEQ ID No. 1;
(d) an amino acid sequence shown as amino acid residues 163-175 of SEQ ID No. 3 or SEQ ID No. 1;
(e) an amino acid sequence shown as amino acid residues 304-311 of SEQ ID No. 3 or SEQ ID No. 1; or
(f) an amino acid sequence which has 75% or more, preferably 85% or more, more preferably 90% or more, even more preferably 95% or more identity to any one of the amino acid sequences defined in (a)-(e) above.

In one aspect, nucleotide sequence encoding a lipid acyl transferase enzyme for use any one of the host cells, vectors, methods and uses of the present invention encodes a lipid acyltransferase that may be the lipid acyl transferase from *Candida parapsilosis* as taught in EP 1 275 711. Thus in one aspect the lipid acyl transferase for use in the method and uses of the present invention may be a lipid acyl transferase comprising one of the amino acid sequences taught in SEQ ID No. 17 or SEQ ID No. 18.

Much by preference, the nucleotide sequence encoding a lipid acyl transferase enzyme for use in any one of the host cells, vectors, methods and uses of the present invention encodes a lipid acyltransferase that may be a lipid acyl transferase (lipid acyltransferase) comprising the amino acid sequence shown as SEQ ID No. 16, or an amino acid sequence which has 75% or more, preferably 85% or more, more preferably 90% or more, even more preferably 95% or more, even more preferably 98% or more, or even more preferably 99% or more identity to SEQ ID No. 16. This enzyme could be considered a variant enzyme.

In one aspect, the nucleotide sequence encoding a lipid acyltransferase enzyme for use any one of the host cells, vectors, methods and uses of the present invention encodes a lipid acyltransferase that may be a lecithin:cholesterol acyltransferase (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the nucleotide sequence encoding a lipid acyltransferase enzyme for use any one of the host cells, vectors, methods and uses of the present invention encodes a lipid acyltransferase that may be the lipid acyltransferase obtainable, preferably obtained, from the *E. coli* strains TOP 10 harbouring pPet12aAhydro and pPet12aASalmo deposited by Danisco NS of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NCIMB 41204 and NCIMB 41205, respectively.

A nucleotide sequence encoding a lipid acyltransferase enzyme for use any one of the host cells, vectors, methods and uses of the present invention may encode a phospholipid glycerol acyl transferase. Phospholipid glycerol acyl transferases include those isolated from *Aeromonas* spp., preferably *Aeromonas hydrophila* or *A. salmonicida*, most preferable *A. salmonicida* or variants thereof. Most preferred lipid acyl transferases for use in the present invention are encoded by SEQ ID Nos. 1, 3, 4, and 16. It will be recognised by the skilled person that it is preferable that the signal peptides of the acyl transferase has been cleaved during expression of the transferase. The signal peptide of SEQ ID 1, 3, 4, 15 and 16 are amino acids 1-18. Therefore the most preferred regions are amino acids 19-335 for SEQ ID No. 1 and SEQ ID No. 3 (*A. hydrophilia*) and amino acids 19-336 for SEQ ID No. 4, SEQ ID No. 15 and SEQ ID No. 16. (*A. salmonicida*). When used to determine the homology of identity of the amino acid sequences, it is preferred that the alignments as herein described use the mature sequence.

Therefore the most preferred regions for determining homology (identity) are amino acids 19-335 for SEQ ID No. 1 and 3 (*A. hydrophilia*) and amino acids 19-336 for SEQ ID Nos. 4, 15 and 16. (*A. salmonicida*). SEQ ID 34 and 35 are mature protein sequences of a lipid acyl transferase from *A. hydrophilia* and *A. salmonicida* respectively.

A nucleotide sequence encoding a lipid acyltransferase enzyme for use any one of the host cells, vectors, methods and uses of the present invention encodes a lipid acyltransferase that may also be isolated from *Thermobifida*, preferably *T. fusca*, most preferably that encoded by SEQ ID No. 28.

A nucleotide sequence encoding a lipid acyltransferase enzyme for use any one of the host cells, vectors, methods and uses of the present invention encodes a lipid acyltransferase that may also be isolated from *Streptomyces*, preferable *S. avermitis*, most preferably that encoded by SEQ ID No. 32. Other possible enzymes for use in the present invention from *Streptomyces* include those encoded by SEQ ID Nos. 5, 6, 9, 10, 11, 12, 13, 14, 31, and 33.

An enzyme for use in the invention may also be isolated from *Corynebacterium*, preferably *C. efficiens*, most preferably that encoded by SEQ ID No. 29.

Suitably, the nucleotide sequence encoding a lipid acyltransferase enzyme for use any one of the host cells, vectors, methods and uses of the present invention may encode a lipid acyltransferase that comprises any one of the amino acid sequences shown as SEQ ID Nos. 37, 38, 40, 41, 43, 45, or 47 or an amino acid sequence which has at least 70%, 75%, 80%, 85%, 90%, 95%, 96%, 97% or 98% identity therewith, or encoded by any one of the nucleotide sequences shown as SEQ ID Nos. 36, 39, 42, 44, 46, or 48 or a nucleotide sequence which has at least 70%, 75%, 80%, 85%, 90%, 95%, 96%, 97% or 98% identity therewith.

In one embodiment, the nucleic sequence encoding a lipid acyltransferase enzyme for use any one of the host cells, vectors, methods and uses of the present invention is selected from the group consisting of:
a) a nucleic acid comprising a nucleotide sequence shown in SEQ ID No. 36;
b) a nucleic acid which is related to the nucleotide sequence of SEQ ID No. 36 by the degeneration of the genetic code; and
c) a nucleic acid comprising a nucleotide sequence which has at least 70% identity with the nucleotide sequence shown in SEQ ID No. 36.

In one embodiment, a nucleotide sequence encoding a lipid acyltransferase enzyme for use any one of the host cells, vectors, methods and uses of the present invention encodes a lipid acyltransferase that comprises an amino acid sequence as shown in SEQ ID No. 37 or an amino acid sequence which has at least 60% identity thereto.

In a further embodiment the nucleotide sequence encoding a lipid acyltransferase enzyme for use any one of the host cells, vectors, methods and uses of the present invention may encode a lipid acyltransferase comprising any one of the amino acid sequences shown as SEQ ID No. 37, 38, 40, 41, 43, 45 or 47 or an amino acid sequence which has at least 70%, 75%, 80%, 85%, 90%, 95%, 96%, 97% or 98% identity therewith, or encoded by any one of the nucleotide sequences shown as SEQ ID No. 39, 42, 44, 46 or 48 or a nucleotide sequence which has at least 70%, 75%, 80%, 85%, 90%, 95%, 96%, 97% or 98% identity therewith.

In a further embodiment the nucleotide sequence encoding a lipid acyltransferase enzyme for use any one of the host cells, vectors, methods and uses of the present invention may encode a lipid acyltransferase comprising any one of amino sequences shown as SEQ ID No. 38, 40, 41, 45 or 47 or an amino acid sequence which has at least 70%, 75%, 80%, 85%, 90%, 95%, 96%, 97% or 98% identity therewith for the uses described herein.

In a further embodiment the nucleotide sequence encoding a lipid acyltransferase for use in any one of the host cells, vectors, methods and uses of the present invention may encode a lipid acyltransferase comprising any one of amino sequences shown as SEQ ID No. 38, 40, or 47 or an amino acid sequence which has at least 70%, 75%, 80%, 85%, 90%, 95%, 96%, 97% or 98% identity therewith for the uses described herein.

More preferably in one embodiment the nucleotide sequence encoding a lipid acyltransferase for use in any one of the host cells, vectors, methods and uses of the present invention may encode a lipid acyltransferase comprising the amino acid sequence shown as SEQ ID No. 47 or an amino acid sequence which has at least 70%, 75%, 80%, 85%, 90%, 95%, 96%, 97% or 98% identity therewith.

In another embodiment the nucleotide sequence encoding a lipid acyltransferase for use in any one of the host cells, vectors, methods and uses of the present invention may encode a lipid acyltransferase comprising the amino acid sequence shown as SEQ ID No. 43 or 44 or an amino acid sequence which has at least 80%, 85%, 90%, 95%, 96%, 97% or 98% identity therewith.

In another embodiment the nucleotide sequence encoding a lipid acyltransferase for use in any one of the host cells, vectors, methods and uses of the present invention may encode a lipid acyltransferase comprising the amino acid sequence shown as SEQ ID No. 41 or an amino acid sequence which has at least 70%, 75%, 80%, 85%, 90%, 95%, 96%, 97% or 98% identity therewith.

In one embodiment the nucleotide sequence encoding a lipid acyltransferase for use in any one of the host cells, vectors, methods and uses of the present invention is selected from the group consisting of:
a) a nucleic acid comprising a nucleotide sequence shown in SEQ ID No. 36;
b) a nucleic acid which is related to the nucleotide sequence of SEQ ID No. 36 by the degeneration of the genetic code; and
c) a nucleic acid comprising a nucleotide sequence which has at least 70% identity with the nucleotide sequence shown in SEQ ID No. 36.

In one embodiment the lipid acyltransferase according to the present invention may be a lipid acyltransferase obtainable, preferably obtained, from the *Streptomyces* strains L130 or L131 deposited by Danisco NS of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable nucleotide sequences encoding a lipid acyltransferase for use in any one of the host cells, vectors, methods and uses of the present invention may encode a polynucleotide encoding a lipid acyltransferase (SEQ ID No. 16); or may encode an amino acid sequence of a lipid acyltransferase (SEQ ID No. 17).

A suitable nucleotide sequence encoding a lipid acyltransferase for use in any one of the host cells, vectors, methods and uses of the present invention may encode an amino acid sequence which may be identified by alignment to the L131 (SEQ ID No. 37) sequence using Align X, the Clustal W pairwise alignment algorithm of VectorNTI using default settings.

An alignment of the L131 and homologues from *S. avermitilis* and *T. fusca* illustrates that the conservation of the GDSX (SEQ ID NO: 117) motif (GDSY (SEQ ID NO: 122) in L131 and *S. avermitilis* and *T. fusca*), the GANDY (SEQ ID NO: 118) box, which is either GGNDA (SEQ ID NO: 120) or GGNDL (SEQ ID NO: 121), and the HPT block (considered to be the conserved catalytic histidine). These three conserved blocks are highlighted in FIG. 42.

When aligned to either the pfam Pfam00657 consensus sequence (as described in WO04/064987) and/or the L131 sequence herein disclosed (SEQ ID No 37) it is possible to identify three conserved regions, the GDSX (SEQ ID NO: 117) block, the GANDY (SEQ ID NO: 118) block and the HTP block (see WO04/064987 for further details).

When aligned to either the pfam Pfam00657 consensus sequence (as described in WO04/064987) and/or the L131 sequence herein disclosed (SEQ ID No 37)
i) The nucleotide sequence encoding a lipid acyltransferase for use in any one of the host cells, vectors, methods and uses of the present invention may encode a lipid acyltransferase that, has a GDSX (SEQ ID NO: 117) motif, more preferably a GDSX (SEQ ID NO: 117) motif selected from GDSL (SEQ ID NO: 119) or GDSY (SEQ ID NO: 122) motif.

and/or
ii) The nucleotide sequence encoding a lipid acyltransferase for use in any one of the host cells, vectors, methods and uses of the present invention may encode a lipid acyltransferase that, has a GANDY (SEQ ID NO: 118) block, more preferably a GANDY (SEQ ID NO: 118) block comprising amino GGNDX (SEQ ID NO: 123), more preferably GGNDA (SEQ ID NO: 120) or GGNDL (SEQ ID NO: 121).

and/or
iii) The nucleotide sequence encoding a lipid acyltransferase for use in any one of the host cells, vectors, methods and uses of the present invention encodes a lipid acyltransferase that has preferably an HTP block.

and preferably
iv) nucleotide sequence encoding a lipid acyltransferase for use in anyone of the host cells, vectors, methods and uses of the present invention may encode a lipid acyltransferase that has preferably a GDSX (SEQ ID NO: 117) or GDSY (SEQ ID NO: 122) motif, and a GANDY (SEQ ID NO: 118) block comprising amino GGNDX (SEQ ID NO: 123), preferably GGNDA (SEQ ID NO: 120) or GGNDL (SEQ ID NO: 121), and a HTP block (conserved histidine).

Variant Lipid Acyl Transferase

In a preferred embodiment the nucleotide sequence encoding a lipid acyltransferase for use in any one of the host cells, vectors, methods and uses of the present invention may encode a lipid acyltransferase that is a variant lipid acyl transferase.

Variants which have an increased activity on phospholipids, such as increased hydrolytic activity and/or increased transferase activity, preferably increased transferase activity on phospholipids may be used.

Preferably the variant lipid acyltransferase is prepared by one or more amino acid modifications of the lipid acyl transferases as defined hereinabove.

Suitably, when the nucleotide sequence encoding a lipid acyltransferase for use in anyone of the host cells, vectors, methods and uses of the present invention may encode a lipid acyltransferase that may be a variant lipid acyltransferase, in which case the enzyme may be characterised in that the enzyme comprises the amino acid sequence motif GDSX (SEQ ID NO: 117), wherein X is one or more of the following amino acid residues L, A, V, I, F, Y, H, Q, T, N, M or S, and wherein the variant enzyme comprises one or more amino acid modifications compared with a parent sequence at anyone or more of the amino acid residues defined in set 2 or set 4 or set 6 or set 7 (as defined WO2005/066347 and hereinbelow).

For instance the variant lipid acyltransferase may be characterised in that the enzyme comprises the amino acid sequence motif GDSX (SEQ ID NO: 117), wherein X is one or more of the following amino acid residues L, A, V, I, F, Y, H, Q, T, N, M or S, and wherein the variant enzyme comprises one or more amino acid modifications compared with a parent sequence at anyone or more of the amino acid residues detailed in set 2 or set 4 or set 6 or set 7 (as defined in WO2005/066347 and hereinbelow) identified by said parent sequence being structurally aligned with the structural model of P10480 defined herein, which is preferably obtained by structural alignment of P1 0480 crystal structure coordinates with 1IVN.PDB and/or 1DEO.PDB as defined WO2005/066347 and hereinbelow.

In a further embodiment a nucleotide sequence encoding a lipid acyltransferase for use in anyone of the host cells, vectors, methods and uses of the present invention may encode a variant lipid acyltransferase that may be characterised in that the enzyme comprises the amino acid sequence motif GDSX (SEQ ID NO: 117), wherein X is one or more of the following amino acid residues L, A, V, I, F, Y, H, Q, T, N, M or S, and wherein the variant enzyme comprises one or more amino acid modifications compared with a parent sequence at anyone or more of the amino acid residues taught in set 2 identified when said parent sequence is aligned to the pfam consensus sequence (SEQ ID No. 2—FIG. 3) and modified according to a structural model of P10480 to ensure best fit overlap as defined WO2005/066347 and hereinbelow.

Suitably the nucleotide sequence encoding a lipid acyltransferase for use in any one of the host cells, vectors, methods and uses of the present invention may encode a variant lipid acyltransferase enzyme that may comprise an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues defined in set 2 or set 4 or set 6 or set 7 (as defined WO2005/066347 and hereinbelow) identified by sequence alignment with SEQ ID No. 34.

Alternatively the nucleotide sequence encoding a lipid acyltransferase may encode a variant lipid acyltransferase enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues defined in set 2 or set 4 or set 6 or set 7 as defined WO2005/066347 and hereinbelow, identified by said parent sequence being structurally aligned with the structural model of P10480 defined herein, which is preferably obtained by structural alignment of P10480 crystal structure coordinates with 1IVN.PDB and/or 1DEO.PDB as taught within WO2005/066347 and hereinbelow.

Alternatively, the nucleotide sequence encoding a lipid acyltransferase may encode a variant lipid acyltransferase enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues taught in set 2 identified when said parent sequence is aligned to the pfam consensus sequence (SEQ ID No. 2) and modified according to a structural model of P10480 to ensure best fit overlap as taught within WO2005/066347 and hereinbelow.

Preferably, the parent enzyme is an enzyme which comprises, or is homologous to, the amino acid sequence shown as SEQ ID No. 34 and/or SEQ ID No. 15 and/or SEQ ID No. 35.

Preferably, the nucleotide sequence encoding a lipid acyltransferase may encode a variant enzyme which comprises an amino acid sequence, which amino acid sequence is shown as SEQ ID No. 34 or SEQ ID No. 35 except for one or more amino acid modifications at any one or more of the amino acid residues defined in set 2 or set 4 or set 6 or set 7 as defined in WO2005/066347 and hereinbelow.

DEFINITION OF SETS

Amino Acid Set 1:
Amino acid set 1 (note that these are amino acids in 1IVN—FIG. 53 and FIG. 54) Gly8, Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158

The highly conserved motifs, such as GDSX (SEQ ID NO: 117) and catalytic residues, were deselected from set 1 (residues underlined). For the avoidance of doubt, set 1 defines the amino acid residues within 10A of the central carbon atom of a glycerol in the active site of the 11 VN model.

Amino Acid Set 2
Amino acid set 2 (note that the numbering of the amino acids refers to the amino acids in the P10480 mature sequence)
Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

Table of selected residues in Set 1 compared with Set 2:

| IVN model | | | P10480 Mature sequence |
|---|---|---|---|
| | A. hyd homologue | | Residue |
| IVN | PFAM | Structure | Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |
| Pro110 | | 180 to 190 | Pro162 |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |

| IVN model | | | P10480 Mature sequence |
|---|---|---|---|
| | A. hyd homologue | | Residue |
| IVN | PFAM | Structure | Number |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino Acid Set 3:

Amino acid set 3 is identical to set 2 but refers to the *Aeromonas salmonicida* (SEQ ID No. 4) coding sequence, i.e. the amino acid residue numbers are 18 higher in set 3 as this reflects the difference between the amino acid numbering in the mature protein (SEQ ID No. 34) compared with the protein including a signal sequence (SEQ ID No. 25).

The mature proteins of *Aeromonas salmonicida* GDSX (SEQ ID No. 4) and *Aeromonas hydrophila* GDSX (SEQ ID No. 34) differ in five amino acids. These are Thr3Ser, Gln182Lys, Glu309Ala, Ser310Asn, and Gly318-, where the salmonicida residue is listed first and the hydrophila residue is listed last. The hydrophila protein is only 317 amino acids long and lacks a residue in position 318. The *Aeromonas salmonicida* GDSX has considerably high activity on polar lipids such as galactolipid substrates than the *Aeromonas hydrophila* protein. Site scanning was performed on all five amino acid positions.

Amino Acid Set 4:

Amino acid set 4 is S3, Q182, E309, S310, and –318.

Amino Acid Set 5:

F135, D15N, 518G, 518V, Y30F, D116N, D116E, D157N, Y226F, D228N Y230F.

Amino Acid Set 6:

Amino acid set 6 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, –318.

The numbering of the amino acids in set 6 refers to the amino acids residues in P10480 (SEQ ID No. 25)—corresponding amino acids in other sequence backbones can be determined by homology alignment and/or structural alignment to P10480 and/or 1IVN.

Amino Acid Set 7:

Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, –318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y).

The numbering of the amino acids in set 7 refers to the amino acids residues in P10480 (SEQ ID No. 25)—corresponding amino acids in other sequence backbones can be determined by homology alignment and/or structural alignment to P10480 and/or 1IVN).

Suitably, the variant enzyme comprises one or more of the following amino acid modifications compared with the parent enzyme:

S3E, A, G, K, M, Y, R, P, N, T or G

E309Q, R or A, preferably Q or R

–318Y, H, S or Y, preferably Y.

Preferably, X of the GDSX (SEQ ID NO: 117) motif is L. Thus, preferably the parent enzyme comprises the amino acid motif GDSL (SEQ ID NO: 119).

Suitably, said first parent lipid acyltransferase may comprise any one of the following amino acid sequences: SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32 or SEQ ID No. 33.

Suitably, said second related lipid acyltransferase may comprise any one of the following amino acid sequences: SEQ ID No. 3, SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32 or SEQ ID No. 33.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID No. 34 or SEQ ID No. 35.

In one aspect preferably the variant enzyme comprises one or more of the following amino acid substitutions:

S3A, C, D, E, F, G, H, I, K, L, M, N, P, Q, R, T, V, W, or Y; and/or

L17A, C, D, E, F, G, H, I, K, M, N, P, Q, R, S, T, V, W, or Y; and/or

S18A, C, D, E, F, H, I, K, L, M, N, P, Q, R, T, W, or Y; and/or

K22A, C, D, E, F, G, H, I, L, M, N, P, Q, R, S, T, V, W, or Y; and/or

M23A, C, D, E, F, G, H, I, K, L, N, P, Q, R, S, T, V, W, or Y; and/or

Y30A, C, D, E, G, H, I, K, L, M, N, P, Q, R, S, T, V, or W; and/or

G40A, C, D, E, F, H, I, K, L, M, N, P, Q, R, S, T, V, W, or Y; and/or

N80A, C, D, E, F, G, H, I, K, L, M, P, Q, R, S, T, V, W, or Y; and/or

P81A, C, D, E, F, G, H, I, K, L, M, N, Q, R, S, T, V, W, or Y; and/or

K82A, C, D, E, F, G, H, I, L, M, N, P, Q, R, S, T, V, W, or Y; and/or

N87A, C, D, E, F, G, H, I, K, L, M, P, Q, R, S, T, V, W, or Y; and/or
N88A, C, D, E, F, G, H, I, K, L, M, P, Q, R, S, T, V, W, or Y; and/or
W111A, C, D, E, F, G, H, I, K, L, M, N, P, Q, R, S, T, V, W or Y; and/or
V112A, C, D, E, F, G, H, I, K, L, M, N, P, Q, R, S, T, W, or Y; and/or
A114C, D, E, F, G, H, I, K, L, M, N, P, Q, R, S, T, V, W, or Y; and/or
Y117A, C, D, E, F, G, H, I, K, L, M, N, P, Q, R, S, T, V, or W; and/or
L118A, C, D, E, F, G, H, I, K, M, N, P, Q, R, S, T, V, W, or Y; and/or
P156A, C, D, E, F, G, H, I, K, L, M, N, Q, R, S, T, V, W, or Y; and/or
D157A, C, E, F, G, H, I, K, L, M, P, Q, R, S, T, V, W, or Y; and/or
G159A, C, D, E, F, H, I, K, L, M, N, P, Q, R, S, T, V, W, or Y; and/or
Q160A, C, D, E, F, G, H, I, K, L, M, N, P, R, S, T, V, W, or Y; and/or
N161A, C, D, E, F, G, H, I, K, L, M P, Q, R, S, T, V, W, or Y; and/or
P162A, C, D, E, F, G, H, I, K, L, M, N, Q, R, S, T, V, W, or Y; and/or
S163A, C, D, E, F, G, H, I, K, L, M, N, P, Q, R, T, V, W, or Y; and/or
A164C, D, E, F, G, H, I, K, L, M, N, P, Q, R, S, T, V, W, or Y; and/or
R165A, C, D, E, F, G, H, I, K, L, M, N, P, Q, S, T, V, W, or Y; and/or
S166A, C, D, E, F, G, H, I, K, L, M, N, P, Q, R, T, V, W, or Y; and/or
Q167A, C, D, E, F, G, H, I, K, L, M, N, P, R, S, T, V, W, or Y; and/or
K168A, C, D, E, F, G, H, I, L, M, N, P, Q, R, S, T, V, W, or Y; and/or
V169A, C, D, E, F, G, H, I, K, L, M, N, P, Q, R, S, T, W, or Y; and/or
V170A, C, D, E, F, G, H, I, K, L, M, N, P, Q, R, S, T, W, or Y; and/or
E171A, C, D, F, G, H, I, K, L, M, N, P, Q, R, S, T, V, W, or Y; and/or
A172C, D, E, F, G, H, I, K, L, M, N, P, Q, R, S, T, V, W, or Y; and/or
Y179A, C, D, E, F, G, H, I, K, L, M, N, P, Q, R, S, T, V, or W; and/or
H180A, C, D, E, F, G, I, K, L, M, P, Q, R, S, T, V, W, or Y; and/or
N181A, C, D, E, F, G, H, I, K, L, M, P, Q, R, S, T, V, W, or Y; and/or
Q182A, C, D, E, F, G, H, I, K, L, M, N, P, R, S, T, V, W, or Y, preferably K; and/or
M209A, C, D, E, F, G, H, I, K, L, N, P, Q, R, S, T, V, W, or Y; and/or
L210 A, C, D, E, F, G, H, I, K, M, N, P, Q, R, S, T, V, W, or Y; and/or
R211A, C, D, E, F, G, H, I, K, L, M, N, P, Q, R, S, T, V, W, or Y; and/or
N215 A, C, D, E, F, G, H, I, K, L, M, N, P, Q, R, S, T, V, W, or Y; and/or
Y226A, C, D, E, G, H, I, K, L, M, N, P, Q, R, S, T, V, or W; and/or
Y230A, C, D, E, G, H, I, K, L, M, N, P, Q, R, S, T, V or W; and/or
K284A, C, D, E, F, G, H, I, L, M, N, P, Q, R, S, T, V, W, or Y; and/or
M285A, C, D, E, F, G, H, I, K, L, N, P, Q, R, S, T, V, W, or Y; and/or
Q289A, C, D, E, F, G, H, I, K, L, M, N, P, R, S, T, V, W, or Y; and/or
V290A, C, D, E, F, G, H, I, K, L, M, N, P, Q, R, S, T, W, or Y; and/or
E309A, C, D, F, G, H, I, K, L, M, N, P, Q, R, S, T, V, W, or Y; and/or
S310A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

Preferred variant enzymes may have a decreased hydrolytic activity against a phospholipid, such as phosphatidylcholine (PC), may also have an increased transferase activity from a phospholipid.

Preferred variant enzymes may have an increased transferase activity from a phospholipid, such as phosphatidylcholine (PC), these may also have an increased hydrolytic activity against a phospholipid.

Modification of one or more of the following residues may result in a variant enzyme having an increased absolute transferase activity against phospholipid:

S3, D157, S310, E309, Y179, N215, K22, Q289, M23, H180, M209, L210, R211, P81, V112, N80, L82, N88; N87

Specific preferred modifications which may provide a variant enzyme having an improved transferase activity from a phospholipid may be selected from one or more of the following:

S3A, C, D, E, F, G, H, I, K, L, M, N, P, Q, R, T, V, W or Y; preferably N, E, K, R, A, P or M, most preferably S3A
D157A, C, E, F, G, H, I, K, L, M, N, P, Q, R, S, T, V, W or Y; preferably D157S, R, E, N, G, T, V, Q, K or C
S310A, C, D, E, F, G, H, I, K, L, M, N, P, Q, R, T, V W or Y; preferably S310T –318 E
E309A, C, D, E, F, G, H, I, K, L, M, N, P, Q, R, T, V, W or Y; preferably E309 R, E, L, R or A
Y179A, C, D, E, F, G, H, I, K, L, M, N, P, Q, R, S, T, V or W; preferably Y179 D, T, E, R, N, V, K, Q or S, more preferably E, R, N, V, K or Q
N215A, C, D, E, F, G, H, I, K, L, M, P, Q, R, S, T, V, W or Y; preferably N215 S, L, R or Y
K22A, C, D, E, F, G, H, I, L, M, N, P, Q, R, S, T, V, W or Y; preferably K22 E, R, C or A
Q289A, C, D, E, F, G, H, I, K, L, M, N, P, R, S, T, V, W or Y; preferably Q289 R, E, G, P or N
M23A, C, D, E, F, G, H, I, K, L N, P, Q, R, S, T, V, W or Y; preferably M23 K, Q, L, G, T or S
H180A, C, D, E, F, G, I, K, L, M, P, Q, R, S, T, V, W or Y; preferably H180 Q, R or K
M209 A, C, D, E, F, G, H, I, K, L, N, P, Q, R, S, T, V, W or Y; preferably M209 Q, S, R, A, N, Y, E, V or L
L210A, C, D, E, F, G, H, I, K, M, N, P, Q, R, S, T, V, W or Y; preferably L210 R, A, V, S, T, I, W or M
R211A, C, D, E, F, G, H, I, K, L, M, N, P, Q, S, T, V, W or Y; preferably R211T
P81A, C, D, E, F, G, H, I, K, L, M, N, Q, R, S, T, V, W or Y; preferably P81G
V112A, C, D, E, F, G, H, I, K, L, M, N, P, Q, R, S, T, W or Y; preferably V112C N80 A, C, D, E, F, G, H, I, K, L, M, P, Q, R, S, T, V, W or Y; preferably N80 R, G, N, D, P, T, E, V, A or G
L82 A, C, D, E, F, G, H, I, M, N, P, Q, R, S, T, V, W or Y; preferably L82 N, S or E
N88 A, C, D, E, F, G, H, I, K, L, M, P, Q, R, S, T, V, W or Y; preferably N88 C
N87 A, C, D, E, F, G, H, I, K, L, M, P, Q, R, S, T, V, W or Y; preferably N87 M or G Preferred modification of one or more of the following residues results in a variant enzyme having an increased absolute transferase activity against phospholipid:
S3 N, R, A, G
M23 K, Q, L, G, T, S
H180 R
L82 G
Y179 E, R, N, V, K or Q
E309 R, S, L or A One preferred modification is N80D. This is particularly the case when using the reference sequence SEQ ID No. 35 as the backbone. Thus, the reference sequence may be SEQ ID No. 16. This modification may be in combination with one or more further modifications. Therefore in a preferred embodiment of the present invention the nucleotide sequence encoding a lipid acyltransferase for use in any one of the host cells, vectors, methods and uses of the present invention may encode a lipid acyltransferase that comprises SEQ ID No. 35 or an amino acid sequence which has 75% or more, preferably 85% or more, more preferably 90% or more, even more preferably 95% or more, even more preferably 98% or more, or even more preferably 99% or more identity to SEQ ID No. 35.

As noted above, when referring to specific amino acid residues herein the numbering is that obtained from alignment of the variant sequence with the reference sequence shown as SEQ ID No. 34 or SEQ ID No. 35

Much by preference, the nucleotide sequence encoding a lipid acyltransferase for use in any one of the host cells, vectors, methods and uses of the present invention may encode a lipid comprising the amino acid sequence shown as SEQ ID No. 16, or an amino acid sequence which has 75% or more, preferably 85% or more, more preferably 90% or more, even more preferably 95% or more, even more preferably 98% or more, or even more preferably 99% or more identity to SEQ ID No. 16. This enzyme may be considered a variant enzyme.

For the purposes of the present invention, the degree of identity is based on the number of sequence elements which are the same. The degree of identity in accordance with the present invention for amino acid sequences may be suitably determined by means of computer programs known in the art, such as Vector NTI 10 (Invitrogen Corp.). For pairwise alignment the score used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

Suitably, the nucleotide sequence encoding a lipid acyltransferase/lipid acyl transferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

Suitably, the nucleotide sequence encoding a lipid acyltransferase/lipid acyl transferase enzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus sp, Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis Thermobifida fusca* and *Corynebacterium efficiens*.

In one aspect, preferably the nucleotide sequence encoding a nucleotide sequence encoding a lipid acyltransferase for use in any one of the host cells, vectors, methods and uses of the present invention encodes a lipid acyl transferase enzyme according to the present invention is obtainable, preferably obtained or derived, from one or more of *Aeromonas* spp., *Aeromonas hydrophila* or *Aeromonas salmonicida*.

Enzymes which function as lipid acyltransferases in accordance with the present invention can be routinely identified using the assay taught in Example 12 of WO2004/064537. Using this assay, in which there is a very high water content approximately 95%, lipid acyltransferases/lipid acyl transferase in accordance with the present invention are those which have at least 2% acyltransferase activity (relative transferase activity), preferably at least 5% relative transferase activity, preferably at least 10% relative transferase activity, preferably at least 15%, 20%, 25% 26%, 28%, 30%, 40% 50%, 60% or 75% relative transferase activity.

Phospholipases may act as acyl-transferase enzymes in low water environments. Therefore it is considered that in place of or in addition to the phospholipid acyltransferase enzyme a phospholipase enzyme may be used when process for the modification of the edible oil of fat takes place in a low water environment.

The term "high water" as used herein means any substrate or foodstuff with more than 3% water content, preferably more than 4%, more than 5%, more than 6%, more than 7%, more than 8%, more than 9%, more than 10%, more than 20%, more than 30%, more than 40%, more than 50%, more than 60%, more than 70%, more than 80% or more than 90%.

The term "low water" as used herein means any substrate or foodstuff with less than 3% water content, preferably less than 2%, less than 1% or less than 0.5%, less than 0.3%, less than 0.2, less than 0.1, less than 0.05, or less than 0.01%

For avoidance of doubt milk is a high water environment where as butterfat is a low water environment.

Suitable phospholipases for use in the invention include phospholipase A1, phospholipase A2, or phospholipase B. Phospholipase A1, phospholipase A2, or phospholipase B may also be used in co-ordination with the lipid acyl transferase activity. Phospholipase C and/or D may also be used in co-ordination with the lipid acyl transferase activity/phospholipase A1, A2 and/or B activity in analogy with WO2005/089562. Preferred phospholipases may include phospholipase A2, such as Lecitase™ or the *Fusarium venenatum* and *Tuber albidum* phospholipase disclosed in WO2004/97012

(Novozymes/Chr. Hansen). A *Fusarium venenatum* phospholipase is sold by Novozymes as MAX YIELD™.

Isolated

In one aspect, the method of the present invention comprises the additional step of recovering/isolating the lipid acyltransferase. Thus, the lipid acyltransferase produced may be in an isolated form.

In another aspect, the nucleotide sequence encoding a lipid acyltransferase for use in the present invention may be in an isolated form.

The term "isolated" means that the sequence or protein is at least substantially free from at least one other component with which the sequence or protein is naturally associated in nature and as found in nature.

Purified

In one aspect, the method of the present invention comprises the additional step of purifying the lipid acyltransferase.

In another aspect, the nucleotide sequence encoding a lipid acyltransferase for use in the present invention may be in a purified form.

The term "purified" means that the sequence is in a relatively pure state e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the nucleotide sequence encoding a lipid acyltransferase used in the invention may encode a variant lipid acyltransferase, i.e. the lipid acyltransferase may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx (SEQ ID NO: 117), GANDY (SEQ ID NO: 118) and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the nucleotide sequence encoding a lipid acyltransferase for use in any one of the vectors, host cells, methods and/or uses of the present invention may encode a lipid acyltransferase that may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 Jan. 15: 266 (2): 997-1000; Robertson et al J. Biol. Chem. 1994 Jan. 21; 269(3):2146-50; Brumlik et al J. Bacteriol 1996 April; 178 (7): 2060-4; Peelman et al Protein Sci. 1998 March; 7(3):587-99.

Amino Acid Sequences

The present invention also encompasses amino acid sequences encoded by a nucleotide sequence which encodes a lipid acyltransferase for use in any one of the vectors, host cells, methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 μl of water and 5 μg of endoproteinase Lys-C in 5 μl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 μm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturers instructions (Applied Biosystems, California, USA).

Sequence Identity or Sequence Homology

Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST package (see Ausubel et al 1999 Short Protocols in Molecular Biology, $4^{th}$ Ed Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI program. A new tool, called BLAST 2 Sequences is also available for comparing protein and nucleotide sequence (see FEMS Microbiol Lett 1999 174(2): 247-50; FEMS Microbiol Lett 1999 177(1): 187-8)

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | | |
|---|---|---|
| GAP OPEN | 0 | |
| GAP EXTENSION | 0 | |

| FOR CLUSTAL | DNA | PROTEIN | |
|---|---|---|---|
| WORD SIZE | 2 | 1 | K triple |
| GAP PENALTY | 15 | 10 | |
| GAP EXTENSION | 6.66 | 0.1 | |

In one embodiment, preferably the sequence identity for the nucleotide sequences is determined using CLUSTAL with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

In one embodiment the degree of amino acid sequence identity in accordance with the present invention may be suitably determined by means of computer programs known in the art, such as Vector NTI 10 (Invitrogen Corp.). For pairwise alignment the matrix used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Organism

The term "organism" in relation to the present invention includes any organism that could comprise a nucleotide sequence according to the present invention or a nucleotide sequence encoding for a polypeptide having the specific properties as defined herein and/or products obtained therefrom.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a lipid acyltransferase in nature.

Transformation of Host Cells/Organism

Teachings on the transformation of prokaryotic hosts are well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Various methods are known for the transformation of *Bacillus* species.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

In the method of the present invention the lipid acyltransferase may be produced as a fusion protein, for example to aid in extraction and purification thereof. Examples of fusion protein partners include glutathione-S-transferase (GST), 6×His (SEQ ID NO: 124), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a non-native sequence to encode a fusion protein. For example, for screening of peptide libraries for agents capable of affecting the substance activity, it may be useful to encode a chimeric substance expressing a non-native epitope that is recognised by a commercially available antibody.

The invention will now be described, by way of example only, with reference to the following Figures and Examples.

FIG. 1 shows the amino acid sequence of a mutant *Aeromonas salmonicida* mature lipid acyltransferase (GCAT) with a mutation of Asn80Asp (notably, amino acid 80 is in the mature sequence) (SEQ ID 16);

FIG. 2 shows an amino acid sequence (SEQ ID No. 1) a lipid acyl transferase from *Aeromonas hydrophila* (ATCC #7965);

FIG. 3 shows a pfam00657 consensus sequence from database version 6 (SEQ ID No. 2);

FIG. 4 shows an amino acid sequence (SEQ ID No. 3) obtained from the organism *Aeromonas hydrophila* (P10480; GI: 121051);

FIG. 5 shows an amino acid sequence (SEQ ID No. 4) obtained from the organism *Aeromonas salmonicida* (AAG098404; GI: 9964017);

FIG. 6 shows an amino acid sequence (SEQ ID No. 5) obtained from the organism *Streptomyces coelicolor* A3(2) (Genbank accession number NP_631558);

FIG. 7 shows an amino acid sequence (SEQ ID No. 6) obtained from the organism *Streptomyces coelicolor* A3(2) (Genbank accession number: CAC42140);

FIG. 8 shows an amino acid sequence (SEQ ID No. 7) obtained from the organism *Saccharomyces cerevisiae* (Genbank accession number P41734);

FIG. 9 shows an amino acid sequence (SEQ ID No. 8) obtained from the organism Ralstonia (Genbank accession number: AL646052);

FIG. 10 shows SEQ ID No. 9. Scoe1 NCBI protein accession code CAB39707.1 GI: 4539178 conserved hypothetical protein [*Streptomyces coelicolor* A3(2)];

FIG. 11 shows an amino acid shown as SEQ ID No. 10. Scoe2 NCBI protein accession code CAC01477.1 GI: 9716139 conserved hypothetical protein [*Streptomyces coelicolor* A3(2)];

FIG. 12 shows an amino acid sequence (SEQ ID No. 11) Scoe3 NCBI protein accession code CAB88833.1 GI: 7635996 putative secreted protein. [*Streptomyces coelicolor* A3(2)];

FIG. 13 shows an amino acid sequence (SEQ ID No. 12) Scoe4 NCBI protein accession code CAB89450.1 GI: 7672261 putative secreted protein. [*Streptomyces coelicolor* A3(2)];

FIG. 14 shows an amino acid sequence (SEQ ID No. 13) Scoe5 NCBI protein accession code CAB62724.1 GI: 6562793 putative lipoprotein [*Streptomyces coelicolor* A3(2)];

FIG. 15 shows an amino acid sequence (SEQ ID No. 14) Srim1 NCBI protein accession code AAK84028.1 GI: 15082088 GDSL-lipase [*Streptomyces rimosus*];

FIG. 16 shows an amino acid sequence (SEQ ID No. 15) of a lipid acyltransferase from *Aeromonas salmonicida* subsp. *Salmonicida* (ATCC#14174);

FIG. 17 shows SEQ ID No. 19. Scoe1 NCBI protein accession code CAB39707.1 GI: 4539178 conserved hypothetical protein [*Streptomyces coelicolor* A3(2)];

FIG. 18 shows an amino acid sequence (SEQ ID No. 25) of the fusion construct used for mutagenesis of the *Aeromonas hydrophila* lipid acyltransferase gene. The underlined amino acids is a xylanase signal peptide;

FIG. 19 shows a polypeptide sequence of a lipid acyltransferase enzyme from *Streptomyces* (SEQ ID No. 26);

FIG. 20 shows a polypeptide sequence of a lipid acyltransferase enzyme from *Thermobifida* (SEQ ID No. 27);

FIG. 21 shows a polypeptide sequence of a lipid acyltransferase enzyme from *Thermobifida* (SEQ ID No. 28);

FIG. 22 shows a polypeptide of a lipid acyltransferase enzyme from *Corynebacterium efficiens* GDSx 300 amino acid (SEQ ID No. 29, "GDSX" disclosed as SEQ ID NO: 117);

FIG. 23 shows a polypeptide of a lipid acyltransferase enzyme from *Novosphingobium aromaticivorans* GDSx 284 amino acid (SEQ ID No. 30, "GDSX" disclosed as SEQ ID NO: 117);

FIG. 24 shows a polypeptide of a lipid acyltransferase enzyme from *Streptomyces coelicolor* GDSx 269 aa (SEQ ID No. 31, "GDSX" disclosed as SEQ ID NO: 117);

FIG. 25 shows a polypeptide of a lipid acyltransferase enzyme from *Streptomyces avermitilis*\GDSx 269 amino acid (SEQ ID No. 32, "GDSX" disclosed as SEQ ID NO: 117);

FIG. 26 shows a polypeptide of a lipid acyltransferase enzyme from *Streptomyces* (SEQ ID No. 33);

FIG. 27 shows an amino acid sequence (SEQ ID No. 34) obtained from the organism *Aeromonas hydrophila* (P10480; GI: 121051) (notably, this is the mature sequence);

FIG. 28 shows the amino acid sequence (SEQ ID No. 35) of a mutant *Aeromonas salmonicida* mature lipid acyltransferase (GCAT) (notably, this is the mature sequence);

FIG. 29 shows a nucleotide sequence (SEQ ID No. 36) from *Streptomyces thermosacchari*;

FIG. 30 shows an amino acid sequence (SEQ ID No. 37) from *Streptomyces thermosacchari*;

FIG. 31 shows an amino acid sequence (SEQ ID No. 38) from *Thermobifida fuscal*/GDSx ("GDSX" disclosed as SEQ ID NO: 117) 548 amino acid;

FIG. 32 shows a nucleotide sequence (SEQ ID No. 39) from *Thermobifida fusca*;

FIG. 33 shows an amino acid sequence (SEQ ID No. 40) from *Thermobifida fusca*/GDSx;

FIG. 34 shows an amino acid sequence (SEQ ID No. 41) from *Corynebacterium efficiens*/GDSx ("GDSX" disclosed as SEQ ID NO: 117) 300 amino acid;

FIG. 35 shows a nucleotide sequence (SEQ ID No. 42) from *Corynebacterium efficiens*;

FIG. 36 shows an amino acid sequence (SEQ ID No. 43) from *S. coelicolor*/GDSx ("GDSX" disclosed as SEQ ID NO: 117) 268 amino acid;

FIG. 37 shows a nucleotide sequence (SEQ ID No. 44) from *S. coelicolor*;

FIG. 38 shows an amino acid sequence (SEQ ID No. 45) from *S. avermitilis*;

FIG. 39 shows a nucleotide sequence (SEQ ID No. 46) from *S. avermitilis*;

FIG. 40 shows an amino acid sequence (SEQ ID No. 47) from *Thermobifida fusca*/GDSx ("GDSX" disclosed as SEQ ID NO: 117);

FIG. 41 shows a nucleotide sequence (SEQ ID No. 48) from *Thermobifida fusca*/GDSx ("GDSX" disclosed as SEQ ID NO: 117);

Figure 45:
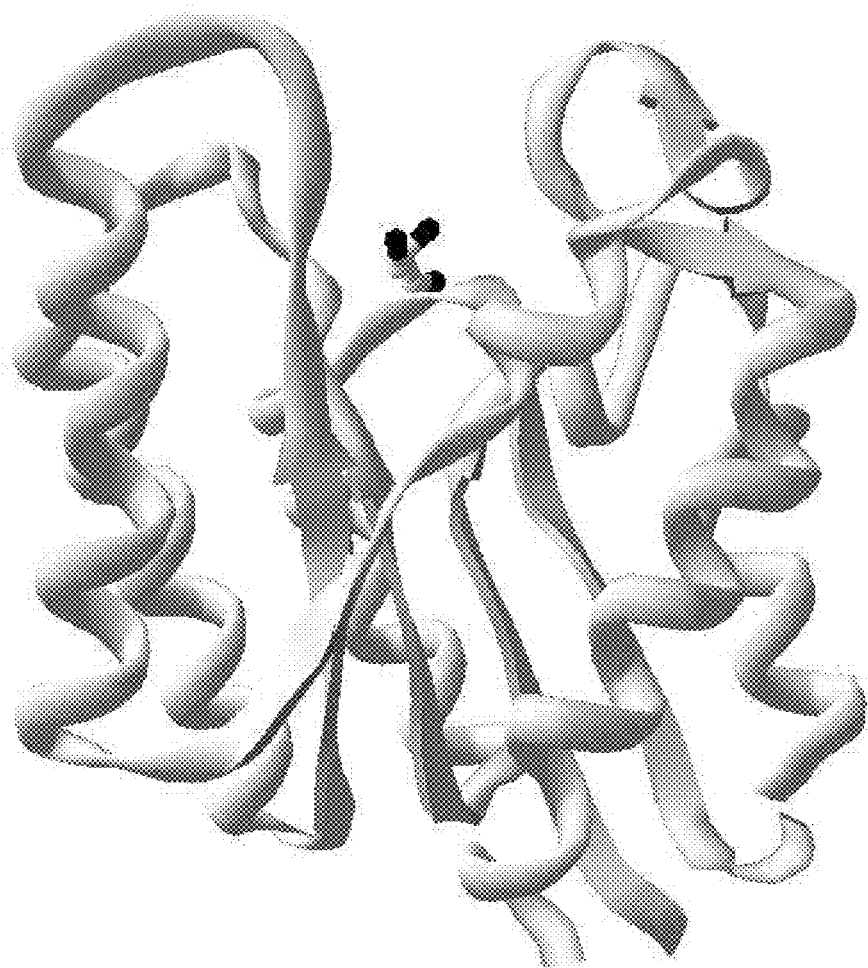
Figure 46:
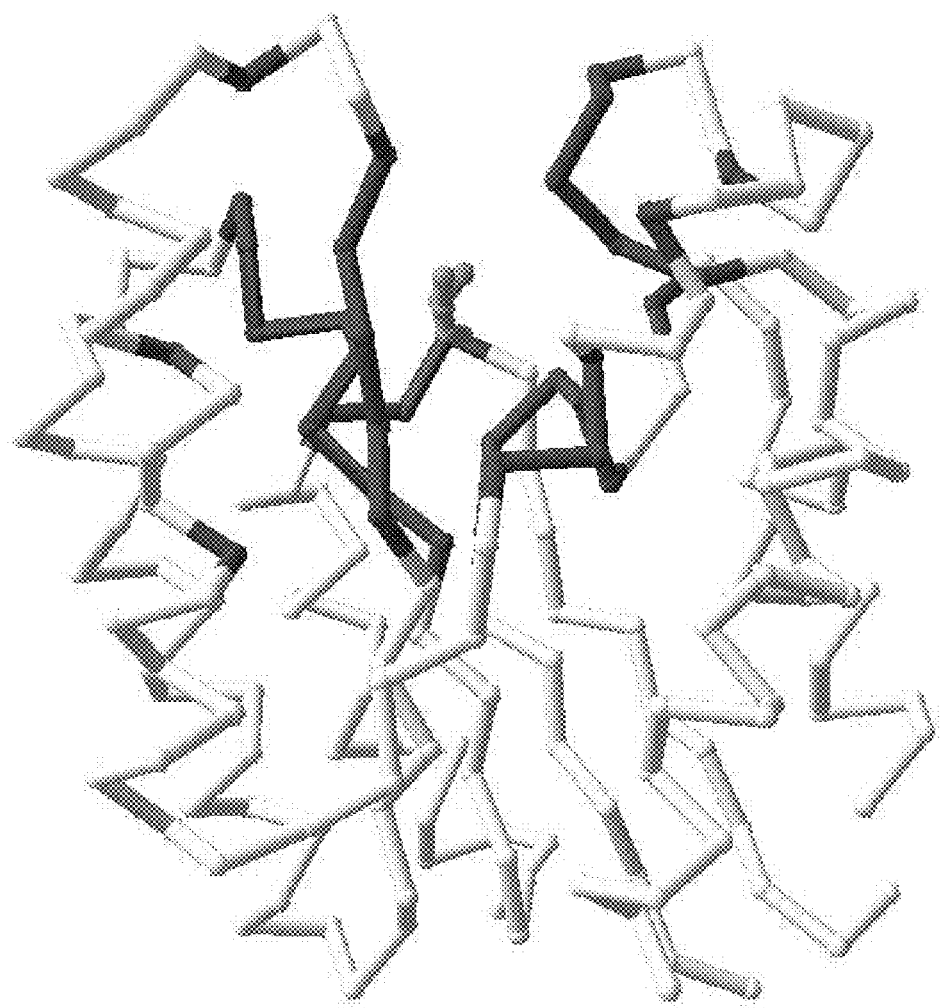
Figure 47:
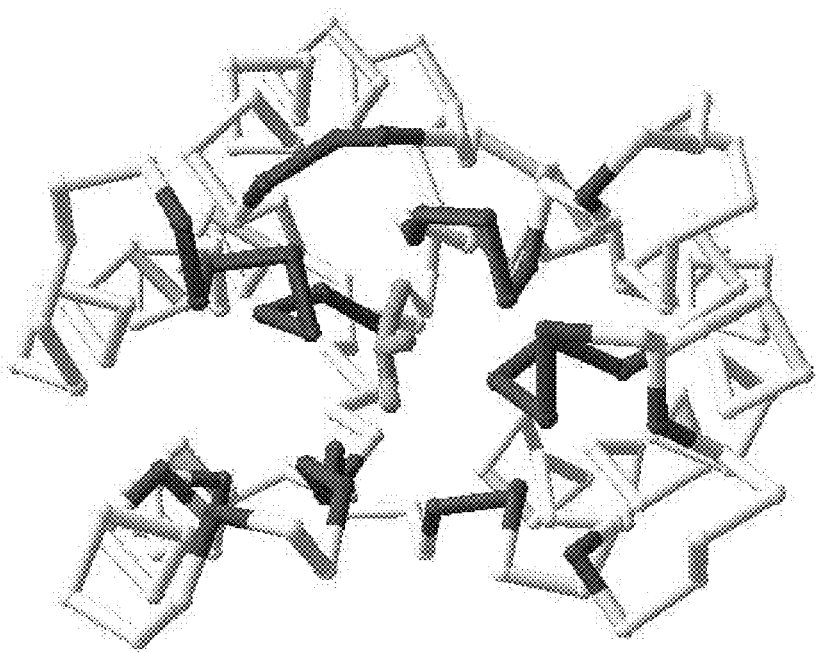

FIG. 42 shows an alignment of the L131 and homologues from *S. avermitilis* and *T. fusca* illustrates that the conservation of the GDSx motif (SEQ ID NO: 117) (GDSY (SEQ ID NO: 122) in L131 and *S. avermitilis* and *T. fusca*), the GANDY box (SEQ ID NO: 118), which is either GGNDA (SEQ ID NO: 120) or GGNDL (SEQ ID NO: 121), and the HPT block (considered to be the conserved catalytic histidine). These three conserved blocks are highlighted;

FIG. 43 shows SEQ ID No 17 which is the amino acid sequence of a lipid acyltransferase from *Candida parapsilosis*;

FIG. 44 shows SEQ ID No 18 which is the amino acid sequence of a lipid acyltransferase from *Candida parapsilosis*;

FIG. 45 shows a ribbon representation of the 1IVN.PDB crystal structure which has glycerol in the active site. The Figure was made using the Deep View Swiss-PDB viewer;

FIG. 46 shows 1 IVN.PDB Crystal Structure—Side View using Deep View Swiss-PDB viewer, with glycerol in active site—residues within 10 Å of active site glycerol are coloured black;

FIG. 47 shows 1IVN.PDB Crystal Structure—Top View using Deep View Swiss-PDB viewer, with glycerol in active site—residues within 10 Å of active site glycerol are coloured black;

Figure 48:
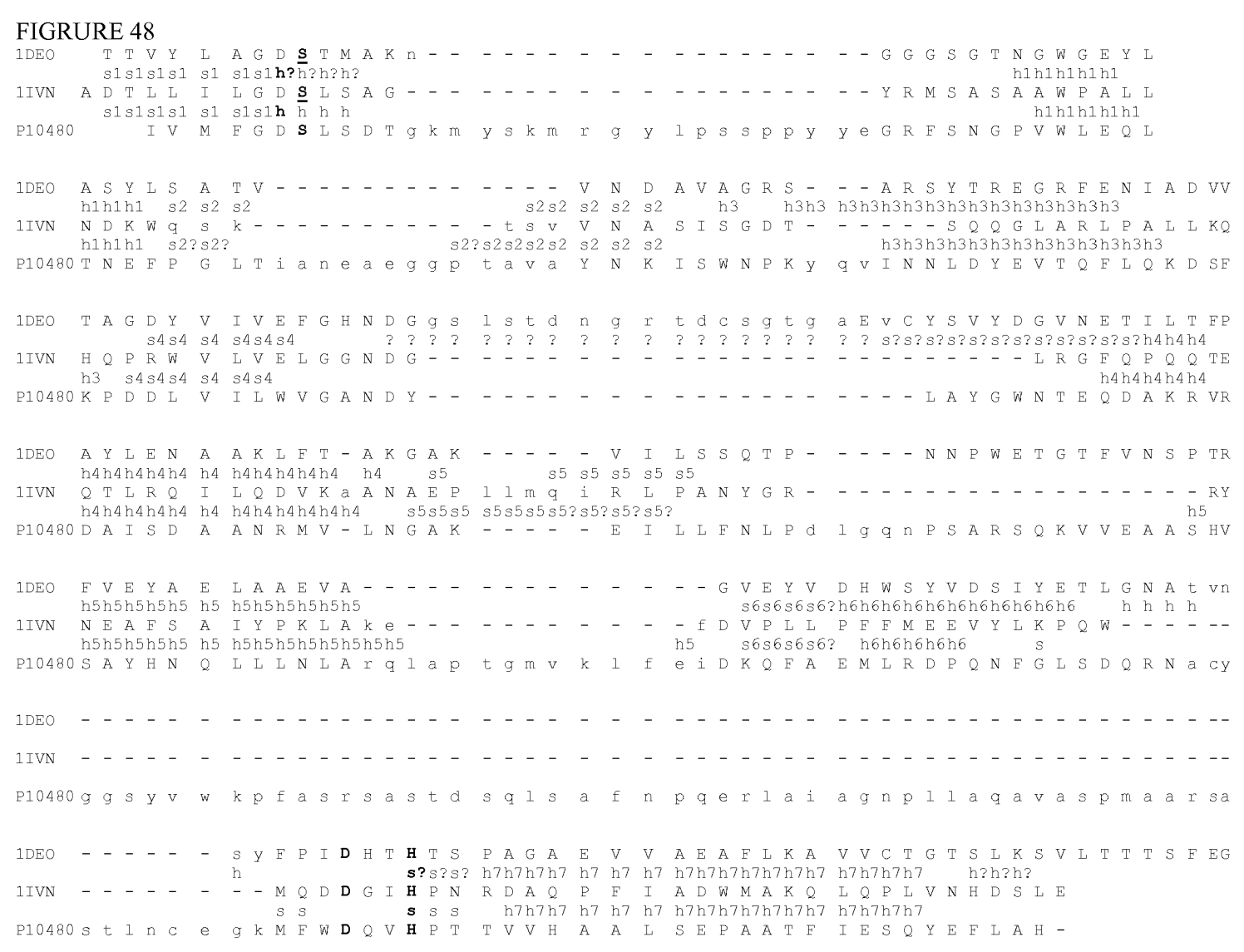

FIG. 48 shows alignment 1 ("1DEO," "1IVN" and "P10480" are disclosed as SEQ ID NOS 20 and 96-97, respectively);

FIG. 49 shows alignment 2 ("1DEOm," "1IVNm" and "P10480 m" are disclosed as SEQ ID NOS 95-97, respectively);

Figure 50A:
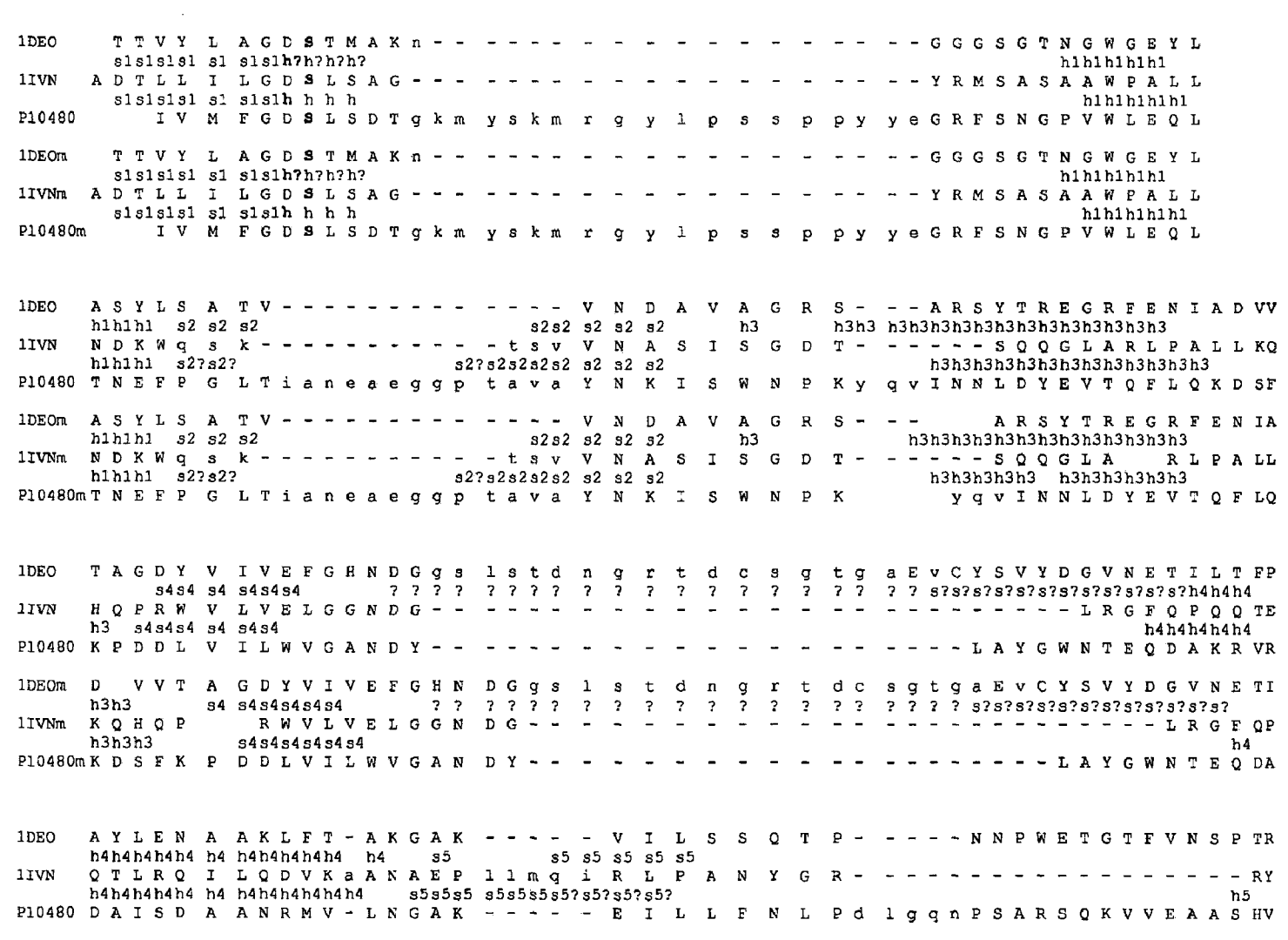
Figure 50B:
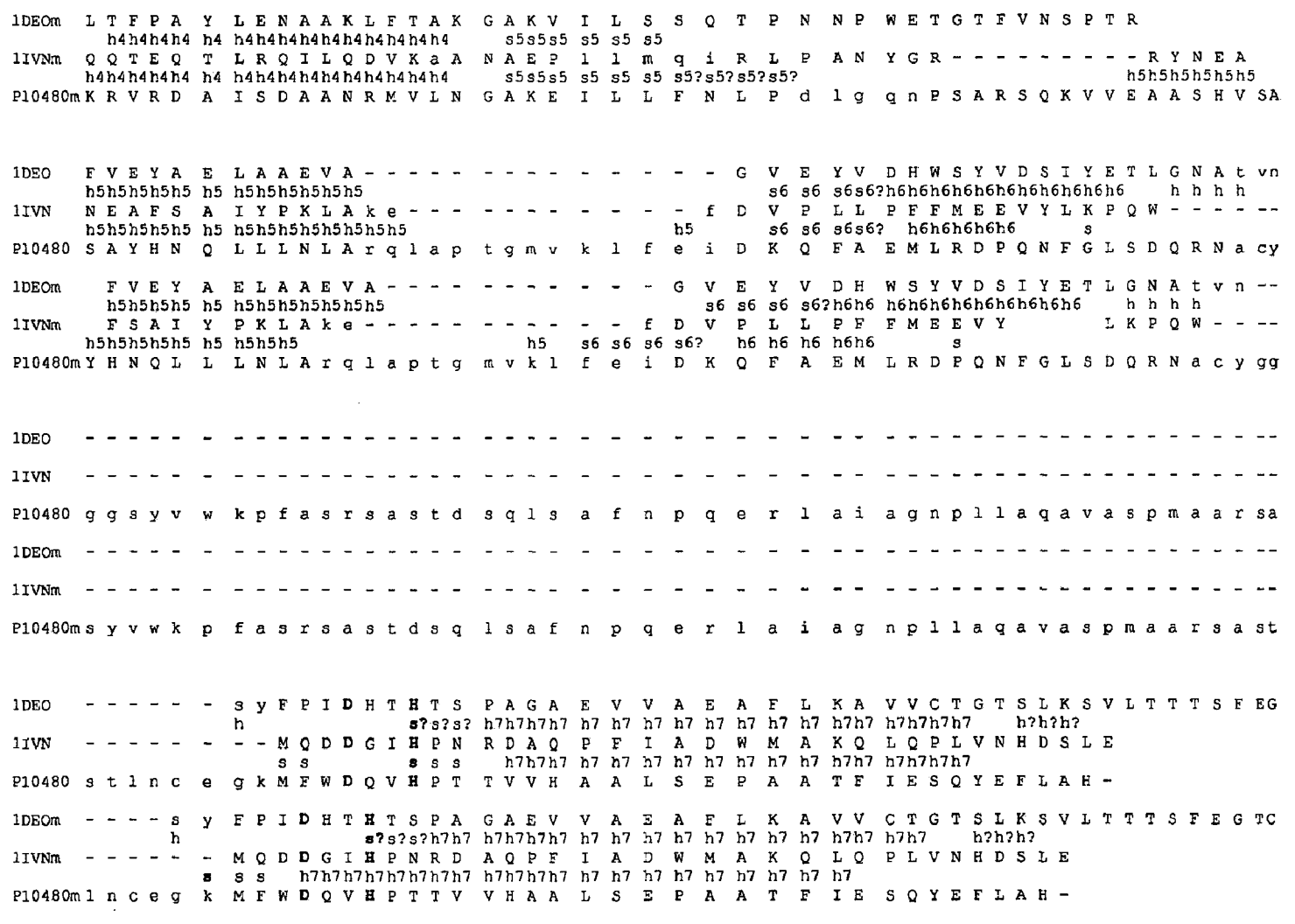

FIGS. 50 and 51 show an alignment of 1IVN to P10480 (P10480 is the database sequence for A. hydrophila enzyme), this alignment was obtained from the PFAM database and used in the model building process (FIG. 50 discloses "1DEO," "1IVN," "P10480," "1DEOm," "1IVNm" and "P10480 m" as SEQ ID NOS 20, 96-97 and 95-97, respectively and FIG. 51 discloses "1IVGN A" and "P10480" as SEQ ID NOS 98-99, respectively); and FIG. 52 shows an alignment where P10480 (SEQ ID NO: 100) is the database sequence for *Aeromonas hydrophila*. This sequence is used for the model construction and the site selection. Note that the full protein (SEQ ID No. 25) is depicted, the mature protein (equivalent to SEQ ID No. 34) starts at residue 19. A. sal is *Aeromonas salmonicida* (Residues 19-336 of SEQ ID No. 4) GDSX (SEQ ID NO: 117) lipase, A. hyd is *Aeromonas hydrophila* (SEQ ID No. 34) GDSX (SEQ ID NO: 117) lipase. The consensus sequence contains a * at the position of a difference between the listed sequences.

Figure 54:
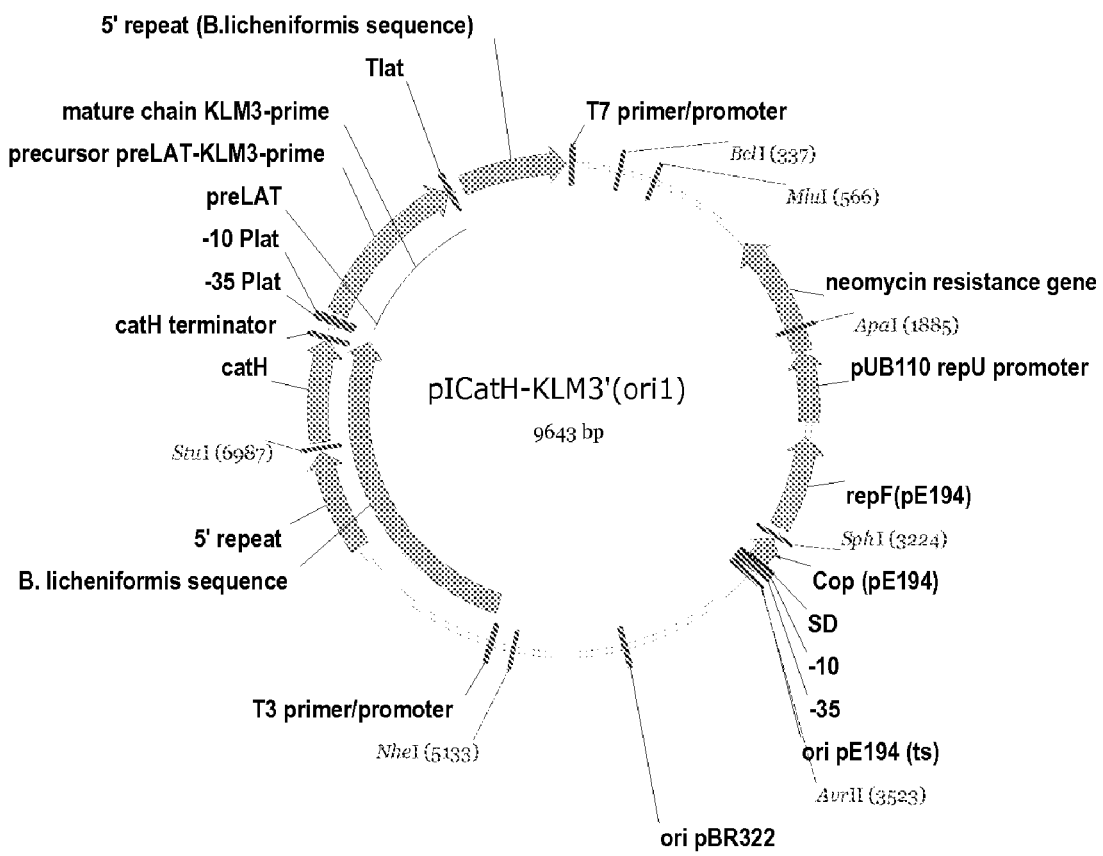
Figure 56:
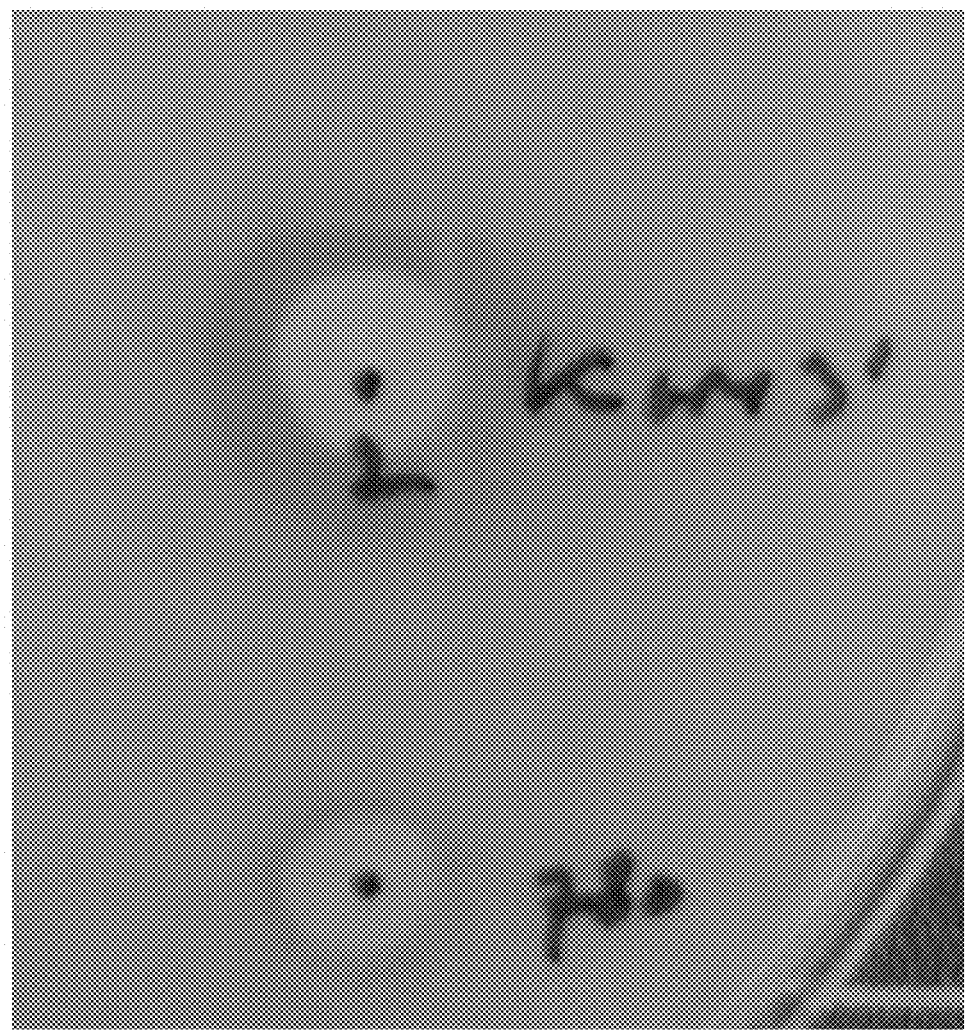

FIG. 53 shows a gene construct used in Example 1;

FIG. 54 shows a codon optimised gene construct (no. 052907) used in Example 1; and FIG. 55 shows the sequence of the XhoI insert (Nucleotide sequence and coded amino acid sequence are disclosed as SEQ ID NOS 115-116, respectively) containing the LAT-KLM3' precursor gene, the −35 and −10 boxes are underlined;

FIG. 56 shows BML780-KLM3'CAP50 (comprising SEQ ID No. 16—upper colony) and BML780 (the empty host strain—lower colony) after 48 h growth at 37° C. on 1% tributyrin agar;

FIG. 57 shows a nucleotide sequence from *Aeromonas salmonicida* (SEQ ID No. 49) including the signal sequence (preLAT—positions 1 to 87);

FIG. 58 shows a nucleotide sequence (SEQ ID No. 50) encoding a lipid acyl transferase according to the present invention obtained from the organism *Aeromonas hydrophila*;

FIG. 59 shows a nucleotide sequence (SEQ ID No. 51) encoding a lipid acyl transferase according to the present invention obtained from the organism *Aeromonas salmonicida*;

FIG. 60 shows a nucleotide sequence (SEQ ID No. 52) encoding a lipid acyl transferase according to the present invention obtained from the organism *Streptomyces coelicolor* A3(2) (Genbank accession number NC_003888.1: 8327480.8328367);

FIG. 61 shows a nucleotide sequence (SEQ ID No. 53) encoding a lipid acyl transferase according to the present invention obtained from the organism *Streptomyces coelicolor* A3(2) (Genbank accession number AL939131.1: 265480 ... 266367);

FIG. 62 shows a nucleotide sequence (SEQ ID No. 54) encoding a lipid acyl transferase according to the present invention obtained from the organism *Saccharomyces cerevisiae* (Genbank accession number Z75034);

FIG. 63 shows a nucleotide sequence (SEQ ID No. 55) encoding a lipid acyl transferase according to the present invention obtained from the organism Ralstonia;

FIG. 64 shows a nucleotide sequence shown as SEQ ID No. 56 encoding NCBI protein accession code CAB39707.1 GI: 4539178 conserved hypothetical protein [*Streptomyces coelicolor* A3(2)];

FIG. 65 shows a nucleotide sequence shown as SEQ ID No. 57 encoding Scoe2 NCBI protein accession code CAC01477.1 GI: 9716139 conserved hypothetical protein [*Streptomyces coelicolor* A3(2)];

FIG. 66 shows a nucleotide sequence shown as SEQ ID No. 58 encoding Scoe3 NCBI protein accession code CAB88833.1 GI: 7635996 putative secreted protein. [*Streptomyces coelicolor* A3(2)];

FIG. 67 shows a nucleotide sequence shown as SEQ ID No. 59 encoding Scoe4 NCBI protein accession code CAB89450.1 GI: 7672261 putative secreted protein. [*Streptomyces coelicolor* A3(2)];

FIG. 68 shows a nucleotide sequence shown as SEQ ID No. 60, encoding Scoe5 NCBI protein accession code CAB62724.1 GI: 6562793 putative lipoprotein [*Streptomyces coelicolor* A3(2)];

FIG. 69 shows a nucleotide sequence shown as SEQ ID No. 61 encoding Srim1 NCBI protein accession code AAK84028.1 GI: 15082088 GDSL-lipase [*Streptomyces rimosus*];

FIG. 70 shows a nucleotide sequence (SEQ ID No. 62) encoding a lipid acyltransferase from *Aeromonas hydrophila* (ATCC #7965);

FIG. 71 shows a nucleotide sequence (SEQ ID No 63) encoding a lipid acyltransferase from *Aeromonas salmonicida* subsp. *Salmonicida* (ATCC#14174); and FIG. 72 shows a nucleotide sequence (SEQ ID No. 24) encoding an enzyme from *Aeromonas hydrophila* including a xylanase signal peptide.

EXAMPLE 1

Expression of KLM3' in *Bacillus licheniformis*

A nucleotide sequence (SEQ ID No. 49) encoding a lipid acyltransferase (SEQ. ID No. 16, hereinafter KLM3') was expressed in *Bacillus licheniformis* as a fusion protein with the signal peptide of *B. licheniformis* [alpha]-amylase (LAT) (see FIGS. 53 and 54). For optimal expression in *Bacillus*, a codon optimized gene construct (no. 052907) was ordered at Geneart (Geneart AG, Regensburg, Germany).

Construct no. 052907 contains an incomplete LAT promoter (only the ±10 sequence) in front of the LAT-KLM3' precursor gene and the LAT transcription (Tlat) downstream of the LAT-KLM3' precursor gene (see FIGS. 53 and 55). To create a XhoI fragment that contains the LAT-KLM3' precursor gene flanked by the complete LAT promoter at the 5' end and the LAT terminator at the 3' end, a PCR (polymerase chain reaction) amplification was performed with the primers Plat5XhoI_FW and EBS2XhoI_RV and gene construct 052907 as template.

```
Plat5XhoI_FW: ccccgctcgaggcttttcttttggaagaaaatatagg
              gaaatggtacttgttaaaaattcggaatatttatac
              aatatcatatgtttcacattgaaagggg
              (SEQ ID NO: 69)

EBS2XhoI_RV: tggaatctcgaggttttatcctttaccttgtctcc
             (SEQ ID NO: 70)
```

PCR was performed on a thermocycler with Phusion High Fidelity DNA polymerase (Finnzymes O Y, Espoo, Finland) according to the instructions of the manufacturer (annealing temperature of 55 [deg.] C.).

The resulting PCR fragment was digested with restriction enzyme XhoI and ligated with T4 DNA ligase into XhoI digested pICatH according to the instructions of the supplier (Invitrogen, Carlsbad, Calif. USA).

The ligation mixture was transformed into B. subtilis strain SC6.1 as described in U.S. Patent Application US20020182734 (International Publication WO 02/14490). The sequence of the XhoI insert containing the LAT-KLM3' precursor gene was confirmed by DNA sequencing (Base-Clear, Leiden, The Netherlands) and one of the correct plasmid clones was designated pICatH-KLM3'(ori1) (FIG. 53). pICatH-KLM3'(ori1) was transformed into B. licheniformis strain BML780 (a derivative of BRA7 and BML612, see WO2005111203) at the permissive temperature (37° C.).

One neomycin resistant (neoR) and chloramphenicol resistant (CmR) transformant was selected and designated BML780(pICatH-KLM3'(ori1)). The plasmid in BML780 (pICatH-KLM3'(ori1)) was integrated into the catH region on the B. licheniformis genome by growing the strain at a non-permissive temperature (50° C.) in medium with 5 [mu]g/ml chloramphenicol. One CmR resistant clone was selected and designated BML780-pICatH-KLM3'(ori1). BML780-pICatH—KLM3'(ori1) was grown again at the permissive temperature for several generations without antibiotics to loop-out vector sequences and then one neomycin sensitive (neoS), CmR clone was selected. In this clone, vector sequences of pICatH on the chromosome are excised (including the neomycin resistance gene) and only the catH—LATKLM3' cassette is left. Next, the catH—LATKLM3' cassette on the chromosome was amplified by growing the strain in/on media with increasing concentrations of chloramphenicol. After various rounds of amplification, one clone (resistant against 50 [mu]g/ml chloramphenicol) was selected and designated BML780-KLM3'CAP50. To verify KLM3' expression, BML780-KLM3'CAP50 and BML780 (the empty host strain) were grown for 48 h at 37° C. on a Heart Infusion (Bacto) agar plate with 1% tributyrin. A clearing zone, indicative for lipid acyltransferase activity, was clearly visible around the colony of BML780-KLM3'CAP50 but not around the host strain BML780 (see FIG. 56). This result shows that a substantial amount of KLM3' is expressed in B. licheniformis strain BML780-KLM3'CAP50 and that these KLM3' molecules are functional.

COMPARATIVE EXAMPLE 1

Vector Construct

The plasmid construct is pCS32new N80D, which is a pCCmini derivative carrying the sequence encoding the mature form of the native Aeromonas salmonicida Glycerophospholipid-cholesterol acyltransferase with a Asn to Asp substitution at position 80 (KLM3'), under control of the p32 promoter and with a CGTase signal sequence.

The host strain used for the expression, is in the bacillus subtilis OS21ΔAprE strain The expression level is measured as transferase activity, expressed as % cholesterol esterified, calculated from the difference in free cholesterol in the reference sample and free cholesterol in the enzyme sample in reactions with PC ($T_{PC}$) as donor and cholesterol as acceptor molecule.

Culture Conditions 5 ml of LB broth (Casein enzymatic digest, 10 g/l; low-sodium Yeast extract, 5 g/l; Sodium Chloride, 5 g/l; Inert tableting aids, 2 g/l) supplemented with 50 mg/l kanamycin, was inoculated with a single colony and incubated at 30° C. for 6 hours at 205 rpm. 0.7 ml of this culture was used to inoculate 50 ml of SAS media ($K_2HPO_4$, 10 g/l; MOPS (3-morpholinopropane sulfonic acid), 40 g/l; Sodium Chloride, 5 g/l; Antifoam (Sin 260), 5 drops/l; Soy flour degreased, 20 g/l; Biospringer 106 (100% dw YE), 20 g/l) supplemented with 50 mg/l kanamycin and a solution of high maltose starch hydrolysates (60 g/l). Incubation was continued for 40 hours at 30° C. and 180 rpm before the culture supernatant was separated by centrifugation at 19000 rpm for 30 min. The supernatant was transferred into a clean tube and directly used for transferase activity measurement.

Preparation of Substrates and Enzymatic Reaction

PC (Avanti Polar Lipids #441601) and cholesterol (Sigma C8503) was scaled in the ratio 9:1, dissolved in chloroform, and evaporated to dryness.

The substrate was prepared by dispersion of 3% PC:Cholesterol 9:1 in 50 mM Hepes buffer pH 7.

0.250 ml substrate solution was transferred into a 3 ml glass tube with screw lid.

0.025 ml culture supernatant was added and the mixture was incubated at 40° C. for 2 hours. A reference sample with water instead of enzyme was also prepared. Heating the reaction mixture in a boiling water bath for 10 minutes stopped the enzyme reaction. 2 ml of 99% ethanol was added to the reaction mixture before submitted to cholesterol assay analysis.

Cholesterol Assay

100 µl substrate containing 1.4 U/ml Cholesterol oxidase (SERVA Electrophoresis GmbH cat. No 17109), 0.4 mg/ml ABTS (Sigma A-1888), 6 U/ml Peroxidase (Sigma 6782) in 0.1 M Tris-HCl, pH 6.6 and 0.5% Triton X-100 (Sigma X-100) was incubated at 37° C. for 5 minutes before 5 µl enzyme reaction sample was added and mixed. The reaction mixture was incubated for further 5 minutes and $OD_{405}$ was measured. The content of cholesterol was calculated from the analyses of standard solutions of cholesterol containing 0.4 mg/ml, 0.3 mg/ml, 0.20 mg/ml, 0.1 mg/ml, 0.05 mg/ml, and 0 mg/ml cholesterol in 99% EtOH.

Results

The table shows the average of 8 separate expression cultures

| Strain | $T_{PC}$[a] |
|---|---|
| OS21ΔAprE[pCS32new] | 74.2 ± 10.1[b] |

[a]$T_{PC}$ is the transferase activity, expressed as % cholesterol esterified, calculated from the difference in free cholesterol in the reference sample and free cholesterol in the enzyme sample in reactions with PC as donor molecule and cholesterol as acceptor molecule.
[b]Average of 8 separate expression cultures All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An expression vector comprising a nucleotide sequence encoding a heterologous lipid acyltransferase operably linked to a promoter for expression of the nucleotide sequence in a *Bacillus* host cell, wherein the nucleotide sequence encoding the heterologous lipid acyltransferase is shown as SEQ ID NO: 49.

2. An expression vector according to claim 1, wherein the promoter sequence is not natively associated with the nucleotide sequence.

3. An expression vector according to claim 1, further comprising a nucleotide sequence encoding a signal peptide fused to the nucleotide sequence encoding the heterologous lipid acyltransferase,
   wherein the nucleotide sequence encoding the signal peptide is operably linked to the nucleotide sequence encoding the heterologous lipid acyltransferase.

4. An expression vector according to claim 1, wherein the promoter is selected from the group consisting of an α-amylase promoter sequence, a protease promoter sequence, and a levansucrase promoter sequence.

5. A *Bacillus* host cell comprising a nucleotide sequence encoding a heterologous lipid acyltransferase,
   wherein the nucleotide sequence encoding the heterologous lipid acyltransferase is shown as SEQ ID NO: 49, and
   wherein the *Bacillus* host cell is one other than *B. subtilis*.

6. A method of producing a heterologous lipid acyltransferase, comprising: transforming a *Bacillus* host cell with an expression vector comprising a nucleotide sequence encoding the heterologous lipid acyltransferase shown as SEQ ID NO: 49, wherein the *Bacillus* host cell is one other than *B. subtilis*; and expressing the heterologous lipid acyltransferase in the *Bacillus* host cell, thereby producing heterologous lipid.

7. The *Bacillus* host cell according to claim 1 or 5, wherein the *Bacillus* host cell is a *Bacillus licheniformis* host cell.

8. The method according to claim 6, wherein the *Bacillus* host cell is a *Bacillus licheniformis* host cell.

9. The method according to claim 6 or 8, wherein there is increased expression of the heterologous lipid acyltransferase as compared with lipid acyltransferase expression in a *B. subtilis* host cell which has been transformed with the expression vector comprising the nucleotide sequence encoding the heterologous lipid acyltransferase shown as SEQ ID NO: 49.

10. An isolated nucleic acid sequence encoding a heterologous lipid acyltransferase shown as SEQ ID NO: 49.

11. An expression vector according to claim 1, wherein the promoter is selected from the group consisting of a subtilisin promoter sequence, and a glutamic acid-specific protease promoter sequence.

* * * * *

SEQUENCE LISTING

<160> NUMBER OF SEQ ID NOS: 124

<210> SEQ ID NO 1
<211> LENGTH: 335
<212> TYPE: PRT
<213> ORGANISM: Aeromonas hydrophila

<400> SEQUENCE: 1

```
Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Gln Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335
```

<210> SEQ ID NO 2
<211> LENGTH: 361
<212> TYPE: PRT
<213> ORGANISM: Artificial Sequence

```
<220> FEATURE:
<223> OTHER INFORMATION: Description of Artificial Sequence: Synthetic
      consensus polypeptide

<400> SEQUENCE: 2

Ile Val Ala Phe Gly Asp Ser Leu Thr Asp Gly Glu Ala Tyr Tyr Gly
1               5                   10                  15

Asp Ser Asp Gly Gly Gly Trp Gly Ala Gly Leu Ala Asp Arg Leu Thr
            20                  25                  30

Ala Leu Leu Arg Leu Arg Ala Arg Pro Arg Gly Val Asp Val Phe Asn
        35                  40                  45

Arg Gly Ile Ser Gly Arg Thr Ser Asp Gly Arg Leu Ile Val Asp Ala
    50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
                85                  90                  95

Ala Gly Ala Thr Ile Leu Pro Thr Ser Gly Pro Phe Leu Ile Gln Val
            100                 105                 110

Gln Phe Lys Asp Phe Lys Ser Gln Val Leu Glu Leu Arg Gln Ala Leu
        115                 120                 125

Gly Leu Leu Gln Glu Leu Leu Arg Leu Leu Pro Val Leu Asp Ala Lys
    130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
    210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
    290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
            340                 345                 350

Gly Tyr Lys Ala Val Ala Glu Ala Leu
        355                 360

<210> SEQ ID NO 3
<211> LENGTH: 335
<212> TYPE: PRT
<213> ORGANISM: Aeromonas hydrophila
```

<400> SEQUENCE: 3

```
Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
    290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335
```

<210> SEQ ID NO 4
<211> LENGTH: 336
<212> TYPE: PRT
<213> ORGANISM: Aeromonas salmonicida

<400> SEQUENCE: 4

```
Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30
```

```
Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
 50                  55                  60

Val Trp Leu Glu Gln Leu Thr Lys Gln Phe Pro Gly Leu Thr Ile Ala
 65                  70                  75                  80

Asn Glu Ala Glu Gly Gly Ala Thr Ala Val Ala Tyr Asn Lys Ile Ser
                 85                  90                  95

Trp Asn Pro Lys Tyr Gln Val Tyr Asn Asn Leu Asp Tyr Glu Val Thr
                100                 105                 110

Gln Phe Leu Gln Lys Asp Ser Phe Lys Pro Asp Leu Val Ile Leu
        115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
                180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
 1               5                  10                  15

Val Gly Thr Leu Ala Leu Gly Leu Thr Asp Ala Thr Ala His Ala Ala
                 20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
 50                  55                  60

Cys Leu Arg Ser Thr Ala Asn Tyr Pro His Val Ile Ala Asp Thr Thr
 65                  70                  75                  80
```

```
Gly Ala Arg Leu Thr Asp Val Thr Cys Gly Ala Ala Gln Thr Ala Asp
                 85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295

<210> SEQ ID NO 6
<211> LENGTH: 295
<212> TYPE: PRT
<213> ORGANISM: Streptomyces coelicolor

<400> SEQUENCE: 6

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
```

```
                        165                 170                 175
Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295

<210> SEQ ID NO 7
<211> LENGTH: 238
<212> TYPE: PRT
<213> ORGANISM: Saccharomyces cerevisiae

<400> SEQUENCE: 7

Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Ile Gly Pro Gly Leu Val Asp Arg Glu Lys
        115                 120                 125

Trp Glu Lys Glu Lys Ser Glu Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235
```

```
<210> SEQ ID NO 8
<211> LENGTH: 347
<212> TYPE: PRT
<213> ORGANISM: Ralstonia sp.

<400> SEQUENCE: 8

Met Asn Leu Arg Gln Trp Met Gly Ala Ala Thr Ala Ala Leu Ala Leu
1               5                   10                  15

Gly Leu Ala Ala Cys Gly Gly Gly Thr Asp Gln Ser Gly Asn Pro
            20                  25                  30

Asn Val Ala Lys Val Gln Arg Met Val Val Phe Gly Asp Ser Leu Ser
                35                  40                  45

Asp Ile Gly Thr Tyr Thr Pro Val Ala Gln Ala Val Gly Gly Gly Lys
        50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95

Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Ala Gly Ala
        115                 120                 125

Leu Thr Tyr Pro Val Gln Gln Gln Leu Ala Asn Phe Tyr Ala Ala Ser
130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Thr Ser Gly Ser
            165                 170                 175

Gly Val Thr Pro Ala Ile Ala Thr Ala Gln Val Gln Ala Ala Thr
        180                 185                 190

Asp Leu Val Gly Tyr Val Lys Asp Met Ile Ala Lys Gly Ala Thr Gln
            195                 200                 205

Val Tyr Val Phe Asn Leu Pro Asp Ser Ser Leu Thr Pro Asp Gly Val
210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
            260                 265                 270

Phe Gly Phe Ala Asn Thr Ser Ala Arg Ala Cys Asp Ala Thr Lys Ile
        275                 280                 285

Asn Ala Leu Val Pro Ser Ala Gly Gly Ser Ser Leu Phe Cys Ser Ala
            290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
            340                 345

<210> SEQ ID NO 9
<211> LENGTH: 261
<212> TYPE: PRT
<213> ORGANISM: Streptomyces coelicolor

<400> SEQUENCE: 9
```

```
Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
                35                  40                  45

Asn Leu Ala Val Arg Gly Arg Leu Leu Asp Gln Ile Val Ala Glu Gln
        50                  55                  60

Val Pro Arg Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                    85                  90                  95

Glu Arg Phe Glu Leu Ala Val Ala Ala Leu Thr Ala Ala Ala Gly Thr
                100                 105                 110

Val Leu Val Thr Thr Gly Phe Asp Thr Arg Gly Val Pro Val Leu Lys
                115                 120                 125

His Leu Arg Gly Lys Ile Ala Thr Tyr Asn Gly His Val Arg Ala Ile
        130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Leu Pro Pro Arg
        195                 200                 205

Gly Thr Leu Asp Val Arg Arg Asp Asp Val His Trp Ala Arg Glu Tyr
        210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                    245                 250                 255

Ile Ala Ala Val Ala
            260

<210> SEQ ID NO 10
<211> LENGTH: 260
<212> TYPE: PRT
<213> ORGANISM: Streptomyces coelicolor

<400> SEQUENCE: 10

Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
                35                  40                  45

Arg Tyr Ala Asn Leu Ala Val Arg Gly Lys Leu Ile Gly Gln Ile Val
        50                  55                  60

Asp Glu Gln Val Asp Val Ala Ala Ala Met Gly Ala Asp Val Ile Thr
65                  70                  75                  80

Leu Val Gly Gly Leu Asn Asp Thr Leu Arg Pro Lys Cys Asp Met Ala
                    85                  90                  95

Arg Val Arg Asp Leu Leu Thr Gln Ala Val Glu Arg Leu Ala Pro His
                100                 105                 110
```

```
Cys Glu Gln Leu Val Leu Met Arg Ser Pro Gly Arg Gln Gly Pro Val
            115                 120                 125

Leu Glu Arg Phe Arg Pro Arg Met Glu Ala Leu Phe Ala Val Ile Asp
130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                    165                 170                 175

Thr Ala Glu Gly His Arg Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Arg Thr Ala Asp Val Arg Phe Ala
    210                 215                 220

Arg Gln His Leu Leu Pro Trp Ile Gly Arg Arg Leu Thr Gly Arg Ser
225                 230                 235                 240

Ser Gly Asp Gly Leu Pro Ala Lys Arg Pro Asp Leu Leu Pro Tyr Glu
                245                 250                 255

Asp Pro Ala Arg
            260

<210> SEQ ID NO 11
<211> LENGTH: 454
<212> TYPE: PRT
<213> ORGANISM: Streptomyces coelicolor

<400> SEQUENCE: 11

Met Thr Arg Gly Arg Asp Gly Ala Gly Ala Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
        35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Ala Glu
65                  70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
            100                 105                 110

Leu Tyr Gly Gln Ser Pro Leu Thr Val Thr His Ala Ser Ile Ala Leu
        115                 120                 125

Ala Ala Gly Pro Asp Thr Ala Ala Ala Ile Ala Asp Thr Met Arg Arg
    130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
        195                 200                 205

Asp Val Thr Ala Val Ala Tyr Thr Thr Pro Thr Pro Tyr Trp Arg Tyr
    210                 215                 220
```

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
            245                 250                 255

Asn His Arg Trp Thr Asp Val Leu Ala Arg Leu His Glu Ala Ala
                260                 265                 270

Gly Asp Gly Arg Asp Thr Pro Arg Tyr Ser Val Val Asn Glu Gly Ile
            275                 280                 285

Ser Gly Asn Arg Leu Leu Thr Ser Arg Pro Gly Arg Pro Ala Asp Asn
        290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
                325                 330                 335

Pro Glu Leu Ala Asp Arg Asp Ala Ile Leu Thr Gly Leu Arg Thr Leu
            340                 345                 350

Val Asp Arg Ala His Ala Arg Gly Leu Arg Val Val Gly Ala Thr Ile
        355                 360                 365

Thr Pro Phe Gly Gly Tyr Gly Gly Tyr Thr Glu Ala Arg Glu Thr Met
    370                 375                 380

Arg Gln Glu Val Asn Glu Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415

Met Arg Ser Asp Tyr Asp Ser Gly Asp His Leu His Pro Gly Asp Lys
            420                 425                 430

Gly Tyr Ala Arg Met Gly Ala Val Ile Asp Leu Ala Ala Leu Lys Gly
        435                 440                 445

Ala Ala Pro Val Lys Ala
    450

<210> SEQ ID NO 12
<211> LENGTH: 340
<212> TYPE: PRT
<213> ORGANISM: Streptomyces coelicolor

<400> SEQUENCE: 12

Met Thr Ser Met Ser Arg Ala Arg Val Ala Arg Arg Ile Ala Ala Gly
1               5                   10                  15

Ala Ala Tyr Gly Gly Gly Ile Gly Leu Ala Gly Ala Ala Val
            20                  25                  30

Gly Leu Val Val Ala Glu Val Gln Leu Ala Arg Arg Val Gly Val
        35                  40                  45

Gly Thr Pro Thr Arg Val Pro Asn Ala Gln Gly Leu Tyr Gly Gly Thr
    50                  55                  60

Leu Pro Thr Ala Gly Asp Pro Pro Leu Arg Leu Met Met Leu Gly Asp
65                  70                  75                  80

Ser Thr Ala Ala Gly Gln Gly Val His Arg Ala Gly Gln Thr Pro Gly
                85                  90                  95

Ala Leu Leu Ala Ser Gly Leu Ala Ala Val Ala Glu Arg Pro Val Arg
            100                 105                 110

Leu Gly Ser Val Ala Gln Pro Gly Ala Cys Ser Asp Asp Leu Asp Arg
        115                 120                 125

Gln Val Ala Leu Val Leu Ala Glu Pro Asp Arg Val Pro Asp Ile Cys
    130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Arg Leu Arg Thr Ala
            165                 170                 175

Gly Ala Glu Val Val Gly Thr Cys Pro Asp Leu Gly Thr Ile Glu
        180                 185                 190

Arg Val Arg Gln Pro Leu Arg Trp Leu Ala Arg Ala Ser Arg Gln
    195                 200                 205

Leu Ala Ala Ala Gln Thr Ile Gly Ala Val Glu Gln Gly Gly Arg Thr
210                 215                 220

Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala
            245                 250                 255

Thr Ala Ala Met Ala Val Leu Pro Ser Val Cys Ala Ala Leu Gly Leu
        260                 265                 270

Trp Pro Ala Asp Glu Glu His Pro Asp Ala Leu Arg Arg Glu Gly Phe
    275                 280                 285

Leu Pro Val Ala Arg Ala Ala Glu Ala Ala Ser Glu Ala Gly Thr
290                 295                 300

Glu Val Ala Ala Ala Met Pro Thr Gly Pro Arg Gly Pro Trp Ala Leu
305                 310                 315                 320

Leu Lys Arg Arg Arg Arg Arg Val Ser Glu Ala Glu Pro Ser Ser
            325                 330                 335

Pro Ser Gly Val
        340

<210> SEQ ID NO 13
<211> LENGTH: 305
<212> TYPE: PRT
<213> ORGANISM: Streptomyces coelicolor

<400> SEQUENCE: 13

Met Gly Arg Gly Thr Asp Gln Arg Thr Arg Tyr Gly Arg Arg Ala
1               5                   10                  15

Arg Val Ala Leu Ala Ala Leu Thr Ala Ala Val Leu Gly Val Gly Val
        20                  25                  30

Ala Gly Cys Asp Ser Val Gly Gly Asp Ser Pro Ala Pro Ser Gly Ser
        35                  40                  45

Pro Ser Lys Arg Thr Arg Thr Ala Pro Ala Trp Asp Thr Ser Pro Ala
50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
            85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
            165                 170                 175

```
Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
            195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270

Thr Asp Gln Leu Ser His Trp Asp Trp Phe His Pro Ser Val Asp Gly
            275                 280                 285

Gln Ala Arg Leu Ala Glu Ile Ala Tyr Arg Ala Val Thr Ala Lys Asn
    290                 295                 300

Pro
305

<210> SEQ ID NO 14
<211> LENGTH: 268
<212> TYPE: PRT
<213> ORGANISM: Streptomyces rimosus

<400> SEQUENCE: 14

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
            35                  40                  45

Val Gly Ala Gly Ser Tyr Asp Ser Ser Ser Gly Ser Cys Lys Arg Ser
    50                  55                  60

Thr Lys Ser Tyr Pro Ala Leu Trp Ala Ala Ser His Thr Gly Thr Arg
65              70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Leu Gly Tyr Pro
                165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Ala Asp Asp Ile Asn Ala Val Thr
        195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240
```

```
Val Thr Leu Pro Val Glu Asn Ser Tyr His Pro Thr Ala Asn Gly Gln
            245                 250                 255

Ser Lys Gly Tyr Leu Pro Val Leu Asn Ser Ala Thr
            260                 265

<210> SEQ ID NO 15
<211> LENGTH: 336
<212> TYPE: PRT
<213> ORGANISM: Aeromonas salmonicida

<400> SEQUENCE: 15

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 16
```

```
<211> LENGTH: 318
<212> TYPE: PRT
<213> ORGANISM: Aeromonas salmonicida

<400> SEQUENCE: 16

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315

<210> SEQ ID NO 17
<211> LENGTH: 465
<212> TYPE: PRT
<213> ORGANISM: Candida parapsilosis

<400> SEQUENCE: 17

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30
```

-continued

```
Pro Gln Gly Tyr Glu Ala Gln Pro Leu Gly Ser Ile Leu Lys Thr Arg
     35                  40                  45
Asn Val Pro Asn Pro Leu Thr Asn Val Phe Thr Pro Val Lys Val Gln
 50                  55                  60
Asn Ala Trp Gln Leu Leu Val Arg Ser Glu Asp Thr Phe Gly Asn Pro
 65                  70                  75                  80
Asn Ala Ile Val Thr Thr Ile Ile Gln Pro Phe Asn Ala Lys Lys Asp
                 85                  90                  95
Lys Leu Val Ser Tyr Gln Thr Phe Glu Asp Ser Gly Lys Leu Asp Cys
                100                 105                 110
Ala Pro Ser Tyr Ala Ile Gln Tyr Gly Ser Asp Ile Ser Thr Leu Thr
                115                 120                 125
Thr Gln Gly Glu Met Tyr Tyr Ile Ser Ala Leu Leu Asp Gln Gly Tyr
        130                 135                 140
Tyr Val Val Thr Pro Asp Tyr Glu Gly Pro Lys Ser Thr Phe Thr Val
145                 150                 155                 160
Gly Leu Gln Ser Gly Arg Ala Thr Leu Asn Ser Leu Arg Ala Thr Leu
                165                 170                 175
Lys Ser Gly Asn Leu Thr Gly Val Ser Ser Asp Ala Glu Thr Leu Leu
                180                 185                 190
Trp Gly Tyr Ser Gly Gly Ser Leu Ala Ser Gly Trp Ala Ala Ala Ile
        195                 200                 205
Gln Lys Glu Tyr Ala Pro Glu Leu Ser Lys Asn Leu Leu Gly Ala Ala
210                 215                 220
Leu Gly Gly Phe Val Thr Asn Ile Thr Ala Thr Ala Glu Ala Val Asp
225                 230                 235                 240
Ser Gly Pro Phe Ala Gly Ile Ile Ser Asn Ala Leu Ala Gly Ile Gly
                245                 250                 255
Asn Glu Tyr Pro Asp Phe Lys Asn Tyr Leu Leu Lys Lys Val Ser Pro
                260                 265                 270
Leu Leu Ser Ile Thr Tyr Arg Leu Gly Asn Thr His Cys Leu Leu Asp
                275                 280                 285
Gly Gly Ile Ala Tyr Phe Gly Lys Ser Phe Ser Arg Ile Ile Arg
        290                 295                 300
Tyr Phe Pro Asp Gly Trp Asp Leu Val Asn Gln Glu Pro Ile Lys Thr
305                 310                 315                 320
Ile Leu Gln Asp Asn Gly Leu Val Tyr Gln Pro Lys Asp Leu Thr Pro
                325                 330                 335
Gln Ile Pro Leu Phe Ile Tyr His Gly Thr Leu Asp Ala Ile Val Pro
                340                 345                 350
Ile Val Asn Ser Arg Lys Thr Phe Gln Gln Trp Cys Asp Trp Gly Leu
                355                 360                 365
Lys Ser Gly Glu Tyr Asn Glu Asp Leu Thr Asn Gly His Ile Thr Glu
        370                 375                 380
Ser Ile Val Gly Ala Pro Ala Ala Leu Thr Trp Ile Ile Asn Arg Phe
385                 390                 395                 400
Asn Gly Gln Pro Pro Val Asp Gly Cys Gln His Asn Val Arg Ala Ser
                405                 410                 415
Asn Leu Glu Tyr Pro Gly Thr Pro Gln Ser Ile Lys Asn Tyr Phe Glu
                420                 425                 430
Ala Ala Leu His Ala Ile Leu Gly Phe Asp Leu Gly Pro Asp Val Lys
                435                 440                 445
Arg Asp Lys Val Thr Leu Gly Gly Leu Leu Lys Leu Glu Arg Phe Ala
450                 455                 460
```

Phe
465

<210> SEQ ID NO 18
<211> LENGTH: 471
<212> TYPE: PRT
<213> ORGANISM: Candida parapsilosis

<400> SEQUENCE: 18

```
Met Arg Tyr Phe Ala Ile Ala Phe Leu Leu Ile Asn Thr Ile Ser Ala
 1               5                  10                  15

Phe Val Leu Ala Pro Lys Lys Pro Ser Gln Asp Asp Phe Tyr Thr Pro
             20                  25                  30

Pro Gln Gly Tyr Glu Ala Gln Pro Leu Gly Ser Ile Leu Lys Thr Arg
         35                  40                  45

Asn Val Pro Asn Pro Leu Thr Asn Val Phe Thr Pro Val Lys Val Gln
     50                  55                  60

Asn Ala Trp Gln Leu Leu Val Arg Ser Glu Asp Thr Phe Gly Asn Pro
 65                  70                  75                  80

Asn Ala Ile Val Thr Thr Ile Ile Gln Pro Phe Asn Ala Lys Lys Asp
                 85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365
```

```
Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe His His His His His His
465                 470

<210> SEQ ID NO 19
<211> LENGTH: 261
<212> TYPE: PRT
<213> ORGANISM: Streptomyces coelicolor

<400> SEQUENCE: 19

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260
```

<210> SEQ ID NO 20
<211> LENGTH: 230
<212> TYPE: PRT
<213> ORGANISM: Aspergillus aculeatus

<400> SEQUENCE: 20

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
    210                 215                 220

Thr Thr Ser Phe Glu Gly
225                 230

<210> SEQ ID NO 21
<211> LENGTH: 18
<212> TYPE: PRT
<213> ORGANISM: Aeromonas sp.

<400> SEQUENCE: 21

Met Lys Lys Trp Phe Val Cys Leu Leu Gly Leu Ile Ala Leu Thr Val
1               5                   10                  15

Gln Ala

<210> SEQ ID NO 22
<211> LENGTH: 29
<212> TYPE: PRT
<213> ORGANISM: Bacillus subtilis

<400> SEQUENCE: 22

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 23
<211> LENGTH: 29
<212> TYPE: PRT
<213> ORGANISM: Bacillus licheniformis

<400> SEQUENCE: 23

Met Met Arg Lys Lys Ser Phe Trp Phe Gly Met Leu Thr Ala Phe Met
1               5                   10                  15

Leu Val Phe Thr Met Glu Phe Ser Asp Ser Ala Ser Ala
            20                  25

<210> SEQ ID NO 24
<211> LENGTH: 1047
<212> TYPE: DNA
<213> ORGANISM: Aeromonas hydrophila

<400> SEQUENCE: 24
atgtttaagt ttaaaaagaa tttcttagtt ggattatcgg cagctttaat gagtattagc      60
ttgtttccgg caaccgcctc tgcagctagc gccgacagcc gtcccgcctt ttcccggatc     120
gtgatgttcg cgacagcct ctccgatacc ggcaaaatgt acagcaagat gcgcggttac     180
ctccccctcca gcccgcccta ctatgagggc cgtttctcca acggacccgt ctggctggag    240
cagctgacca aacagttccc gggtctgacc atcgccaacg aagcggaagg cggtgccact    300
gccgtggctt acaacaagat ctcctggaat cccaagtatc aggtcatcaa caacctggac    360
tacgaggtca cccagttctt gcagaaagac agcttcaagc cggacgatct ggtgatcctc    420
tgggtcggtg ccaatgacta tctggcctat ggctggaaca cggagcagga tgccaagcgg    480
gttcgcgatg ccatcagcga tgcggccaac cgcatggtac tgaacggtgc caagcagata    540
ctgctgttca acctgccgga tctgggccag aacccgtcag ctcgcagtca gaaggtggtc    600
gaggcggtca gccatgtctc cgcctatcac aaccagctgc tgctgaacct ggcacgccag    660
ctggccccca ccggcatggt aaagctgttc gagatcgaca gcaatttgc cgagatgctg    720
cgtgatccgc agaacttcgg cctgagcgac gtcgagaacc cctgctacga cggcggctat    780
gtgtggaagc cgtttgccac ccgcagcgtc agcaccgacc gccagctctc cgccttcagt    840
ccgcaggaac gcctcgccat cgccggcaac ccgctgctgg cacaggccgt tgccagtcct    900
atggcccgcc gcagcgccag ccccctcaac tgtgagggca agatgttctg ggatcaggta    960
cacccgacca ctgtcgtgca cgcagccctg agcgagcgcg ccgccacctt catcgcgaac   1020
cagtacgagt tcctcgccca ctgatga                                        1047

<210> SEQ ID NO 25
<211> LENGTH: 347
<212> TYPE: PRT
<213> ORGANISM: Artificial Sequence
<220> FEATURE:
<223> OTHER INFORMATION: Description of Artificial Sequence: Synthetic
      fusion construct polypeptide

<400> SEQUENCE: 25

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
        35                  40                  45

Asp Thr Gly Lys Met Tyr Ser Lys Met Arg Gly Tyr Leu Pro Ser Ser

```
                    50                  55                  60
Pro Pro Tyr Tyr Glu Gly Arg Phe Ser Asn Gly Pro Val Trp Leu Glu
 65                  70                  75                  80

Gln Leu Thr Lys Gln Phe Pro Gly Leu Thr Ile Ala Asn Glu Ala Glu
                 85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
            115                 120                 125

Lys Asp Ser Phe Lys Pro Asp Asp Leu Val Ile Leu Trp Val Gly Ala
130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
            195                 200                 205

Tyr His Asn Gln Leu Leu Leu Asn Leu Ala Arg Gln Leu Ala Pro Thr
210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255

Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
            275                 280                 285

Gly Asn Pro Leu Leu Ala Gln Ala Val Ala Ser Pro Met Ala Arg Arg
290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
            340                 345

<210> SEQ ID NO 26
<211> LENGTH: 267
<212> TYPE: PRT
<213> ORGANISM: Streptomyces sp.

<400> SEQUENCE: 26

Met Arg Leu Thr Arg Ser Leu Ser Ala Ala Ser Val Ile Val Phe Ala
 1               5                  10                  15

Leu Leu Leu Ala Leu Leu Gly Ile Ser Pro Ala Gln Ala Ala Gly Pro
                20                  25                  30

Ala Tyr Val Ala Leu Gly Asp Ser Tyr Ser Ser Gly Asn Gly Ala Gly
             35                  40                  45

Ser Tyr Ile Asp Ser Ser Gly Asp Cys His Arg Ser Asn Asn Ala Tyr
         50                  55                  60

Pro Ala Arg Trp Ala Ala Ala Asn Ala Pro Ser Ser Phe Thr Phe Ala
 65                  70                  75                  80

Ala Cys Ser Gly Ala Val Thr Thr Asp Val Ile Asn Asn Gln Leu Gly
```

```
                    85                  90                  95
Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
            130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
            195                 200                 205

Ala Thr Ala His Gly Phe Arg Phe Gly Asp Val Arg Pro Thr Phe Asn
            210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 27
<211> LENGTH: 548
<212> TYPE: PRT
<213> ORGANISM: Thermobifida sp.

<400> SEQUENCE: 27

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
            35                  40                  45

Val Pro Pro Leu Thr Leu Pro Gly Asp Gly Val Leu Cys Thr Thr Ser
50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
            115                 120                 125

Gly Asp Ser Ser Pro Pro Phe Arg Ala Gly Trp Ser Leu Pro Pro Lys
            130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Arg Leu Phe Leu Gly
            180                 185                 190

Ile Pro Ala Leu Val Leu Val Thr Ala Leu Thr Leu Val Leu Ala Val
```

```
            195                 200                 205
Pro Thr Gly Arg Glu Thr Leu Trp Arg Met Trp Cys Glu Ala Thr Gln
210                 215                 220

Asp Trp Cys Leu Gly Val Pro Val Asp Ser Arg Gly Gln Pro Ala Glu
225                 230                 235                 240

Asp Gly Glu Phe Leu Leu Ser Pro Val Gln Ala Ala Thr Trp Gly
            245                 250                 255

Asn Tyr Tyr Ala Leu Gly Asp Ser Tyr Ser Gly Asp Gly Ala Arg
            260                 265                 270

Asp Tyr Tyr Pro Gly Thr Ala Val Lys Gly Gly Cys Trp Arg Ser Ala
            275                 280                 285

Asn Ala Tyr Pro Glu Leu Val Ala Glu Ala Tyr Asp Phe Ala Gly His
            290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                    325                 330                 335

Ser Leu Val Thr Ile Gly Ile Gly Gly Asn Asp Leu Gly Phe Ser Thr
                    340                 345                 350

Val Leu Lys Thr Cys Met Val Arg Val Pro Leu Leu Asp Ser Lys Ala
                    355                 360                 365

Cys Thr Asp Gln Glu Asp Ala Ile Arg Lys Arg Met Ala Lys Phe Glu
    370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                    405                 410                 415

Thr Gly Ala Tyr Tyr Thr Leu Thr Ala Ser Asn Gln Arg Trp Leu Asn
                    420                 425                 430

Glu Thr Ile Gln Glu Phe Asn Gln Gln Leu Ala Glu Ala Val Ala Val
                    435                 440                 445

His Asp Glu Glu Ile Ala Ala Ser Gly Val Gly Ser Val Glu Phe
450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                    485                 490                 495

Val Asp Arg Ser Thr Phe His Pro Asn Ala Ala Gly His Arg Ala Val
                500                 505                 510

Gly Glu Arg Val Ile Glu Gln Ile Glu Thr Gly Pro Gly Arg Pro Leu
                515                 520                 525

Tyr Ala Thr Phe Ala Val Val Ala Gly Ala Thr Val Asp Thr Leu Ala
            530                 535                 540

Gly Glu Val Gly
545

<210> SEQ ID NO 28
<211> LENGTH: 372
<212> TYPE: PRT
<213> ORGANISM: Thermobifida sp.

<400> SEQUENCE: 28

Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
```

```
                20                  25                  30
Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
 50                  55                  60

Asp Gly Glu Phe Leu Leu Leu Ser Pro Val Gln Ala Ala Thr Trp Gly
 65                  70                  75                  80

Asn Tyr Tyr Ala Leu Gly Asp Ser Tyr Ser Gly Asp Gly Ala Arg
                85                  90                  95

Asp Tyr Tyr Pro Gly Thr Ala Val Lys Gly Gly Cys Trp Arg Ser Ala
                100                 105                 110

Asn Ala Tyr Pro Glu Leu Val Ala Glu Ala Tyr Asp Phe Ala Gly His
            115                 120                 125

Leu Ser Phe Leu Ala Cys Ser Gly Gln Arg Gly Tyr Ala Met Leu Asp
        130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                    165                 170                 175

Val Leu Lys Thr Cys Met Val Arg Val Pro Leu Leu Asp Ser Lys Ala
                180                 185                 190

Cys Thr Asp Gln Glu Asp Ala Ile Arg Lys Arg Met Ala Lys Phe Glu
                195                 200                 205

Thr Thr Phe Glu Glu Leu Ile Ser Glu Val Arg Thr Arg Ala Pro Asp
        210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
            275                 280                 285

Val Asp Val Tyr His Ala Leu Asp Gly His Glu Ile Gly Ser Asp Glu
        290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
            355                 360                 365

Gly Glu Val Gly
        370

<210> SEQ ID NO 29
<211> LENGTH: 300
<212> TYPE: PRT
<213> ORGANISM: Corynebacterium efficiens

<400> SEQUENCE: 29

Met Arg Thr Thr Val Ile Ala Ala Ser Ala Leu Leu Leu Leu Ala Gly
 1               5                  10                  15

Cys Ala Asp Gly Ala Arg Glu Glu Thr Ala Gly Ala Pro Pro Gly Glu
```

```
            20                  25                  30
Ser Ser Gly Gly Ile Arg Glu Glu Gly Ala Glu Ala Ser Thr Ser Ile
        35                  40                  45

Thr Asp Val Tyr Ile Ala Leu Gly Asp Ser Tyr Ala Ala Met Gly Gly
50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
        275                 280                 285

Val Arg Asp Ala Leu Gly Leu Glu Pro Val Gln Pro
    290                 295                 300

<210> SEQ ID NO 30
<211> LENGTH: 284
<212> TYPE: PRT
<213> ORGANISM: Novosphingobium aromaticivorans

<400> SEQUENCE: 30

Met Gly Gln Val Lys Leu Phe Ala Arg Arg Cys Ala Pro Val Leu Leu
1               5                   10                  15

Ala Leu Ala Gly Leu Ala Pro Ala Ala Thr Val Ala Arg Glu Ala Pro
            20                  25                  30

Leu Ala Glu Gly Ala Arg Tyr Val Ala Leu Gly Ser Ser Phe Ala Ala
        35                  40                  45

Gly Pro Gly Val Gly Pro Asn Ala Pro Gly Ser Pro Glu Arg Cys Gly
    50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
```

```
                      100                 105                 110
Thr Arg Leu Val Thr Leu Thr Ile Gly Gly Asn Asp Val Ser Phe Val
            115                 120                 125
Gly Asn Ile Phe Ala Ala Ala Cys Glu Lys Met Ala Ser Pro Asp Pro
        130                 135                 140
Arg Cys Gly Lys Trp Arg Glu Ile Thr Glu Glu Trp Gln Ala Asp
145                 150                 155                 160
Glu Glu Arg Met Arg Ser Ile Val Arg Gln Ile His Ala Arg Ala Pro
                165                 170                 175
Leu Ala Arg Val Val Val Val Asp Tyr Ile Thr Val Leu Pro Pro Ser
            180                 185                 190
Gly Thr Cys Ala Ala Met Ala Ile Ser Pro Asp Arg Leu Ala Gln Ser
        195                 200                 205
Arg Ser Ala Ala Lys Arg Leu Ala Arg Ile Thr Ala Arg Val Ala Arg
    210                 215                 220
Glu Glu Gly Ala Ser Leu Leu Lys Phe Ser His Ile Ser Arg Arg His
225                 230                 235                 240
His Pro Cys Ser Ala Lys Pro Trp Ser Asn Gly Leu Ser Ala Pro Ala
                245                 250                 255
Asp Asp Gly Ile Pro Val His Pro Asn Arg Leu Gly His Ala Glu Ala
            260                 265                 270
Ala Ala Ala Leu Val Lys Leu Val Lys Leu Met Lys
        275                 280

<210> SEQ ID NO 31
<211> LENGTH: 268
<212> TYPE: PRT
<213> ORGANISM: Streptomyces coelicolor

<400> SEQUENCE: 31

Met Arg Arg Phe Arg Leu Val Gly Phe Leu Ser Ser Leu Val Leu Ala
1               5                   10                  15
Ala Gly Ala Ala Leu Thr Gly Ala Ala Thr Ala Gln Ala Ala Gln Pro
            20                  25                  30
Ala Ala Ala Asp Gly Tyr Val Ala Leu Gly Asp Ser Tyr Ser Ser Gly
        35                  40                  45
Val Gly Ala Gly Ser Tyr Ile Ser Ser Ser Gly Asp Cys Lys Arg Ser
    50                  55                  60
Thr Lys Ala His Pro Tyr Leu Trp Ala Ala Ala His Ser Pro Ser Thr
65                  70                  75                  80
Phe Asp Phe Thr Ala Cys Ser Gly Ala Arg Thr Gly Asp Val Leu Ser
                85                  90                  95
Gly Gln Leu Gly Pro Leu Ser Ser Gly Thr Gly Leu Val Ser Ile Ser
            100                 105                 110
Ile Gly Gly Asn Asp Ala Gly Phe Ala Asp Thr Met Thr Thr Cys Val
        115                 120                 125
Leu Gln Ser Glu Ser Ser Cys Leu Ser Arg Ile Ala Thr Ala Glu Ala
    130                 135                 140
Tyr Val Asp Ser Thr Leu Pro Gly Lys Leu Asp Gly Val Tyr Ser Ala
145                 150                 155                 160
Ile Ser Asp Lys Ala Pro Asn Ala His Val Val Ile Gly Tyr Pro Arg
                165                 170                 175
Arg Phe Tyr Lys Leu Gly Thr Thr Cys Ile Gly Leu Ser Glu Thr Lys
            180                 185                 190
Arg Thr Ala Ile Asn Lys Ala Ser Asp His Leu Asn Thr Val Leu Ala
```

```
                195              200                205
Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265

<210> SEQ ID NO 32
<211> LENGTH: 269
<212> TYPE: PRT
<213> ORGANISM: Streptomyces avermitilis

<400> SEQUENCE: 32

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Thr Gly Leu Val Ser Leu Thr
            100                 105                 110

Ile Gly Gly Asn Asp Ala Gly Phe Ser Asp Val Met Thr Thr Cys Val
            115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 33
<211> LENGTH: 267
<212> TYPE: PRT
<213> ORGANISM: Streptomyces sp.

<400> SEQUENCE: 33
```

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65              70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 34
<211> LENGTH: 317
<212> TYPE: PRT
<213> ORGANISM: Aeromonas hydrophila

<400> SEQUENCE: 34

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65              70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110
```

```
Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Asn Leu Ala Arg Gln Leu Ala
            180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Gln Arg Asn Ala
            210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
            275                 280                 285

Gln Val His Pro Thr Thr Val Val His Ala Ala Leu Ser Glu Pro Ala
            290                 295                 300

Ala Thr Phe Ile Glu Ser Gln Tyr Glu Phe Leu Ala His
305                 310                 315

<210> SEQ ID NO 35
<211> LENGTH: 318
<212> TYPE: PRT
<213> ORGANISM: Aeromonas salmonicida

<400> SEQUENCE: 35

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175
```

Ser Ala Tyr His Asn Lys Leu Leu Asn Leu Ala Arg Gln Leu Ala
        180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
        210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
                260                 265                 270

Arg Arg Ser Ala Ser Pro Leu Asn Cys Glu Gly Lys Met Phe Trp Asp
                275                 280                 285

Gln Val His Pro Thr Thr Val Val His Ala Ala Leu Ser Glu Arg Ala
                290                 295                 300

Ala Thr Phe Ile Glu Thr Gln Tyr Glu Phe Leu Ala His Gly
305                 310                 315

<210> SEQ ID NO 36
<211> LENGTH: 1371
<212> TYPE: DNA
<213> ORGANISM: Streptomyces thermosacchari

<400> SEQUENCE: 36

```
acaggccgat gcacggaacc gtacctttcc gcagtgaagc gctctccccc catcgttcgc      60
cgggacttca tccgcgattt tggcatgaac acttccttca acgcgcgtag cttgctacaa     120
gtgcggcagc agacccgctc gttggaggct cagtgagatt gacccgatcc ctgtcggccg     180
catccgtcat cgtcttcgcc ctgctgctcg cgctgctggg catcagcccg gccaggcag      240
ccggcccggc ctatgtggcc ctgggggatt cctattcctc gggcaacggc gccggaagtt     300
acatcgattc gagcggtgac tgtcaccgca gcaacaacgc gtaccccgcc cgctgggcgg     360
cggccaacgc accgtcctcc ttcaccttcg cggcctgctc gggagcggtg accacggatg     420
tgatcaacaa tcagctgggc gccctcaacg cgtccaccgg cctggtgagc atcaccatcg     480
gcggcaatga cgcgggcttc gcggacgcga tgaccacctg cgtcaccagc tcggacagca     540
cctgcctcaa ccggctggcc accgccacca actacatcaa caccaccctg ctcgcccggc     600
tcgacgcggt ctacagccag atcaaggccg tgcccccaa cgcccgcgtg gtcgtcctcg      660
gctacccgcg catgtacctg gcctcgaacc cctggtactg cctgggcctg agcaacacca     720
agcgcgcggc catcaacacc accgccgaca ccctcaactc ggtgatctcc tcccgggcca     780
ccgcccacgg attccgattc ggcgatgtcc gcccgacctt caacaaccac gaactgttct     840
tcggcaacga ctggctgcac tcactcaccc tgccggtgtg ggagtcgtac cacccccacca    900
gcacgggcca tcagagcggc tatctgccgg tcctcaacgc caacagctcg acctgatcaa    960
cgcacggccg tgcccgcccc gcgcgtcacg ctcggcgcgg cgccgcagc gcgttgatca    1020
gcccacagtg ccggtgacgg tccaccgtc acggtcgagg gtgtacgtca cggtggcgcc    1080
gctccagaag tggaacgtca gcaggaccgt ggagccgtcc ctgacctcgt cgaagaactc    1140
cggggtcagc gtgatcaccc ctcccccgta gccgggggcg aaggcggcgc cgaactcctt    1200
gtaggacgtc cagtcgtgcg gcccggcgtt gccaccgtcc gcgtagaccg cttccatggt    1260
cgccagccgg tccccgcgga actcggtggg gatgtccgtg cccaaggtgg tcccggtggt    1320
```

```
gtccgagagc accgggggct cgtaccggat gatgtgcaga tccaaagaat t         1371
```

<210> SEQ ID NO 37
<211> LENGTH: 267
<212> TYPE: PRT
<213> ORGANISM: Streptomyces thermosacchari

<400> SEQUENCE: 37

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265
```

<210> SEQ ID NO 38
<211> LENGTH: 548
<212> TYPE: PRT
<213> ORGANISM: Thermobifida fusca

<400> SEQUENCE: 38

```
Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60
```

```
Ser Thr Arg Asp Ala Glu Thr Val Trp Arg Lys His Leu Gln Pro Arg
 65                  70                  75                  80

Pro Asp Gly Gly Phe Arg Pro His Leu Gly Val Gly Cys Leu Leu Ala
                 85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
            115                 120                 125

Gly Asp Ser Ser Pro Pro Phe Arg Ala Gly Trp Ser Leu Pro Pro Lys
        130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Leu Phe Leu Gly
            180                 185                 190

Ile Pro Ala Leu Val Leu Val Thr Ala Leu Thr Leu Val Leu Ala Val
            195                 200                 205

Pro Thr Gly Arg Glu Thr Leu Trp Arg Met Trp Cys Glu Ala Thr Gln
210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
                260                 265                 270

Asp Tyr Tyr Pro Gly Thr Ala Val Lys Gly Gly Cys Trp Arg Ser Ala
            275                 280                 285

Asn Ala Tyr Pro Glu Leu Val Ala Glu Ala Tyr Asp Phe Ala Gly His
        290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
            340                 345                 350

Val Leu Lys Thr Cys Met Val Arg Val Pro Leu Leu Asp Ser Lys Ala
            355                 360                 365

Cys Thr Asp Gln Glu Asp Ala Ile Arg Lys Arg Met Ala Lys Phe Glu
370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
            420                 425                 430

Glu Thr Ile Gln Glu Phe Asn Gln Gln Leu Ala Glu Ala Val Ala Val
        435                 440                 445

His Asp Glu Glu Ile Ala Ala Ser Gly Gly Val Gly Ser Val Glu Phe
        450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
```

```
                        485                 490                 495
Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
            515                 520                 525

Tyr Ala Thr Phe Ala Val Val Ala Gly Ala Thr Val Asp Thr Leu Ala
            530                 535                 540

Gly Glu Val Gly
545

<210> SEQ ID NO 39
<211> LENGTH: 3000
<212> TYPE: DNA
<213> ORGANISM: Thermobifida fusca

<400> SEQUENCE: 39
ggtggtgaac cagaacaccc ggtcgtcggc gtgggcgtcc aggtgcaggt gcaggttctt      60
caactgctcc agcaggatgc cgccgtggcc gtgcacgatg ccttgggca ggcctgtggt     120 ccccgacgag tacagcaccc atagcggatg tcgaacggc agcggggtga actccagttc     180
cgcgccttcg cccgcggctt cgaactccgc ccaggacagg gtgtcggcga cagggccgca     240
gcccaggtac ggcaggacga cggtgtgctg caggctgggc atgccgtcgc gcagggcttt     300
gagcacgtca cggcggtcga agtccttacc gccgtagcgg tagccgtcca cggccagcag     360
cactttcggt tcgatctgcg cgaaccggtc gaggacgctg cgcaccccga agtcggggga     420
acaggacgac caggtcgcac cgatcgcggc gcaggcgagg aatgcggccg tcgcctcggc     480
gatgttcggc aggtaggcca cgaccccgtc gccgggccc accccgaggc tgcggagggc     540
cgcagcgatc gcggcggtgc gggtccgcag ttctccccag gtccactcgg tcaacggccg     600
gagttcggac gcgtgccgga tcgccacggc tgatgggtca cggtcgcgga agatgtgctc     660
ggcgtagttg agggtggcgc cggggaacca cgacggcgccg gcatggcgt cggaggcgag     720 cactgtggtg tacggggtgg cggcgcgcac ccggtagtac tcccagatcg cggaccagaa     780
tccttcgagg tcggttaccg accagcgcca cagtgcctcg tagtccggtg cgtccacacc     840
gcggtgctcc cgcacccagc gggtgaacgc ggtgaggttg gcgcgttctt tgcgctcctc     900
gtcgggactc cacaggatcg gcggctgcgg cttgagtgtc atgaaacgcg accccttcgt     960
ggacggtgcg gatgcggtga gcgtcgggtg cctcccctaa cgctccccgg tgacggagtg    1020
ttgtgcacca catctagcac gcgggacgcg gaaaccgtat ggagaaaaca cctacaaccc    1080
cggccggacg gtgggtttcg gccacactta ggggtcgggt gcctgcttgc cgggcagggc    1140
agtcccgggg tgctgtggtg cgggcgggag ggctgtcgct tcgaggtgtg ccggcgggac    1200
actccgggcc tcagccgtac ccgcaacggg gacagttctc ctcccttccg ggctggatgg    1260
tcccttcccc cgaaatgcgg cgagatctcc cagtcagccc ggaaaacacc cgctgtgccc    1320
aggtactctt tgcttcgaac agacaggccg gacggtccac gggggaggtt tgtgggcagc    1380
ggaccacgtg cggcgaccag acgacggttg ttcctcggta tccccgctct tgtacttgtg    1440
acagcgctca cgctggtctt ggctgtcccg acggggcgcg agacgctgtg cgcatgtgg    1500 tgtgaggcca cccaggactg gtgcctgggg gtgccggtcg actcccgcgg acagcctgcg    1560
gaggacggcg agtttctgct gctttctccg gtccaggcag cgacctgggg gaactattac    1620
gcgctcgggg attcgtactc ttcggggggac ggggcccgcg actactatcc cggcaccgcg    1680
gtgaagggcg gttgctggcg gtccgctaac gcctatccgg agctggtcgc cgaagcctac    1740
```

```
gacttcgccg acacttgtc gttcctggcc tgcagcggcc agcgcggcta cgccatgctt    1800
gacgctatcg acgaggtcgg ctcgcagctg gactggaact cccctcacac gtcgctggtg    1860
acgatcggga tcggcggcaa cgatctgggg ttctccacgg ttttgaagac ctgcatggtg    1920
cgggtgccgc tgctgacag caaggcgtgc acggaccagg aggacgctat ccgcaagcgg    1980
atggcgaaat tcgagacgac gttgaagag ctcatcagcg aagtgcgcac ccgcgcgccg    2040
gacgcccgga tccttgtcgt gggctacccc cggattttc cggaggaacc gaccggcgcc    2100
tactacacgc tgaccgcgag caaccagcgg tggctcaacg aaaccattca ggagttcaac    2160
cagcagctcg ccgaggctgt cgcggtccac gacgaggaga ttgccgcgtc gggcggggtg    2220
ggcagcgtgg agttcgtgga cgtctaccac gcgttggacg ccacgagat cggctcggac    2280 gagccgtggg tgaacggggt gcagttgcgg gacctcgcca ccggggtgac tgtggaccgc    2340
agtaccttcc accccaacgc cgctgggcac cgggcggtcg gtgagcgggt catcgagcag    2400
atcgaaaccg gccgggccg tccgctctat gccactttcg cggtggtggc ggggcgacc    2460 gtggacactc tcgcgggcga ggtggggtga cccggcttac cgtccggccc gcaggtctgc    2520
gagcactgcg gcgatctggt ccactgccca gtgcagttcg tcttcggtga tgaccagcgg    2580
cggggagagc cggatcgttg agccgtgcgt gtctttgacg agcacacccc gctgcaggag    2640
ccgttcgcac agttctcttc cggtggccag agtcgggtcg acgtcgatcc cagcccacag    2700
gccgatgctg cgggccgcga ccacgccgtt gccgaccagt tggtcgaggc gggcgcgcag    2760 cacggggcg agggcgcgga catggtccag gtaagggccg tcgcggacga ggctcaccac    2820
ggcagtgccg accgcgcagg cgagggcgtt gccgccgaag gtgctgccgt gctggccggg    2880
gcggatcacg tcgaagactt ccgcgtcgcc taccgccgcc gcacgggca ggatgccgcc    2940 gcccagcgct ttgccgaaca ggtagatatc ggcgtcgact ccgctgtggt cgcaggcccg    3000
```

<210> SEQ ID NO 40
<211> LENGTH: 372
<212> TYPE: PRT
<213> ORGANISM: Thermobifida fusca

<400> SEQUENCE: 40

```
Val Gly Ser Gly Pro Arg Ala Ala Thr Arg Arg Leu Phe Leu Gly
 1               5                  10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
        50                  55                  60

Asp Gly Glu Phe Leu Leu Leu Ser Pro Val Gln Ala Ala Thr Trp Gly
    65                  70                  75                  80

Asn Tyr Tyr Ala Leu Gly Asp Ser Tyr Ser Gly Asp Gly Ala Arg
                85                  90                  95

Asp Tyr Tyr Pro Gly Thr Ala Val Lys Gly Gly Cys Trp Arg Ser Ala
                100                 105                 110

Asn Ala Tyr Pro Glu Leu Val Ala Glu Ala Tyr Asp Phe Ala Gly His
            115                 120                 125

Leu Ser Phe Leu Ala Cys Ser Gly Gln Arg Gly Tyr Ala Met Leu Asp
        130                 135                 140

Ala Ile Asp Glu Val Gly Ser Gln Leu Asp Trp Asn Ser Pro His Thr
    145                 150                 155                 160
```

```
Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 41
<211> LENGTH: 300
<212> TYPE: PRT
<213> ORGANISM: Corynebacterium efficiens

<400> SEQUENCE: 41

Met Arg Thr Thr Val Ile Ala Ala Ser Ala Leu Leu Leu Ala Gly
1               5                   10                  15

Cys Ala Asp Gly Ala Arg Glu Glu Thr Ala Gly Ala Pro Pro Gly Glu
            20                  25                  30

Ser Ser Gly Gly Ile Arg Glu Glu Gly Ala Glu Ala Ser Thr Ser Ile
        35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160
```

```
Leu Leu Gly Glu Thr Ile Gly Glu Gln Leu Asp Gln Leu Pro Pro Gln
                165                 170                 175

Leu Asp Arg Val His Glu Ala Ile Asp Arg Ala Gly Asp Ala Gln
        180                 185                 190

Val Val Val Thr Gly Tyr Leu Pro Leu Val Ser Ala Gly Asp Cys Pro
            195                 200                 205

Glu Leu Gly Asp Val Ser Glu Ala Asp Arg Arg Trp Ala Val Glu Leu
        210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Gln Thr Asp Ala
            260                 265                 270

Tyr Pro Leu His Pro Thr Ser Ala Gly His Glu Ala Met Ala Ala Ala
            275                 280                 285

Val Arg Asp Ala Leu Gly Leu Glu Pro Val Gln Pro
            290                 295                 300

<210> SEQ ID NO 42
<211> LENGTH: 3000
<212> TYPE: DNA
<213> ORGANISM: Corynebacterium efficiens

<400> SEQUENCE: 42
ttctggggtg ttatggggtt gttatcggct cgtcctgggt ggatcccgcc aggtggggta      60
ttcacggggg acttttgtgt ccaacagccg agaatgagtg ccctgagcgg tgggaatgag     120
gtgggcgggg ctgtgtcgcc atgaggggc ggcgggctct gtggtgcccc gcgaccccg      180 gccccggtga gcggtgaatg aaatccggct gtaatcagca tcccgtgccc accccgtcgg     240
ggaggtcagc gcccggagtg tctacgcagt cggatcctct cggactcggc catgctgtcg     300
gcagcatcgc gctcccgggt cttggcgtcc ctcggctgtt ctgcctgctg tccctggaag     360
gcgaaatgat caccggggag tgatacaccg gtggtctcat cccggatgcc cacttcggcg     420
ccatccggca attcgggcag ctcccgggtgg aagtaggtgg catccgatgc gtcggtgacg     480
ccatagtggg cgaagatctc atcctgctcg agggtgctca ggccactctc cggatcgata     540 tcggggcgt ccttgatggc gtccttgctg aaaccgaggt gcagcttgtg ggcttccaat     600
ttcgcaccac ggagcgggac gaggctggaa tgacggccga agagcccgtg gtggaccctca     660 acgaaggtgg gtagtcccgt gtcatcattg aggaacacgc cctccaccgc acccagcttg     720
tggccggagt tgtcgtaggc gctggcatcc agaagggaaa cgatctcata tttgtcggtg     780
tgctcagaca tgatcttcct ttgctgtcgg tgtctggtac taccacggta gggctgaatg     840
caactgttat ttttctgtta tttaggaat tggtccatat cccacaggct ggctgtggtc     900
aaatcgtcat caagtaatcc ctgtcacaca aatggtgtgg tggagccct ggtcgcggtt     960 ccgtgggagg cgccgtgccc cgcaggatcg tcggcatcgg cggatctggc cggtaccccg    1020
cggtgaataa aatcattctg taaccttcat cacggttggt tttaggtatc cgcccctttc    1080
gtcctgaccc cgtccccggc gcgcgggagc ccgcgggttg cggtagacag gggagacgtg    1140
gacaccatga ggacaacggt catcgcagca agcgcattac tccttctcgc cggatgcgcg    1200
gatgggcccg ggaggagac cgccggtgca ccgccgggtg agtcctccgg gggcatccgg    1260
gaggaggggg cggaggcgtc gacaagcatc accgacgtct acatcgccct cgggggattcc   1320 tatgcggcga tgggcgggcg ggatcagccg ttacggggtg agccgttctg cctgcgctcg    1380
```

```
tccggtaatt accoggaact cctccacgca gaggtcaccg atctcacctg ccagggggcg      1440
gtgaccgggg atctgctcga acccaggacg ctggggagc gcacgctgcc ggcgcaggtg      1500
gatgcgctga cggaggacac caccctggtc accctctcca tcgggggcaa tgacctcgga     1560
ttcggggagg tggcgggatg catccgggaa cggatcgccg gggagaacgc tgatgattgc     1620
gtggacctgc tgggggaaac catcggggag cagctcgatc agcttccccc gcagctggac     1680
cgcgtgcacg aggctatccg ggaccgcgcc ggggacgcgc aggttgtggt caccggttac     1740
ctgccgctcg tgtctgccgg ggactgcccc gaactggggg atgtctccga ggcggatcgt     1800
cgttgggcgg ttgagctgac cgggcagatc aacgagaccg tgcgcgaggc ggccgaacga     1860
cacgatgccc tctttgtcct gcccgacgat gccgatgagc acaccagttg tgcaccccca     1920
cagcagcgct gggcggatat ccagggccaa cagaccgatg cctatccgct gcacccgacc     1980
tccgccggcc atgaggcgat ggccgccgcc gtccgggacg cgctgggcct ggaaccggtc     2040
cagccgtagc gccgggcgcg cgcttgtcga cgaccaaccc atgccaggct gcagtcacat     2100
ccgcacatag cgcgcgcggg cgatggagta cgcaccatag aggatgagcc cgatgccgac     2160
gatgatgagc agcacactgc cgaagggttg ttccccgagg gtgcgcagag ccgagtccag     2220
acctgcggcc tgctccggat catgggccca accggcgatg acgatcaaca ccccccaggat    2280 cccgaaggcg ataccacggg cgacataacc ggctgttccg gtgatgatga tcgcggtccc     2340
gacctgccct gaccccgcac ccgcctccag atcctcccgg aaatcccggg tggcccccctt    2400 ccagaggttg tagacacccg ccccagtac caccagcccg cgaccacaa ccagcaccac       2460 accccagggt tgggatagga cggtggcggt gacatcggtg gcggtctccc catcggaggt     2520
gctgccgccc cgggcgaagg tggaggtggt caccgccagg gagaagtaga ccatggccat     2580
gaccgccccc ttggccctttt ccttgaggtc ctcgcccgcc agcagctggc tcaattgcca    2640
gagtcccagg gccgccaggg cgatgacggc aacccacagg aggaactgcc cacccggagc    2700
ctccgcgatg gtggccaggg cacctgaatt cgaggcctca tcacccgaac cgccggatcc     2760
agtggcgatg cgcaccgcga tccaccgat gaggatgtgc agtatgccca ggacaatgaa      2820
accacctctg gccagggtgg tcagcgcggg gtggtcctcg gcctggtcgg cagcccgttc     2880
gatcgtccgt ttcgcggatc tggtgtcgcc cttatccata gctcccattg aaccgccttg     2940
aggggtgggc ggccactgtc agggcggatt gtgatctgaa ctgtgatgtt ccatcaaccc     3000
```

<210> SEQ ID NO 43
<211> LENGTH: 268
<212> TYPE: PRT
<213> ORGANISM: Streptomyces coelicolor

<400> SEQUENCE: 43

Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

```
Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
            115                 120                 125

Leu Gln Ser Glu Ser Ser Cys Leu Ser Arg Ile Thr Ala Glu Ala
        130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
                180                 185                 190

Arg Thr Ala Ile Asn Lys Ala Ser Asp His Leu Asn Thr Val Leu Ala
            195                 200                 205

Gln Arg Ala Ala Ala His Gly Phe Thr Phe Gly Asp Val Arg Thr Thr
        210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
                260                 265
```

<210> SEQ ID NO 44
<211> LENGTH: 2000
<212> TYPE: DNA
<213> ORGANISM: Streptomyces coelicolor

<400> SEQUENCE: 44

```
cccggcggcc cgtgcaggag cagcagccgg cccgcgatgt cctcgggcgt cgtcttcatc      60
aggccgtcca tcgcgtcggc gaccggcgcc gtgtagttgg cccggacctc gtcccaggtg     120
cccgcggcga tctggcgggt ggtgcggtgc gggccgcgcc gaggggagac gtaccagaag     180
cccatcgtca cgttctccgg ctgcggttcg ggctcgtccg ccgctccgtc cgtcgcctcg     240
ccgagcacct tctcggcgag gtcggcgctg gtcgccgtca ccgtgacgtc ggcgccccgg     300
ctccagcgcg agatcagcag cgtccagccg tcgccctccg ccagcgtcgc gctgcggtcg     360
tcgtcgcggg cgatccgcag cacgcgcgcg ccgggcggca gcagcgtggc gccggaccgt     420
acgcggtcga tgttcgccgc gtgcgagtac ggctgctcac ccgtggcgaa cggccgagg     480
aacagcgcgt cgacgacgtc ggacggggag tcgctgtcgt ccacgttgag ccggatcggc     540
agggcttcgt gcgggttcac ggacatgtcg ccatgatcgg gcacccggcc gccgcgtgca     600
cccgctttcc cgggcacgca cgacaggggc tttctcgccg tcttccgtcc gaacttgaac     660
gagtgtcagc catttcttgg catggacact tccagtcaac gcgcgtagct gctaccacgg     720
ttgtggcagc aatcctgcta agggaggttc catgagacgt ttccgacttg tcggcttcct     780
gagttcgctc gtcctcgccg ccggcgccgc cctcaccggg gcagcgaccg cccaggcggc     840
ccaacccgcc gccgccgacg gctatgtggc cctcggcgac tcctactcct ccggggtcgg     900
agcgggcagc tacatcagct cgagcggcga ctgcaagcgc agcacgaagg cccatcccta     960
cctgtgggcg gccgcccact cgccctccac gttcgacttc accgcctgtt ccggcgcccg    1020
tacgggtgat gttctctccg acagctcggc ccgctcagc tccggcaccg gctcgtctc    1080
gatcagcatc ggcggcaacg acgccggttt cgccgacacc atgacgacct gtgtgctcca    1140
```

-continued

```
gtccgagagc tcctgcctgt cgcggatcgc caccgccgag gcgtacgtcg actcgacgct    1200
gcccggcaag ctcgacggcg tctactcggc aatcagcgac aaggcgccga acgcccacgt    1260
cgtcgtcatc ggctacccgc gcttctacaa gctcggcacc acctgcatcg gcctgtccga    1320
gaccaagcgg acggcgatca acaaggcctc cgaccacctc aacaccgtcc tcgcccagcg    1380
cgccgccgcc cacggcttca ccttcggcga cgtacgcacc accttcaccg gccacgagct    1440
gtgctccggc agccctggc tgcacagcgt caactggctg aacatcggcg agtcgtacca    1500
ccccaccgcg gccggccagt ccggtggcta cctgccggtc ctcaacggcg ccgcctgacc    1560
tcaggcggaa ggagaagaag aaggagcgga gggagacgag gagtgggagg ccccgcccga    1620
cggggtcccc gtccccgtct ccgtctccgt cccggtcccg caagtcaccg agaacgccac    1680
cgcgtcggac gtggcccgca ccggactccg cacctccacg cgcacggcac tctcgaacgc    1740
gccggtgtcg tcgtgcgtcg tcaccaccac gccgtcctgg cgcgagcgct cgccgcccga    1800
cgggaaggac agcgtccgcc accccggatc ggagaccgac ccgtccgcgg tcacccaccg    1860
gtagccgacc tccgcgggca gccgcccgac cgtgaacgtc gccgtgaacg cgggtgcccg    1920
gtcgtgcggc ggcggacagg cccccgagta gtgggtgcgc gagcccacca cggtcacctc    1980
caccgactgc gctgcggggc                                                 2000
```

<210> SEQ ID NO 45
<211> LENGTH: 269
<212> TYPE: PRT
<213> ORGANISM: Streptomyces avermitilis

<400> SEQUENCE: 45

```
Met Arg Arg Ser Arg Ile Thr Ala Tyr Val Thr Ser Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Asp Tyr Leu Asn Ser Ala Ile
        195                 200                 205

Ala Lys Arg Ala Ala Asp His Gly Phe Thr Phe Gly Asp Val Lys Ser
    210                 215                 220
```

```
Thr Phe Thr Gly His Glu Ile Cys Ser Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 46
<211> LENGTH: 1980
<212> TYPE: DNA
<213> ORGANISM: Streptomyces avermitilis

<400> SEQUENCE: 46
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggccct     120
tgcccttgct cgacgcggcc ttgaagccgg tgcccttctt gagcgtgacg atgtagctgc     180
ccttgatcgc ggtgggggag ccggcggcga gcaccgtgcc ctcggccggg gtggcctggg     240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacggggt ggctcaaggg      480 agttgagacc ctgtcatgag tctgacatga gcacgcaatc aacggggccg tgagcacccc     540
ggggcgaccc cggaaagtgc cgagaagtct tggcatggac acttcctgtc aacacgcgta     600
gctggtacga cggttacggc agagatcctg ctaaagggag gttccatgag acgttcccga     660
attacggcat acgtgacctc actcctcctc gccgtcggct gcgccctcac cggggcagcg     720
acggcgcagg cgtccccagc cgccgcggcc acgggctatg tggccctcgg cgactcgtac     780
tcgtccggtg tcgcgccgg cagctacctc agctccagcg gcgactgcaa gcgcagttcg      840
aaggcctatc cgtacctctg gcaggccgcg cattcaccct cgtcgttcag tttcatggct     900
tgctcgggcg ctcgtacggg tgatgtcctg gccaatcagc tcggcaccct gaactcgtcc     960
accggcctgg tctccctcac catcggaggc aacgacgcgg gcttctccga cgtcatgacg    1020
acctgtgtgc tccagtccga cagcgcctgc ctctcccgca tcaacacggc gaaggcgtac    1080
gtcgactcca ccctgcccgg ccaactcgac agcgtgtaca cggcgatcag cacgaaggcc    1140
ccgtcggccc atgtggccgt gctgggctac ccccgcttct acaaactggg cggctcctgc    1200
ctcgcgggcc tctcggagac caagcggtcc gccatcaacg acgcggccga ctatctgaac    1260
agcgccatcg ccaagcgcgc cgccgaccac ggcttcacct tcggcgacgt caagagcacc    1320
ttcaccggcc atgagatctg ctccagcagc acctggctgc acagtctcga cctgctgaac    1380
atcggccagt cctaccaccc gaccgcggcc ggccagtccg gcggctatct gccggtcatg    1440
aacagcgtgg cctgagctcc cacggcctga atttttaagg cctgaatttt taaggcgaag    1500
gtgaaccgga agcggaggcc ccgtccgtcg gggtctccgt cgcacaggtc accgagaacg    1560
gcacggagtt ggacgtcgtg cgcaccgggt cgcgcacctc gacggcgatc tcgttcgaga    1620
tcgttccgct cgtgtcgtac gtggtgacga cacctgcttc tgctgggtc tttccgccgc     1680 tcgccgggaa ggacagcgtc ttccagcccg gatccggac ctcgcccttc ttggtcaccc     1740
agcggtactc cacctcgacc ggcaccggcc ccaccgtgaa ggtcgccgtg aacgtgggcg    1800
cctgggcggt gggcggcggg caggcaccgg agtagtcggt gtgcacgccg gtgaccgtca    1860
ccttcacgga ctgggccggc ggggtcgtcg taccgccgcc gccaccgccg cctcccggag    1920
```
tggagcccga gctgtggtcg cccccgccgt cggcgttgtc gtcctcgggg gttttcgaac    1980

<210> SEQ ID NO 47
<211> LENGTH: 372
<212> TYPE: PRT
<213> ORGANISM: Thermobifida fusca

<400> SEQUENCE: 47

Met Gly Ser Gly Pro Arg Ala Ala Thr Arg Arg Leu Phe Leu Gly
1               5                  10                  15

Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 48
<211> LENGTH: 968
<212> TYPE: DNA
<213> ORGANISM: Thermobifida fusca

<400> SEQUENCE: 48

| | | | | | | |
|---|---|---|---|---|---|---|
| ctgcagacac | ccgccccgcc | ttctcccgga | tcgtcatgtt | cggcgactcc | ctcagcgaca | 60 |
| ccggcaagat | gtactccaag | atgcgcggct | acctgccgtc | ctccccgccg | tactacgagg | 120 |
| gccgcttctc | gaacggcccg | gtctggctgg | agcagctgac | gaagcagttc | cccggcctga | 180 |
| cgatcgccaa | cgaggccgag | gggggcgcga | ccgcagtcgc | ctacaacaag | atctcctgga | 240 |
| acccgaagta | ccaggtcatt | aacaacctcg | actacgaggt | cacccagttc | ttgcagaagg | 300 |
| actcgttcaa | gcccgacgac | ctggtcatcc | tgtgggtggg | cgccaacgac | tacctggcct | 360 |
| acggttggaa | cacggagcag | gacgccaagc | gggtgcgcga | cgccatctcg | gacgcggcaa | 420 |
| accgcatggt | cctgaacggc | gcgaagcaga | tcctgctgtt | caacctgccc | gacctgggcc | 480 |
| agaacccgtc | cgcccgctcc | cagaaggtcg | tcgaggccgt | ctcgcacgtg | tccgcctacc | 540 |
| acaacaagct | gctcctcaac | ctcgcccggc | agctcgcccc | gacgggcatg | gtcaagctgt | 600 |
| tcgagatcga | caagcagttc | gcggagatgc | tgcgcgaccc | ccagaacttc | ggcctgagcg | 660 |
| acgtggagaa | cccgtgctac | gacggcggct | acgtgtggaa | gccgttcgcc | acccggtccg | 720 |
| tctcgaccga | ccggcagctg | tcggccttct | cgccccagga | gcgcctggcg | atcgctggca | 780 |
| acccgctcct | ggcacaggcg | gtagcttcgc | cgatggcccg | ccgctcggcc | tcgcccctca | 840 |
| actgcgaggg | caagatgttc | tgggaccagg | tccaccccac | caccgtggtc | cacgccgccc | 900 |
| tctcggagcg | cgccgccacc | ttcatcgaga | cccagtacga | gttcctcgcc | cactagtcta | 960 |
| gaggatcc | | | | | | 968 |

<210> SEQ ID NO 49
<211> LENGTH: 1044
<212> TYPE: DNA
<213> ORGANISM: Aeromonas salmonicida

<400> SEQUENCE: 49

| | | | | | | |
|---|---|---|---|---|---|---|
| atgaaacaac | aaaaacggct | ttacgcccga | ttgctgacgc | tgttatttgc | gctcatcttc | 60 |
| ttgctgcctc | attctgcagc | ttcagcagca | gatacaagac | cggcgtttag | ccggatcgtc | 120 |
| atgtttggag | atagcctgag | cgatacgggc | aaaatgtata | gcaaaatgag | aggctatctt | 180 |
| ccgtcaagcc | cgccgtatta | tgaaggccgc | tttagcaatg | gaccggtctg | gctgaacaa | 240 |
| ctgacgaaac | aatttccggg | actgacgatc | gctaatgaag | cagaaggagg | agcaacagcg | 300 |
| gtcgcctata | caaaaatcag | ctgggacccg | aaatatcagg | tcatcaacaa | cctggactat | 360 |
| gaagtcacac | agtttcttca | gaaagacagc | tttaaaccgg | atgatctggt | catcctttgg | 420 |
| gtcggcgcca | atgattatct | ggcgtatggc | tggaacacag | aacaagatgc | caaaagagtc | 480 |
| agagatgcca | tcagcgatgc | cgctaataga | atggtcctga | acgcgccaa | acaaatcctg | 540 |
| ctgtttaacc | tgccggatct | gggacaaaat | ccgagcgcca | gaagccaaaa | agtcgtcgaa | 600 |
| gcagtcagcc | atgtcagcgc | ctatcataac | aaactgctgc | tgaacctggc | aagacaattg | 660 |
| gcaccgacgg | gaatggttaa | attgtttgaa | attgacaaac | agtttgccga | aatgctgaga | 720 |
| gatccgcaaa | attttggcct | gagcgatgtc | gaaaacccgt | gctatgatgg | cggatatgtc | 780 |
| tggaaaccgt | ttgccacaag | aagcgtcagc | acggatagac | aactgtcagc | gtttagcccg | 840 |

| caagaaagac tggcaatcgc cggaaatccg cttttggcac aagcagttgc ttcaccgatg | 900 |
| gcaagaagat cagcaagccc gctgaattgc gaaggcaaaa tgttttggga tcaggtccat | 960 |
| ccgacaacag ttgtccatgc tgcccttttca gaaagagcgg cgacgtttat cgaaacacag | 1020 |
| tatgaatttc tggcccatgg ctga | 1044 |

```
<210> SEQ ID NO 50
<211> LENGTH: 1005
<212> TYPE: DNA
<213> ORGANISM: Aeromonas hydrophila

<400> SEQUENCE: 50
```

| atgaaaaaat ggtttgtgtg tttattggga ttggtcgcgc tgacagttca ggcagccgac | 60 |
| agccgtcccg ccttctcccg gatcgtgatg tttggcgaca gcctctccga taccggcaag | 120 |
| atgtacagca agatgcgcgg ttacctcccc tccagccccc cctactatga gggccgcttc | 180 |
| tccaacgggc ccgtctggct ggagcagctg accaacgagt tcccgggcct gaccatagcc | 240 |
| aacgaggcgg aaggcggacc gaccgccgtg gcttacaaca agatctcctg gaatcccaag | 300 |
| tatcaggtca tcaacaacct ggactacgag gtcacccagt tcctgcaaaa agacagcttc | 360 |
| aagccggacg atctggtgat cctctgggtc ggcgccaacg actatctggc ctatggctgg | 420 |
| aacacagagc aggatgccaa gcgggtgcgc gacgccatca gcgatgcggc caaccgcatg | 480 |
| gtgctgaacg gcgccaagga gatactgctg ttcaacctgc cggatctggg ccagaacccc | 540 |
| tcggcccgca gccagaaggt ggtcgaggcg ccagccatg tctccgccta ccacaaccag | 600 |
| ctgctgctga acctggcacg ccagctggct cccaccggca tggtgaagct gttcgagatc | 660 |
| gacaagcagt tgccgagat gctgcgtgat ccgcagaact tcggcctgag cgaccagagg | 720 |
| aacgcctgct acggtggcag ctatgtatgg aagccgtttg cctcccgcag cgccagcacc | 780 |
| gacagccagc tctccgcctt caacccgcag gagcgcctcg ccatcgccgg caacccgctg | 840 |
| ctggcccagg ccgtcgccag ccccatggct gcccgcagcg ccagcaccct caactgtgag | 900 |
| ggcaagatgt tctgggatca ggtccacccc accactgtcg tgcacgccgc cctgagcgag | 960 |
| cccgccgcca ccttcatcga gagccagtac gagttcctcg cccac | 1005 |

```
<210> SEQ ID NO 51
<211> LENGTH: 1011
<212> TYPE: DNA
<213> ORGANISM: Aeromonas salmonicida

<400> SEQUENCE: 51
```

| atgaaaaaat ggtttgtttg tttattgggg ttgatcgcgc tgacagttca ggcagccgac | 60 |
| actcgccccg ccttctcccg gatcgtgatg ttcggcgaca gcctctccga taccggcaaa | 120 |
| atgtacagca agatgcgcgg ttacctcccc tccagcccgc cctactatga gggccgtttc | 180 |
| tccaacggac ccgtctggct ggagcagctg accaagcagt tcccgggtct gaccatcgcc | 240 |
| aacgaagcgg aaggcggtgc cactgccgtg gcttacaaca agatctcctg gaatcccaag | 300 |
| tatcaggtct acaacaacct ggactacgag gtcacccagt tcttgcagaa agacagcttc | 360 |
| aagccggacg atctggtgat cctctgggtc ggtgccaatg actatctggc atatggctgg | 420 |
| aatacggagc aggatgccaa gcgagttcgc gatgccatca gcgatgcggc caaccgcatg | 480 |
| gtactgaacg gtgccaagca gatactgctg ttcaacctgc cggatctggg ccagaacccg | 540 |
| tcagcccgca gtcagaaggt ggtcgaggcg gtcagccatg tctccgccta tcacaacaag | 600 |
| ctgctgctga acctggcacg ccagctggcc cccaccggca tggtaaagct gttcgagatc | 660 |

```
gacaagcaat tgccgagat gctgcgtgat ccgcagaact tcggcctgag cgacgtcgag    720
aacccctgct acgacggcgg ctatgtgtgg aagccgtttg ccacccgcag cgtcagcacc    780
gaccgccagc tctccgcctt cagtccgcag gaacgcctcg ccatcgccgg caacccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcga gacccagtac gagttcctcg cccacggatg a           1011

<210> SEQ ID NO 52
<211> LENGTH: 888
<212> TYPE: DNA
<213> ORGANISM: Streptomyces coelicolor

<400> SEQUENCE: 52
atgccgaagc tgcccttcg ccgtgtcatg accgcgacag tcgccgccgt cggcacgctc     60
gccctcggcc tcaccgacgc caccgcccac gccgcgcccg cccaggccac tccgaccctg    120
gactacgtcg ccctcggcga cagctacagc gccggctccg gcgtcctgcc cgtcgacccc    180
gccaacctgc tctgtctgcg ctcgacggcc aactacccc acgtcatcgc ggacacgacg    240
ggcgcccgcc tcacggacgt cacctgcggc gccgcgcaga ccgccgactt cacgcgggcc    300
cagtacccgg gcgtcgcacc ccagttggac gcgctcggca ccggcacgga cctggtcacg    360
ctcaccatcg gcggcaacga caacagcacc ttcatcaacg ccatcacggc ctgcggcacg    420
gcgggtgtcc tcagcggcgg caagggcagc ccctgcaagg acaggcacgg cacctccttc    480
gacgacgaga tcgaggccaa cacgtacccc gcgctcaagg aggcgctgct cggcgtccgc    540
gccagggctc cccacgccag ggtggcggct ctcggctacc cgtggatcac cccggccacc    600
gccgacccgt cctgcttcct gaagctcccc ctcgccgccg gtgacgtgcc ctacctgcgg    660
gccatccagg cacacctcaa cgacgcgtc cggcgggccg ccgaggagac cggagccacc    720
tacgtggact tctccggggt gtccgacggc cacgacgcct gcgaggcccc cggcacccgc    780
tggatcgaac cgctgctctt cgggcacagc ctcgttcccg tccacccccaa cgccctgggc    840 gagcggcgca tggccgagca cacgatggac gtcctcggcc tggactga                888

<210> SEQ ID NO 53
<211> LENGTH: 888
<212> TYPE: DNA
<213> ORGANISM: Streptomyces coelicolor

<400> SEQUENCE: 53
tcagtccagg ccgaggacgt ccatcgtgtg ctcggccatg cgccgctcgc ccagggcgtt     60
ggggtggacg ggaacgaggc tgtgcccgaa gagcagcggt tcgatccagc gggtgccggg    120
ggcctcgcag gcgtcgtggc cgtcggacac cccggagaag tccacgtagg tggctccggt    180
ctcctcggcg gcccgccgga ccgcgtcgtt gaggtgtgcc tggatggccc gcaggtaggg    240
cacgtcaccg gcggcgaggg ggagcttcag gaagcaggac gggtcggcgg tggccggggt    300
gatccacggg tagccgagag ccgccaccct ggcgtgggga gccctggcgc ggacgccgag    360
cagcgcctcc ttgagcgcgg ggtacgtgtt ggcctcgatc tcgtcgtcga aggaggtgcc    420
gtgcctgtcc ttgcagggggc tgcccttgcc gccgctgagg acacccgccg tgccgcaggc    480
cgtgatggcg ttgatgaagg tgctgttgtc gttgccgccg atggtgagcg tgaccaggtc    540
cgtgccggtg ccgagcgcgt ccaactgggg tgcgacgccc gggtactggg cccgcgtgaa    600
gtcggcggtc tgcgcggcgc cgcaggtgac gtccgtgagg cggcgcccg tcgtgtccgc    660
```

```
gatgacgtgg gggtagttgg ccgtcgagcg cagacagagc aggttggcgg ggtcgacggg      720
caggacgccg gagccggcgc tgtagctgtc gccgagggcg acgtagtcca gggtcggagt      780
ggcctgggcg ggcgcggcgt gggcggtggc gtcggtgagg ccgagggcga gcgtgccgac      840
ggcggcgact gtcgcggtca tgacacggcg aagggcaggc ttcggcat                   888

<210> SEQ ID NO 54
<211> LENGTH: 717
<212> TYPE: DNA
<213> ORGANISM: Saccharomyces cerevisiae

<400> SEQUENCE: 54
atggattacg agaagtttct gttatttggg gattccatta ctgaatttgc ttttaatact       60
aggcccattg aagatggcaa agatcagtat gctcttggag ccgcattagt caacgaatat      120
acgagaaaaa tggatattct tcaaagaggg ttcaaagggt acacttctag atgggcgttg      180
aaaatacttc ctgagatttt aaagcatgaa tccaatattg tcatggccac aatattttg      240 ggtgccaacg atgcatgctc agcaggtccc caaagtgtcc ccctccccga atttatcgat      300
aatattcgtc aaatggtatc tttgatgaag tcttaccata tccgtcctat tataatagga      360
ccggggctag tagatagaga gaagtgggaa aagaaaaat ctgaagaaat agctctcgga      420
tacttccgta ccaacgagaa ctttgccatt tattccgatg ccttagcaaa actagccaat      480
gaggaaaaag ttcccttcgt ggctttgaat aaggcgtttc aacaggaagg tggtgatgct      540
tggcaacaac tgctaacaga tggactgcac ttttccggaa aagggtacaa aattttcat      600 gacgaattat tgaaggtcat tgagacattc taccccaat atcatccaa aaacatgcag      660 tacaaactga agattggag agatgtgcta gatgatggat ctaacataat gtcttga       717

<210> SEQ ID NO 55
<211> LENGTH: 1044
<212> TYPE: DNA
<213> ORGANISM: Ralstonia sp.

<400> SEQUENCE: 55
atgaacctgc gtcaatggat gggcgccgcc acggctgccc ttgccttggg cttggccgcg       60 tgcggggcg gtgggaccga ccagagcggc aatcccaatg tcgccaaggt gcagcgcatg      120
gtggtgttcg gcgacagcct gagcgatatc ggcacctaca ccccgtcgc gcaggcggtg      180 ggcggcggca gttcaccac caacccgggc ccgatctggg ccgagaccgt ggccgcgcaa      240
ctgggcgtga cgctcacgcc ggcggtgatg ggctacgcca cctccgtgca gaattgcccc      300
aaggccggct gcttcgacta tgcgcagggc ggctcgcgcg tgaccgatcc gaacggcatc      360
ggccacaacg gcgcgcggg ggcgctgacc tacccggttc agcagcagct cgccaacttc      420
tacgcggcca gcaacaacac attcaacggc aataacgatg tcgtcttcgt gctggccggc      480
agcaacgaca ttttcttctg gaccactgcg gcggccacca gcggctccgg cgtgacgccc      540
gccattgcca cggcccaggt gcagcaggcc gcgacggacc tggtcggcta tgtcaaggac      600
atgatcgcca agggtgcgac gcaggtctac gtgttcaacc tgcccgacag cagcctgacg      660
ccggacggcg tggcaagcgg cacgaccggc caggcgctgc tgcacgcgct ggtgggcacg      720
ttcaacacga cgctgcaaag cgggctggcc ggcacctcgg cgcgcatcat cgacttcaac      780
gcacaactga ccgcggcgat ccagaatggc gcctcgttcg gcttcgccaa caccagcgcc      840
cgggcctgcg acgccaccaa gatcaatgcc ctggtgccga gcgccggcgg cagctcgctg      900
ttctgctcgg ccaacacgct ggtggcttcc ggtgcggacc agagctacct gttcgccgac      960
```

```
ggcgtgcacc cgaccacggc cggccatcgc ctgatcgcca gcaacgtgct ggcgcgcctg   1020
ctggcggata acgtcgcgca ctga                                         1044
```

<210> SEQ ID NO 56
<211> LENGTH: 786
<212> TYPE: DNA
<213> ORGANISM: Streptomyces coelicolor

<400> SEQUENCE: 56

```
gtgatcgggt cgtacgtggc ggtgggggac agcttcaccg agggcgtcgg cgaccccggc    60
cccgacgggg cgttcgtcgg ctgggccgac cggctcgccg tactgctcgc ggaccggcgc   120
cccgagggcg acttcacgta cacgaacctc gccgtgcgcg gcaggctcct cgaccagatc   180
gtggcggaac aggtcccgcg ggtcgtcgga ctcgcgcccg acctcgtctc gttcgcggcg   240
ggcggcaacg acatcatccg gcccggcacc gatcccgacg aggtcgccga gcggttcgag   300
ctggcggtgg ccgcgctgac cgccgcggcc ggaaccgtcc tggtgaccac cgggttcgac   360
acccgggggg tgcccgtcct caagcacctg cgcggcaaga tcgccacgta caacgggcac   420
gtccgcgcca tcgccgaccg ctacggctgc ccggtgctcg acctgtggtc gctgcggagc   480
gtccaggacc gcagggcgtg ggacgccgac cggctgcacc tgtcgccgga ggggcacacc   540
cgggtggcgc tgcgcgcggg gcaggccctg gcctgcgcg tcccggccga ccctgaccag   600
ccctggccgc cctgccgcc gcgcggcacg ctcgacgtcc ggcgcgacga cgtgcactgg   660
gcgcgcgagt acctggtgcc gtggatcggg cgccggctgc ggggcgagtc gtcgggcgac   720
cacgtgacgg ccaaggggac gctgtcgccg gacgccatca gacgcggat cgccgcggtg   780 gcctga                                                              786
```

<210> SEQ ID NO 57
<211> LENGTH: 783
<212> TYPE: DNA
<213> ORGANISM: Streptomyces coelicolor

<400> SEQUENCE: 57

```
atgcagacga accccgcgta caccagtctc gtcgccgtcg gcgactcctt caccgagggc    60
atgtcggacc tgctgcccga cggctcctac cgtggctggg ccgacctcct cgccacccgg   120
atggcggccc gctcccccgg cttccggtac gccaacctgg cggtgcgcgg gaagctgatc   180
ggacagatcg tcgacgagca ggtggacgtg gccgccgcca tggagccga cgtgatcacg   240 ctggtcggcg ggctcaacga cacgctgcgg cccaagtgcg acatggcccg ggtgcgggac   300
ctgctgaccc aggccgtgga acggctcgcc ccgcactgcg agcagctggt gctgatgcgc   360
agtcccggtc gccagggtcc ggtgctggag cgcttccggc cccgcatgga ggccctgttc   420
gccgtgatcg acgacctggc cgggcggcac ggcgccgtgg tcgtcgacct gtacggggcc   480
cagtcgctgg ccgaccctcg gatgtgggac gtggaccggc tgcacctgac cgccgagggc   540
caccgccggg tcgcggaggc ggtgtggcag tcgctcggcc acgagcccga ggaccccgag   600
tggcacgcgc cgatcccggc gacgccgccg ccggggtggg tgacgcgcag gaccgcggac   660
gtccggttcg cccggcagca cctgctgccc tggataggcc gcaggctgac cgggcgctcg   720
tccggggacg gcctgccggc caagcgcccg gacctgctgc cctacgagga ccccgcacgg   780
tga                                                                 783
```

<210> SEQ ID NO 58
<211> LENGTH: 1365

```
<212> TYPE: DNA
<213> ORGANISM: Streptomyces coelicolor

<400> SEQUENCE: 58
atgacccggg gtcgtgacgg gggtgcgggg gcgcccccca ccaagcaccg tgccctgctc      60
gcggcgatcg tcaccctgat agtggcgatc tccgcggcca tatacgccgg agcgtccgcg     120
gacgacggca gcagggacca cgcgctgcag gccggaggcc gtctcccacg aggagacgcc     180
gcccccgcgt ccaccggtgc ctgggtgggc gcctgggcca ccgcaccggc cgcggccgag     240 ccggcaccg agacgaccgg cctgcgggcc cgctccgtgc gcaacgtcgt gcacacctcg      300
gtcggcggca ccggcgcgcg gatcaccctc tcgaacctgt acgggcagtc gccgctgacc     360
gtcacacacg cctcgatcgc cctggccgcc gggcccgaca ccgccgccgc gatcgccgac     420
accatgcgcc ggctcacctt cggcggcagc gcccgggtga tcatcccggc gggcggccag     480
gtgatgagcg acaccgcccg cctcgccatc ccctacgggg cgaacgtcct ggtcaccacg     540 tactcccca tcccgtccgg gccggtgacc taccatccgc aggcccggca gaccagctac      600
ctggccgacg cgaccgcac ggcggacgtc accgccgtcg cgtacaccac ccccacgccc      660
tactggcgct acctgaccgc cctcgacgtg ctgagccacg aggccgacgg cacggtcgtg     720
gcgttcggcg actccatcac cgacggcgcc cgctcgcaga gcgacgccaa ccaccgctgg     780
accgacgtcc tcgccgcacg cctgcacgag gcggcgggcg acggccggga cacgccccgc     840
tacagcgtcg tcaacgaggg catcagcggc aaccggctcc tgaccagcag gccggggcgg     900
ccggccgaca cccgagcgg actgagccgg ttccagcggg acgtgctgga acgcaccaac      960
gtcaaggccg tcgtcgtcgt cctcggcgtc aacgacgtcc tgaacagccc ggaactcgcc    1020
gaccgcgacg ccatcctgac cggcctgcgc accctcgtcg accgggcgca cgcccgggga    1080
ctgcgggtcg tcggcgccac gatcacgccg ttcggcggct acgcggcta caccgaggcc     1140 cgcgagacga tgcggcagga ggtcaacgag gagatccgct ccggccgggt cttcgacacg    1200
gtcgtcgact tcgacaaggc cctgcgcgac ccgtacgacc cgcgccggat gcgctccgac    1260
tacgacagcg cgaccaccct gcaccccggc gacaaggggt acgcgcgcat gggcgcggtc    1320
atcgacctgg ccgcgctgaa gggcgcggcg ccggtcaagg cgtag                    1365

<210> SEQ ID NO 59
<211> LENGTH: 1023
<212> TYPE: DNA
<213> ORGANISM: Streptomyces coelicolor

<400> SEQUENCE: 59
atgacgagca tgtcgagggc gagggtggcg cggcggatcg cggccggcgc ggcgtacggc      60
ggcggcggca tcggcctggc gggagcggcg gcggtcggtc tggtggtggc cgaggtgcag     120
ctggccagac gcagggtggg ggtgggcacg ccgacccggg tgccgaacgc gcagggactg     180 tacgcggca ccctgcccac ggccggcgac ccgccgctgc ggctgatgat gctgggcgac     240
tccacggccg ccgggcaggg cgtgcaccgg gccgggcaga gccgggcgc gctgctggcg     300 tccgggctcg cggcggtggc ggagcggccg gtgcggctgg ggtcggtcgc ccagccgggg     360
gcgtgctcgg acgacctgga ccggcaggtg gcgctggtgc tcgccgagcc ggaccggtg      420 cccgacatct gcgtgatcat ggtcggcgcc aacgacgtca cccaccggat gccggcgacc     480
cgctcggtgc ggcacctgtc ctcggcggta cggcggctgc gcacggccgg tgcggaggtg     540
gtggtcggca cctgtccgga cctgggcacg atcgagcggg tgcggcagcc gctgcgctgg     600
ctggcccggc gggcctcacg gcagctcgcg gcggcacaga ccatcggcgc cgtcgagcag     660
```

```
ggcgggcgca cggtgtcgct gggcgacctg ctgggtccgg agttcgcgca gaacccgcgg    720
gagctcttcg gccccgacaa ctaccacccc tccgccgagg ggtacgccac ggccgcgatg    780
gcggtactgc cctcggtgtg cgccgcgctc ggcctgtggc cggccgacga ggagcacccg    840
gacgcgctgc gccgcgaggg cttcctgccg gtggcgcgcg cggcggcgga ggcggcgtcc    900
gaggcgggta cggaggtcgc cgccgccatg cctacggggc ctcggggggcc ctgggcgctg    960 ctgaagcgcc ggagacggcg tcgggtgtcg gaggcggaac cgtccagccc gtccggcgtt   1020
tga                                                                 1023

<210> SEQ ID NO 60
<211> LENGTH: 918
<212> TYPE: DNA
<213> ORGANISM: Streptomyces coelicolor

<400> SEQUENCE: 60
atgggtcgag ggacggacca gcggacgcgg tacggccgtc gccgggcgcg tgtcgcgctc     60
gccgccctga ccgccgccgt cctgggcgtg ggcgtggcgg gctgcgactc cgtgggcggc    120
gactcacccg ctccttccgg cagcccgtcg aagcggacga ggacggcgcc cgcctgggac    180
accagcccgg cgtccgtcgc cgccgtgggc gactccatca cgcgcggctt cgacgcctgt    240
gcggtgctgt cggactgccc ggaggtgtcg tgggcgaccg gcagcagcgc gaaggtcgac    300
tcgctggccg tacggctgct ggggaaggcg gacgcggccg agcacagctg gaactacgcg    360
gtcaccgggg cccggatggc ggacctgacc gctcaggtga cgcgggcggc gcagcgcgag    420
ccggagctgg tggcggtgat ggccggggcg aacgacgcgt gccggtccac gacctcggcg    480
atgacgccgg tggcggactt ccgggcgcag ttcgaggagg cgatggccac cctgcgcaag    540
aagctcccca aggcgcaggt gtacgtgtcg agcatcccgg acctcaagcg gctctggtcc    600
cagggccgca ccaacccgct gggcaagcag gtgtggaagc tcggcctgtg cccgtcgatg    660
ctgggcgacg cggactccct ggactcggcg gcgaccctgc ggcgcaacac ggtgcgcgac    720
cgggtggcgc actacaacga ggtgctgcgg gaggtctgcg cgaaggaccg gcggtgccgc    780
agcgacgacg gcgcggtgca cgagttccgg ttcggcacgg accagttgag ccactgggac    840
tggttccacc cgagtgtgga cggccaggcc cggctggcgg agatcgccta ccgcgcggtc    900
accgcgaaga atccctga                                                 918

<210> SEQ ID NO 61
<211> LENGTH: 1068
<212> TYPE: DNA
<213> ORGANISM: Streptomyces rimosus

<400> SEQUENCE: 61
ttcatcacaa cgatgtcaca acaccggcca tccgggtcat ccctgatcgt gggaatgggt     60
gacaagcctt cccgtgacga aagggtcctg ctacatcaga aatgacagaa atcctgctca    120
gggaggttcc atgagactgt cccgacgcgc ggccacggcg tccgcgctcc tcctcacccc    180
ggcgctcgcg ctcttcggcg cgagcgccgc cgtgtccgcg ccgcgaatcc aggccaccga    240
ctacgtggcc ctcggcgact cctactcctc ggggtcggc gcgggcagct acgacagcag    300
cagtggctct tgtaagcgca gcaccaagtc ctacccggcc ctgtgggccg cctcgcacac    360
cggtacgcgg ttcaacttca ccgcctgttc gggcgcccgc acaggagacg tgctggccaa    420
gcagctgacc ccggtcaact ccggcaccga cctggtcagc attaccatcg gcggcaacga    480
cgcgggcttc gccgacacca tgaccacctg caacctccag ggcgagagcg cgtgcctggc    540
```

```
gcggatcgcc aaggcgcgcg cctacatcca gcagacgctg cccgcccagc tggaccaggt    600
ctacgacgcc atcgacagcc gggccccgc agcccaggtc gtcgtcctgg gctacccgcg     660
cttctacaag ctgggcggca gctgcgccgt cggtctctcg gagaagtccc gcgcggccat    720
caacgccgcc gccgacgaca tcaacgccgt caccgccaag cgcgccgccg accacggctt    780
cgccttcggg gacgtcaaca cgaccttcgc cgggcacgag ctgtgctccg gcgcccctg    840 gctgcacagc gtcacccttc ccgtggagaa ctcctaccac cccacggcca acggacagtc    900
caagggctac ctgcccgtcc tgaactccgc cacctgatct cgcggctact ccgcccctga    960
cgaagtcccg ccccgggcg gggcttcgcc gtaggtgcgc gtaccgccgt cgcccgtcgc    1020
gccggtggcc ccgccgtacg tgccgccgcc cccggacgcg gtcggttc                 1068
```

<210> SEQ ID NO 62
<211> LENGTH: 1008
<212> TYPE: DNA
<213> ORGANISM: Aeromonas hydrophila

<400> SEQUENCE: 62

```
atgaaaaaat ggtttgtgtg tttattggga ttggtcgcgc tgacagttca ggcagccgac     60
agtcgccccg cctttcccg gatcgtgatg ttcggcgaca gcctctccga taccggcaaa    120
atgtacagca agatgcgcgg ttacctcccc tccagcccgc cctactatga gggccgtttc    180
tccaacggac ccgtctggct ggagcagctg accaaacagt tcccgggtct gaccatcgcc    240
aacgaagcgg aaggcggtgc cactgccgtg gcttacaaca agatctcctg gaatcccaag    300
tatcaggtca tcaacaacct ggactacgag gtcacccagt tcttgcagaa agacagcttc    360
aagccggacg atctggtgat cctctgggtc ggtgccaatg actatctggc ctatggctgg    420
aacacggagc aggatgccaa gcgggttcgc gatgccatca gcgatgcggc caaccgcatg    480
gtactgaacg gtgccaagca gatactgctg ttcaacctgc cggatctggg ccagaacccg    540
tcagctcgca gtcagaaggt ggtcgaggcg gtcagccatg tctccgccta tcacaaccag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag    720 aaccctgct acgacggcgg ctatgtgtgg aagccgtttg ccacccgcag cgtcagcacc    780
gaccgccagc tctccgcctt cagtccgcag gaacgcctcg ccatcgccgg caacccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcgc gaaccagtac gagttcctcg cccactga                1008
```

<210> SEQ ID NO 63
<211> LENGTH: 1011
<212> TYPE: DNA
<213> ORGANISM: Aeromonas salmonicida

<400> SEQUENCE: 63

```
atgaaaaaat ggtttgtttg tttattgggg ttgatcgcgc tgacagttca ggcagccgac     60
actcgccccg ccttctcccg gatcgtgatg ttcggcgaca gcctctccga taccggcaaa    120
atgtacagca agatgcgcgg ttacctcccc tccagcccgc cctactatga gggccgtttc    180
tccaacggac ccgtctggct ggagcagctg accaagcagt tcccgggtct gaccatcgcc    240
aacgaagcgg aaggcggtgc cactgccgtg gcttacaaca agatctcctg gaatcccaag    300
tatcaggtca tcaacaacct ggactacgag gtcacccagt tcttgcagaa agacagcttc    360
```

```
aagccggacg atctggtgat cctctgggtc ggtgccaatg actatctggc atatggctgg      420
aatacggagc aggatgccaa gcgagttcgc gatgccatca gcgatgcggc caaccgcatg      480
gtactgaacg gtgccaagca gatactgctg ttcaacctgc cggatctggg ccagaacccg      540
tcagcccgca gtcagaaggt ggtcgaggcg gtcagccatg tctccgccta tcacaacaag      600
ctgctgctga acctggcacg ccagctggcc cccaccggca tggtaaagct gttcgagatc      660
gacaagcaat tgccgagat gctgcgtgat ccgcagaact tcggcctgag cgacgtcgag        720 aaccccctgct acgacggcgg ctatgtgtgg aagccgtttg ccacccgcag cgtcagcacc     780
gaccgccagc tctccgcctt cagtccgcag gaacgcctcg ccatcgccgg caacccgctg      840
ctggcacagg ccgttgccag tcctatggcc cgccgcagcg ccagccccct caactgtgag      900
ggcaagatgt tctgggatca ggtacacccg accactgtcg tgcacgcagc cctgagcgag      960
cgcgccgcca ccttcatcga gacccagtac gagttcctcg cccacggatg a              1011
```

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      terminator oligonucleotide sequence

<400> SEQUENCE: 64

```
cgggacttac cgaaagaaac catcaatgat ggtttctttt ttgttcataa a              51
```

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
      terminator oligonucleotide sequence

<400> SEQUENCE: 65

```
caagactaaa gaccgttcgc ccgttttttgc aataagcggg cgaatcttac ataaaaata     59
```

<210> SEQ ID NO 66
<211> LENGTH: 61
<212> TYPE: DNA
<213> ORGANISM: Artificial Sequence
<220> FEATURE:
<223> OTHER INFORMATION: Description of Artificial Sequence: Synthetic
      terminator oligonucleotide sequence

<400> SEQUENCE: 66

```
acggccgtta gatgtgacag cccgttccaa aaggaagcgg gctgtcttcg tgtattattg      60
t                                                                     61
```

<210> SEQ ID NO 67
<211> LENGTH: 54
<212> TYPE: DNA
<213> ORGANISM: Artificial Sequence
<220> FEATURE:
<223> OTHER INFORMATION: Description of Artificial Sequence: Synthetic
      terminator oligonucleotide sequence

<400> SEQUENCE: 67

```
tcttttaaag gaaaggctgg aatgcccggc attccagcca catgatcatc gttt            54
```

<210> SEQ ID NO 68
<211> LENGTH: 56

```
<212> TYPE: DNA
<213> ORGANISM: Artificial Sequence
<220> FEATURE:
<223> OTHER INFORMATION: Description of Artificial Sequence: Synthetic
      terminator oligonucleotide sequence

<400> SEQUENCE: 68
gctgacaaat aaaagaagc aggtatggag gaacctgctt cttttttacta ttattg        56

<210> SEQ ID NO 69
<211> LENGTH: 102
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccccgctcga ggcttttctt ttggaagaaa atatagggaa aatggtactt gttaaaaatt    60
cggaatattt atacaatatc atatgtttca cattgaaagg gg                       102

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggaatctcg aggtttttatc ctttaccttg tctcc                              35

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 71

Met Arg Arg Ser Arg Phe Leu Ala
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 72

Ala Leu Ile Leu Leu Thr Leu Ala
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 73

Ala Arg Ala Ala Pro
1               5
```

-continued

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 74

Tyr Val Ala Leu Gly Asp Ser Tyr Ser Ser Gly
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 75

Gly Ala Gly Ser Tyr
1               5

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 76

Ser Ser Gly Asp
1

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 77

Arg Ser Thr Lys Ala Tyr Pro Ala Leu Trp Ala Ala Ala His Ala
1               5                   10                  15

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 78

Ser Ser Phe Ser Phe
1               5

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 79

```
Ala Cys Ser Gly Ala Arg Thr Tyr Asp Val Leu Ala
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 80

Leu Val Ser Ile Thr Ile Gly Gly Asn Asp Ala Gly Phe Ala Asp
1               5                   10                  15

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 81

Met Thr Thr Cys Val Leu
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 82

Ser Asp Ser Ala Cys Leu
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 83

Thr Leu Pro Ala
1

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 84

Arg Leu Asp Ser Val Tyr Ser Ala Ile
1               5

<210> SEQ ID NO 85
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      consensus peptide

<400> SEQUENCE: 85

Thr Arg Ala Pro
1

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 86

Ala Arg Val Val Val Leu Gly Tyr Pro Arg Ile Tyr
1               5                   10

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 87

Leu Gly Leu Ser
1

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 88

Thr Lys Arg Ala Ala Ile Asn Asp Ala Ala Asp
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 89

Leu Asn Ser Val Ile Ala Lys Arg Ala Ala Asp His
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 90

Gly Phe Thr Phe Gly Asp Val
1               5

<210> SEQ ID NO 91
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 91

Gly His Glu Leu Cys Ser Ala
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 92

Pro Trp Leu His Ser Leu Thr Leu Pro
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 93

Ser Tyr His Pro Thr Ala
1               5

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 94

Gly His Ala Ala Gly Tyr Leu Pro Val Leu Asn Ser Ile
1               5                   10

<210> SEQ ID NO 95
<211> LENGTH: 232
<212> TYPE: PRT
<213> ORGANISM: Aspergillus aculeatus

<400> SEQUENCE: 95

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95
```

```
Tyr Ser Val Tyr Asp Gly Val Asn Glu Thr Ile Leu Thr Phe Pro Ala
                100                 105                 110

Tyr Leu Glu Asn Ala Ala Lys Leu Phe Thr Ala Lys Gly Ala Lys Val
            115                 120                 125

Ile Leu Ser Ser Gln Thr Pro Asn Asn Pro Trp Glu Thr Gly Thr Phe
130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Ala Glu Ala Phe
                195                 200                 205

Leu Lys Ala Val Val Cys Thr Gly Thr Ser Leu Lys Ser Val Leu Thr
            210                 215                 220

Thr Thr Ser Phe Glu Gly Thr Cys
225                 230

<210> SEQ ID NO 96
<211> LENGTH: 184
<212> TYPE: PRT
<213> ORGANISM: Escherichia coli

<400> SEQUENCE: 96

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 97
<211> LENGTH: 308
<212> TYPE: PRT
<213> ORGANISM: Aeromonas hydrophila

<400> SEQUENCE: 97

Ile Val Met Phe Gly Asp Ser Leu Ser Asp Thr Gly Lys Met Tyr Ser
```

```
                1               5                   10                  15
Lys Met Arg Gly Tyr Leu Pro Ser Ser Pro Tyr Tyr Glu Gly Arg
                    20                  25                  30

Phe Ser Asn Gly Pro Val Trp Leu Glu Gln Leu Thr Asn Glu Phe Pro
                    35                  40                  45

Gly Leu Thr Ile Ala Asn Glu Ala Glu Gly Gly Pro Thr Ala Val Ala
                50                  55                  60

Tyr Asn Lys Ile Ser Trp Asn Pro Lys Tyr Gln Val Ile Asn Asn Leu
65                      70                  75                      80

Asp Tyr Glu Val Thr Gln Phe Leu Gln Lys Asp Ser Phe Lys Pro Asp
                    85                  90                  95

Asp Leu Val Ile Leu Trp Val Gly Ala Asn Asp Tyr Leu Ala Tyr Gly
                    100                 105                 110

Trp Asn Thr Glu Gln Asp Ala Lys Arg Val Arg Asp Ala Ile Ser Asp
                    115                 120                 125

Ala Ala Asn Arg Met Val Leu Asn Gly Ala Lys Glu Ile Leu Leu Phe
                130                 135                 140

Asn Leu Pro Asp Leu Gly Gln Asn Pro Ser Ala Arg Ser Gln Lys Val
145                     150                 155                     160

Val Glu Ala Ala Ser His Val Ser Ala Tyr His Asn Gln Leu Leu Leu
                    165                 170                 175

Asn Leu Ala Arg Gln Leu Ala Pro Thr Gly Met Val Lys Leu Phe Glu
                    180                 185                 190

Ile Asp Lys Gln Phe Ala Glu Met Leu Arg Asp Pro Gln Asn Phe Gly
                    195                 200                 205

Leu Ser Asp Gln Arg Asn Ala Cys Tyr Gly Gly Ser Tyr Val Trp Lys
                210                 215                 220

Pro Phe Ala Ser Arg Ser Ala Ser Thr Asp Ser Gln Leu Ser Ala Phe
225                     230                 235                     240

Asn Pro Gln Glu Arg Leu Ala Ile Ala Gly Asn Pro Leu Leu Ala Gln
                    245                 250                 255

Ala Val Ala Ser Pro Met Ala Ala Arg Ser Ala Ser Thr Leu Asn Cys
                    260                 265                 270

Glu Gly Lys Met Phe Trp Asp Gln Val His Pro Thr Thr Val Val His
                    275                 280                 285

Ala Ala Leu Ser Glu Pro Ala Ala Thr Phe Ile Glu Ser Gln Tyr Glu
                290                 295                 300

Phe Leu Ala His
305

<210> SEQ ID NO 98
<211> LENGTH: 167
<212> TYPE: PRT
<213> ORGANISM: Escherichia coli

<400> SEQUENCE: 98

Leu Leu Ile Leu Gly Asp Ser Leu Ser Ala Gly Tyr Arg Met Ser Ala
1               5                   10                  15

Ser Ala Ala Trp Pro Ala Leu Leu Asn Asp Lys Trp Gln Ser Lys Thr
                    20                  25                  30

Ser Val Val Asn Ala Ser Ile Ser Gly Asp Thr Ser Gln Gln Gly Leu
                35                  40                  45

Ala Arg Leu Pro Ala Leu Leu Lys Gln His Gln Pro Arg Trp Val Leu
            50                  55                  60

Val Glu Leu Gly Gly Asn Asp Gly Leu Arg Gly Phe Gln Pro Gln Gln
```

```
                65                  70                  75                  80
Thr Glu Gln Thr Leu Arg Gln Ile Leu Gln Asp Val Lys Ala Ala Asn
                    85                  90                  95

Ala Glu Pro Leu Leu Met Gln Ile Arg Leu Pro Ala Asn Tyr Gly Arg
                100                 105                 110

Arg Tyr Asn Glu Ala Phe Ser Ala Ile Tyr Pro Lys Leu Ala Lys Glu
            115                 120                 125

Phe Asp Val Pro Leu Leu Pro Phe Phe Met Glu Glu Val Tyr Leu Lys
        130                 135                 140

Pro Gln Trp Met Gln Asp Asp Gly Ile His Pro Asn Arg Asp Ala Gln
145                 150                 155                 160

Pro Phe Ile Ala Asp Trp Met
                165

<210> SEQ ID NO 99
<211> LENGTH: 295
<212> TYPE: PRT
<213> ORGANISM: Aeromonas hydrophila

<400> SEQUENCE: 99

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
                20                  25                  30

Phe Ser Asn Gly Pro Val Trp Leu Glu Gln Leu Thr Asn Glu Phe Pro
            35                  40                  45

Gly Leu Thr Ile Ala Asn Glu Ala Glu Gly Gly Pro Thr Ala Val Ala
        50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Glu Ile Leu Leu Phe
        130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Arg Ser Ala Ser Thr Leu Asn Cys
            260                 265                 270

Glu Gly Lys Met Phe Trp Asp Gln Val His Pro Thr Thr Val Val His
```

```
                275                 280                 285

Ala Ala Leu Ser Glu Pro Ala
    290                 295

<210> SEQ ID NO 100
<211> LENGTH: 335
<212> TYPE: PRT
<213> ORGANISM: Aeromonas hydrophila

<400> SEQUENCE: 100

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
    290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 101
<211> LENGTH: 318
<212> TYPE: PRT
```

<213> ORGANISM: Aeromonas salmonicida

<400> SEQUENCE: 101

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Tyr Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315

<210> SEQ ID NO 102
<211> LENGTH: 50
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 102

Arg Pro Ala Phe Ser Arg Ile Val Met Phe Gly Asp Ser Leu Ser Asp
1               5                   10                  15

Thr Gly Lys Met Tyr Ser Lys Met Arg Gly Tyr Leu Pro Ser Ser Pro
            20                  25                  30

```
Pro Tyr Tyr Glu Gly Arg Phe Ser Asn Gly Pro Val Trp Leu Glu Gln
        35                  40                  45

Leu Thr
    50

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 103

Phe Pro Gly Leu Thr Ile Ala Asn Glu Ala Glu Gly Gly
1               5                   10

<210> SEQ ID NO 104
<211> LENGTH: 79
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 104

Thr Ala Val Ala Tyr Asn Lys Ile Ser Trp Asn Pro Lys Tyr Gln Val
1               5                   10                  15

Ile Asn Asn Leu Asp Tyr Glu Val Thr Gln Phe Leu Gln Lys Asp Ser
            20                  25                  30

Phe Lys Pro Asp Asp Leu Val Ile Leu Trp Val Gly Ala Asn Asp Tyr
        35                  40                  45

Leu Ala Tyr Gly Trp Asn Thr Glu Gln Asp Ala Lys Arg Val Arg Asp
    50                  55                  60

Ala Ile Ser Asp Ala Ala Asn Arg Met Val Leu Asn Gly Ala Lys
65                  70                  75

<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 105

Ile Leu Leu Phe Asn Leu Pro Asp Leu Gly Gln Asn Pro Ser Ala Arg
1               5                   10                  15

Ser Gln Lys Val Val Glu Ala
            20

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 106

Ser His Val Ser Ala Tyr His Asn
1               5

<210> SEQ ID NO 107
```

```
<211> LENGTH: 38
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 107

Leu Leu Leu Asn Leu Ala Arg Gln Leu Ala Pro Thr Gly Met Val Lys
1               5                   10                  15

Leu Phe Glu Ile Asp Lys Gln Phe Ala Glu Met Leu Arg Asp Pro Gln
            20                  25                  30

Asn Phe Gly Leu Ser Asp
            35

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 108

Tyr Val Trp Lys Pro Phe Ala
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 109

Gln Leu Ser Ala Phe
1               5

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 110

Pro Gln Glu Arg Leu Ala Ile Ala Gly Asn Pro Leu Leu Ala Gln Ala
1               5                   10                  15

Val Ala Ser Pro Met Ala
            20

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 111

Arg Ser Ala Ser
1

<210> SEQ ID NO 112
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 112

Leu Asn Cys Glu Gly Lys Met Phe Trp Asp Gln Val His Pro Thr Thr
1               5                   10                  15

Val Val His Ala Ala Leu Ser Glu
            20

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 113

Ala Ala Thr Phe Ile
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 114

Gln Tyr Glu Phe Leu Ala His
1               5

<210> SEQ ID NO 115
<211> LENGTH: 1225
<212> TYPE: DNA
<213> ORGANISM: Artificial Sequence
<220> FEATURE:
<223> OTHER INFORMATION: Description of Artificial Sequence: Synthetic
      XhoI insert polynucleotide containing the LAT-KLM3' precursor
      gene
<220> FEATURE:
<221> NAME/KEY: CDS
<222> LOCATION: (101)..(1141)

<400> SEQUENCE: 115
gcttttcttt tggaagaaaa tatagggaaa atggtacttg ttaaaaattc ggaatattta      60
tacaatatca tatgtttcac attgaaaggg gaggagaatc atg aaa caa caa aaa      115
                                             Met Lys Gln Gln Lys
                                             1               5 cgg ctt tac gcc cga ttg ctg acg ctg tta ttt gcg ctc atc ttc ttg      163
Arg Leu Tyr Ala Arg Leu Leu Thr Leu Leu Phe Ala Leu Ile Phe Leu
                10                  15                  20 ctg cct cat tct gca gct tca gca gca gat aca aga ccg gcg ttt agc      211
Leu Pro His Ser Ala Ala Ser Ala Ala Asp Thr Arg Pro Ala Phe Ser
            25                  30                  35 cgg atc gtc atg ttt gga gat agc ctg agc gat acg ggc aaa atg tat      259
Arg Ile Val Met Phe Gly Asp Ser Leu Ser Asp Thr Gly Lys Met Tyr
        40                  45                  50 agc aaa atg aga ggc tat ctt ccg tca agc ccg ccg tat tat gaa ggc      307
Ser Lys Met Arg Gly Tyr Leu Pro Ser Ser Pro Pro Tyr Tyr Glu Gly
    55                  60                  65 cgc ttt agc aat gga ccg gtc tgg ctg gaa caa ctg acg aaa caa ttt      355
```

```
                Arg Phe Ser Asn Gly Pro Val Trp Leu Glu Gln Leu Thr Lys Gln Phe
                70              75                  80                  85 ccg gga ctg acg atc gct aat gaa gca gaa gga gga gca aca gcg gtc                 403
Pro Gly Leu Thr Ile Ala Asn Glu Ala Glu Gly Gly Ala Thr Ala Val
                90                  95                  100 gcc tat aac aaa atc agc tgg gac ccg aaa tat cag gtc atc aac aac                 451
Ala Tyr Asn Lys Ile Ser Trp Asp Pro Lys Tyr Gln Val Ile Asn Asn
            105                 110                 115 ctg gac tat gaa gtc aca cag ttt ctt cag aaa gac agc ttt aaa ccg                 499
Leu Asp Tyr Glu Val Thr Gln Phe Leu Gln Lys Asp Ser Phe Lys Pro
        120                 125                 130 gat gat ctg gtc atc ctt tgg gtc ggc gcc aat gat tat ctg gcg tat                 547
Asp Asp Leu Val Ile Leu Trp Val Gly Ala Asn Asp Tyr Leu Ala Tyr
    135                 140                 145 ggc tgg aac aca gaa caa gat gcc aaa aga gtc aga gat gcc atc agc                 595
Gly Trp Asn Thr Glu Gln Asp Ala Lys Arg Val Arg Asp Ala Ile Ser
150                 155                 160                 165 gat gcc gct aat aga atg gtc ctg aac ggc gcc aaa caa atc ctg ctg                 643
Asp Ala Ala Asn Arg Met Val Leu Asn Gly Ala Lys Gln Ile Leu Leu
                170                 175                 180 ttt aac ctg ccg gat ctg gga caa aat ccg agc gcc aga agc caa aaa                 691
Phe Asn Leu Pro Asp Leu Gly Gln Asn Pro Ser Ala Arg Ser Gln Lys
            185                 190                 195 gtc gtc gaa gca gtc agc cat gtc agc gcc tat cat aac aaa ctg ctg                 739
Val Val Glu Ala Val Ser His Val Ser Ala Tyr His Asn Lys Leu Leu
        200                 205                 210 ctg aac ctg gca aga caa ttg gca ccg acg gga atg gtt aaa ttg ttt                 787
Leu Asn Leu Ala Arg Gln Leu Ala Pro Thr Gly Met Val Lys Leu Phe
    215                 220                 225 gaa att gac aaa cag ttt gcc gaa atg ctg aga gat ccg caa aat ttt                 835
Glu Ile Asp Lys Gln Phe Ala Glu Met Leu Arg Asp Pro Gln Asn Phe
230                 235                 240                 245 ggc ctg agc gat gtc gaa aac ccg tgc tat gat ggc gga tat gtc tgg                 883
Gly Leu Ser Asp Val Glu Asn Pro Cys Tyr Asp Gly Gly Tyr Val Trp
                250                 255                 260 aaa ccg ttt gcc aca aga agc gtc agc acg gat aga caa ctg tca gcg                 931
Lys Pro Phe Ala Thr Arg Ser Val Ser Thr Asp Arg Gln Leu Ser Ala
            265                 270                 275 ttt agc ccg caa gaa aga ctg gca atc gcc gga aat ccg ctt ttg gca                 979
Phe Ser Pro Gln Glu Arg Leu Ala Ile Ala Gly Asn Pro Leu Leu Ala
        280                 285                 290 caa gca gtt gct tca ccg atg gca aga aga tca gca agc ccg ctg aat                1027
Gln Ala Val Ala Ser Pro Met Ala Arg Arg Ser Ala Ser Pro Leu Asn
    295                 300                 305 tgc gaa ggc aaa atg ttt tgg gat cag gtc cat ccg aca aca gtt gtc                1075
Cys Glu Gly Lys Met Phe Trp Asp Gln Val His Pro Thr Thr Val Val
310                 315                 320                 325 cat gct gcc ctt tca gaa aga gcg gcg acg ttt atc gaa aca cag tat                1123
His Ala Ala Leu Ser Glu Arg Ala Ala Thr Phe Ile Glu Thr Gln Tyr
                330                 335                 340 gaa ttt ctg gcc cat ggc tgagttaaca gaggacggat ttcctgaagg                       1171
Glu Phe Leu Ala His Gly
            345 aaatccgttt ttttatttta agcttggaga caaggtaaag gataaaacct cgag                    1225

<210> SEQ ID NO 116
<211> LENGTH: 347
<212> TYPE: PRT
<213> ORGANISM: Artificial Sequence
<220> FEATURE:
<223> OTHER INFORMATION: Description of Artificial Sequence: Synthetic
```

XhoI insert polypeptide containing the LAT-KLM3' precursor gene

<400> SEQUENCE: 116

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Asp Thr
            20                  25                  30

Arg Pro Ala Phe Ser Arg Ile Val Met Phe Gly Asp Ser Leu Ser Asp
        35                  40                  45

Thr Gly Lys Met Tyr Ser Lys Met Arg Gly Tyr Leu Pro Ser Ser Pro
    50                  55                  60

Pro Tyr Tyr Glu Gly Arg Phe Ser Asn Gly Pro Val Trp Leu Glu Gln
65                  70                  75                  80

Leu Thr Lys Gln Phe Pro Gly Leu Thr Ile Ala Asn Glu Ala Glu Gly
                85                  90                  95

Gly Ala Thr Ala Val Ala Tyr Asn Lys Ile Ser Trp Asp Pro Lys Tyr
            100                 105                 110

Gln Val Ile Asn Asn Leu Asp Tyr Glu Val Thr Gln Phe Leu Gln Lys
        115                 120                 125

Asp Ser Phe Lys Pro Asp Asp Leu Val Ile Leu Trp Val Gly Ala Asn
    130                 135                 140

Asp Tyr Leu Ala Tyr Gly Trp Asn Thr Glu Gln Asp Ala Lys Arg Val
145                 150                 155                 160

Arg Asp Ala Ile Ser Asp Ala Ala Asn Arg Met Val Leu Asn Gly Ala
                165                 170                 175

Lys Gln Ile Leu Leu Phe Asn Leu Pro Asp Leu Gly Gln Asn Pro Ser
            180                 185                 190

Ala Arg Ser Gln Lys Val Val Glu Ala Val Ser His Val Ser Ala Tyr
        195                 200                 205

His Asn Lys Leu Leu Leu Asn Leu Ala Arg Gln Leu Ala Pro Thr Gly
    210                 215                 220

Met Val Lys Leu Phe Glu Ile Asp Lys Gln Phe Ala Glu Met Leu Arg
225                 230                 235                 240

Asp Pro Gln Asn Phe Gly Leu Ser Asp Val Glu Asn Pro Cys Tyr Asp
                245                 250                 255

Gly Gly Tyr Val Trp Lys Pro Phe Ala Thr Arg Ser Val Ser Thr Asp
            260                 265                 270

Arg Gln Leu Ser Ala Phe Ser Pro Gln Glu Arg Leu Ala Ile Ala Gly
        275                 280                 285

Asn Pro Leu Leu Ala Gln Ala Val Ala Ser Pro Met Ala Arg Arg Ser
    290                 295                 300

Ala Ser Pro Leu Asn Cys Glu Gly Lys Met Phe Trp Asp Gln Val His
305                 310                 315                 320

Pro Thr Thr Val Val His Ala Ala Leu Ser Glu Arg Ala Ala Thr Phe
                325                 330                 335

Ile Glu Thr Gln Tyr Glu Phe Leu Ala His Gly
            340                 345
```

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
motif peptide
<220> FEATURE:
<221> NAME/KEY: MOD_RES

```
<222> LOCATION: (4)..(4)
<223> OTHER INFORMATION: Leu, Ala, Val, Ile, Phe, Tyr, His, Gln, Thr,
      Asn, Met or Ser

<400> SEQUENCE: 117

Gly Asp Ser Xaa
1

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 118

Gly Ala Asn Asp Tyr
1               5

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 119

Gly Asp Ser Leu
1

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 120

Gly Gly Asn Asp Ala
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 121

Gly Gly Asn Asp Leu
1               5

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 122

Gly Asp Ser Tyr
1
```

```
-continued

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide
<220> FEATURE:
<221> NAME/KEY: MOD_RES
<222> LOCATION: (5)..(5)
<223> OTHER INFORMATION: Any amino acid

<400> SEQUENCE: 123

Gly Gly Asn Asp Xaa
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 124

His His His His His His
1               5
```